United States Patent
Yousef et al.

(10) Patent No.: US 12,209,137 B2
(45) Date of Patent: Jan. 28, 2025

(54) ANTIGEN BINDING PROTEINS SPECIFICALLY BINDING CT45

(71) Applicant: Immatics Biotechnologies GmbH, Tuebingen (DE)

(72) Inventors: Sara Yousef, Tuebingen (DE); Fabian Brunk, Tuebingen (DE); Andreas Moritz, Tuebingen (DE); Sebastian Bunk, Tuebingen (DE); Claudia Wagner, Tuebingen (DE); Dominik Maurer, Tuebingen (DE); Felix Unverdorben, Tuebingen (DE)

(73) Assignee: Emmatics Biotechmiogieg GmbH, Tübingen (DE)

( * ) Notice: Subject to any disclaimer, the term of this patent is extended or adjusted under 35 U.S.C. 154(b) by 0 days.

(21) Appl. No.: 17/874,711

(22) Filed: Jul. 27, 2022

(65) Prior Publication Data

US 2023/0057987 A1 Feb. 23, 2023

Related U.S. Application Data

(60) Provisional application No. 63/335,399, filed on Apr. 27, 2022, provisional application No. 63/203,582, filed on Jul. 27, 2021.

(30) Foreign Application Priority Data

Jul. 27, 2021 (EP) .................................... 21188018

(51) Int. Cl.
| | | |
|---|---|---|
| C07K 16/30 | (2006.01) | |
| C07K 14/725 | (2006.01) | |
| G01N 33/574 | (2006.01) | |

(52) U.S. Cl.
CPC ...... *C07K 16/3069* (2013.01); *C07K 14/7051* (2013.01); *G01N 33/57496* (2013.01); *C07K 2317/34* (2013.01)

(58) Field of Classification Search
CPC ............ C07K 16/3069; C07K 14/7051; C07K 2317/34; C07K 14/70539; C07K 14/4702; C07K 2317/30; C07K 2317/734; C07K 2317/92; G01N 33/57496; A61P 35/00
See application file for complete search history.

(56) References Cited

U.S. PATENT DOCUMENTS

| | | |
|---|---|---|
| 4,861,719 A | 8/1989 | Miller |
| 4,975,278 A | 12/1990 | Senter et al. |
| 5,202,238 A | 4/1993 | Fell et al. |
| 5,204,244 A | 4/1993 | Fell et al. |
| 5,208,020 A | 5/1993 | Chari et al. |
| 5,278,056 A | 1/1994 | Bank et al. |
| 5,882,877 A | 3/1999 | Gregory et al. |
| 6,013,516 A | 1/2000 | Verma et al. |
| 6,018,032 A | 1/2000 | Koike et al. |
| 6,127,175 A | 10/2000 | Vigne et al. |
| 6,464,998 B1 | 10/2002 | Beuzard et al. |
| 6,805,861 B2 | 10/2004 | Stauss |
| 7,811,828 B2 | 10/2010 | Lemmel et al. |
| 9,791,443 B2 | 10/2017 | Weinschenk et al. |
| 9,791,444 B2 | 10/2017 | Weinschenk et al. |
| 10,106,805 B2 | 10/2018 | Spangenberg et al. |
| 11,072,645 B2 | 7/2021 | Bunk et al. |
| 2008/0038285 A1 | 2/2008 | Lemmel et al. |
| 2011/0257890 A1 | 10/2011 | Weinschenk et al. |
| 2013/0096016 A1 | 4/2013 | Weinschenk et al. |
| 2016/0187351 A1 | 6/2016 | Weinschenk et al. |
| 2018/0162922 A1 | 6/2018 | Bunk et al. |
| 2019/0016801 A1 | 1/2019 | Hofmann et al. |
| 2019/0016802 A1 | 1/2019 | Hofmann et al. |
| 2019/0016803 A1 | 1/2019 | Hofmann et al. |

(Continued)

FOREIGN PATENT DOCUMENTS

| | | |
|---|---|---|
| AU | 2003236645 B2 | 6/2009 |
| WO | 81/01145 A1 | 4/1981 |

(Continued)

OTHER PUBLICATIONS

Almagro, Juan C., et al. "Humanization of antibodies" Frontiers in Bioscience, vol. 13, pp. 1619-1633, Jan. 1, 2008.
Andrade, Valeria C.C., et al. "Frequency and prognostic relevance of cancer testis antigen 45 expression in multiple myeloma" Experimental Hematology, vol. 37, pp. 446-449, Apr. 2009.
Bragado, Rafael, et al. "Allelic polymorphism in the coding region of human TCR Cα gene and characterization of structural variability in the α chain constant domain" International Immunology, vol. 6, Issue 2, pp. 223-230, Feb. 1994.

(Continued)

*Primary Examiner* — Nelson B Moseley, II
*Assistant Examiner* — Alyssa Rae Stonebraker
(74) *Attorney, Agent, or Firm* — McBee, Moore & Vanik IP, LLC

(57) ABSTRACT

The present invention provides an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions CDRa1, CDRa2 and CDRa3 and a second polypeptide comprising a variable domain $V_B$ comprising CDRb1, CDRb2 and CDRb3. Also provided are nucleic acids encoding the antigen binding proteins, vectors comprising the nucleic acids, recombinant cells expressing the antigen binding proteins and pharmaceutical compositions comprising the antigen binding proteins. The invention further provides the antigen binding proteins for use in medicine and a method of producing the antigen binding protein.

64 Claims, 13 Drawing Sheets

Specification includes a Sequence Listing.

(56) References Cited

U.S. PATENT DOCUMENTS

| | | |
|---|---|---|
| 2019/0016804 A1 | 1/2019 | Hofmann et al. |
| 2021/0380659 A1 | 12/2021 | Bunk et al. |
| 2022/0185888 A1 | 6/2022 | Hofmann et al. |
| 2022/0195044 A1 | 6/2022 | Hofmann et al. |

FOREIGN PATENT DOCUMENTS

| | | |
|---|---|---|
| WO | 88/07378 A1 | 10/1988 |
| WO | 94/19478 A1 | 9/1994 |
| WO | 95/14785 A1 | 6/1995 |
| WO | 96/22378 A1 | 7/1996 |
| WO | 97/10354 A1 | 3/1997 |
| WO | 2001/48145 A1 | 7/2001 |
| WO | 03/100432 A2 | 12/2003 |
| WO | 2004/04404 A2 | 1/2004 |
| WO | 2004/091668 A1 | 10/2004 |
| WO | 2005/076009 A2 | 8/2005 |
| WO | 2006/029176 A2 | 3/2006 |
| WO | 2011/044186 A1 | 4/2011 |
| WO | 2011/128448 A1 | 10/2011 |
| WO | 2014/018863 A1 | 1/2014 |
| WO | 2014/091034 A1 | 6/2014 |
| WO | 2016/107740 A1 | 7/2016 |
| WO | 2017/195153 A1 | 11/2017 |
| WO | 2018/104407 A1 | 6/2018 |
| WO | 2019/012138 A1 | 1/2019 |
| WO | 2020/210202 A1 | 10/2020 |

OTHER PUBLICATIONS

Cerveira, Nuno, et al. "A novel spliced fusion of MLL with CT45A2 in a pediatric biphenotypic acute leukemia" BMC Cancer, vol. 58, Article No. 518, Sep. 2010.
Chen, Li, et al. "Increased Proteasome Activity, Ubiquitin-Conjugating Enzymes, and eEF1A Translation Factor Detected in Breast Cancer Tissue" Cancer Research, vol. 65, No. 13, Jul. 1, 2005.
Chen, Yao-Tseng, et al. "Cancer/testis antigen CT45: Analysis of mRNA and protein expression in human cancer" International Journal of Cancer, vol. 124, No. 12, pp. 2893-2898, Jun. 2009.
Chervin, Adam S., et al. "Engineering higher affinity T cell receptors using a T cell display system" Journal Immunol. Methods, vol. 339, No. 2, pp. 175-184, Dec. 2008.
Cole, David K., et al., T-cell Receptor (TCR)-Peptide Specificity Overrides Affinity-enhancing TCR-Major Histocompatibility Complex Interactions* Journal of Biological Chemistry, vol. 289, No. 2, pp. 628-638, Jan. 2014.
Coscia, Fabian, et al. "Multi-level Proteomics Identifies CT45 as a Chemosensitivity Mediator and Immunotherapy Target in Ovarian Cancer" Cell, vol. 175, No. 1, pp. 159-170, Sep. 20, 2018.
Dengjel, Jorn, et al. "Unexpected Abundance of HLA Class II Presented Peptides in Primary Renal Cell Carcinomas" Human Cancer Biology, vol. 12, No. 14, pp. 4163-4170, Jul. 15, 2006.
Folch, Géraldine, et al. "The Human T cell Receptor Beta Variable (TRBV) Genes" Experimental and Clinical Immunogenetics, vol. 17, pp. 42-54, 2000.
Gattinoni, Luca, et al. "Adoptive immunotherapy for cancer: building on success" National Review Immunology, vol. 6, No. 5, pp. 383-393, May 2006.
Gillies, Stephen D., et al. "Expression of cloned immunoglobulin genes introduced into mouse L cells" Nucleic Acids Research, vol. 11, No. 22, pp. 7981-7997, Nov. 1983.
Guo, Haiwei, et al. "Protein tolerance to random amino acid change" PNAS, vol. 101, No. 25, pp. 205-9210, Jun. 22, 2004.
Hosken, Nancy A., et al. "Defective Presentation of Endogenous Antigen by a Cell Line Expressing Class I Molecules" Science, vol. 248, pp. 367-370, Apr. 20, 1990.
Hudecz, Ferenc. "Synthesis of Peptide Bioconjugates" Methods in Molecular Biology, vol. 298, pp. 209-223, 2005.
International Search Report and Written Opinion mailed Nov. 21, 2022 in International Application No. PCT/EP2022/071104 (17 pages).
Jin, Benjamin Y., et al. "Engineered T cells targeting E7 mediate regression of human papillomavirus cancers in a murine model" JCI Insight, vol. 3, No. 8, Apr. 2018.
Kirin, Srecko I., et al. "Amino Acid and Peptide Bioconjugates of Copper(II) and Zinc(II) Complexes with a Modified N, N-Bis(2-picolyl)amine Ligand" Inorganic Chemistry, vol. 44, pp. 5405-5415, Jul. 2005.
Koop, A, et al. "MS7-5: Identification of the Microtubule Associated Protein EML4 as a Cancer/Testis Antigen (CT45) Interacting Protein" European Journal of Cell Biology, vol. 89, p. 39, Mar. 1, 2010.
Koop, Anja, et al. "Down-regulation of the cancer/testis antigen 45(CT45) is associated with altered tumor cell morphology, adhesion and migration" Cell Communication & Signaling, vol. 11, No. 1, Jun. 10, 2013 (12 pages).
Kuwana, Yoshihisa, et al. "Expression of Chimeric Receptor Composed of Immunoglobulin-Derived V Resions and T-Cell Receptor-Derived C Regions", vol. 149, No. 3, pp. 960-968, Dec. 31, 1987.
Lefranc, Marie-Paule, et al. "IMGT unique numbering for immunoglobulin and T cell receptor variable domains and Ig superfamily V-like domains" Developmental & Comparative Immunology, vol. 27, pp. 55-77, Jan. 2003.
LeFranc, Marie-Paule, et al. "IMGT(R) , the international ImMunoGeneTics information system(R) 25 years on" Nucleic Acids Research, vol. 43, Database issue D413-D422, Jan. 2015.
Mason, John O., et al. "Transcription Cell Type Specificity is Conferred by an Immunoglobulin VH Gene Promoter That Includes a Functional Consensus Sequence" Cell, vol. 41, pp. 479-487, Jun. 1985.
Mizukami, Yuji, et al. "Primary T-Cell Lymphoma of the Thyroid" Pathology International, vol. 37, Issue 12, pp. 1987-1995, Dec. 1987.
Morgan, Richard A., et al. "Cancer Regression in Patients After Transfer of Genetically Engineered Lymphocytes" Science, vol. 314, No. 5796, pp. 126-129, Oct. 6, 2006.
Morrison, Sherie L., et al. "Chimeric human antibody molecules: Mouse antigen-binding domains with human constant region domains" Proc. Natl. Acad. Sci., vol. 81, pp. 6851-6855, Nov. 1984.
Needleman, Saul B., et al. "A General Method Applicable to the Search for Similarities in the Amino Acid Sequence of Two Proteins" Journal of Molecular Biology, vol. 48, No. 3, pp. 443-453, Mar. 1970.
Neuberger, M.S., et al. "A hapten-specific chimaeric IgE antibody with human physiological effector function" Nature, vol. 314, pp. 268-270, Mar. 1985.
Nielsen, Peter E., et al. "Sequence-Selective Recognition of DNA by Strand Displacement with a Thymine-Substituted Polyamide" Science, vol. 254, pp. 1497-1500, Dec. 1991.
Plebanski, Magdalena, et al. "Induction of peptide-specific primary cytotoxic T lymphocyte responses from human peripheral blood" European Journal of Immunology, vol. 25, Issue 6, pp. 1783-1787, Jun. 1995.
Rice, Peter, et al. "EMBOSS:The European Molecular Biology Open Software Suite" vol. 16, No. 6, Jun. 2000.
Riechmann, Lutz, et al. "Reshaping human antibodies for therapy" Nature, vol. 332, pp. 323-327, Mar. 1988.
Scaviner, Dominique, et al. "The Human T Cell Receptor Alpha Variable (TRAV) Genes" Experimental and Clinical Immunogenetics, vol. 17, No. 2, pp. 83-96, 2000.
Shimasaki, Noriko, et al. "NK cells for cancer immunotherapy" Nature Reviews Drug Discovery, vol. 19, No. 3, pp. 200-218, Mar. 2020.
Shitara, Kenya, et al. "A new vector for the high level expression of chimeric antibodies in myeloma cells" Journal of Immunological Methods, vol. 167, Issues 1-2, pp. 271-27, Jan. 1994.
Soto, Carolina M., et al. "MHC-class I-restricted CD4 T cells: a nanomolar affinity TCR has improved anti-tumor efficacy in vivo compared to the micromolar wild type TCR" Cancer Immunology, Immunotherapy, vol. 62, No. 2, pp. 359-369, Feb. 2013.

(56) References Cited

OTHER PUBLICATIONS

Stadinski, Brian D., et al. "Effect of CDR3 Sequences and Distal V Gene Residues in Regulating TCR-MHC Contacts and Ligand Specificity" The Journal of Immunology, vol. 192, No. 12, pp. 6071-6082, Jun. 2014.

Urlaub, Gail, et al. "Isolation of Chinese hamster cell mutants deficient in dihydrofolate reductase activity" Proc. Natl. Acad. Sci., vol. 77, No. 7, pp. 4216-4220, Jul. 1980.

Walter, Steffen, et al. "Cutting Edge: Predetermined Avidity of Human CD8 T Cells Expanded on Calibrated MHC/Anti-CD28-Coated Microspheres" Journal of Immunology, vol. 171, No. 10, pp. 4974-4978, Nov. 2003.

Yang, Ping, et al. "Cancer/Testis Antigens Trigger Epithelial-Mesenchymal Transition and Genesis of Cancer Stem-Like Cells" Current Pharmaceutical Design, vol. 21, No. 10, pp. 1292-1300, Mar. 2015.

Yang, Ping, et al. "Oncogenic cancer/testis antigens are a hallmarker of cancer and a sensible target for cancer immunotherapy" BBA—Reviews on Cancer, vol. 1876, No. 1, Apr. 29, 2021 (10 pages).

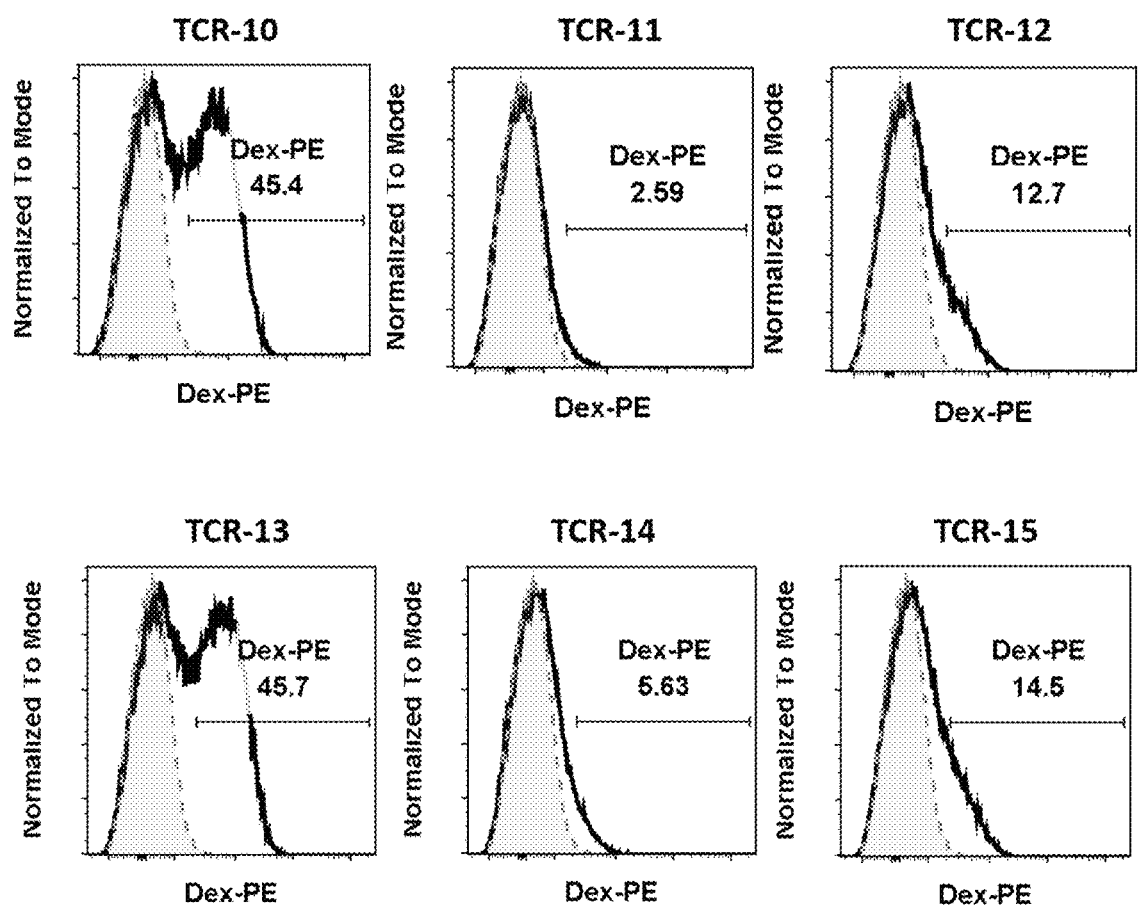

ANTIGEN BINDING PROTEINS SPECIFICALLY BINDING CT45

CROSS-REFERENCE TO RELATED APPLICATIONS

This application claims priority to U.S. Provisional Patent Application No. 63/335,399, filed 27 Apr. 2022, U.S. Provisional Patent Application No. 63/203,582, filed 27 Jul. 2021, and European Patent Application No. 21188018.2, filed 27 Jul. 2021. Each of these applications is incorporated by reference in its entirety.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "3000058-020002_Sequence_Listing" created on 27 Jul. 2022, and 714,614 bytes in size) is submitted concurrently with the instant application, and the entire contents of the Sequence Listing are incorporated herein by reference.

The present invention relates to antigen binding proteins directed against CT45 protein-derived antigens, in particular antigen binding proteins which are specifically binding to the tumor expressed CT45-IP antigenic peptide in a complex with MHC. The antigen binding proteins are provided for use in the diagnosis, treatment and prevention of CT45 expressing proliferative diseases. Further provided are nucleic acids encoding the antigen binding proteins, vectors comprising the nucleic acids, recombinant cells expressing the antigen binding proteins and pharmaceutical compositions comprising the antigen binding proteins.

BACKGROUND

T-cell based immunotherapy targets peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are specifically expressed by cancer cells, and/or upregulated in cancer cells. Unlike CAR-T therapy and current antibody-based approaches, which can only target cell surface proteins, T-cell based immunotherapy enables the targeting of otherwise inaccessible intracellular proteins and thus significantly increases the number and diversity of the targets.

"Cancer Testis antigen 45 (CT45)" is a multigene family of nine almost identical genes in direct tandem repeats (typically named A1, A2, A3, A5, A6, A7, A8, A9 and A10). All nine CT45 genes encode putative proteins of 189 amino acids. The CT45A1 protein, which is usually only expressed in testicular germ cells, was shown to be also expressed in lung cancer, breast cancer and ovarian cancer (Chen, Y. T. et al., Int. J Cancer 124 (2009): 2893-2898). CT45A1 was also shown to be associated with poor prognosis and poor outcomes in multiple myeloma (Andrade, V. C. et al., Exp. Hematol. 37 (2009): 446-449). CT45A1 was described as gene up-regulating epithelial-mesenchymal transition (EMT) and metastatic genes, promoting EMT and tumor dissemination. Furthermore, CT45A1 was described as being implicated in the initiation or maintenance of cancer stem-like cells, promoting tumorigenesis and malignant progression (Yang, P. et al., Curr. Pharm. Des 21 (2015): 1292-1300). CT45A1 over-expression in a breast cancer model was shown to result in the up-regulation of various oncogenic and metastatic genes, constitutively activated ERK and CREB signalling pathways and increased tumorigenesis, invasion and metastasis. Silencing of CT45A1 was shown to reduce cancer cell migration and invasion. CT45A2 was shown to be a novel spliced MLL fusion partner in a pediatric patient with de novo bi-phenotypic acute leukemia and thus might be relevant for leukemogenesis (Cerveira, N. et al., BMC. Cancer 10 (2010): 518). CT45 was shown to be frequently expressed in both cancer cell lines and lung cancer specimens (Chen, L. et al., Cancer Res 65 (2005): 5599-5606). Since it has limited or no expression in normal adult tissues, CT45 is an attractive target for immunotherapeutic intervention.

The development of new anti-cancer agents that specifically recognize intracellular targets in a complex with MHC is one of the most important keys to unlock hard-to-treat cancers, particularly solid tumors. Thus, there is a need to develop new anti-cancer agents that specifically target intracellular proteins highly specific to cancer cells. The present invention addresses that need by providing novel antigen binding proteins specifically binding to a CT45 antigenic peptide comprising the amino acid sequence of SEQ ID NO: 138 (KIFEMLEGV), and methods of using such molecules in the treatment of proliferative diseases, in particular cancer. The antigen binding proteins of the invention are characterized by a high stability, high affinity, high functional avidity, high efficacy and high specificity. Compared to previously described antigen binding proteins binding to CT45 antigenic peptides, the antigen binding proteins of the invention exhibit at least one of: an increased stability, an increased affinity, an increased functional avidity, an increased efficacy and/or an increased specificity. The antigen binding proteins of the invention are thus both more effective and safer than prior art antigen binding proteins.

SUMMARY

In a first aspect, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 80, CDRa3 comprises or consists of the amino acid sequence of SEQ ID NO: 82, CDRb1 comprises or consists of the amino acid sequence of SEQ ID NO: 85, and CDRb3 comprises or consists of the amino acid sequence of SEQ ID NO: 87, CDRa1 comprises or consists of the amino acid sequence of SEQ ID NO: 71, CDRa3 comprises or consists of the amino acid sequence of SEQ ID NO: 72, CDRb1 comprises or consists of the amino acid sequence of SEQ ID NO: 75, and CDRb3 comprises or consists of the amino acid sequence of SEQ ID NO: 77, CDRa1 comprises or consists of the amino acid sequence of SEQ ID NO: 24, CDRa3 comprises or consists of the amino acid sequence of SEQ ID NO: 63, CDRb1 comprises or consists of the amino acid sequence of SEQ ID NO: 66, and CDRb3 comprises or consists of the amino acid sequence of SEQ ID NO: 68, CDRa1 comprises or consists of the amino acid sequence of SEQ ID NO: 90, CDRa3 comprises or consists of the amino acid sequence of SEQ ID NO: 92, CDRb1 comprises or consists of the amino acid sequence of SEQ ID NO: 66, and CDRb3 comprises or consists of the amino acid sequence of SEQ ID NO: 96, CDRa1 comprises or consists of the amino acid sequence of SEQ ID NO: 2, CDRa3 comprises or consists of the amino acid sequence of SEQ ID NO: 4, CDRb1 comprises or consists of the amino acid sequence of SEQ ID NO: 8, and CDRb3 comprises or consists of the amino acid sequence of SEQ ID NO: 10, CDRa1 comprises or consists of the amino acid sequence of SEQ ID NO: 53, CDRa3 comprises or consists of the amino acid sequence of SEQ ID NO: 55, CDRb1 comprises or consists of the amino acid sequence of SEQ ID NO: 58, and CDRb3 comprises or consists of the amino acid sequence of SEQ ID NO: 60, CDRa1 comprises or consists of the amino acid sequence of SEQ ID NO: 24, CDRa3 comprises or consists of the amino acid sequence of SEQ ID NO: 133, CDRb1 comprises or consists of the amino acid sequence of SEQ ID NO: 75, and CDRb3 comprises or consists of the amino acid sequence of SEQ ID NO: 136, CDRa1 comprises or consists of the amino acid sequence of SEQ ID NO: 99, CDRa3 comprises or consists of the amino acid sequence of SEQ ID NO: 101, CDRb1 comprises or consists of the amino acid sequence of SEQ ID NO: 75, and CDRb3 comprises or consists of the amino acid sequence of SEQ ID NO: 104, CDRa1 comprises or consists of the amino acid sequence of SEQ ID NO: 14, CDRa3 comprises or consists of the amino acid sequence of SEQ ID NO: 16, CDRb1 comprises or consists of the amino acid sequence of SEQ ID NO: 19, and CDRb3 comprises or consists of the amino acid sequence of SEQ ID NO: 21, CDRa1 comprises or consists of the amino acid sequence of SEQ ID NO: 107, CDRa3 comprises or consists of the amino acid sequence of SEQ ID NO: 109, CDRb1 comprises or consists of the amino acid sequence of SEQ ID NO: 112, and CDRb3 comprises or consists of the amino acid sequence of SEQ ID NO: 114, CDRa1 comprises or consists of the amino acid sequence of SEQ ID NO: 125, CDRa3 comprises or consists of the amino acid sequence of SEQ ID NO: 127, CDRb1 comprises or consists of the amino acid sequence of SEQ ID NO: 112, and CDRb3 comprises or consists of the amino acid sequence of SEQ ID NO: 130, or CDRa1 comprises or consists of the amino acid sequence of SEQ ID NO: 117, CDRa3 comprises or consists of the amino acid sequence of SEQ ID NO: 119, CDRb1 comprises or consists of the amino acid sequence of SEQ ID NO: 58, and CDRb3 comprises or consists of the amino acid sequence of SEQ ID NO: 122, CDRa1 comprises or consists of the amino acid sequence of SEQ ID NO: 24, CDRa3 comprises or consists of the amino acid sequence of SEQ ID NO: 35, CDRb1 comprises or consists of the amino acid sequence of SEQ ID NO: 38, and CDRb3 comprises or consists of the amino acid sequence of SEQ ID NO: 40, CDRa1 comprises or consists of the amino acid sequence of SEQ ID NO: 24, CDRa3 comprises or consists of the amino acid sequence of SEQ ID NO: 26, CDRb1 comprises or consists of the amino acid sequence of SEQ ID NO: 29, and CDRb3 comprises or consists of the amino acid sequence of SEQ ID NO: 31, or CDRa1 comprises or consists of the amino acid sequence of SEQ ID NO: 43, CDRa3 comprises or consists of the amino acid sequence of SEQ ID NO: 45, CDRb1 comprises or consists of the amino acid sequence of SEQ ID NO: 48, and CDRb3 comprises or consists of the amino acid sequence of SEQ ID NO: 50, wherein the antigen binding protein comprises said CDRa1, CDRa3, CDRb1 and CDRb3 sequences with not more than one, two or three amino acid mutations.

In a second aspect, the invention relates to a nucleic acid comprising a sequence encoding the antigen binding protein of the first aspect of the invention.

In a third aspect, the invention relates to a vector comprising the nucleic acid of the second aspect of the invention.

In a fourth aspect, the invention relates to a host cell comprising the antigen binding protein of the first aspect of the invention, the nucleic acid of the second aspect of the invention, or the vector of the third aspect of the invention.

In a fifth aspect, the invention relates to a pharmaceutical composition comprising the antigen binding protein of the first aspect of the invention, the nucleic acid of the second aspect of the invention, the vector of the third aspect of the invention or the host cell of the fourth aspect of the invention and optionally a pharmaceutically acceptable carrier.

In a sixth aspect, the invention relates to a method of producing the antigen binding protein according to the first aspect of the invention, comprising the steps of (a) providing a host cell, (b) providing a genetic construct comprising a coding sequence encoding the antigen binding protein of any of the first aspect of the invention, (c) introducing the genetic construct into the host cell, and (d) expressing the genetic construct by the host cell.

In a seventh aspect, the invention relates to the antigen binding protein of the first aspect of the invention, the nucleic acid of the second aspect of the invention, the vector of the third aspect of the invention, the host cell of the fourth aspect of the invention, or the pharmaceutical composition of the fourth aspect of the invention for use in medicine.

In an eighth aspect, the invention relates to the antigen binding protein of the first aspect of the invention, the nucleic acid of the second aspect of the invention, the vector of the third aspect of the invention, the host cell of the fourth aspect of the invention, or the pharmaceutical composition of the fourth aspect of the invention for use in a method of treatment and/or diagnosis of a proliferative disease.

In a ninth aspect, the invention relates to an in-vitro method of detecting cancer in a biological sample comprising the steps of (a) contacting the biological sample with the antigen binding protein of the first aspect of the invention, and (b) detecting binding of the antigen binding protein to the biological sample.

Definitions

The "CT45 antigenic peptide" comprises or consists of the amino acid sequence KIFEMLEGV (SEQ ID NO: 138) which corresponds to amino acids 143-151 of CT45A1 (SEQ ID NO: 749 as accessible under the Uniprot accession number Q5HYN5), CT45A2, CT45A3, CT45A5, CT45A6, CT45A7, CT45A8, CT45A9 and CT45A10. This CT45 antigenic peptide is also herein referred to as "CT45 peptide" or "CT45-IP". The CT45 antigenic peptide is a peptide epitope derived from a tumor-associated or tumor-specific protein and is presented on the cell surface by molecules of the major histocompatibility complex (MHC), preferably MHC I. More particularly, the CT45 antigenic peptide is presented on the cell surface in complex with a HLA protein, preferably HLA-A, more preferably HLA-A*02. In most preferred embodiments, the CT45 antigenic peptide consists of the amino acid sequence KIFEMLEGV (SEQ ID NO: 138). In instances where the CT45 antigenic peptide comprises further amino acids in addition to the amino acid sequence KIFEMLEGV (SEQ ID NO: 138), it is preferred that the overall length of the CT45 antigenic peptide does not exceed 30 or 20 amino acids, more preferably does not exceed 15 amino acids, even more preferably does not exceed 12 amino acids. In instances where the CT45 antigenic peptide comprises further amino acids in addition to SEQ ID NO: 138, the amino acids of SEQ ID NO: 138 are preferably located within the peptide binding groove of the MHC protein when the antigenic peptide is in a complex with an MHC protein. The skilled in the art is aware that antigenic peptides presented on MHC I are usually no longer than 12 amino acids. However, in instances where peptides are artificially loaded on MHC proteins, it is plausible that an antigenic peptide artificially loaded on MHC I may be longer than 12 amino acids. The term "antigen" or "target antigen" as used herein refers to a molecule or a portion of a molecule or complex that is capable of being bound by an antigen binding site, wherein said antigen binding site is present in an antigen binding protein, preferably an antigen binding protein of the present invention. The antigen in the context of the present invention is the CT45 antigenic peptide, more particularly the CT45 antigenic peptide in a complex with a MHC protein, such as an HLA protein, for instance HLA-A*02.

A "CT45-IP:MHC complex presenting cell" herein refers to a cell that presents on its surface CT45-IP in a complex with a MHC molecule. In preferred embodiments, the CT45-IP:MHC complex presenting cell is a tumor cell, wherein the tumor is preferably a cancer as defined herein below in the section 'Therapeutic methods and uses'. In the context of the present invention, the CT45-IP:MHC complex is over-presented on the cell surface of a CT45-IP:MHC complex presenting cell, compared to levels of said complex on the surface of cells in normal (healthy) tissue (also referred to as "healthy cells") or on the surface of control cells loaded with a different antigen presenting peptide or no peptide. By "over-presented" is meant that the CT45-IP:MHC complex is present at a level at least 2-fold, preferably between 5-fold to 10-fold of the level present in healthy tissue or control cells.

An example for "CT45-IP:MHC complex presenting cells" are the CT45-IP loaded T2 cells or the NCIH1703 or A375 tumor cells used in the examples of this application.

A "domain" may be any region of a protein, generally defined on the basis of sequence homologies and often referring to a specific structural or functional entity.

The term "immunoglobulin (Ig) domain" in the context of the present invention refers to a protein domain that consists of a 2-layer sandwich of 7-9 antiparallel β-strands arranged in two β-sheets with a Greek key topology. The Ig domain is probably the most frequently used "building block" in naturally occurring proteins. Proteins containing Ig domains are subsumed into the immunoglobulin superfamily, including e.g. antibodies, T-cell receptors (TCRs) and cell adhesion molecules. Examples of Ig domains are the variable and constant domains of antibodies and TCRs.

"$V_A$" in the context of the present invention refers to a TCR variable domain comprising TCR-derived CDR sequences and TCR-derived framework sequences. The CDR and framework sequences may be derived from a variable domain of a TCR α-chain ($V_\alpha$), β-chain ($V_\beta$), γ-chain ($V_\gamma$) or δ-chain ($V_\delta$), preferably from a $V_\alpha$. The CDR and framework sequences of the $V_A$ domain in context of the present invention do not necessarily have to be derived from the same TCR chain. In some embodiments, CDRs derived from one TCR variable domain (of the donor TCR) are grafted onto another TCR variable domain (of the acceptor TCR). For example, the donor TCR may comprise a $V_\alpha$ encoded by TRAV5 and TRAJ17, and the acceptor TCR may comprise a $V_A$ encoded by TRAV14 and TRAJ33. If the CDR1, CDR3 and optionally CDR2 of the donor TCR are grafted onto the acceptor TCR, the CDRs will be present in the context of different framework regions, but the affinity and specificity for the antigenic peptide conveyed by the CDRs will not be changed, i.e. after grafting the variable domain of the acceptor TCR will have substantially the same affinity and specificity for the antigenic peptide as the variable domain of the donor TCR.

"$V_B$" in the context of the present invention refers to a variable domain comprising TCR-derived CDR sequences and TCR-derived framework sequences. The CDR and framework sequences may be derived from a variable domain of a TCR α-chain ($V_\alpha$), β-chain ($V_\beta$), γ-chain ($V_\gamma$) or δ-chain ($V_\delta$), preferably from a $V_\beta$. The CDR and framework sequences of the $V_B$ domain in context of the present invention do not necessarily have to be derived from the same TCR. In some embodiments, CDRs derived from one TCR variable domain (of the donor TCR) are grafted onto another TCR variable domain (of the acceptor TCR). For example, the donor TCR may comprise a $V_\gamma$ encoded by TRBV2 and TRBJ2-1, and the acceptor TCR may comprise a $V_A$ encoded by TRBV27 and TRBJ1-5. If the CDR1, CDR3 and optionally CDR2 of the donor TCR are grafted onto the acceptor TCR, the CDRs will be present in the context of different framework regions, but the affinity and specificity for the antigenic peptide conveyed by the CDRs will not be changed, i.e. after grafting the variable domain of the acceptor TCR will have substantially the same affinity and specificity for the antigenic peptide as the variable domain of the donor TCR.

CDRs may not only be exchanged/grafted between different alpha variable domains or different beta variable domains, but also may be grafted from a TCR alpha to a TCR beta, gamma or delta variable domain, or from a TCR beta to a TCR alpha, gamma or delta variable domain.

$V_\alpha$ in the context of the present invention refers to a variable domain of a TCR α-chain.

$V_\beta$ in the context of the present invention refers to a variable domain of a TCR β-chain.

$V_\gamma$ in the context of the present invention refers to a variable domain of a TCR γ-chain.

$V_\delta$ in the context of the present invention refers to a variable domain of a TCR δ-chain.

$V_L$ in the context of the present invention refers to a variable domain of an antibody light chain.

$V_H$ in the context of the present invention refers to a variable domain of an antibody heavy chain.

$C_L$ in the context of the present invention refers to a constant domain of an antibody light chain.

$C_{H1}$, $C_{H2}$ and $C_{H3}$ in the context of the present invention refer to constant domains of an antibody heavy chain, in particular an IgG heavy chain.

The term "epitope", also known as antigenic determinant, is the part of an antigen that is recognized by the immune system. As used herein, the term epitope comprises the terms "structural epitope" and "functional epitope". The "structural epitope" are those amino acids of the antigen, e.g.

peptide-MHC complex, that are covered by the antigen binding protein when bound to the antigen. Typically, all amino acids of the antigen are considered covered that are within 5 Å of any atom of an amino acid of the antigen binding protein. The structural epitope of an antigen may be determined by art known methods including X-ray crystallography or NMR analysis. The structural epitope of an antibody typically comprises 20 to 30 amino acids. The structural epitope of a TCR typically comprises 20 to 30 amino acids. The "functional epitope" as herein defined is a subset of those amino acids forming the structural epitope and comprises the amino acids of the antigen that are critical for formation of the interface with the antigen binding protein of the invention or functional fragment thereof, either by directly forming non-covalent interactions such as H-bonds, salt bridges, aromatic stacking or hydrophobic interactions or by indirectly stabilizing the binding conformation of the antigen and is, for instance, determined by mutational scanning. In the context of the present invention, the functional epitope is also referred to as "binding motif". Typically, the functional epitope of an antigen bound by an antibody comprises between 4 and 6 amino acids. Typically, the functional epitope of a peptide-MHC complex comprises between 2 to 6 or 7 amino acids of the peptide and 2 to 7 amino acids of the MHC molecule. Since MHC I presented peptides typically have a length between 8 to 10 amino acids only a subset of amino acids of each given peptide is part of the functional epitope of a peptide-MHC complex. The epitope, in particular the functional epitope bound by the antigen binding proteins of the present invention comprises or consists of the amino acids of the antigen that are required for formation of the binding interface.

The "Major Histocompatibility Complex" (MHC) is a set of cell surface proteins essential for the acquired immune system to recognize foreign molecules in vertebrates, which in turn determines histocompatibility. The main function of MHC molecules is to bind to antigens derived from pathogens and display them on the cell surface for recognition by the appropriate T cells. The human MHC is also called the HLA (human leukocyte antigen) complex (or just HLA). Thus, in a preferred embodiment, MHC is HLA. The MHC gene family is divided into three subgroups: class I, class II, and class III. Complexes of peptide and MHC class I molecules (MHC I) are usually recognized by CD8-positive T cells (CD8+ T cells) bearing the appropriate T cell receptor (TCR), whereas complexes of peptide and MHC class II molecules (MHC II) are usually recognized by CD4-positive helper-T cells (CD4+ T cells) bearing the appropriate TCR. CD4 and CD8 usually function as co-receptors of a TCR in binding to MHC I and MHC II, respectively. In some exceptional cases, complexes of peptide and MHC I are recognized by CD8-negative (in particular CD8-negative, CD4-positive) T cells (Soto et al., 2013, Cancer Immunol Immunother. 2013 February; 62(2): 359-369). Since the responses of CD8-positive and CD4-positive T cells contribute jointly and synergistically to the anti-tumor effect, the identification and characterization of tumor-associated antigens and corresponding T cell receptors is important in the development of cancer immunotherapies such as vaccines and cell therapies. The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface. The MHC class I HLA protein in the context of the present disclosure may be an HLA-A, HLA-B or HLA-C protein, suitably HLA-A protein, for example HLA-A*02. In the MHC class I dependent immune reaction, peptides not only have to be able to bind to certain MHC class I molecules expressed by tumor cells, they subsequently also have to be recognized by T cells bearing specific T cell receptors (TCR).

"Antigenic peptide in a complex with an MHC protein", herein refers to an antigenic peptide that is non-covalently bound to an MHC molecule. In particular, the antigenic peptide is located to a "peptide-binding groove" formed by the MHC molecule. A complex of an MHC molecule and an antigenic peptide is herein also referred to as "peptide-MHC complex" or "pMHC complex". In the case of the CT45 antigenic peptide, the complex is also referred to as "CT45 antigenic peptide-MHC complex" or "CT45-IP:MHC complex".

"HLA-A*02" signifies a specific HLA allele, wherein the letter A signifies the allele and the prefix "*02 prefix" indicates the A2 serotype.

The term "Antigen Binding Protein" herein refers to a polypeptide or a complex of two or more polypeptides comprising an antigen binding site that is able to specifically bind to an antigen, in particular an antigenic peptide in a complex with MHC. As used in the context of the present specification, the term antigen binding protein includes antigen binding proteins of multiple different formats as described below, including soluble antigen binding proteins, membrane bound antigen binding proteins, monovalent, bivalent and multivalent antigen binding proteins, monospecifc, bispecific and multispecific antigen binding proteins, single chain antigen binding proteins and antigen binding proteins comprising two or more chains, fusion proteins and chimeric proteins. The term includes antigen binding proteins having the overall structure of a TCR, an antibody or a chimeric antigen receptor (CAR). The antigen binding protein of the present invention comprises TCR-derived CDRs, in particular a variable domain $V_A$ comprising TCR-derived CDRa1, CDRa3, and optionally CDRa2, and a variable domain $V_B$ comprising TCR-derived CDRb1, CDRb3, and optionally CDRb2. In a particular embodiment, the entire $V_A$ domain and/or the entire $V_B$ domain are TCR-derived and are thus TCR alpha, beta, gamma or delta variable domains ($V_\alpha$, $V_\beta$, $V_\gamma$ or $V_\delta$). In preferred embodiments, the antigen binding protein is a TCR. In some embodiments, the antigen binding protein of the present invention comprises $V_A$ and $V_B$ as herein defined, and further an additional domain fused directly or indirectly to $V_A$ or $V_B$. Such an antigen binding protein can be referred to as "fusion protein". Examples of additional domains comprised in an antigen binding protein of the invention that is a fusion protein" are listed below. If the antigen binding protein is a bispecific or multispecific antigen-binding protein, it comprises—in addition to $V_A$ and $V_B$ as herein defined—at least one more variable domain, preferably two variable domains, and optionally a constant domain, wherein the variable and/or constant domains may be derived from an antibody or TCR. The antigen-binding protein thus comprises two different antigen binding sites (one formed by $V_A$ and $V_B$ and one formed by the additional at least one, preferably two, variable domains) and is able to specifically bind to two different antigens simultaneously, as it is known from, for example bispecific antibodies. In some embodiments, the antigen binding protein comprises TCR-derived $V_A$ and $V_B$ and in addition two antibody-derived variable domains, in particular $V_L$ and $V_H$. Such constructs comprising elements of both antibodies and TCRs represent hybrid formats and may be e.g. referred to as "bispecific TCR-antibody fusion protein". In such bispecific fusion proteins, the variable domains may be arranged in various orientations. Techniques to produce such bispecific fusion proteins are known to the skilled in the art, who can thus easily use the variable domains as herein defined to generate and produce bispecific antigen binding proteins in various formats. The skilled person is entirely capable of selecting suitable linkers to ensure folding in the desired conformation.

"At least one" herein refers to one or more of the specified objects such as 1, 2, 3, 4, 5 or 6 or more of the specified objects. For example, at least one binding site herein refers to 1, 2, 3, 4, 5 or 6 or more binding sites.

The term "bispecific" in the context of the present invention refers to antigen binding proteins with at least two valences and binding specificities for two different antigens and thus comprises at least two antigen binding sites. The term "valence" refers to the number of binding sites of an antigen binding protein, e.g. a bivalent antigen binding protein relates to an antigen binding protein that has two binding sites. The binding sites may bind to the same or different targets, i.e. a bivalent antigen binding protein may be monospecific, i.e. binding one target, or bispecific, i.e. binding two different targets. The antigen binding molecules of the present invention comprise at least one antigen-binding site comprising TCR-derived CDRs. In preferred embodiments, the antigen binding molecules of the present invention comprise at least one TCR-derived antigen-binding site.

It is preferred that the antigen binding protein is a TCR. The term "TCR" as used herein includes both native and engineered TCRs.

A "native TCR" refers to a wildtype TCR that can be isolated from nature. Native TCRs are heterodimeric cell surface proteins of the immunoglobulin super-family, which are associated with invariant proteins of the CD3 complex involved in mediating signal transduction. Native heterodimeric TCRs exist in αβ and γδ forms, which are structurally similar but have distinct locations and probably functions. Native, full-length αβ heterodimeric TCRs consist of an α-chain and a β-chain. The α-chain comprises a variable region (V region) encoded by a TRAV gene, a joining region (J region) encoded by a TRAJ gene, and a constant region (C region) encoded by a TRAC gene. The β-chain comprises a variable region (V region) encoded by a TRBV gene, a joining region (J region) encoded by a TRBJ gene and a constant region (C region) encoded by a TRBC gene, and usually a short diversity region (D region) encoded by a TRBD gene between the V and J regions, although this D region is often considered as part of the J region (Lefranc, (2001), Curr Protoc Immunol Appendix 1: Appendix 10). The genes encoding different α-chain and β-chain variable, joining and constant regions are referred to in IMGT nomenclature by unique numbers (Folch and Lefranc, (2000), Exp Clin Immunogenet 17 (1): 42-54; Scaviner and Lefranc, (2000), Exp Clin Immunogenet 17 (2): 83-96; LeFranc and LeFranc, (2001), "T cell Receptor Factsbook", Academic Press). Further information on TCR genes can be found in the international ImMunoGeneTics information system®, Lefranc M-P et al., (Nucleic Acids Res. 2015 January; 43 (Database issue): D413-22).

On protein level, TCR α-, β-, γ- and δ-chains comprise two immunoglobulin domains, the variable domain and the constant domain. The variable domain corresponds to the V(D)J region. The constant domain corresponds to the C region. The constant domain is the membrane-proximal domain and in the context of the present invention also includes the transmembrane (TM) domain and a short cytoplasmic tail. Each of the constant and variable domains include an intra-chain disulfide bond. The variable domains ($V_\alpha$ and $V_\beta$ in αβ TCRs and $V_\gamma$ and $V_\delta$ in γδ TCRs) contain highly polymorphic loops comprising the complementarity determining regions (CDRs).

Each TCR variable domain comprises three "TCR complementarity determining regions (CDRs)" embedded in a framework sequence, one being the hypervariable region named CDR3. In the context of the present invention, CDRa1, CDRa2 and CDRa3 denote α-chain CDRs, and CDRb1, CDRb2 and CDRb3 denote β-chain CDRs. The sequences encoding CDRa1 and CDRa2 are comprised in TRAV, the sequences encoding CDRa3 are comprised in TRAV and TRAJ, the sequences encoding CDRb1 and CDRb2 are comprised in TRBV, and the sequences encoding CDRb3 are comprised in TRBV, TRBD and TRBJ. In TCRs, the CDR1 and CDR3 amino acid residues make contact with the antigenic peptide, while the CDR2 amino acid residues mainly contact the HLA molecule (Stadinski et al., J Immunol. 2014 Jun. 15; 192(12): 6071-6082; Cole et al., J Biol Chem. 2014 Jan. 10; 289(2):628-38). The antigen specificity of a TCR is thus defined by the CDR3 and CDR1 sequences. The CDR2 sequences are not required for the determination of antigen specificity, but may play a role in the overall affinity of a TCR towards a peptide-MHC complex.

"TCR framework regions" (FRs) refer to amino acid sequences interposed between the CDRs, i.e. to those portions of the variable domains that are to some extent conserved among different TCRs. The α-, β-, γ- and δ-chain variable domains each have four FRs, herein designated FR1-a, FR2-a, FR3-a, FR4-a (for an α- or γ-chain), and FR1-b, FR2-b, FR3-b, FR4-b (for a β-or δ-chain), respectively. Accordingly, an α-chain or γ-chain variable domain may be described as (FR1-a)-(CDRa1)-(FR2-a)-(CDRa2)-(FR3-a)-(CDRa3)-(FR4-a) and a β-or δ-chain variable domain may be described as (FR1-b)-(CDRb1)-(FR2-b)-(CDRb2)-(FR3-b)-(CDRb3)-(FR4-b). In the context of the present invention, the CDR/FR sequences in an α-, β-, γ-or δ-chain variable domain is determined based on IMGT definition (Lefranc et al., Dev. Comp. Immunol., 2003, 27 (1): 55-77). Accordingly, CDR/FR amino acid positions when related to TCR or TCR-derived domains are indicated according to said IMGT definition. Preferably, the IMGT position of the CDR/FR amino acid positions of the variable domain $V_\alpha$ is given in analogy to the IMGT numbering of TRAV24*01 and/or the IMGT position of the CDR/FR amino acid positions of the variable domain $V_\beta$ is given in analogy to the IMGT numbering of TRBV12-3*01.

An "engineered TCR" may be a protein closely resembling a native TCR, but comprising minor modifications in the variable and/or constant domains, e.g. a humanized TCR or a TCR with improved heterodimerization or expression level, or may be a single chain TCR, a soluble TCR, a monovalent, bivalent or multivalent TCR, a monospecific, bispecific or multispecific TCR, a functional fragment of a TCR, or a fusion protein or chimeric protein comprising a functional fragment of a TCR.

"Functional fragment of a TCR" refers to a fragment of a TCR that retains or substantially retains the affinity, functional avidity and/or specificity of the parental TCR from which it is derived for a target antigen. "Parental TCR" in this context refers to a full length TCR from which a functional fragment is derived. As binding to the target antigenic peptide is defined by the CDR1 and CDR3 sequences, and binding to the target antigenic peptide MHC complex is defined by CDR1, CDR2 and CDR3, antigen binding proteins comprising the CDR1 and CDR3 and optionally CDR2 sequences of a parental TCR retain the affinity, functional avidity and/or specificity of the parental TCR for a target antigen. The skilled in the art is aware that the CDRs have to be interspersed with framework regions (FRs), however the specific amino acid sequences of the framework regions are not directly involved in target antigen specificity. Examples of functional TCR fragments include single variable domains, such as TCR alpha, beta, gamma or delta variable domains, or fragments of the α, β, δ or γ chain, such as an α, β, δ or γ chain without transmembrane domain and short cytoplasmic tail. The term "fragment" as used herein refers to naturally occurring fragments (e.g. splice variants or peptide fragments) as well as artificially constructed fragments, in particular to those obtained by gene-technological means.

A functional fragment of a TCR is considered to have retained or substantially retained the affinity for a target antigen, if, for example, the $K_D$ for binding to the target antigen measured as outlined below is identical to the $K_D$ of the parental TCR or is increased or reduced, preferably reduced, no more than 10×, 5×, 3×, or 2×.

A functional fragment of a TCR is considered to have retained or substantially retained the functional avidity for a target antigen, if, for example, the functional avidity for the target antigen is identical to that of the parental TCR or is increased or reduced, preferably reduced, no more than 50%, 40%, 30%, 20%, 15%, 10%, 8%, 5%, 3%, 2% or 1%. In particular, a functional fragment of a TCR is considered to have retained or substantially retained the functional avidity for a target antigen, if, for example, its cytotoxic activity in response to the target of the parent protein measured in a cytotoxicity assay, preferably a luciferase release assay as described below is identical to the cytotoxic activity of the parental TCR or is increased or reduced, preferably reduced, no more than 50%, 40%, 30%, 20%, 15%, 10%, 8%, 5%, 3%, 2% or 1%, preferably 10%, 8%, 5%, 3%, 2% or 1%.

A functional fragment of a TCR is considered to have retained or substantially retained the specificity for a target antigen (i.e. the ability to specifically bind to a target antigen), if it does not significantly bind to peptides other than the target antigenic peptide of the parental TCR.

The terms "α/β TCR" or a "γ/δ TCR" refer to a TCR comprising an α-chain and a β-chain as described above, or a γ-chain and a δ-chain, respectively. Such a TCR may also be described as "full length TCR" or "conventional TCR". An α/β TCR or a γ/δ TCR may be a native TCR or may be an engineered TCR that retains the structure of a native TCR, i.e. an engineered TCR comprising minor modifications in the variable and/or constant domains as described above, such as a humanized TCR.

"Single chain TCR (scTCR)" as used herein denotes a TCR in which the variable domains of the TCR are located on a single polypeptide. Typically, the variable domains in scTCRs are separated by a linker, wherein said linker typically comprises 10 to 30 amino acids, such as 25 amino acids.

A "chimeric protein" herein refers to a protein comprising sequences from multiple species. A "chimeric TCR" herein refers to a TCR comprising sequences from multiple species. Preferably, a chimeric TCR in the context of the invention may comprise an α-chain comprising at least one domain from a human and one domain from mouse. More preferably, a chimeric TCR in the context of the invention may comprise an α-chain comprising a variable domain of a human α-chain and, for example, a constant domain of a murine TCR α-chain.

The term "antibody" as used herein is meant to include native and engineered antibodies. The term "engineered antibody includes functional antibody fragments, single chain antibodies, single domain antibodies, bispecific or multispecific antibodies.

A native "antibody" comprises two heavy and two light chains, wherein the heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct domains (also referred to as regions). The light chain includes two domains, a variable domain ($V_L$) and a constant domain (CO. The heavy chain includes four or five domains depending on the antibody isotype; a variable domain ($V_H$) and three or four constant domains ($C_{H1}$, $C_{H2}$ and $C_{H3}$, and optionally $C_{H4}$, collectively referred to as $C_H$). The variable domains of both light ($V_L$) and heavy ($V_H$) chains determine binding recognition and specificity to the antigen. The constant domains of the light ($C_L$ and heavy ($C_H$) chains confer important biological properties such as antibody chain association, secretion, trans-placental mobility, complement binding, and binding to $F_c$ receptors ($F_cR$).

The specificity of the antibody resides in the structural complementarity between the antibody binding site and the antigenic determinant. Antibody binding sites are made up of residues that are primarily from the "antibody complementarity determining regions" (CDRs) or hypervariable regions. Occasionally, residues from non-hypervariable or framework regions (FR) influence the overall domain structure and hence the binding site. CDRs refer to amino acid sequences that together define the binding affinity and specificity of the natural Fv region of a native antibody binding site. The light and heavy chains of an antibody each have three CDRs, designated CDR1-L, CDR2-L, CDR3-L and CDR1-H, CDR2-H, CDR3-H, respectively. An antibody antigen-binding site, therefore, includes six CDRs, comprising the CDR set from each of a heavy and a light chain V region. "Antibody framework regions" (FRs) refer to amino acid sequences interposed between CDRs, i.e. to those portions of antibody light and heavy chain variable regions that are relatively conserved among different antibodies in a single species. The light and heavy chains of an antibody each have four FRs, designated FR1-L, FR2-L, FR3-L, FR4-L, and FR1-H, FR2-H, FR3-H, FR4-H, respectively. Accordingly, the light chain variable domain may be described as (FR1-L)-(CDR1-L)-(FR2-L)-(CDR2-L)-(FR3-L)-(CDR3-L)-(FR4-L) and the heavy chain variable domain may be described as (FR1-H)-(CDR1-H)-(FR2-H)-(CDR2-H)-(FR3-H)-(CDR3-H)-(FR4-H). As used herein, a "human framework region" is a framework region that is substantially identical (about 85%, or more, in particular 90%, 95%, 97%, 99% or 100%) to the framework region of a naturally occurring human antibody. In the context of the invention, CDR/FR definition in an antibody light or heavy chain variable domain is determined based on IMGT definition (Lefranc et al., Dev. Comp. Immunol., 2003, 27 (1): 55-77). Accordingly, amino acid sequences of the CDR1, CDR2 and CDR3 of a given variable chain and the amino acid sequences of FR1, FR2, FR3 and FR4 are indicated according to said IMGT definition.

Knowing the amino acid sequence of the CDRs of an antibody, a TCR or an antigen binding protein of the invention, one skilled in the art can easily determine the framework regions, such as the TCR framework regions or antibody framework regions. In cases where the CDRs are not indicated, the skilled in the art can first determine the CDR amino acid sequences based on the IMGT definition for TCRs or the IMGT definition for antibodies and then determine the amino acid sequences of the framework regions.

Engineered antibody formats include functional antibody fragments, single chain antibodies, single domain antibodies, and chimeric, humanized, bispecific or multispecific antibodies. Engineered antibody formats further include constructs in which the light chain variable domain of an antibody may be replaced with the α-chain variable domain of a TCR and the heavy chain variable domain may be replaced with the β-chain variable domain of a TCR, or vice versa. A "functional antibody fragment" refers to a portion of a full-length antibody that retains the ability to bind to its target antigen, in particular the affinity and/or specificity for its target antigen. Preferably, a functional antibody fragment comprises the antigen binding region or variable region of the full-length antibody. Examples of functional antibody fragments include Fv, Fab, F(ab')2, Fab', dsFv, (dsFv)2, scFv, sc(Fv)2 and diabodies. A functional antibody fragment may also be a single domain antibody, such as a heavy chain antibody. The term "Fab" denotes an antibody fragment having a molecular weight of about 50,000 Dalton and antigen binding activity, in which about a half of the N-terminal side of H chain and the entire L chain, among fragments obtained by treating IgG with a protease, e.g. papain, are bound together through a disulfide bond. The Fv fragment is the N-terminal part of the Fab fragment of an antibody and consists of the variable portions of one light chain and one heavy chain.

As used herein, a "format" of an antigen binding protein specifies a defined spatial arrangement of domains, in particular of variable and optionally constant domains. Important characteristics of such antigen binding protein formats are the number of polypeptide chains (single chain, double chain or multiple chains), the type and length of linkers connecting different domains, the number of variable domains (and thus the number of valences), the number of different variable domains (and thus the number of specificities for different antigens, e.g. bispecific, multispecific), and the order and orientation of variable domains (e.g. cross-over, parallel).

The term "humanized antibody" refers to an antibody which is completely or partially of non-human origin and which has been modified by replacing certain amino acids, in particular in the framework regions of the heavy and light chains, in order to avoid or minimize an immune response in humans. The constant domains of a humanized antibody are mainly human $C_H$ and $C_L$ domains. Numerous methods for humanization of an antibody sequence are known in the art; see e.g. the review by Almagro & Fransson (2008) Front Biosci. 13: 1619-1633.

In the context of the present application, a sequence that is "at least 85% identical to a reference sequence" is a sequence having, over its entire length, 85%, or more, in particular 90%, 91%, 92%, 93%, 94%, 95%, 96%, 97%, 98% or 99% sequence identity with the entire length of a reference sequence. Proteins consisting of an amino acid sequence "At least 80%, 85%, 90%, 95%, 96%, 97%, 98% or 99% Identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

In the context of the present application, the "percentage of identity" can be calculated using a global pairwise alignment (i.e. the two sequences are compared over their entire length). Methods for comparing the identity of two or more sequences are well known in the art. For example, the "needle" program, which uses the Needleman-Wunsch global alignment algorithm (Needleman and Wunsch, 1970 J. Mol. Biol. 48:443-453) to find the optimum alignment (including gaps) of two sequences when considering their entire length, may be used. The needle program is for example available on the ebi.ac.uk World Wide Web site and is further described in the following publication (EMBOSS: The European Molecular Biology Open Software Suite (2000) Rice, P. Longden, I. and Bleasby, A. Trends in Genetics 16, (6) pp. 276-277). The percentage of identity between two polypeptides, in accordance with the invention, is calculated using the EMBOSS: needle (global) program with a "Gap Open" parameter equal to 10.0, a "Gap Extend" parameter equal to 0.5, and a Blosum62 matrix.

"Amino acid mutations" may be deletions, insertions or substitutions.

"Amino acid substitutions" may be conservative or non-conservative. In an embodiment, substitutions are conservative substitutions, in which one amino acid is substituted for another amino acid with similar structural and/or chemical properties.

In one embodiment, a conservative amino acid substitution may include the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety).

In another embodiment, conservative substitutions may be made in accordance with Table 1. Methods for predicting tolerance to protein modification may be found in, for example, Guo et al., Proc. Natl. Acad. Sci., USA, 101(25): 9205-9210 (2004), the contents of which are incorporated by reference in their entirety.

TABLE 1

Conservative Amino Acid substitutions
Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |

TABLE 1-continued

Conservative Amino Acid substitutions
Conservative Amino Acid Substitutions

| Amino Acid | Substitutions (others are known in the art) |
|---|---|
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

The antigen binding proteins of the present invention can comprise synthetic amino acids in place of one or more naturally-occurring amino acids. Such synthetic amino acids are known in the art, and may include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

In one embodiment, the antigen binding protein of the present invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

A "covalent link" herein refers for example to a disulfide bond or a peptide link or a covalent link via a linker or a linker sequence, such as a polypeptide linker.

The term "linker" as used herein refers to one or more amino acid residues inserted between domains or a domain and an agent to provide sufficient mobility for the domains or elements, for example the variable domains of bispecific antigen binding to fold correctly to form the antigen binding sites.

In some embodiments, a linker consists of 0 amino acid meaning that the linker is absent. A linker is inserted at the transition between variable domains or between variable domains and constant domains (or dimerization domains), respectively, at the amino acid sequence level. The transition between domains can be identified because the approximate size of the antibody domains as well as of the TCR domains is well understood. The precise location of a domain transition can be determined by locating peptide stretches that do not form secondary structural elements such as beta-sheets or alpha-helices as demonstrated by experimental data or as can be assumed by techniques of modelling or secondary structure prediction.

A linker, as long as it is not specified otherwise in the respective context, can be from at least 1 to 30 amino acids in length. In some embodiments, a linker can be 2-25, 2-20, or 3-18 amino acids long. In some embodiments, a linker can be a peptide of a length of no more than 14, 13, 12, 11, 10, 9, 8, 7, 6, or 5 amino acids. In other embodiments, a linker can be 5-25, 5-15, 4-11, 10-20, or 20-30 amino acids long. In other embodiments, a linker can be about, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids long. In a particular embodiment, a linker can be less than 24, less than 20, less than 16, is less than 12, less than 10, for example from 5 to 24, 10 to 24 or 5-10 amino acid residues in length. In some embodiments, said linker is equal to 1 or more amino acid residues in length, such as more than 1, more than 2, more than 5, more than 10, more than 20 amino acid residues in length, more than 22 amino acid residues in length. In preferred embodiments, the linker is a glycine/serine linker, i.e. a linker consisting of or essentially consisting of glycine and serine residues.

The antigen binding protein of the present disclosure can be synthetic, recombinant, isolated, engineered and/or purified.

An "engineered" antigen binding protein, in particular an engineered TCR in the context of the present invention refers to a protein that has been modified by biotechnological methods, in particular by introducing amino acid mutations into the native protein sequence. Such biotechnological methods are well known to the skilled in the art.

By "purified" is meant, when referring to a polypeptide, e.g. to the antigen binding protein of the invention) or a nucleotide sequence, e.g. encoding antigen binding proteins or functional fragment thereof described herein, that the indicated molecule is present in the substantial absence of other biological macromolecules of the same type. The term "purified" as used herein in particular means that at least 75%, 85%, 95%, or 98% by weight, of biological macromolecules of the same type are present. The term "purified" as used herein may further indicate that the antigen binding protein is free from DNA, RNA, proteins, polypeptides or cells that would interfere with its therapeutic, diagnostic, prophylactic, research or other use.

A purified nucleic acid molecule that encodes a particular polypeptide refers to a nucleic acid molecule that is substantially free of other nucleic acid molecules that do not encode the subject polypeptide; however, the molecule may include some additional bases or moieties, which do not deleteriously affect the basic characteristics of the composition.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated". An isolated nucleic acid or protein can exist in substantially purified form, or can exist in a non-native environment such as, for example, a host cell. An isolated antigen binding protein is substantially free of other antigen binding proteins having different antigenic specificities (e.g., an antigen binding protein that specifically binds CT45-IP is substantially free of antigen binding proteins that specifically bind antigens other than CT45-IP). Moreover, an isolated antigen binding protein may be substantially free of other cellular material and/or chemicals.

A "recombinant" molecule is one that has been prepared, expressed, created, or isolated by recombinant means. Recombinant molecules do not exist in nature.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

"Affinity" is defined, in the context of the present invention by the equilibrium binding between the antigen binding protein and its antigen, namely the CT45-IP peptide in a complex with a MHC protein. Affinity is usually expressed as equilibrium dissociation constant ($K_D$).

"$K_D$" is the equilibrium dissociation constant, a ratio of $k_{off}/k_{on}$, between the antigen binding protein and its antigen. $K_D$ and affinity are inversely related. The $K_D$ value relates to the concentration of the antigen binding protein and the lower the $K_D$ value, the higher the affinity of the antigen binding protein. The $K_D$ value can be experimentally assessed by a variety of known methods, such as measuring association and dissociation rates with surface plasmon resonance (SPR) or bio-layer interferometry (BLI). As is known to the skilled in the art, the experimental conditions used for those experiments, such as buffer used, concentration of the protein, can strongly influence the results.

"Functional avidity" is defined, in the context of the present invention, as a parameter that describes the capability of an antigen binding protein, preferably a TCR, to activate an effector cell, preferably a T cell, upon binding to its target antigenic peptide in a complex with MHC. The activation of the effector cell, preferably T cell, can be measured in a functional assay, in particular a cytokine production assay or a cytotoxicity assay as described below. In some embodiments, the functional avidity of an antigen binding protein is considered high if the $EC_{50}$ determined in a functional assay is low, such as less than about 60 nM, less than about 10 nM, or less than about 1 nM in a cytotoxicity assay as described below, and/or the activity determined in a functional assay is high, such as at least 50%, at least 60%, at least 70%, at least 75%, preferably at least 80%, at least 85%, at least 90%, or at least 95% of a maximal activity defined in the respective functional assay. Depending on the functional assay, the maximal activity may be the activity of a reference protein with known high functional avidity or the activity of a "maximum lysis control" as described below.

"Efficacy" is defined, in the context of the present invention, as a parameter that describes the capability of an antigen binding protein, preferably a TCR, to activate an effector cell, preferably a T cell, to kill a cancer cell presenting on its surface the target antigenic peptide in a complex with MHC. The efficacy can be determined in a functional assay, in particular a live-cell monitoring cytotoxicity assay as described below.

In a "functional assay", an antigen binding protein is, for example, expressed in an "effector cell (E)", and the effector cell is co-cultured with "target cells (T)", i.e. with antigen presenting cells presenting a peptide-MHC complex. Functional assays can thus also be described as "co-culture assays". For all cell culture assays described herein, the cell culture temperature preferably is at about 37° C. Preferably, the antigen binding protein is a TCR and the effector cell is a T cell. The target cells may be cells that are artificially loaded with the antigenic peptide (e.g. T2 cells) or may be cells that endogenously present the target antigenic peptide on their surface (e.g. cancer cells expressing CT45). Binding of the antigen binding protein to the peptide-MHC complex leads to activation of the effector cell. Depending of the type of functional assay, there are different readouts for measuring the degree of activation. In a cytokine production assay, the production of cytokines (e.g. TNF-α, IFN-γ, CD107a+, IL-2 and/or Granzyme B) by the effector cells is determined.

In a cytotoxicity assay, the killing of target cells by the effector cells is determined, e.g. by measuring a decline in proliferation of target cells, in particular cancer cells (e.g. in a live-cell monitoring cytotoxicity assay) or by measuring the release of intracellular proteins from the target cells. Suitable intracellular proteins to be measured in a cytotoxicity assay can be endogenous proteins, e.g. LDH or a transgenic protein expressed by the antigen presenting cell, e.g. luciferase.

In the context of the present invention, the term "T2 cell" refers to a cell that expresses an MHCI molecule (HLA-A2) that lacks TAP function. T2 cells can be easily artificially loaded with different concentrations of exogenous antigenic peptides. T2 cell are described e.g. in (Hosken and Bevan, Science 1990 Apr. 20; 248(4953):367-70). T2 cells are commercially available, e.g. from ATCC (American Type Culture Collection). Loading of T2 cells can be achieved under standard cell culture conditions known to the skilled in the art by incubating the T2 cells for about 2 hours with a desired concentration of antigenic peptide. In the context of the present invention, T2 cells that are incubated with a certain concentration of antigenic peptide, such as 1 µM, 100 nM, 10 nM, 1 nM, 100 pM, 10 pM, 1 pM, are referred to as T2 cells loaded with said concentration of antigenic peptide, e.g. T2 cells incubated with 10 µM of antigenic peptide are referred to as T2 cells loaded with 10 µM of antigenic peptide.

The term "E:T ratio" refers to the ratio of effector cells (i.e. immune cells, in particular T cells, expressing the antigen binding protein, in particular the TCR) to target cells. In some embodiments, the E:T ratio corresponds to the seeding ratio, i.e. the ratio of the total number of immune cells, in particular T cells, to target cells. In some embodiments, the E:T ratio is lower than the seeding ratio. This applies to cases where not all immune cells express the antigen binding protein, i.e. not all immune cells are effector cells, for example due to a low electroporation efficiency. In some embodiments, the seeding ratio is used as approximation of the E:T ratio. In some embodiments, the E:T ratio is determined by adjusting the seeding ratio taking into account the electroporation efficiency.

An exemplary luciferase release assay is described in the methods section and performed in examples 1 and 2. In particular embodiments of a luciferase release assay, the effector cells are T cells, preferably pre-stimulated T cells, transiently or stably expressing the TCR, such as T cells electroporated with mRNA encoding the TCR or T cells stably transduced with a nucleic acid encoding the TCR, e.g. T cells transduced with a lentiviral vector comprising a nucleic acid encoding the TCR. These effector cells are co-cultured with target cells expressing luciferase. Preferably, the target cells are T2 cells loaded with an antigenic peptide. Preferably, the effector cells and the target cells are seeded at a ratio between 2:1 and 1:2, preferably 1:1. After a defined time of co-culture, e.g. 12-38 hours, preferably 18-30 hours, more preferably about 24 hours, the amount of luciferase in the supernatant is measured, wherein a high luciferase concentration indicates a high killing activity and thus a high functional avidity of the antigen binding protein, preferably the TCR, for the presented peptide.

The functional avidity of an antigen binding protein is considered high if in a cytotoxicity assay, preferably a luciferase release assay as defined above, the cytotoxic activity of the effector cells against the target cells is at least 50%, at least 60%, at least 70%, at least 75%, preferably at least 80%, at least 85%, at least 90%, or at least 95% of the cytotoxic activity of a control toxic reagent. The skilled in the art is aware that the cytotoxic activity can be higher than 100%. This is due to the fact that 100% cytotoxic activity is defined by a "maximum lysis control", which refers to incubation of the target cells with the toxic reagent. In some embodiments, the toxic reagent is a detergent, e.g. Triton-X100, Tween-20, Tween-80 or NP-40, that effects lysis of the target cells. In some specific examples, the maximum lysis control comprises adding a 0.2% Triton-X100 solution to the target cell culture. The cytotoxic activity of the toxic reagent, i.e. the number of target cells killed by the toxic reagent is defined as 100%. Since the target cells can still proliferate during the co-culture, the effector cells may eventually kill an even higher number of target cells during the cytotoxicity assay than the toxic reagent killed during the maximum lysis control. In such instances, the calculated cytotoxic activity will be higher than 100%.

An exemplary cytokine production assay is described in the methods section and performed in example 3. In particular embodiments of a cytokine production assay, the effector cells are T cells, preferably pre-stimulated T cells, expressing the TCR, such as T cells transiently transfected or stably transduced with a nucleic acid encoding the TCR, preferably T cells electroporated with mRNA encoding the TCR. These effector cells are co-cultured with target cells that are preferably T2 cells loaded with an antigenic peptide. Preferably, the effector cells and the target cells are seeded at a ratio between 2:1 and 1:2, preferably 1:1. The co-culture preferably occurs in the presence of a secretion-blocking agent. After a defined time of co-culture, e.g. 3-7 hours, preferably about 5 hours, the effector cells are stained for at least one intracellular cytokine selected from, for example CD107a+, IFN-gamma, TNF alpha, IL-2 and Granzyme B, to determine the amount of effector cells that produce cytokines. The functional avidity of an antigen binding protein is considered high if the antigen is capable of activating effector cells in a cytokine production assay as defined above, in particular if the number of effector cells that produce cytokines upon co-culture with target cells is at least 2%, at least 2.5%, preferably at least 3% per population of immune cells, such as living CD4+, CD8+ and/or CD3+ cells. Preferably, the number of effector cells that produce cytokines upon co-culture with target cells is at least 10%, at least 25%, at least 50% per total number of effector cells. As explained above, not all immune cells express the antigen binding protein, i.e. not all immune cells seeded in the co-culture assay are effector cells, for example due to a low electroporation efficiency.

An exemplary live-cell monitoring cytotoxicity assay is described in the methods section and performed in example 5. In particular embodiments of a live-cell monitoring cytotoxicity assay, the effector cells are T cells, preferably pre-stimulated T cells, transiently or stably expressing the TCR, such as T cells electroporated with mRNA encoding the TCR. These effector cells are co-cultured with tumor cells endogenously expressing and presenting the CT45-IP antigenic peptide and optionally additionally loaded with the CT45-IP antigenic peptide. In some embodiments, the tumor cells are A375 cells or NCIH-1703 cells. The tumor cells are preferably fluorescently labelled. In some embodiments of the live-cell monitoring cytotoxicity assay, the seeding ratio of total T cells (including T cells expressing the TCR (=effector cells) and T cells not expressing the TCR) is between 9:1 and 0.5:1, such as 9:1, 6:1, 3:1, 2:1 or 1:1. In some embodiments, the E:T ratio is between 6:1 and 0.2:1. The efficacy of an antigen binding protein is considered high if in a live-cell monitoring cytotoxicity assay as defined above, killing of tumor cells (as determined by a reduction in tumor cell proliferation) is observed at an E:T ratio of 6:1 or less, 5:1 or less, 4:1 or less, 3:1 or less, preferably 2:1 or less, more preferably 1:1 or less, even more preferably 0.5:1 or less.

"Half maximal effective concentration" also called "$EC_{50}$", typically refers to the concentration of a molecule, which induces a response halfway between the baseline and maximum after a specified exposure time. The lower the $EC_{50}$ value, the higher the functional avidity of the molecule. $EC_{50}$ values can be experimentally assessed by a variety of known methods, for example using the functional assays described above or other ELISA- or flow cytometry-based killing assays.

To determine the $EC_{50}$ in a functional assay as described above, different concentrations of antigenic peptide loaded on antigen presenting cells, such as T2 cells have to be used in a "peptide titration experiment". An exemplary luciferase release assay with peptide titration is described in the methods section and performed in example 1. In particular embodiments, the "$EC_{50}$" refers to the concentration of the antigenic peptide loaded on target cells, in particular T2 cells loaded with the CT45 antigenic peptide, which induces a response halfway between the baseline and maximum, when said target cells are co-cultured with effector cells in a luciferase release as defined above. The functional avidity of an antigen binding protein is considered high if the $EC_{50}$ determined in a cytotoxicity assay, preferably a luciferase release assay as defined above, is less than about 60 nM, less than about 50 nM, less than about 30 nM, less than about 25 nM, preferably less than about 20 nM, less than about 15 nM, less than about 10 nM, more preferably less than about 5 nM, less than about 2.5 nM, less than about 1.5 nM or less than about 1 nM.

A "dextramer staining" involves contacting cells expressing an antigen binding protein with fluorescently labelled multimers comprising ten CT45-IP:MHC complexes.

The term "specificity" in the context of the present invention denotes the capacity of an antigen binding protein to discriminate its target peptide from peptides having a different amino acid sequence, e.g. similar peptides as defined below. An antigen binding protein is considered specific for a target peptide if binding to the target peptide occurs with a significantly higher affinity and/or higher functional avidity than the binding to similar peptides. The specificity of the antigen binding protein is determined by the amino acid sequences CDRa1, CDRa3, CDRb1 and CDRb3. The amino acid sequences of CDRa2 and CDRb2 contact the MHC molecule and are not required for antigen specificity.

In the context of the present invention "similar peptides" herein refers to potential off-target peptides, i.e. peptides that may potentially be bound by the antigen binding proteins of the invention based on their biochemical/biophysical characteristics, including but not limited to a homologous sequence or a similar motif. Similar peptides comprise typically 8 to 12 amino acids in length. The similar peptides in the context of the present invention are typically MHC, in particular MHCI, presented. Furthermore, similar peptides in the context of the present invention include peptides that comprise or consists of an amino acid sequence that is similar to the amino acid sequence of the CT45 antigenic peptide, more particular, peptides that, in comparison to the epitope of the CT45 antigenic peptide, comprise an epitope wherein some or all amino acids have identical and/or similar biochemical/biophysical characteristics as the amino acids that constitute the epitope of the CT45 antigenic peptide. In some examples, similar peptides investigated in the context of the present invention were selected from a database of tumor and normal tissue-presented HLA-A*02 bound peptides (XPRESIDENT® database) using a similarity scoring within the binding-relevant positions of CT45-IP and the requirement of at least one detection on normal tissues. Binding of an antigen binding protein to a similar peptide presented by an MHC protein may lead to adverse reactions. Such adverse reactions may be "off-tumor" side effects, such as cross-reactivity of a specific TCR with a similar peptide in healthy tissues as reported in Lowdell et al., Cytotherapy, published on Dec. 4, 2018).

In particular, the following peptides are similar peptides in the context of the present invention: SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010).

The skilled person is aware that among the similar peptides, there are some that are not bound by the antigen binding proteins of the invention to a detectable degree, e.g. peptides for which no binding signal or response in a functional assay beyond the background level is detectable. "Background level" in this context refers to a binding signal or response in a functional assay observed for a non-homologous, "non similar" peptide, e.g. control peptide NYESO1-001, or in the absence of a peptide.

For other similar peptides, a low, but non-significant binding may be detectable. These latter similar peptides may also be described as "potentially relevant" similar peptides. An antigen binding protein is considered to not significantly bind to a similar peptide and to be specific for its target antigenic peptide if at least one of the following applies when binding to the similar peptide and the target antigenic peptide is compared under similar, preferably identical experimental conditions:

The functional avidity in response to the similar peptide, determined in a functional assay as described above, is 25% or less, 20% or less, 15% or less, 10% or less of the functional avidity in response to the target antigenic peptide CT45-IP.

The cytotoxic activity in response to the similar peptide, determined in a cytotoxicity assay as described above, is 25% or less, 20% or less, 15% or less, 10% or less of the cytotoxic activity in response to the target antigenic peptide CT45-IP.

The $EC_{50}$ of the similar peptide, determined in a functional assay, preferably a cytotoxicity assay, as described above, is increased by a factor of at least 50, at least 100, at least 200 or at least 500, compared to the $EC_{50}$ of the target antigenic peptide CT45-IP.

The $K_D$ for the similar peptide is increased by a factor at least 25, at least 30, at least 40, at least 50, at least 75, or at least 100, compared to the $K_D$ for the target antigenic peptide CT45-IP.

In the context of the present specification, the term "about" when referring to a specific value is meant to indicate that the value may deviate by ±10%, ±9%, ±8%, ±7%, ±6%, ±5%, ±4%, ±3%, ±2% or ±1%.

Antigen Binding Proteins

In a first aspect, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein 1) CDRa1 comprises or consists of the amino acid sequence of SEQ ID NO: 14, CDRa3 comprises the amino acid sequence of SEQ ID NO: 489, preferably SEQ ID NO: 519, CDRb1 comprises or consists of the amino acid sequence of SEQ ID NO: 19, and CDRb3 comprises the amino acid sequence of SEQ ID NO: 504, 2) CDRa1 comprises or consists of the amino acid sequence of SEQ ID NO: 24, CDRa3 comprises the amino acid sequence of SEQ ID NO: 490, preferably SEQ ID NO: 520, CDRb1 comprises or consists of the amino acid sequence of SEQ ID NO: 75, and CDRb3 comprises the amino acid sequence of SEQ ID NO: 505, preferably SEQ ID NO: 526, 3) CDRa1 comprises or consists of the amino acid sequence of SEQ ID NO: 24, CDRa3 comprises the amino acid sequence of SEQ ID NO: 491, CDRb1 comprises or consists of the amino acid sequence of SEQ ID NO: 66, and CDRb3 comprises the amino acid sequence of SEQ ID NO: 506, preferably SEQ ID NO: 527, 4) CDRa1 comprises or consists of the amino acid sequence of SEQ ID NO: 90, CDRa3 comprises the amino acid sequence of SEQ ID NO: 492, CDRb1 comprises or consists of the amino acid sequence of SEQ ID NO: 66, and CDRb3 comprises the amino acid sequence of SEQ ID NO: 507, preferably SEQ ID NO: 528, 5) CDRa1 comprises or consists of the amino acid sequence of SEQ ID NO: 2, CDRa3 comprises the amino acid sequence of SEQ ID NO: 493, CDRb1 comprises or consists of the amino acid sequence of SEQ ID NO: 8, and CDRb3 comprises the amino acid sequence of SEQ ID NO: 508, preferably SEQ ID NO: 529, 6) CDRa1 comprises or consists of the amino acid sequence of SEQ ID NO: 53, CDRa3 comprises the amino acid sequence of SEQ ID NO: 494, preferably SEQ ID NO: 521, CDRb1 comprises or consists of the amino acid sequence of SEQ ID NO: 58, and CDRb3 comprises the amino acid sequence of SEQ ID NO: 509, preferably SEQ ID NO: 530, 7) CDRa1 comprises or consists of the amino acid sequence of SEQ ID NO: 71, CDRa3 comprises the amino acid sequence of SEQ ID NO: 495, CDRb1 comprises or consists of the amino acid sequence of SEQ ID NO: 75, and CDRb3 comprises the amino acid sequence of SEQ ID NO: 510, preferably SEQ ID NO: 531, 8) CDRa1 comprises or consists of the amino acid sequence of SEQ ID NO: 99, CDRa3 comprises the amino acid sequence of SEQ ID NO: 496, preferably SEQ ID NO: 522, CDRb1 comprises or consists of the amino acid sequence of SEQ ID NO: 75, and CDRb3 comprises the amino acid sequence of SEQ ID NO: 511, 9) CDRa1 comprises or consists of the amino acid sequence of SEQ ID NO: 80, CDRa3 comprises the amino acid sequence of SEQ ID NO: 497, CDRb1 comprises or consists of the amino acid sequence of SEQ ID NO: 85, and CDRb3 comprises the amino acid sequence of SEQ ID NO: 512, preferably SEQ ID NO: 532, 10) CDRa1 comprises or consists of the amino acid sequence of SEQ ID NO: 107, CDRa3 comprises the amino acid sequence of SEQ ID NO: 498, preferably SEQ ID NO: 523, CDRb1 comprises or consists of the amino acid sequence of SEQ ID NO: 112, and CDRb3 comprises the amino acid sequence of SEQ ID NO: 513, preferably SEQ ID NO: 533, 11) CDRa1 comprises or consists of the amino acid sequence of SEQ ID NO: 125, CDRa3 comprises the amino acid sequence of SEQ ID NO: 499, CDRb1 comprises or consists of the amino acid sequence of SEQ ID NO: 112, and CDRb3 comprises the amino acid sequence of SEQ ID NO: 514, preferably SEQ ID NO: 534, 12) CDRa1 comprises or consists of the amino acid sequence of SEQ ID NO: 117, CDRa3 comprises the amino acid sequence of SEQ ID NO: 500, CDRb1 comprises or consists of the amino acid sequence of SEQ ID NO: 58, and CDRb3 comprises the amino acid sequence of SEQ ID NO: 515, preferably SEQ ID NO: 535, 13) CDRa1 comprises or consists of the amino acid sequence of SEQ ID NO: 24, CDRa3 comprises the amino acid sequence of SEQ ID NO: 501, preferably SEQ ID NO: 524, CDRb1 comprises or consists of the amino acid sequence of SEQ ID NO: 38, and CDRb3 comprises the amino acid sequence of SEQ ID NO: 516, preferably SEQ ID NO: 536, 14) CDRa1 comprises or consists of the amino acid sequence of SEQ ID NO: 24, CDRa3 comprises the amino acid sequence of SEQ ID NO: 502, preferably SEQ ID NO: 525, CDRb1 comprises or consists of the amino acid sequence of SEQ ID NO: 29, and CDRb3 comprises the amino acid sequence of SEQ ID NO: 517, preferably SEQ ID NO: 537, or 15) CDRa1 comprises or consists of the amino acid sequence of SEQ ID NO: 43, CDRa3 comprises the amino acid sequence of SEQ ID NO: 503, CDRb1 comprises or consists of the amino acid sequence of SEQ ID NO: 48, and CDRb3 comprises the amino acid sequence of SEQ ID NO: 518, preferably SEQ ID NO: 538, wherein the antigen binding protein comprises said CDRa1, CDRa3, CDRb1 and CDRb3 sequences with not more than one, two or three amino acid mutations.

The above-mentioned amino acid sequences comprised in CDRa3 and CDRb3 are the central amino acids of CDRa3 and CDRb3 (also referred to herein as "CDR3 core"). The inventors have found that within the CDR3 sequences, a core sequence can be defined that comprises the amino acids that are most relevant for specific binding to the antigenic peptide, while the amino acids outside the CDR3 core are less relevant for specific binding to the antigenic peptide (data not shown). The CDR3 core comprises the central 8 amino acids of a CDR3. In some embodiments, the CDR3 core consists of the central 8 amino acids of a CDR3, in particular in cases where the CDR3 sequence is no longer than 12 amino acids. In case of CDR3 sequences that are longer than 12 amino acids, the CDR3 core may comprise further amino acids, in particular the central 9-13 amino acids.

All embodiments described herein as embodiment 1 (of 15) are preferably combined with other embodiments 1 (of 15). In the same manner, all embodiments described herein as embodiment 2, 3, 4, 5, 6, 7, 8, 9, 10, 11, 12, 13, 14 or 15 (of 15), respectively, are preferably combined with other embodiments 2, 3, 4, 5, 6, 7, 8, 9, 10, 11, 12, 13, 14 or 15 (of 15), respectively. For example, CDR1 and CDR3 sequences of an embodiment 1 (of 15) are preferably combined with CDR2 sequences of an embodiment 1 (of 15).

In preferred embodiments,

1) CDRa3 comprises or consists of the amino acid sequence of SEQ ID NO: 16, and CDRb3 comprises or consists of the amino acid sequence of SEQ ID NO: 21, 2) CDRa3 comprises or consists of the amino acid sequence of SEQ ID NO: 133, and CDRb3 comprises or consists of the amino acid sequence of SEQ ID NO: 136, 3) CDRa3 comprises or consists of the amino acid sequence of SEQ ID NO: 63, and CDRb3 comprises or consists of the amino acid sequence of SEQ ID NO: 68, 4) CDRa3 comprises or consists of the amino acid sequence of SEQ ID NO: 92, and CDRb3 comprises or consists of the amino acid sequence of SEQ ID NO: 96, 5) CDRa3 comprises or consists of the amino acid sequence of SEQ ID NO: 4, and CDRb3 comprises or consists of the amino acid sequence of SEQ ID NO: 10, 6) CDRa3 comprises or consists of the amino acid sequence of SEQ ID NO: 55, and CDRb3 comprises or consists of the amino acid sequence of SEQ ID NO: 60, 7) CDRa3 comprises or consists of the amino acid sequence of SEQ ID NO: 72, and CDRb3 comprises or consists of the amino acid sequence of SEQ ID NO: 77, 8) CDRa3 comprises or consists of the amino acid sequence of SEQ ID NO: 101, and CDRb3 comprises or consists of the amino acid sequence of SEQ ID NO: 104, 9) CDRa3 comprises or consists of the amino acid sequence of SEQ ID NO: 82, and CDRb3 comprises or consists of the amino acid sequence of SEQ ID NO: 87, 10) CDRa3 comprises or consists of the amino acid sequence of SEQ ID NO: 109, and CDRb3 comprises or consists of the amino acid sequence of SEQ ID NO: 114, 11) CDRa3 comprises or consists of the amino acid sequence of SEQ ID NO: 127, and CDRb3 comprises or consists of the amino acid sequence of SEQ ID NO: 130, or 12) CDRa3 comprises or consists of the amino acid sequence of SEQ ID NO: 119, and CDRb3 comprises or consists of the amino acid sequence of SEQ ID NO: 122, 13) CDRa3 comprises or consists of the amino acid sequence of SEQ ID NO: 35, and CDRb3 comprises or consists of the amino acid sequence of SEQ ID NO: 40, 14) CDRa3 comprises or consists of the amino acid sequence of SEQ ID NO: 26, and CDRb3 comprises or consists of the amino acid sequence of SEQ ID NO: 31, or 15) CDRa3 comprises or consists of the amino acid sequence of SEQ ID NO: 45, and CDRb3 comprises or consists of the amino acid sequence of SEQ ID NO: 50, wherein the antigen binding protein comprises said CDRa1, CDRa3, CDRb1 and CDRb3 sequences with not more than one, two or three amino acid mutations.

An antigen binding protein comprising CDRa1, CDRa3, CDRb1 and CDRb3 sequences with not more than one, two or three amino acid mutations, herein refers to an antigen binding protein that may comprise one, two or three amino acid mutations in each of CDRa1, CDRa3, CDRb1 and/or CDRb3.

In preferred embodiments of the antigen binding protein,
1) CDRa2 comprises or consists of the amino acid sequence of SEQ ID NO: 15, and CDRb2 comprises or consists of the amino acid sequence of SEQ ID NO: 20,
2) CDRa2 comprises or consists of the amino acid sequence of SEQ ID NO: 25, and CDRb2 comprises or consists of the amino acid sequence of SEQ ID NO: 76,
3) CDRa2 comprises or consists of the amino acid sequence of SEQ ID NO: 25, and CDRb2 comprises or consists of the amino acid sequence of SEQ ID NO: 67,
4) CDRa2 comprises or consists of the amino acid sequence of SEQ ID NO: 91, and CDRb2 comprises or consists of the amino acid sequence of SEQ ID NO: 95,
5) CDRa2 comprises or consists of the amino acid sequence of SEQ ID NO: 3, and CDRb2 comprises or consists of the amino acid sequence of SEQ ID NO: 9
6) CDRa2 comprises or consists of the amino acid sequence of SEQ ID NO: 54, and CDRb2 comprises or consists of the amino acid sequence of SEQ ID NO: 59,
7) CDRa2 comprises or consists of the amino acid sequence of SEQ ID NO: 15, and CDRb2 comprises or consists of the amino acid sequence of SEQ ID NO: 76,
8) CDRa2 comprises or consists of the amino acid sequence of SEQ ID NO: 100, and CDRb2 comprises or consists of the amino acid sequence of SEQ ID NO: 76,
9) CDRa2 comprises or consists of the amino acid sequence of SEQ ID NO: 81, and CDRb2 comprises or consists of the amino acid sequence of SEQ ID NO: 86,
10) CDRa2 comprises or consists of the amino acid sequence of SEQ ID NO: 108, and CDRb2 comprises or consists of the amino acid sequence of SEQ ID NO: 113,
11) CDRa2 comprises or consists of the amino acid sequence of SEQ ID NO: 126, and CDRb2 comprises or consists of the amino acid sequence of SEQ ID NO: 113,
12) CDRa2 comprises or consists of the amino acid sequence of SEQ ID NO: 118, and CDRb2 comprises or consists of the amino acid sequence of SEQ ID NO: 59
13) CDRa2 comprises or consists of the amino acid sequence of SEQ ID NO: 25, and CDRb2 comprises or consists of the amino acid sequence of SEQ ID NO: 39,
14) CDRa2 comprises or consists of the amino acid sequence of SEQ ID NO: 25, and CDRb2 comprises or consists of the amino acid sequence of SEQ ID NO: 30, or
15) CDRa2 comprises or consists of the amino acid sequence of SEQ ID NO: 44, and CDRb2 comprises or consists of the amino acid sequence of SEQ ID NO: 49,
wherein the antigen binding protein comprises said CDRa2 and CDRb2 sequences with not more than one, two, three or four amino acid mutations.

An antigen binding protein comprising CDRa2 and CDRb2 sequences with not more than one, two, three or four amino acid mutations, herein refers to an antigen binding protein that may comprise one, two, three or four amino acid mutations in each of CDRa2 and/or CDRb2.

In all embodiments of the antigen binding protein of the invention, amino acid mutations within the CDRa1, CDRa2, CDRa3, CDRb1, CDRb2 and CDRb3 sequences—if present—are preferably amino acid substitutions, more preferably conservative amino acid substitutions (see Table 1). It is preferred that the CDR sequences comprise not more than two, preferably not more than one, amino acid mutation. It is further preferred that the amino acid mutations—if present—are at the first or last position of the respective CDR sequence. In most preferred embodiments, the CDR sequences do not comprise any amino acid mutation.

Introducing a mutation into a known amino acid sequence is standard procedure well-known in the art and routine work for the skilled person. Respective methods are known in the field (e.g. Stratagene's QuikChange Site Directed Mutagenesis Kit since 2007). The skilled person is thus very well capable of introducing specific mutations such as substitutions into an amino acid sequence in general and into a CDR sequence in particular.

Screening of variants of a CDR for binding to its target is also a standard procedure applied by the skilled person. The present application mentions functional assays, including cytokine production and luciferase release assays to determine binding of an antigen binding protein of the invention to the CT45-IP peptide. Binding of an antigen binding protein of the invention to the CT45-IP peptide can also be determined by dextramer staining.

While the outcome of an amino acid mutation in a CDR may not be readily predictable, the skilled person would be well capable of generating and screening multiple mutants without undue burden. The skilled person would thus be able to generate antigen binding protein carrying one, two or three amino acid mutations within their CDRs and subsequently identify antigen binding proteins having the same binding characteristics as an antigen binding protein comprising the CDR sequences of Table 3.

In preferred embodiments, not more than 1 or 2 amino acid mutations, preferably not more than 1 amino acid mutation, more preferably not more than 1 amino acids substitution, most preferably not more than 1 conservative amino acid substitution is comprised within the central 8 amino acids of the CDRa3 and/or CDRb3, i.e. within the CDR3 core. In cases where the CDR3 comprises more than 12 amino acids, it is even more preferred that not more than 1 or 2 amino acid mutations, preferably not more than 1 amino acid mutation, more preferably not more than 1 amino acids substitution, most preferably not more than 1 conservative amino acid substitution is comprised within the central 9-13 amino acids of the CDRa3 and/or CDRb3, i.e. within the CDR3 core max (Table 3).

In some embodiments, the antigen binding protein induces an immune response, for example, in the cell expressing the antigen binding protein (if the antigen binding protein is membrane-bound), preferably a lymphocyte, more preferably a T cell or an NK cell, more preferably a T cell. In some embodiments, the immune response may also be induced in a cell recruited by an antigen binding protein of the invention (if the antigen binding protein is a soluble, bispecific antigen binding protein capable of binding to and thereby recruiting e.g. a T cell or an NK cell). Preferably, the immune response is characterized by an increased production of interferon (IFN) γ and/or tumor necrosis factor (TNF) α. The immune response is preferably directed against a tumor cell presenting on its surface a complex of the CT45 antigenic peptide and an MHC protein.

In some embodiments, the antigen binding protein specifically binds to a complex of the CT45 antigenic peptide and an MHC protein. In some embodiments, the CT45 antigenic peptide consists of SEQ ID NO: 138. In some embodiments, the antigen binding protein specifically binds to the amino acid sequence of SEQ ID NO: 138 in a complex with an MHC protein.

In all aspects of the present invention, it is preferred that the CT45 antigenic peptide is in a complex with an MHC class I HLA protein, such as HLA-A, HLA-B or HLA-C, preferably HLA-A, more preferably HLA-A*02.

The antigen binding proteins of the invention are characterized by a high stability, a high affinity for the CT45-IP antigenic peptide, a high functional avidity for the CT45-IP antigenic peptide, high efficacy in killing tumor cells presenting the CT45-IP antigenic peptide and/or a high specificity for the CT45-IP antigenic peptide.

The antigen binding proteins of the invention have an increased stability, increased binding affinity, increased functional avidity, increased efficacy and/or an increased specificity, preferably an increased binding affinity, increased functional avidity, increased efficacy and/or an increased specificity in comparison to a reference protein when measured under similar, preferably identical experimental conditions.

A "reference protein" herein refers to a protein to which the antigen binding protein of the invention is compared. The comparison of the antigen binding protein of the invention and the reference protein is carried out under similar, preferably identical experimental conditions, preferably in parallel. Depending on the parameter that is compared, such a reference protein may be e.g. a TCR binding to the CT45 antigenic peptide that does not comprise the CDR sequences as defined in context of the present invention, a TCR binding to a different antigenic peptide derived from CT45, or a TCR binding to an unrelated antigenic peptide, e.g. antigenic peptide NYESO1-001 (SEQ ID NO: 188). The reference protein is preferably in the same format as the antigen binding protein with which it is compared. In instances where the antigen binding protein is a TCR, a suitable reference protein is also a TCR.

"Increased stability" herein refers, for example, to an increased expression level of the antigen binding protein in comparison to a reference protein under the same experimental conditions. The antigen binding proteins of the invention have a high expression level, in particular an increased expression level in comparison to a reference protein when measured under similar, preferably identical experimental conditions. The inventors have shown in example 4 that the antigen binding proteins exhibit high expression levels in T cells. Expression levels of antigen binding proteins can be measured e.g. by dextramer staining.

The antigen binding proteins of the invention have a high affinity for the CT45-IP antigenic peptide, in particular an increased affinity in comparison to a reference protein when measured under similar, preferably identical experimental conditions.

The antigen binding proteins of the invention have a high functional avidity for the CT45-IP antigenic peptide, in particular an increased functional avidity in comparison to a reference protein when measured under similar, preferably identical experimental conditions. The inventors have shown in example 1 that the antigen binding proteins exhibit a high functional avidity for the CT45-IP antigenic peptide. Functional avidity can be determined in a functional assay, in particular a cytotoxicity assay as described above. Measuring functional activity can comprise determining the $EC_{50}$ in a peptide titration experiment.

The antigen binding proteins of the invention have a high efficacy in killing tumor cells presenting the CT45-IP antigenic peptide, in particular an increased efficacy in comparison to a reference protein when measured under similar, preferably identical experimental conditions. The inventors have shown in example 5 that the antigen binding proteins exhibit a high efficacy in killing tumor cells presenting the CT45-IP antigenic peptide. Efficacy can be determined in a functional assay, in particular a live-cell monitoring cytotoxicity assay as described above.

In a preferred embodiment, the antigen binding protein specifically binds to a structural epitope of CT45-IP. In a more preferred embodiment, the antigen binding protein specifically binds to a functional epitope of CT45-IP. The inventors performed experiments in order to identify residues of CT45-IP that are relevant for binding by the antigen binding proteins of the invention (Example 2, Table 4). The inventors identified amino acid positions 3, 4, 5, 6 and 7 of SEQ ID NO: 138 to be relevant for binding. Thus, in some embodiments, the antigen binding protein specifically binds to a functional epitope comprising or consisting of 2, 3 or 4 amino acid positions selected from the group consisting of positions 3, 4, 5, 6 and 7 of SEQ ID NO: 138. Residues relevant for binding by the antigen binding proteins can also be referred to as "binding motif" of CT45-IP. The skilled in the art is aware that determination of the exact epitope or functional epitope might slightly vary depending on the method used and the cut-off values chosen. In context of the present invention the epitope has been determined in a cytotoxicity assay (luciferase release) as described above. The experimental conditions are further defined in example 2.

An amino acid sequence according to SEQ ID NO: 138, wherein at least one position is substituted, is in the context of the present specification referred to as "CT45-IP variant sequence". In particular, one position is substituted into alanine (SEQ ID NOs: 139-145). Peptides having a CT45-IP variant sequence are herein also referred to as CT45-IP variant peptides. In one embodiment, the antigen binding protein of the present invention shows a reduced functional avidity, in particular a reduced cytotoxic activity in a cytotoxicity assay, more particularly a luciferase release assay as described above, to CT45-IP variant peptides, in which at least one of the positions 3, 4, 5, 6 and 7 of SEQ ID NO: 138 is substituted into an alanine, in particular a functional avidity that is reduced by more than 70%, more than 80%, more than 90% or more than 95% compared to the functional avidity for CT45-IP.

The antigen binding proteins of the invention have a high specificity for the CT45-IP antigenic peptide, in particular an increased specificity in comparison to a reference protein when measured under similar, preferably identical experimental conditions. The inventors demonstrate in example 2 that the antigen binding proteins of the present invention bind the target antigen, i.e. the CT45 antigenic peptide in a complex with a MHC protein, with high specificity.

The inventors identified potential off-target peptides that are, for example, similar to the sequence and/or motif of CT45-IP, and thus have an increased risk of being bound by an antigen binding protein binding to CT45-IP.

In some embodiments, the antigen binding protein does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In some embodiments, the antigen binding protein does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In some embodiments, the antigen binding protein does not significantly bind to at least 1, at least 2, at least 3, at least 4, at least 5, or all similar peptides selected from the group consisting of SEQ ID NO: 147 (SP-05-0002), SEQ ID NO: 151 (SP-05-0006), SEQ ID NO: 152 (SP-05-0007) and SEQ ID NO: 155 (SP-05-0010).

In preferred embodiments, $V_A$ and $V_B$ are TCR variable domains, in particular TCR alpha, beta, gamma or delta variable domains. In some embodiments, $V_A$ is a TCR alpha, gamma or delta variable domain and $V_B$ is a TCR beta, gamma or delta variable domain. Preferably, $V_A$ is a TCR alpha variable domain and $V_B$ is a TCR beta variable domain, or $V_A$ is a TCR gamma variable domain and $V_B$ is a TCR delta variable domain, or $V_A$ is a TCR alpha variable domain and $V_B$ is a TCR gamma variable domain, or $V_A$ is a TCR delta variable domain and $V_B$ is a TCR beta variable domain. In preferred embodiments, $V_A$ is a TCR alpha variable domain and $V_B$ is a TCR beta variable domain. In some embodiments, $V_A$ is a TCR gamma variable domain comprising CDR1 and CDR3 and optionally CDR2 derived from a TCR alpha variable domain, and/or $V_B$ is a TCR delta variable domain comprising CDR1 and CDR3 and optionally CDR2 derived from a TCR beta variable domain. Preferably, within $V_A$ 1) FR1-a comprises or consists of SEQ ID NO: 539, 554 or 569;
   FR2-a comprises or consists of SEQ ID NO: 584;
   FR3-a comprises or consists of SEQ ID NO: 599 or 614; and/or
   FR4-a comprises or consists of SEQ ID NO: 629; or
2) FR1-a comprises or consists of SEQ ID NO: 540, 555 or 570;
   FR2-a comprises or consists of SEQ ID NO: 585;
   FR3-a comprises or consists of SEQ ID NO: 600 or 615; and/or
   FR4-a comprises or consists of SEQ ID NO: 630; or
3) FR1-a comprises or consists of SEQ ID NO: 541, 556 or 571;
   FR2-a comprises or consists of SEQ ID NO: 586;
   FR3-a comprises or consists of SEQ ID NO: 601 or 616; and/or
   FR4-a comprises or consists of SEQ ID NO: 631; or
4) FR1-a comprises or consists of SEQ ID NO: 542, 557 or 572;
   FR2-a comprises or consists of SEQ ID NO: 587;
   FR3-a comprises or consists of SEQ ID NO: 602 or 617; and/or
   FR4-a comprises or consists of SEQ ID NO: 632; or
5) FR1-a comprises or consists of SEQ ID NO: 543, 558 or 573;
   FR2-a comprises or consists of SEQ ID NO: 588;
   FR3-a comprises or consists of SEQ ID NO: 603 or 618; and/or
   FR4-a comprises or consists of SEQ ID NO: 633; or
6) FR1-a comprises or consists of SEQ ID NO: 544, 559, or 574;
   FR2-a comprises or consists of SEQ ID NO: 589;
   FR3-a comprises or consists of SEQ ID NO: 604 or 619; and/or
   FR4-a comprises or consists of SEQ ID NO: 634; or
7) FR1-a comprises or consists of SEQ ID NO: 545, 560 or 575;
   FR2-a comprises or consists of SEQ ID NO: 590;
   FR3-a comprises or consists of SEQ ID NO: 605 or 620; and/or
   FR4-a comprises or consists of SEQ ID NO: 635; or
8) FR1-a comprises or consists of SEQ ID NO: 546, 561 or 576;
   FR2-a comprises or consists of SEQ ID NO: 591;
   FR3-a comprises or consists of SEQ ID NO: 606 or 621; and/or
   FR4-a comprises or consists of SEQ ID NO: 636; or
9) FR1-a comprises or consists of SEQ ID NO: 547, 562 or 577;
   FR2-a comprises or consists of SEQ ID NO: 592;
   FR3-a comprises or consists of SEQ ID NO: 607 or 622; and/or
   FR4-a comprises or consists of SEQ ID NO: 637; or
10) FR1-a comprises or consists of SEQ ID NO: 548, 563 or 578;
    FR2-a comprises or consists of SEQ ID NO: 593;
    FR3-a comprises or consists of SEQ ID NO: 608 or 623; and/or
    FR4-a comprises or consists of SEQ ID NO: 638;
11) FR1-a comprises or consists of SEQ ID NO: 549, 564, or 579;
    FR2-a comprises or consists of SEQ ID NO: 594;
    FR3-a comprises or consists of SEQ ID NO: 609 or 624; and/or
    FR4-a comprises or consists of SEQ ID NO: 639; or
12) FR1-a comprises or consists of SEQ ID NO: 550, 565 or 580;
    FR2-a comprises or consists of SEQ ID NO: 595;
    FR3-a comprises or consists of SEQ ID NO: 610 or 625; and/or
    FR4-a comprises or consists of SEQ ID NO: 640; or
13) FR1-a comprises or consists of SEQ ID NO: 551, 566 or 581;
    FR2-a comprises or consists of SEQ ID NO: 596;
    FR3-a comprises or consists of SEQ ID NO: 611 or 626; and/or
    FR4-a comprises or consists of SEQ ID NO: 641; or
14) FR1-a comprises or consists of SEQ ID NO: 552, 567 or 582;
    FR2-a comprises or consists of SEQ ID NO: 597;
    FR3-a comprises or consists of SEQ ID NO: 612 or 627; and/or
    FR4-a comprises or consists of SEQ ID NO: 642; or
15) FR1-a comprises or consists of SEQ ID NO: 553, 568 or 583;
    FR2-a comprises or consists of SEQ ID NO: 598;
    FR3-a comprises or consists of SEQ ID NO: 613 or 628; and/or
    FR4-a comprises or consists of SEQ ID NO: 643; and within $V_B$ 1) FR1-b comprises or consists of SEQ ID NO: 644 or 659;
   FR2-b comprises or consists of SEQ ID NO: 674 or 689;
   FR3-b comprises or consists of SEQ ID NO: 704 or 719; and/or
   FR4-b comprises or consists of SEQ ID NO: 734; or
2) FR1-b comprises or consists of SEQ ID NO: 645 or 660;
   FR2-b comprises or consists of SEQ ID NO: 675 or 690;
   FR3-b comprises or consists of SEQ ID NO: 705 or 720; and/or
   FR4-b comprises or consists of SEQ ID NO: 735; or 3) FR1-b comprises or consists of SEQ ID NO: 646 or 661;
  FR2-b comprises or consists of SEQ ID NO: 676 or 691;
  FR3-b comprises or consists of SEQ ID NO: 706 or 721; and/or
  FR4-b comprises or consists of SEQ ID NO: 736; or
4) FR1-b comprises or consists of SEQ ID NO: 647 or 662;
  FR2-b comprises or consists of SEQ ID NO: 677 or 692;
  FR3-b comprises or consists of SEQ ID NO: 707 or 722; and/or
  FR4-b comprises or consists of SEQ ID NO: 737; or
5) FR1-b comprises or consists of SEQ ID NO: 648 or 663;
  FR2-b comprises or consists of SEQ ID NO: 678 or 693;
  FR3-b comprises or consists of SEQ ID NO: 708 or 723; and/or
  FR4-b comprises or consists of SEQ ID NO: 738; or
6) FR1-b comprises or consists of SEQ ID NO: 649 or 664;
  FR2-b comprises or consists of SEQ ID NO: 679 or 694;
  FR3-b comprises or consists of SEQ ID NO: 709 or 724; and/or
  FR4-b comprises or consists of SEQ ID NO: 739; or
7) FR1-b comprises or consists of SEQ ID NO: 650 or 665;
  FR2-b comprises or consists of SEQ ID NO: 680 or 695;
  FR3-b comprises or consists of SEQ ID NO: 710 or 725; and/or
  FR4-b comprises or consists of SEQ ID NO: 740; or
8) FR1-b comprises or consists of SEQ ID NO: 651 or 666;
  FR2-b comprises or consists of SEQ ID NO: 681 or 696;
  FR3-b comprises or consists of SEQ ID NO: 711 or 726; and/or
  FR4-b comprises or consists of SEQ ID NO: 741; or
9) FR1-b comprises or consists of SEQ ID NO: 652 or 667;
  FR2-b comprises or consists of SEQ ID NO: 682 or 697;
  FR3-b comprises or consists of SEQ ID NO: 712 or 727; and/or
  FR4-b comprises or consists of SEQ ID NO: 742; or
10) FR1-b comprises or consists of SEQ ID NO: 653 or 668;
  FR2-b comprises or consists of SEQ ID NO: 683 or 698;
  FR3-b comprises or consists of SEQ ID NO: 713 or 728; and/or
  FR4-b comprises or consists of SEQ ID NO: 743; or
11) FR1-b comprises or consists of SEQ ID NO: 654 or 669;
  FR2-b comprises or consists of SEQ ID NO: 684 or 699;
  FR3-b comprises or consists of SEQ ID NO: 714 or 729; and/or
  FR4-b comprises or consists of SEQ ID NO: 744; or
12) FR1-b comprises or consists of SEQ ID NO: 655 or 670;
  FR2-b comprises or consists of SEQ ID NO: 685 or 700;
  FR3-b comprises or consists of SEQ ID NO: 715 or 730; and/or
  FR4-b comprises or consists of SEQ ID NO: 745; or
13) FR1-b comprises or consists of SEQ ID NO: 656 or 671;
  FR2-b comprises or consists of SEQ ID NO: 686 or 701;
  FR3-b comprises or consists of SEQ ID NO: 716 or 731; and/or
  FR4-b comprises or consists of SEQ ID NO: 746; or
14) FR1-b comprises or consists of SEQ ID NO: 657 or 672;
  FR2-b comprises or consists of SEQ ID NO: 687 or 702;
  FR3-b comprises or consists of SEQ ID NO: 717 or 732; and/or
  FR4-b comprises or consists of SEQ ID NO: 747; or
15) FR1-b comprises or consists of SEQ ID NO: 658 or 673;
  FR2-b comprises or consists of SEQ ID NO: 688 or 703;
  FR3-b comprises or consists of SEQ ID NO: 718 or 733; and/or
  FR4-b comprises or consists of SEQ ID NO: 748,
wherein each of FR1-a, FR2-a, FR3-a, FR4-a, FR1-b, FR2-b, FR3-b and FR4-b may optionally comprise 8, 7, 6, 5, 4, 3, 2 or 1 amino acid mutations.

In some embodiments, it is preferred that
  1) FR1-a comprises or consists of SEQ ID NO: 539;
  2) FR1-a comprises or consists of SEQ ID NO: 540;
  3) FR1-a comprises or consists of SEQ ID NO: 541;
  4) FR1-a comprises or consists of SEQ ID NO: 542;
  5) FR1-a comprises or consists of SEQ ID NO: 543;
  6) FR1-a comprises or consists of SEQ ID NO: 544;
  7) FR1-a comprises or consists of SEQ ID NO: 545;
  8) FR1-a comprises or consists of SEQ ID NO: 546;
  9) FR1-a comprises or consists of SEQ ID NO: 547;
  10) FR1-a comprises or consists of SEQ ID NO: 548;
  11) FR1-a comprises or consists of SEQ ID NO: 549;
  12) FR1-a comprises or consists of SEQ ID NO: 550;
  13) FR1-a comprises or consists of SEQ ID NO: 551;
  14) FR1-a comprises or consists of SEQ ID NO: 552; or
  15) FR1-a comprises or consists of SEQ ID NO: 553,
wherein each of FR1-a, FR2-a, FR3-a and FR4-a may optionally comprise 8, 7, 6, 5, 4, 3, 2 or 1 amino acid mutations.

In some embodiments, it is preferred that
  1) FR3-a comprises or consists of SEQ ID NO: 599, optionally comprising 8, 7, 6, 5, 4, 3, 2 or 1 amino acid mutations outside position 10 of SEQ ID NO: 599;
  2) FR3-a comprises or consists of SEQ ID NO: 600, optionally comprising 8, 7, 6, 5, 4, 3, 2 or 1 amino acid mutations outside position 11 of SEQ ID NO: 600;
  3) FR3-a comprises or consists of SEQ ID NO: 601, optionally comprising 8, 7, 6, 5, 4, 3, 2 or 1 amino acid mutations outside position 5 of SEQ ID NO: 601;
  4) FR3-a comprises or consists of SEQ ID NO: 602, optionally comprising 8, 7, 6, 5, 4, 3, 2 or 1 amino acid mutations outside position 12 of SEQ ID NO: 602;
  5) FR3-a comprises or consists of SEQ ID NO: 603, optionally comprising 8, 7, 6, 5, 4, 3, 2 or 1 amino acid mutations outside position 22 of SEQ ID NO: 603;
  6) FR3-a comprises or consists of SEQ ID NO: 604, optionally comprising 8, 7, 6, 5, 4, 3, 2 or 1 amino acid mutations outside position 25 of SEQ ID NO: 604;
  7) FR3-a comprises or consists of SEQ ID NO: 605, optionally comprising 8, 7, 6, 5, 4, 3, 2 or 1 amino acid mutations outside position 21 of SEQ ID NO: 605;

8) FR3-a comprises or consists of SEQ ID NO: 606, optionally comprising 8, 7, 6, 5, 4, 3, 2 or 1 amino acid mutations outside position 18 of SEQ ID NO: 606
9) FR3-a comprises or consists of SEQ ID NO: 607, optionally comprising 8, 7, 6, 5, 4, 3, 2 or 1 amino acid mutations outside position 24 of SEQ ID NO: 607;
10) FR3-a comprises or consists of SEQ ID NO: 608, optionally comprising 8, 7, 6, 5, 4, 3, 2 or 1 amino acid mutations outside position 21 of SEQ ID NO: 608;
11) FR3-a comprises or consists of SEQ ID NO: 609, optionally comprising 8, 7, 6, 5, 4, 3, 2 or 1 amino acid mutations outside position 7 of SEQ ID NO: 609;
12) FR3-a comprises or consists of SEQ ID NO: 610, optionally comprising 8, 7, 6, 5, 4, 3, 2 or 1 amino acid mutations outside position 30 of SEQ ID NO: 610;
13) FR3-a comprises or consists of SEQ ID NO: 611, optionally comprising 8, 7, 6, 5, 4, 3, 2 or 1 amino acid mutations outside position 18 of SEQ ID NO: 611;
14) FR3-a comprises or consists of SEQ ID NO: 612, optionally comprising 8, 7, 6, 5, 4, 3, 2 or 1 amino acid mutations outside position 19 of SEQ ID NO: 612; or
15) FR3-a comprises or consists of SEQ ID NO: 613, optionally comprising 8, 7, 6, 5, 4, 3, 2 or 1 amino acid mutations outside position 23 of SEQ ID NO: 613.

In some embodiments, it is preferred that
1) FR2-b comprises or consists of SEQ ID NO: 674;
2) FR2-b comprises or consists of SEQ ID NO: 675;
3) FR2-b comprises or consists of SEQ ID NO: 676;
4) FR2-b comprises or consists of SEQ ID NO: 677;
5) FR2-b comprises or consists of SEQ ID NO: 678;
6) FR2-b comprises or consists of SEQ ID NO: 679;
7) FR2-b comprises or consists of SEQ ID NO: 680;
8) FR2-b comprises or consists of SEQ ID NO: 681;
9) FR2-b comprises or consists of SEQ ID NO: 682;
10) FR2-b comprises or consists of SEQ ID NO: 683;
11) FR2-b comprises or consists of SEQ ID NO: 684;
12) FR2-b comprises or consists of SEQ ID NO: 685;
13) FR2-b comprises or consists of SEQ ID NO: 686;
14) FR2-b comprises or consists of SEQ ID NO: 687; or
15) FR2-b comprises or consists of SEQ ID NO: 688, wherein each of FR1-b, FR2-b, FR3-b and FR4-b may optionally comprise 6, 5, 4, 3, 2 or 1 amino acid mutations.

In some embodiments, it is preferred that
1) FR2-b comprises or consists of SEQ ID NO: 689, optionally comprising 6, 5, 4, 3, 2 or 1 amino acid mutations outside position 16 of SEQ ID NO: 689; or
2) FR2-b comprises or consists of SEQ ID NO: 690, optionally comprising 6, 5, 4, 3, 2 or 1 amino acid mutations outside position 17 of SEQ ID NO: 690;
3) FR2-b comprises or consists of SEQ ID NO: 691, optionally comprising 6, 5, 4, 3, 2 or 1 amino acid mutations outside position 5 of SEQ ID NO: 691;
4) FR2-b comprises or consists of SEQ ID NO: 692, optionally comprising 6, 5, 4, 3, 2 or 1 amino acid mutations outside position 15 of SEQ ID NO: 692;
5) FR2-b comprises or consists of SEQ ID NO: 693, optionally comprising 6, 5, 4, 3, 2 or 1 amino acid mutations outside position 7 of SEQ ID NO: 693;
6) FR2-b comprises or consists of SEQ ID NO: 694, optionally comprising 6, 5, 4, 3, 2 or 1 amino acid mutations outside position 13 of SEQ ID NO: 694;
7) FR2-b comprises or consists of SEQ ID NO: 695, optionally comprising 6, 5, 4, 3, 2 or 1 amino acid mutations outside position 11 of SEQ ID NO: 695;
8) FR2-b comprises or consists of SEQ ID NO: 696, optionally comprising 6, 5, 4, 3, 2 or 1 amino acid mutations outside position 11 of SEQ ID NO: 696;
9) FR2-b comprises or consists of SEQ ID NO: 697, optionally comprising 6, 5, 4, 3, 2 or 1 amino acid mutations outside position 1 of SEQ ID NO: 697;
10) FR2-b comprises or consists of SEQ ID NO: 698, optionally comprising 6, 5, 4, 3, 2 or 1 amino acid mutations outside position 1 of SEQ ID NO: 698;
11) FR2-b comprises or consists of SEQ ID NO: 699, optionally comprising 6, 5, 4, 3, 2 or 1 amino acid mutations outside position 16 of SEQ ID NO: 699;
12) FR2-b comprises or consists of SEQ ID NO: 700, optionally comprising 6, 5, 4, 3, 2 or 1 amino acid mutations outside position 7 of SEQ ID NO: 700;
13) FR2-b comprises or consists of SEQ ID NO: 701, optionally comprising 6, 5, 4, 3, 2 or 1 amino acid mutations outside position 11 of SEQ ID NO: 701;
14) FR2-b comprises or consists of SEQ ID NO: 702, optionally comprising 6, 5, 4, 3, 2 or 1 amino acid mutations outside position 1 of SEQ ID NO: 702; or
15) FR2-b comprises or consists of SEQ ID NO: 703, optionally comprising 6, 5, 4, 3, 2 or 1 amino acid mutations outside position 7 of SEQ ID NO: 703.

In preferred embodiments,
1) $V_A$ comprises SEQ ID NO: 189 or an amino acid sequence having at least 70%, 75%, 80%, 85%, 90%, 95%, 98% or 99% identity to SEQ ID NO: 189 and comprising the CDRa1 comprising SEQ ID NO: 14, the CDRa3 comprising SEQ ID NO: 489, and optionally the CDRa2 comprising SEQ ID NO: 15; and $V_B$ comprises SEQ ID NO: 339 or an amino acid sequence having at least 70%, 75%, 80%, 85%, 90%, 95%, 98% or 99% identity to SEQ ID NO: 339 and comprising the CDRb1 comprising SEQ ID NO: 19, the CDRb3 comprising SEQ ID NO: 504 and optionally the CDRb2 comprising SEQ ID NO: 20, or
2) $V_A$ comprises SEQ ID NO: 190 or an amino acid sequence having at least 70%, 75%, 80%, 85%, 90%, 95%, 98% or 99% identity to SEQ ID NO: 190 and comprising the CDRa1 comprising SEQ ID NO: 24, the CDRa3 comprising SEQ ID NO: 490, and optionally the CDRa2 comprising SEQ ID NO: 25; and $V_B$ comprises SEQ ID NO: 340 or an amino acid sequence having at least 70%, 75%, 80%, 85%, 90%, 95%, 98% or 99% identity to SEQ ID NO: 340 and comprising the CDRb1 comprising SEQ ID NO: 75, the CDRb3 comprising SEQ ID NO: 505 and optionally the CDRb2 comprising SEQ ID NO: 76, or
3) $V_A$ comprises SEQ ID NO: 191 or an amino acid sequence having at least 70%, 75%, 80%, 85%, 90%, 95%, 98% or 99% identity to SEQ ID NO: 191 and comprising the CDRa1 comprising SEQ ID NO: 24, the CDRa3 comprising SEQ ID NO: 491, and optionally the CDRa2 comprising SEQ ID NO: 25; and $V_B$ comprises SEQ ID NO: 341 or an amino acid sequence having at least 70%, 75%, 80%, 85%, 90%, 95%, 98% or 99% identity to SEQ ID NO: 341 and comprising the CDRb1 comprising SEQ ID NO: 66, the CDRb3 comprising SEQ ID NO: 506 and optionally the CDRb2 comprising SEQ ID NO: 67, or
4) $V_A$ comprises SEQ ID NO: 192 or an amino acid sequence having at least 70%, 75%, 80%, 85%, 90%, 95%, 98% or 99% identity to SEQ ID NO: 192 and comprising the CDRa1 comprising SEQ ID NO: 90 the CDRa3 comprising SEQ ID NO: 492, and optionally the CDRa2 comprising SEQ ID NO: 91; and $V_B$ comprises SEQ ID NO: 342 or an amino acid sequence having at least 70%, 75%, 80%, 85%, 90%, 95%, 98% or 99% identity to SEQ ID NO: 342 and comprising the CDRb1 comprising SEQ ID NO: 66, the CDRb3 comprising SEQ ID NO: 507 and optionally the CDRb2 comprising SEQ ID NO: 95, or 5) $V_A$ comprises SEQ ID NO: 193 or an amino acid sequence having at least 70%, 75%, 80%, 85%, 90%, 95%, 98% or 99% identity to SEQ ID NO: 193 and comprising the CDRa1 comprising SEQ ID NO: 2, the CDRa3 comprising SEQ ID NO: 493, and optionally the CDRa2 comprising SEQ ID NO: 3; and $V_B$ comprises SEQ ID NO: 343 or an amino acid sequence having at least 70%, 75%, 80%, 85%, 90%, 95%, 98% or 99% identity to SEQ ID NO: 343 and comprising the CDRb1 comprising SEQ ID NO: 8, the CDRb3 comprising SEQ ID NO: 508 and optionally the CDRb2 comprising SEQ ID NO: 9, or 6) $V_A$ comprises SEQ ID NO: 194 or an amino acid sequence having at least 70%, 75%, 80%, 85%, 90%, 95%, 98% or 99% identity to SEQ ID NO: 194 and comprising the CDRa1 comprising SEQ ID NO: 53, the CDRa3 comprising SEQ ID NO: 494, and optionally the CDRa2 comprising SEQ ID NO: 54; and $V_B$ comprises SEQ ID NO: 344 or an amino acid sequence having at least 70%, 75%, 80%, 85%, 90%, 95%, 98% or 99% identity to SEQ ID NO: 344 and comprising the CDRb1 comprising SEQ ID NO: 58, the CDRb3 comprising SEQ ID NO: 509 and optionally the CDRb2 comprising SEQ ID NO: 59, or 7) $V_A$ comprises SEQ ID NO: 195 or an amino acid sequence having at least 70%, 75%, 80%, 85%, 90%, 95%, 98% or 99% identity to SEQ ID NO: 195 and comprising the CDRa1 comprising SEQ ID NO: 71, the CDRa3 comprising SEQ ID NO: 495, and optionally the CDRa2 comprising SEQ ID NO: 15; and $V_B$ comprises SEQ ID NO: 345 or an amino acid sequence having at least 70%, 75%, 80%, 85%, 90%, 95%, 98% or 99% identity to SEQ ID NO: 345 and comprising the CDRb1 comprising SEQ ID NO: 75, the CDRb3 comprising SEQ ID NO: 510 and optionally the CDRb2 comprising SEQ ID NO: 76, or 8) $V_A$ comprises SEQ ID NO: 196 or an amino acid sequence having at least 70%, 75%, 80%, 85%, 90%, 95%, 98% or 99% identity to SEQ ID NO: 196 and comprising the CDRa1 comprising SEQ ID NO: 99, the CDRa3 comprising SEQ ID NO: 496, and optionally the CDRa2 comprising SEQ ID NO: 100; and $V_B$ comprises SEQ ID NO: 346 or an amino acid sequence having at least 70%, 75%, 80%, 85%, 90%, 95%, 98% or 99% identity to SEQ ID NO: 346 and comprising the CDRb1 comprising SEQ ID NO: 75, the CDRb3 comprising SEQ ID NO: 511 and optionally the CDRb2 comprising SEQ ID NO: 76, or 9) $V_A$ comprises SEQ ID NO: 197 or an amino acid sequence having at least 70%, 75%, 80%, 85%, 90%, 95%, 98% or 99% identity to SEQ ID NO: 197 and comprising the CDRa1 comprising SEQ ID NO: 80, the CDRa3 comprising SEQ ID NO: 497, and optionally the CDRa2 comprising SEQ ID NO: 81; and $V_B$ comprises SEQ ID NO: 347 or an amino acid sequence having at least 70%, 75%, 80%, 85%, 90%, 95%, 98% or 99% identity to SEQ ID NO: 347 and comprising the CDRb1 comprising SEQ ID NO: 85, the CDRb3 comprising SEQ ID NO: 512 and optionally the CDRb2 comprising SEQ ID NO: 86, or 10) $V_A$ comprises SEQ ID NO: 198 or an amino acid sequence having at least 70%, 75%, 80%, 85%, 90%, 95%, 98% or 99% identity to SEQ ID NO: 198 and comprising the CDRa1 comprising SEQ ID NO: 107, the CDRa3 comprising SEQ ID NO: 498, and optionally the CDRa2 comprising SEQ ID NO: 108; and $V_B$ comprises SEQ ID NO: 348 or an amino acid sequence having at least 70%, 75%, 80%, 85%, 90%, 95%, 98% or 99% identity to SEQ ID NO: 348 and comprising the CDRb1 comprising SEQ ID NO: 112, the CDRb3 comprising SEQ ID NO: 513 and optionally the CDRb2 comprising SEQ ID NO: 113, or 11) $V_A$ comprises SEQ ID NO: 199 or an amino acid sequence having at least 70%, 75%, 80%, 85%, 90%, 95%, 98% or 99% identity to SEQ ID NO: 199 and comprising the CDRa1 comprising SEQ ID NO: 125, the CDRa3 comprising SEQ ID NO: 499, and optionally the CDRa2 comprising SEQ ID NO: 126; and $V_B$ comprises SEQ ID NO: 349 or an amino acid sequence having at least 70%, 75%, 80%, 85%, 90%, 95%, 98% or 99% identity to SEQ ID NO: 349 and comprising the CDRb1 comprising SEQ ID NO: 112, the CDRb3 comprising SEQ ID NO: 514 and optionally the CDRb2 comprising SEQ ID NO: 113, or 12) $V_A$ comprises SEQ ID NO: 200 or an amino acid sequence having at least 70%, 75%, 80%, 85%, 90%, 95%, 98% or 99% identity to SEQ ID NO: 200 and comprising the CDRa1 comprising SEQ ID NO: 117, the CDRa3 comprising SEQ ID NO: 500, and optionally the CDRa2 comprising SEQ ID NO: 118; and $V_B$ comprises SEQ ID NO: 350 or an amino acid sequence having at least 70%, 75%, 80%, 85%, 90%, 95%, 98% or 99% identity to SEQ ID NO: 350 and comprising the CDRb1 comprising SEQ ID NO: 58, the CDRb3 comprising SEQ ID NO: 515 and optionally the CDRb2 comprising SEQ ID NO: 59, or 13) $V_A$ comprises SEQ ID NO: 201 or an amino acid sequence having at least 70%, 75%, 80%, 85%, 90%, 95%, 98% or 99% identity to SEQ ID NO: 201 and comprising the CDRa1 comprising SEQ ID NO: 24, the CDRa3 comprising SEQ ID NO: 501, and optionally the CDRa2 comprising SEQ ID NO: 25; and $V_B$ comprises SEQ ID NO: 351 or an amino acid sequence having at least 70%, 75%, 80%, 85%, 90%, 95%, 98% or 99% identity to SEQ ID NO: 351 and comprising the CDRb1 comprising SEQ ID NO: 38, the CDRb3 comprising SEQ ID NO: 516 and optionally the CDRb2 comprising SEQ ID NO: 39, or 14) $V_A$ comprises SEQ ID NO: 202 or an amino acid sequence having at least 70%, 75%, 80%, 85%, 90%, 95%, 98% or 99% identity to SEQ ID NO: 202 and comprising the CDRa1 comprising SEQ ID NO: 24, the CDRa3 comprising SEQ ID NO: 502 and optionally the CDRa2 comprising SEQ ID NO: 25; and $V_B$ comprises SEQ ID NO: 352 or an amino acid sequence having at least 70%, 75%, 80%, 85%, 90%, 95%, 98% or 99% identity to SEQ ID NO: 352 and comprising the CDRb1 comprising SEQ ID NO: 29, the CDRb3 comprising SEQ ID NO: 517 and optionally the CDRb2 comprising SEQ ID NO: 30, or 15) $V_A$ comprises SEQ ID NO: 203 or an amino acid sequence having at least 70%, 75%, 80%, 85%, 90%, 95%, 98% or 99% identity to SEQ ID NO: 203 and comprising the CDRa1 comprising SEQ ID NO: 43, the CDRa3 comprising SEQ ID NO: 503 and optionally the CDRa2 comprising SEQ ID NO: 44; and $V_B$ comprises SEQ ID NO: 353 or an amino acid sequence having at least 70%, 75%, 80%, 85%, 90%, 95%, 98% or 99% identity to SEQ ID NO: 353 and comprising the CDRb1 comprising SEQ ID NO: 48, the CDRb3 comprising SEQ ID NO: 518 and optionally the CDRb2 comprising SEQ ID NO: 49.

In preferred embodiments,
1) $V_A$ comprises SEQ ID NO: 189, 249, 264 or 279; and $V_B$ comprises SEQ ID NO: 339, 399, 414 or 429, or
2) $V_A$ comprises SEQ ID NO: 190, 250, 265 or 280; and $V_B$ comprises SEQ ID NO: 340, 400, 415 or 430, or
3) $V_A$ comprises SEQ ID NO: 191, 251, 266 or 281; and $V_B$ comprises SEQ ID NO: 341, 401, 416 or 431, or
4) $V_A$ comprises SEQ ID NO: 192, 252, 267 or 282; and $V_B$ comprises SEQ ID NO: 342, 402, 417 or 432, or
5) $V_A$ comprises SEQ ID NO: 193, 253, 268 or 283; and $V_B$ comprises SEQ ID NO: 343, 403, 418 or 433, or
6) $V_A$ comprises SEQ ID NO: 194, 254, 269 or 284; and $V_B$ comprises SEQ ID NO: 344, 404, 419 or 434, or
7) $V_A$ comprises SEQ ID NO: 195, 255, 270 or 285; and $V_B$ comprises SEQ ID NO: 345, 405, 420 or 435, or
8) $V_A$ comprises SEQ ID NO: 196, 256, 271 or 286; and $V_B$ comprises SEQ ID NO: 346, 406, 421 or 436, or
9) $V_A$ comprises SEQ ID NO: 197, 257, 272 or 287; and $V_B$ comprises SEQ ID NO: 347, 407, 422, or 437, or
10) $V_A$ comprises SEQ ID NO: 198, 258, 273 or 288; and $V_B$ comprises SEQ ID NO: 348, 408, 423 or 438, or
11) $V_A$ comprises SEQ ID NO: 199, 259, 274 or 289; and $V_B$ comprises SEQ ID NO: 349, 409, 424 or 439, or
12) $V_A$ comprises SEQ ID NO: 200, 260, 275 or 290; and $V_B$ comprises SEQ ID NO: 350, 410, 425 or 440, or
13) $V_A$ comprises SEQ ID NO: 201, 261, 276 or 291; and $V_B$ comprises SEQ ID NO: 351, 411, 426 or 441, or
14) $V_A$ comprises SEQ ID NO: 202, 262, 277 or 292; and $V_B$ comprises SEQ ID NO: 352, 412, 427 or 442, or
15) $V_A$ comprises SEQ ID NO: 203, 263, 278 or 293; and $V_B$ comprises SEQ ID NO: 353, 413, 428 or 443.

In some embodiments,
1) $V_A$ comprises SEQ ID NO: 189; and $V_B$ comprises SEQ ID NO: 414, or
2) $V_A$ comprises SEQ ID NO: 190; and $V_B$ comprises SEQ ID NO: 415, or
3) $V_A$ comprises SEQ ID NO: 191; and $V_B$ comprises SEQ ID NO: 416, or
4) $V_A$ comprises SEQ ID NO: 192; and $V_B$ comprises SEQ ID NO: 417, or
5) $V_A$ comprises SEQ ID NO: 193; and $V_B$ comprises SEQ ID NO: 418, or
6) $V_A$ comprises SEQ ID NO: 194; and $V_B$ comprises SEQ ID NO: 419, or
7) $V_A$ comprises SEQ ID NO: 195; and $V_B$ comprises SEQ ID NO: 420, or
8) $V_A$ comprises SEQ ID NO: 196; and $V_B$ comprises SEQ ID NO: 421, or
9) $V_A$ comprises SEQ ID NO: 197; and $V_B$ comprises SEQ ID NO: 422, or
10) $V_A$ comprises SEQ ID NO: 198; and $V_B$ comprises SEQ ID NO: 423, or
11) $V_A$ comprises SEQ ID NO: 199; and $V_B$ comprises SEQ ID NO: 424, or
12) $V_A$ comprises SEQ ID NO: 200; and $V_B$ comprises SEQ ID NO: 425, or
13) $V_A$ comprises SEQ ID NO: 201; and $V_B$ comprises SEQ ID NO: 426, or
14) $V_A$ comprises SEQ ID NO: 202; and $V_B$ comprises SEQ ID NO: 427, or
15) $V_A$ comprises SEQ ID NO: 203; and $V_B$ comprises SEQ ID NO: 428.

$V_A$ preferably comprises or consists of an amino acid sequence selected from the group consisting of SEQ ID NO: 13, 132, 62, 89, 1, 52, 70, 98, 79, 106, 124, 116, 34, 23, and 42, or an amino acid sequence having at least 70%, 75%, 80%, 85%, 90%, 95%, 98% or 99% identity to SEQ ID NO: 13, 132, 62, 89, 1, 52, 70, 98, 79, 106, 124, 116, 34, 23, and 42 and comprising the CDRa1, CDRa2 and CDRa3 as defined in context of the antigen binding proteins of the invention, wherein the CDRa1, CDRa2 and CDRa3 sequences may comprise one, two or three amino acid mutations. $V_B$ preferably comprises or consists of an amino acid sequence selected from the group consisting of SEQ ID NO: 18, 135, 65, 94, 7, 57, 74, 103, 84, 111, 129, 121, 37, 28 and 47 or an amino acid sequence having at least 70%, 75%, 80%, 85%, 90%, 95%, 98% or 99% identity to SEQ ID NO: 18, 135, 65, 94, 7, 57, 74, 103, 84, 111, 129, 121, 37, 28 and 47 and comprising the CDRa1, CDRa2 and CDRa3 as defined in context of the antigen binding proteins of the invention, wherein the CDRb1, CDRb2 and CDRb3 sequences may comprise one, two or three amino acid mutations.

Modifications and changes may be made in the amino acid sequence of the antigen binding protein of the present invention, and in the corresponding DNA sequences, respectively, and still result in a functional antigen binding protein or polypeptide with desirable characteristics.

In preferred embodiments,
1) $V_A$ comprises or consists of the amino acid sequence of SEQ ID NO: 13 or an amino acid sequence having at least 70%, 75%, 80%, 85%, 90%, 95%, 98% or 99% identity to SEQ ID NO: 13 and $V_B$ comprises or consists of the amino acid sequence of SEQ ID NO: 18 or an amino acid sequence having at least 70%, 75%, 80%, 85%, 90%, 95%, 98% or 99% identity to SEQ ID NO: 18;
2) $V_A$ comprises or consists of the amino acid sequence of SEQ ID NO: 132 or an amino acid sequence having at least 70%, 75%, 80%, 85%, 90%, 95%, 98% or 99% identity to SEQ ID NO: 132 and $V_B$ comprises or consists of the amino acid sequence of SEQ ID NO: 135 or an amino acid sequence having at least 70%, 75%, 80%, 85%, 90%, 95%, 98% or 99% identity to SEQ ID NO: 135;
3) $V_A$ comprises or consists of the amino acid sequence of SEQ ID NO: 62 or an amino acid sequence having at least 70%, 75%, 80%, 85%, 90%, 95%, 98% or 99% identity to SEQ ID NO: 62 and $V_B$ comprises or consists of the amino acid sequence of SEQ ID NO: 65 or an amino acid sequence having at least 70%, 75%, 80%, 85%, 90%, 95%, 98% or 99% identity to SEQ ID NO: 65;
4) $V_A$ comprises or consists of the amino acid sequence of SEQ ID NO: 89 or an amino acid sequence having at least 70%, 75%, 80%, 85%, 90%, 95%, 98% or 99% identity to SEQ ID NO: 89 and $V_B$ comprises or consists of the amino acid sequence of SEQ ID NO: 94 or an amino acid sequence having at least 70%, 75%, 80%, 85%, 90%, 95%, 98% or 99% identity to SEQ ID NO: 94;
5) $V_A$ comprises or consists of the amino acid sequence of SEQ ID NO: 1 or an amino acid sequence having at least 70%, 75%, 80%, 85%, 90%, 95%, 98% or 99% identity to SEQ ID NO: 1 and $V_B$ comprises or consists of the amino acid sequence of SEQ ID NO: 7 or an amino acid sequence having at least 70%, 75%, 80%, 85%, 90%, 95%, 98% or 99% identity to SEQ ID NO: 7;
6) $V_A$ comprises or consists of the amino acid sequence of SEQ ID NO: 52 or an amino acid sequence having at least 70%, 75%, 80%, 85%, 90%, 95%, 98% or 99% identity to SEQ ID NO: 52 and $V_B$ comprises or consists of the amino acid sequence of SEQ ID NO: 57 or an amino acid sequence having at least 70%, 75%, 80%, 85%, 90%, 95%, 98% or 99% identity to SEQ ID NO: 57;

7) $V_A$ comprises or consists of the amino acid sequence of SEQ ID NO: 70 or an amino acid sequence having at least 70%, 75%, 80%, 85%, 90%, 95%, 98% or 99% identity to SEQ ID NO: 70 and $V_B$ comprises or consists of the amino acid sequence of SEQ ID NO: 74 or an amino acid sequence having at least 70%, 75%, 80%, 85%, 90%, 95%, 98% or 99% identity to SEQ ID NO: 74;

8) $V_A$ comprises or consists of the amino acid sequence of SEQ ID NO: 98 or an amino acid sequence having at least 70%, 75%, 80%, 85%, 90%, 95%, 98% or 99% identity to SEQ ID NO: 98 and $V_B$ comprises or consists of the amino acid sequence of SEQ ID NO: 103 or an amino acid sequence having at least 70%, 75%, 80%, 85%, 90%, 95%, 98% or 99% identity to SEQ ID NO: 103;

9) $V_A$ comprises or consists of the amino acid sequence of SEQ ID NO: 79 or an amino acid sequence having at least 70%, 75%, 80%, 85%, 90%, 95%, 98% or 99% identity to SEQ ID NO: 79 and $V_B$ comprises or consists of the amino acid sequence of SEQ ID NO: 84 or an amino acid sequence having at least 70%, 75%, 80%, 85%, 90%, 95%, 98% or 99% identity to SEQ ID NO: 84;

10) $V_A$ comprises or consists of the amino acid sequence of SEQ ID NO: 106 or an amino acid sequence having at least 70%, 75%, 80%, 85%, 90%, 95%, 98% or 99% identity to SEQ ID NO: 106 and $V_B$ comprises or consists of the amino acid sequence of SEQ ID NO: 111 or an amino acid sequence having at least 70%, 75%, 80%, 85%, 90%, 95%, 98% or 99% identity to SEQ ID NO: 111;

11) $V_A$ comprises or consists of the amino acid sequence of SEQ ID NO: 124 or an amino acid sequence having at least 70%, 75%, 80%, 85%, 90%, 95%, 98% or 99% identity to SEQ ID NO: 124 and $V_B$ comprises or consists of the amino acid sequence of SEQ ID NO: 129 or an amino acid sequence having at least 70%, 75%, 80%, 85%, 90%, 95%, 98% or 99% identity to SEQ ID NO: 129;

12) $V_A$ comprises or consists of the amino acid sequence of SEQ ID NO: 116 or an amino acid sequence having at least 70%, 75%, 80%, 85%, 90%, 95%, 98% or 99% identity to SEQ ID NO: 116 and $V_B$ comprises or consists of the amino acid sequence of SEQ ID NO: 121 or an amino acid sequence having at least 70%, 75%, 80%, 85%, 90%, 95%, 98% or 99% identity to SEQ ID NO: 121;

13) $V_A$ comprises or consists of the amino acid sequence of SEQ ID NO: 34 or an amino acid sequence having at least 70%, 75%, 80%, 85%, 90%, 95%, 98% or 99% identity to SEQ ID NO: 34 and $V_B$ comprises or consists of the amino acid sequence of SEQ ID NO: 37 or an amino acid sequence having at least 70%, 75%, 80%, 85%, 90%, 95%, 98% or 99% identity to SEQ ID NO: 37;

14) $V_A$ comprises or consists of the amino acid sequence of SEQ ID NO: 23 or an amino acid sequence having at least 70%, 75%, 80%, 85%, 90%, 95%, 98% or 99% identity to SEQ ID NO: 23 and $V_B$ comprises or consists of the amino acid sequence of SEQ ID NO: 28 or an amino acid sequence having at least 70%, 75%, 80%, 85%, 90%, 95%, 98% or 99% identity to SEQ ID NO: 28; or 15) $V_A$ comprises or consists of the amino acid sequence of SEQ ID NO: 42 or an amino acid sequence having at least 70%, 75%, 80%, 85%, 90%, 95%, 98% or 99% identity to SEQ ID NO: 42 and $V_B$ comprises or consists of the amino acid sequence of SEQ ID NO: 47 or an amino acid sequence having at least 70%, 75%, 80%, 85%, 90%, 95%, 98% or 99% identity to SEQ ID NO: 47, wherein $V_A$ and $V_B$ comprise the CDR sequences as defined in context of the antigen binding proteins of the invention, wherein the CDR sequences may comprise one, two or three amino acid mutations, preferably no amino acid mutation.

In preferred embodiments,

1) $V_A$ comprises or consists of SEQ ID NO: 13, 204, 219 or 234; and $V_B$ comprises or consists of SEQ ID NO: 18, 354, 369 or 384, or 2) $V_A$ comprises or consists of SEQ ID NO: 132, 205, 220 or 235; and $V_B$ comprises or consists of SEQ ID NO: 135, 355, 370 or 385, or 3) $V_A$ comprises or consists of SEQ ID NO: 62, 206, 221 or 236; and $V_B$ comprises or consists of SEQ ID NO: 65, 356, 371 or 386, or 4) $V_A$ comprises or consists of SEQ ID NO: 89, 207, 222 or 237; and $V_B$ comprises or consists of SEQ ID NO: 94, 357, 372 or 387, or 5) $V_A$ comprises or consists of SEQ ID NO: 1, 208, 223 or 238; and $V_B$ comprises or consists of SEQ ID NO: 7, 358, 373 or 388, or 6) $V_A$ comprises or consists of SEQ ID NO: 52, 209, 224 or 239; and $V_B$ comprises or consists of SEQ ID NO: 57, 359, 374 or 389, or 7) $V_A$ comprises or consists of SEQ ID NO: 70, 210, 225 or 240; and $V_B$ comprises or consists of SEQ ID NO: 74, 360, 375 or 390, or 8) $V_A$ comprises or consists of SEQ ID NO: 198, 211, 226 or 241; and $V_B$ comprises or consists of SEQ ID NO: 103, 361, 376 or 391, or 9) $V_A$ comprises or consists of SEQ ID NO: 79, 212, 227 or 242; and $V_B$ comprises or consists of SEQ ID NO: 84, 362, 377, or 392, or 10) $V_A$ comprises or consists of SEQ ID NO: 106, 213, 228 or 243; and $V_B$ comprises or consists of SEQ ID NO: 111, 363, 378 or 393, or 11) $V_A$ comprises or consists of SEQ ID NO: 124, 214, 229 or 244; and $V_B$ comprises or consists of SEQ ID NO: 129, 364, 379 or 394, or 12) $V_A$ comprises or consists of SEQ ID NO: 116, 215, 230 or 245; and $V_B$ comprises or consists of SEQ ID NO: 121, 365, 380 or 395, or 13) $V_A$ comprises or consists of SEQ ID NO: 34, 216, 231 or 246; and $V_B$ comprises or consists of SEQ ID NO: 37, 366, 381 or 396, or 14) $V_A$ comprises or consists of SEQ ID NO: 23, 217, 232 or 247; and $V_B$ comprises or consists of SEQ ID NO: 28, 367, 382 or 397, or 15) $V_A$ comprises or consists of SEQ ID NO: 42, 218, 233 or 248; and $V_B$ comprises or consists of SEQ ID NO: 47, 368, 383 or 398.

More preferably,

1) $V_A$ comprises or consists of the amino acid sequence of SEQ ID NO: 13 and $V_B$ comprises or consists of the amino acid sequence of SEQ ID NO: 18;

2) $V_A$ comprises or consists of the amino acid sequence of SEQ ID NO: 132 and $V_B$ comprises or consists of the amino acid sequence of SEQ ID NO: 135;
3) $V_A$ comprises or consists of the amino acid sequence of SEQ ID NO: 62 and $V_B$ comprises or consists of the amino acid sequence of SEQ ID NO: 65;
4) $V_A$ comprises or consists of the amino acid sequence of SEQ ID NO: 89 and $V_B$ comprises or consists of the amino acid sequence of SEQ ID NO: 94;
5) $V_A$ comprises or consists of the amino acid sequence of SEQ ID NO: 1 and $V_B$ comprises or consists of the amino acid sequence of SEQ ID NO: 7;
6) $V_A$ comprises or consists of the amino acid sequence of SEQ ID NO: 52 and $V_B$ comprises or consists of the amino acid sequence of SEQ ID NO: 57;
7) $V_A$ comprises or consists of the amino acid sequence of SEQ ID NO: 70 and $V_B$ comprises or consists of the amino acid sequence of SEQ ID NO: 74;
8) $V_A$ comprises or consists of the amino acid sequence of SEQ ID NO: 98 and $V_B$ comprises or consists of the amino acid sequence of SEQ ID NO: 103;
9) $V_A$ comprises or consists of the amino acid sequence of SEQ ID NO: 79 and $V_B$ comprises or consists of the amino acid sequence of SEQ ID NO: 84;
10) $V_A$ comprises or consists of the amino acid sequence of SEQ ID NO: 106 and $V_B$ comprises or consists of the amino acid sequence of SEQ ID NO: 111;
11) $V_A$ comprises or consists of the amino acid sequence of SEQ ID NO: 124 and $V_B$ comprises or consists of the amino acid sequence of SEQ ID NO: 129;
12) $V_A$ comprises or consists of the amino acid sequence of SEQ ID NO: 116 and $V_B$ comprises or consists of the amino acid sequence of SEQ ID NO: 121;
13) $V_A$ comprises or consists of the amino acid sequence of SEQ ID NO: 34 and $V_B$ comprises or consists of the amino acid sequence of SEQ ID NO: 37;
14) $V_A$ comprises or consists of the amino acid sequence of SEQ ID NO: 23 and $V_B$ comprises or consists of the amino acid sequence of SEQ ID NO: 28; or
15) $V_A$ comprises or consists of the amino acid sequence of SEQ ID NO: 42 and $V_B$ comprises or consists of the amino acid sequence of SEQ ID NO: 47.

In another embodiment,
1) $V_A$ comprises or consists of SEQ ID NO: 13 and $V_B$ comprises or consists of SEQ ID NO: 369, or
2) $V_A$ comprises or consists of SEQ ID NO: 132 and $V_B$ comprises or consists of SEQ ID NO: 370, or
3) $V_A$ comprises or consists of SEQ ID NO: 62 and $V_B$ comprises or consists of SEQ ID NO: 371, or
4) $V_A$ comprises or consists of SEQ ID NO: 89 and $V_B$ comprises or consists of SEQ ID NO: 372, or
5) $V_A$ comprises or consists of SEQ ID NO: 1 and $V_B$ comprises or consists of SEQ ID NO: 373, or
6) $V_A$ comprises or consists of SEQ ID NO: 52 and $V_B$ comprises or consists of SEQ ID NO: 374, or
7) $V_A$ comprises or consists of SEQ ID NO: 70 and $V_B$ comprises or consists of SEQ ID NO: 375, or
8) $V_A$ comprises or consists of SEQ ID NO: 198 and $V_B$ comprises or consists of SEQ ID NO: 376, or
9) $V_A$ comprises or consists of SEQ ID NO: 79 and $V_B$ comprises or consists of SEQ ID NO: 377, or
10) $V_A$ comprises or consists of SEQ ID NO: 106 and $V_B$ comprises or consists of SEQ ID NO: 378, or
11) $V_A$ comprises or consists of SEQ ID NO: 124 and $V_B$ comprises or consists of SEQ ID NO: 379, or
12) $V_A$ comprises or consists of SEQ ID NO: 116 and $V_B$ comprises or consists of SEQ ID NO: 380, or
13) $V_A$ comprises or consists of SEQ ID NO: 34 and $V_B$ comprises or consists of SEQ ID NO: 381, or
14) $V_A$ comprises or consists of SEQ ID NO: 23 and $V_B$ comprises or consists of SEQ ID NO: 382, or
15) $V_A$ comprises or consists of SEQ ID NO: 42 and $V_B$ comprises or consists of SEQ ID NO: 383.

The antigen binding protein may be monovalent or multivalent, e.g. tetra-, tri- or bivalent.

The antigen binding protein is monospecific or multispecific, e.g. tetra-, tri- or bispecific.

In some embodiments, the antigen binding protein is a soluble protein.

In the antigen binding proteins of the invention, the first and the second polypeptide can be comprised in a single polypeptide chain. Such a single chain construct may e.g. be a single chain TCR (scTCR) or a single chain bispecific antigen binding protein, in particular a single chain bispecific TCR, or a single chain bispecific TCR-antibody molecule.

It is preferred that the first and the second polypeptide are comprised in two polypeptide chains, i.e. $V_A$ is comprised in a first polypeptide chain and $V_B$ is comprised in a second polypeptide chain.

It is preferred that the antigen binding protein is a TCR. The TCR may be selected from the group consisting of an α/β TCR, a γ/δ TCR, a single chain TCR, a membrane-bound TCR, a soluble TCR, a monovalent, bivalent or multivalent TCR, a monospecific, bispecific or multispecific TCR, a functional fragment of a TCR, a fusion protein comprising a functional fragment of a TCR or a chimeric protein comprising a functional fragment of a TCR. In preferred embodiments, the TCR is an α/β TCR or a γ/δ TCR, preferably an α/β TCR. In the context of the present invention, whenever it is stated that an antigen binding protein is preferably a TCR, this further implies that most preferably, the antigen binding protein is an α/β TCR or a γ/δ TCR, preferably an α/β TCR. In one embodiment, the TCR constant domain sequences may be derived from any suitable species, such as any mammal, e.g., human, rat, monkey, rabbit, donkey, or mouse, preferably human or mouse, more preferably human. In one embodiment, the TCR is an αβ TCR and comprises an α-chain constant domain (TRAC) sequence according to SEQ ID NO: 5, 750, 751 or 156, preferably SEQ ID NO: 5, 750 or 751, and a δ-chain constant domain (TRBC1 or TRBC2) sequence according to SEQ ID NO: 11, 32 or 157, preferably SEQ ID NO: 11 or 32.

Preferably, the first polypeptide comprises or consists of an amino acid sequence selected from the group consisting of SEQ ID NO: 17, 134, 64, 93, 6, 56, 73, 102, 83, 110, 128, 120, 36, 27, 46 and 158-172, preferably selected from the group consisting of SEQ ID NO: 17, 134, 64, 93, 6, 56, 73, 102, 83, 110, 128, 120, 36, 27 and 46 or an amino acid sequence having at least 70%, 75%, 80%, 85%, 90%, 95%, 98% or 99% identity to SEQ ID NO: 17, 134, 64, 93, 6, 56, 73, 102, 83, 110, 128, 120, 36, 27, 46 or 158-172, and comprising the CDRa1, CDRa2 and CDRa3 as defined in context of the antigen binding proteins of the invention, wherein the CDRa1, CDRa2 and CDRa3 sequences may comprise one, two or three amino acid mutations; and the second polypeptide comprises or consists of an amino acid sequence selected from the group consisting of SEQ ID NO: 22, 137, 69, 97, 12, 61, 78, 105, 88, 115, 131, 123, 41, 33, 51 and 173-187, preferably selected from the group consisting of SEQ ID NO: 22, 137, 69, 97, 12, 61, 78, 105, 88, 115, 131, 123, 41, 33 and 51, or an amino acid sequence having at least 70%, 75%, 80%, 85%, 90%, 95%, 98% or 99% identity to SEQ ID NO: 22, 137, 69, 97, 12, 61, 78, 105, 88, 115, 131, 123, 41, 33, 51 or 173-187, and comprising the CDRa1, CDRa2 and CDRa3 as defined in context of the antigen binding proteins of the invention, wherein the CDRb1, CDRb2 and CDRb3 sequences may comprise one, two or three amino acid mutations.

More preferably, the first polypeptide comprises or consists of an amino acid sequence selected from the group consisting of SEQ ID NO: 17, 134, 64, 93, 6, 56, 73, 102, 83, 110, 128, 120, 36, 27, 46 and 158-172, preferably selected from the group consisting of SEQ ID NO: 17, 134, 64, 93, 6, 56, 73, 102, 83, 110, 128, 120, 36, 27 and 46, or an amino acid sequence having at least 70%, 75%, 80%, 85%, 90%, 95%, 98% or 99% identity to SEQ ID NO: 17, 134, 64, 93, 6, 56, 73, 102, 83, 110, 128, 120, 36, 27, 46, or 158-172, and comprising the CDRa1, CDRa2 and CDRa3 as defined in context of the antigen binding proteins of the invention without amino acid mutation; and the second polypeptide comprises or consists of an amino acid sequence selected from the group consisting of SEQ ID NO: 22, 137, 69, 97, 12, 61, 78 105, 88, 115, 131, 123, 41, 33, 51 and 173-187, preferably selected from the group consisting of SEQ ID NO:22, 137, 69, 97, 12, 61, 78 105, 88, 115, 131, 123, 41, 33 and 51, or an amino acid sequence having at least 70%, 75%, 80%, 85%, 90%, 95%, 98% or 99% identity to SEQ ID NO: 22, 137, 69, 97, 12, 61, 78 105, 88, 115, 131, 123, 41, 33, 51 or 173-187, and comprising the CDRa1, CDRa2 and CDRa3 as defined in context of the antigen binding proteins of the invention without amino acid mutations.

In preferred embodiments,
1) the first polypeptide comprises or consists of the amino acid sequence of SEQ ID NO: 17 or an amino acid sequence having at least 70%, 75%, 80%, 85%, 90%, 95%, 98% or 99% identity to SEQ ID NO: 17 and the second polypeptide comprises or consists of the amino acid sequence of SEQ ID NO: 22 or an amino acid sequence having at least 70%, 75%, 80%, 85%, 90%, 95%, 98% or 99% identity to SEQ ID NO: 22;
2) the first polypeptide comprises or consists of the amino acid sequence of SEQ ID NO: 134 or an amino acid sequence having at least 70%, 75%, 80%, 85%, 90%, 95%, 98% or 99% identity to SEQ ID NO: 134 and the second polypeptide comprises or consists of the amino acid sequence of SEQ ID NO: 137 or an amino acid sequence having at least 70%, 75%, 80%, 85%, 90%, 95%, 98% or 99% identity to SEQ ID NO: 137;
3) the first polypeptide comprises or consists of the amino acid sequence of SEQ ID NO: 64 or an amino acid sequence having at least 70%, 75%, 80%, 85%, 90%, 95%, 98% or 99% identity to SEQ ID NO: 64 and the second polypeptide comprises or consists of the amino acid sequence of SEQ ID NO: 69 or an amino acid sequence having at least 70%, 75%, 80%, 85%, 90%, 95%, 98% or 99% identity to SEQ ID NO: 69;
4) the first polypeptide comprises or consists of the amino acid sequence of SEQ ID NO: 93 or an amino acid sequence having at least 70%, 75%, 80%, 85%, 90%, 95%, 98% or 99% identity to SEQ ID NO: 93 and the second polypeptide comprises or consists of the amino acid sequence of SEQ ID NO: 97 or an amino acid sequence having at least 70%, 75%, 80%, 85%, 90%, 95%, 98% or 99% identity to SEQ ID NO: 97;
5) the first polypeptide comprises or consists of the amino acid sequence of SEQ ID NO: 6 or an amino acid sequence having at least 70%, 75%, 80%, 85%, 90%, 95%, 98% or 99% identity to SEQ ID NO: 6 and the second polypeptide comprises or consists of the amino acid sequence of SEQ ID NO: 12 or an amino acid sequence having at least 70%, 75%, 80%, 85%, 90%, 95%, 98% or 99% identity to SEQ ID NO: 12;
6) the first polypeptide comprises or consists of the amino acid sequence of SEQ ID NO: 56 or an amino acid sequence having at least 70%, 75%, 80%, 85%, 90%, 95%, 98% or 99% identity to SEQ ID NO: 56 and the second polypeptide comprises or consists of the amino acid sequence of SEQ ID NO: 61 or an amino acid sequence having at least 70%, 75%, 80%, 85%, 90%, 95%, 98% or 99% identity to SEQ ID NO: 61;
7) the first polypeptide comprises or consists of the amino acid sequence of SEQ ID NO: 73 or an amino acid sequence having at least 70%, 75%, 80%, 85%, 90%, 95%, 98% or 99% identity to SEQ ID NO: 73 and the second polypeptide comprises or consists of the amino acid sequence of SEQ ID NO: 78 or an amino acid sequence having at least 70%, 75%, 80%, 85%, 90%, 95%, 98% or 99% identity to SEQ ID NO: 78;
8) the first polypeptide comprises or consists of the amino acid sequence of SEQ ID NO: 102 or an amino acid sequence having at least 70%, 75%, 80%, 85%, 90%, 95%, 98% or 99% identity to SEQ ID NO: 102 and the second polypeptide comprises or consists of the amino acid sequence of SEQ ID NO: 105 or an amino acid sequence having at least 70%, 75%, 80%, 85%, 90%, 95%, 98% or 99% identity to SEQ ID NO: 105;
9) the first polypeptide comprises or consists of the amino acid sequence of SEQ ID NO: 83 or an amino acid sequence having at least 70%, 75%, 80%, 85%, 90%, 95%, 98% or 99% identity to SEQ ID NO: 83 and the second polypeptide comprises or consists of the amino acid sequence of SEQ ID NO: 88 or an amino acid sequence having at least 70%, 75%, 80%, 85%, 90%, 95%, 98% or 99% identity to SEQ ID NO: 88;
10) the first polypeptide comprises or consists of the amino acid sequence of SEQ ID NO: 110 or an amino acid sequence having at least 70%, 75%, 80%, 85%, 90%, 95%, 98% or 99% identity to SEQ ID NO: 110 and the second polypeptide comprises or consists of the amino acid sequence of SEQ ID NO: 115 or an amino acid sequence having at least 70%, 75%, 80%, 85%, 90%, 95%, 98% or 99% identity to SEQ ID NO: 115;
11) the first polypeptide comprises or consists of the amino acid sequence of SEQ ID NO: 128 or an amino acid sequence having at least 70%, 75%, 80%, 85%, 90%, 95%, 98% or 99% identity to SEQ ID NO: 128 and the second polypeptide comprises or consists of the amino acid sequence of SEQ ID NO: 131 or an amino acid sequence having at least 70%, 75%, 80%, 85%, 90%, 95%, 98% or 99% identity to SEQ ID NO: 131;
12) the first polypeptide comprises or consists of the amino acid sequence of SEQ ID NO: 120 or an amino acid sequence having at least 70%, 75%, 80%, 85%, 90%, 95%, 98% or 99% identity to SEQ ID NO: 120 and the second polypeptide comprises or consists of the amino acid sequence of SEQ ID NO: 123 or an amino acid sequence having at least 70%, 75%, 80%, 85%, 90%, 95%, 98% or 99% identity to SEQ ID NO: 123;
13) the first polypeptide comprises or consists of the amino acid sequence of SEQ ID NO: 36 or an amino acid sequence having at least 70%, 75%, 80%, 85%, 90%, 95%, 98% or 99% identity to SEQ ID NO: 36 and the second polypeptide comprises or consists of the amino acid sequence of SEQ ID NO: 41 or an amino acid sequence having at least 70%, 75%, 80%, 85%, 90%, 95%, 98% or 99% identity to SEQ ID NO: 41;
14) the first polypeptide comprises or consists of the amino acid sequence of SEQ ID NO: 27 or an amino acid sequence having at least 70%, 75%, 80%, 85%, 90%, 95%, 98% or 99% identity to SEQ ID NO: 27 and the second polypeptide comprises or consists of the amino acid sequence of SEQ ID NO: 33 or an amino acid sequence having at least 70%, 75%, 80%, 85%, 90%, 95%, 98% or 99% identity to SEQ ID NO: 33; or
15) the first polypeptide comprises or consists of the amino acid sequence of SEQ ID NO: 46 or an amino acid sequence having at least 70%, 75%, 80%, 85%, 90%, 95%, 98% or 99% identity to SEQ ID NO: 46 and the second polypeptide comprises or consists of the amino acid sequence of SEQ ID NO: 51 or an amino acid sequence having at least 70%, 75%, 80%, 85%, 90%, 95%, 98% or 99% identity to SEQ ID NO: 51;

wherein the first and the second polypeptide comprise the CDR sequences as defined in context of the antigen binding proteins of the invention, wherein the CDR sequences may comprise one, two or three amino acid mutations, preferably no amino acid mutation.

In preferred embodiments,
1) the first polypeptide comprises or consists of SEQ ID NO: 17, 294, 309 or 324 and the second polypeptide comprises or consists of SEQ ID NO: 22, 444, 459 or 474;
2) the first polypeptide comprises or consists of SEQ ID NO: 134, 295, 310 or 325 and the second polypeptide comprises or consists of SEQ ID NO: 137, 445, 460 or 475;
3) the first polypeptide comprises or consists of SEQ ID NO: 64, 296, 311 or 326 and the second polypeptide comprises or consists of SEQ ID NO: 69, 446, 461 or 476;
4) the first polypeptide comprises or consists of SEQ ID NO: 93, 297, 312 or 327 and the second polypeptide comprises or consists of SEQ ID NO: 97, 447, 462 or 477;
5) the first polypeptide comprises or consists of SEQ ID NO: 6, 298, 313 or 328 and the second polypeptide comprises or consists of SEQ ID NO: 12, 448, 463 or 478;
6) the first polypeptide comprises or consists of SEQ ID NO: 56, 299, 314 or 329 and the second polypeptide comprises or consists of SEQ ID NO: 61, 449, 464 or 479;
7) the first polypeptide comprises or consists of SEQ ID NO: 73, 300, 315 or 330 and the second polypeptide comprises or consists of SEQ ID NO: 78, 450, 465 or 480;
8) the first polypeptide comprises or consists of SEQ ID NO: 102, 301, 316 or 331 and the second polypeptide comprises or consists of SEQ ID NO: 105, 451, 466 or 481;
9) the first polypeptide comprises or consists of SEQ ID NO: 83, 302, 317 or 332 and the second polypeptide comprises or consists of SEQ ID NO: 88, 452, 467 or 482;
10) the first polypeptide comprises or consists of SEQ ID NO: 110, 303, 318 or 333 and the second polypeptide comprises or consists of SEQ ID NO: 115, 453, 468 or 483;
11) the first polypeptide comprises or consists of SEQ ID NO: 128, 304, 319 or 334 and the second polypeptide comprises or consists of SEQ ID NO: 131, 454, 469 or 484;
12) the first polypeptide comprises or consists of SEQ ID NO: 120, 305, 320 or 335 and the second polypeptide comprises or consists of SEQ ID NO: 123, 455, 470 or 485;
13) the first polypeptide comprises or consists of SEQ ID NO: 36, 306, 321 or 336 and the second polypeptide comprises or consists of SEQ ID NO: 41, 456, 471 or 486;
14) the first polypeptide comprises or consists of SEQ ID NO: 27, 307, 322 or 337 and the second polypeptide comprises or consists of SEQ ID NO: 33, 457, 472 or 487; or
15) the first polypeptide comprises or consists of SEQ ID NO: 46, 308, 323 or 338 and the second polypeptide comprises or consists of SEQ ID NO: 51, 458, 473 or 488.

More preferably,
1) the first polypeptide comprises or consists of SEQ ID NO: 17, and the second polypeptide comprises or consists of SEQ ID NO: 22;
2) the first polypeptide comprises or consists of SEQ ID NO: 134 and the second polypeptide comprises or consists of SEQ ID NO: 137;
3) the first polypeptide comprises or consists of SEQ ID NO: 64 and the second polypeptide comprises or consists of SEQ ID NO: 69;
4) the first polypeptide comprises or consists of SEQ ID NO: 93 and the second polypeptide comprises or consists of SEQ ID NO: 97;
5) the first polypeptide comprises or consists of SEQ ID NO: 6 and the second polypeptide comprises or consists of SEQ ID NO: 12;
6) the first polypeptide comprises or consists of SEQ ID NO: 56 and the second polypeptide comprises or consists of SEQ ID NO: 61;
7) the first polypeptide comprises or consists of SEQ ID NO: 73 and the second polypeptide comprises or consists of SEQ ID NO: 78;
8) the first polypeptide comprises or consists of SEQ ID NO: 102 and the second polypeptide comprises or consists of SEQ ID NO: 105;
9) the first polypeptide comprises or consists of SEQ ID NO: 83 and the second polypeptide comprises or consists of SEQ ID NO: 88;
10) the first polypeptide comprises or consists of SEQ ID NO: 110 and the second polypeptide comprises or consists of SEQ ID NO: 115;
11) the first polypeptide comprises or consists of SEQ ID NO: 128 and the second polypeptide comprises or consists of SEQ ID NO: 131;
12) the first polypeptide comprises or consists of SEQ ID NO: 120 and the second polypeptide comprises or consists of SEQ ID NO: 123;
13) the first polypeptide comprises or consists of SEQ ID NO: 36 and the second polypeptide comprises or consists of SEQ ID NO: 41;
14) the first polypeptide comprises or consists of SEQ ID NO: 27 and the second polypeptide comprises or consists of SEQ ID NO: 33; or
15) the first polypeptide comprises or consists of SEQ ID NO: 46 and the second polypeptide comprises or consists of SEQ ID NO: 51.

In other embodiments,
1) the first polypeptide comprises or consists of SEQ ID NO: 17 and the second polypeptide comprises or consists of SEQ ID NO: 459;
2) the first polypeptide comprises or consists of SEQ ID NO: 134 and the second polypeptide comprises or consists of SEQ ID NO: 460;
3) the first polypeptide comprises or consists of SEQ ID NO: 64 and the second polypeptide comprises or consists of SEQ ID NO: 461;
4) the first polypeptide comprises or consists of SEQ ID NO: 93 and the second polypeptide comprises or consists of SEQ ID NO: 462;
5) the first polypeptide comprises or consists of SEQ ID NO: 6 and the second polypeptide comprises or consists of SEQ ID NO: 463;
6) the first polypeptide comprises or consists of SEQ ID NO: 56 and the second polypeptide comprises or consists of SEQ ID NO: 464;
7) the first polypeptide comprises or consists of SEQ ID NO: 73 and the second polypeptide comprises or consists of SEQ ID NO: 465;
8) the first polypeptide comprises or consists of SEQ ID NO: 102 and the second polypeptide comprises or consists of SEQ ID NO: 466;
9) the first polypeptide comprises or consists of SEQ ID NO: 83 and the second polypeptide comprises or consists of SEQ ID NO: 467;
10) the first polypeptide comprises or consists of SEQ ID NO: 110 and the second polypeptide comprises or consists of SEQ ID NO: 468;
11) the first polypeptide comprises or consists of SEQ ID NO: 128 and the second polypeptide comprises or consists of SEQ ID NO: 469;
12) the first polypeptide comprises or consists of SEQ ID NO: 120 and the second polypeptide comprises or consists of SEQ ID NO: 470;
13) the first polypeptide comprises or consists of SEQ ID NO: 36 and the second polypeptide comprises or consists of SEQ ID NO: 471;
14) the first polypeptide comprises or consists of SEQ ID NO: 27 and the second polypeptide comprises or consists of SEQ ID NO: 472; or
15) the first polypeptide comprises or consists of SEQ ID NO: 46 and the second polypeptide comprises or consists of SEQ ID NO: 473.

In some preferred embodiments, the antigen binding protein of the invention maybe engineered, for example, by the introduction of heterologous sequences, preferably mouse sequences, which may increase expression and stability. Also, further stabilizing mutations as known from the state of the art (e.g. WO2018/104407, PCT/EP2018/069151, WO2011/044186, WO2014/018863) may be introduced, such as replacement of unfavorable amino acids in the variable domains and/or the introduction of a disulfide bonds, e.g. between the constant domains of a TCR and the removal of unpaired cysteine.

In particular, the TCR constant domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. The constant domain may additionally or alternatively contain further mutations, substitutions or deletions relative to the native TRAC and/or TRBC1/2 sequences. The term TRAC and TRBC1/2 encompasses natural polymophic variants, for example N to K at position 4 of TRAC (Bragado et al Int Immunol. 1994 February; 6(2):223-30).

In some embodiments, the antigen binding protein is monovalent or multivalent, e.g. tetra-, tri- or bivalent.

In some embodiments, the antigen binding protein is bispecific, in particular a bispecific TCR, a bispecific antibody or a bispecific TCR-antibody molecule. The skilled person is aware that in instances where the antigen binding protein is a bispecific "antibody", one of the antigen binding sites comprises the TCR-derived CDR1, CDR3 and optionally CDR2 sequences as defined in context of the antigen binding proteins of the invention, while the other antigen-binding site may be entirely antibody-derived.

In some embodiments, the antigen binding protein is a soluble protein. In some embodiments, the antigen binding protein is a soluble TCR. As used herein, the term "soluble TCR" refers to heterodimeric truncated variants of native TCRs, which comprise extracellular portions of the TCR α-chain and δ-chain, for example linked by a disulphide bond, but which lack the transmembrane and cytosolic domains of the native protein.

In one embodiment, the antigen binding protein is of human origin, which is understood as being generated from a human gene locus and therefore comprising human sequences.

In some embodiments, the antigen binding protein is humanized, chimerized and/or murinized.

In one embodiment, the antigen binding protein of the invention further comprises one or more of the following:
(i) one or more further antigen binding sites;
(ii) a transmembrane region, optionally including a cytoplasmic signalling region;
(iii) a diagnostic agent;
(iv) a therapeutic agent.

In instances where the above-listed elements (i) to (v) are polypeptides fused to the antigen binding protein of the invention, the antigen binding proteins can also be referred to as "TCR fusion proteins".

The further antigen binding site—if present—is preferably antibody-derived.

Encompassed by the invention are antigen binding proteins, in particular TCRs, having alternative domains, such as a membrane anchor domain instead of the endogenous transmembrane region. Also encompassed are antigen binding proteins, in particular TCRs, having point mutations in the TCR variable domain or constant domain in order to improve TCR expression or stability and/or chain pairing.

A "transmembrane region", in the context of the present invention may be, for example, a TCR alpha or beta transmembrane domain.

A "cytoplasmic signalling region" may be for example a TCR alpha or beta intracellular domain.

A "diagnostic agent" herein refers to a detectable molecule or substance, such as a fluorescent molecule, a radioactive molecule or any other labels known in the art that provide (either directly or indirectly) a signal.

"Fluorescent molecules" are known in the art include fluorescein isothiocyanate (FITC), phycoerythrin (PE), fluorophores for use in the blue laser (e.g. PerCP, PE-Cy7, PE-Cy5, FL3 and APC or Cy5, FL4), fluorophores for use in the red, violet or UV laser (e.g. Pacific blue, pacific orange).

"Radioactive molecules" include but are not limited radioactive atom for scintigraphic studies such as $I^{123}$, $I^{124}$, $In^{111}$, $Re^{186}$, $Re^{188}$, $Tc^{99}$. Antigen binding proteins of the invention may also comprise a spin label for nuclear magnetic resonance (NMR) imaging (also known as magnetic resonance imaging, MRI), such as iodine-123, indium-111, fluorine-19, carbon-13, nitrogen-15, oxygen-17, gadolinium, manganese or iron.

Such diagnostic agents are may be either directly coupled (i.e., physically linked) to the antigen binding protein or may be indirectly linked.

A "therapeutic agent" herein refers to an agent that has a therapeutic effect. The terms therapeutic agent and drug are used interchangeably herein. In one embodiment, a therapeutic agent may be a growth inhibitory agent, such as a cytotoxic agent or a radioactive isotope.

A "growth inhibitory agent", or "anti-proliferative agent", which can be used indifferently, refers to a compound or composition which inhibits growth of a cell, especially a tumour cell, either in vitro or in vivo.

The term "cytotoxic agent" as used herein refers to a substance that inhibits or prevents the function of cells and/or causes destruction of cells. The term "cytotoxic agent" is intended to include chemotherapeutic agents, enzymes, antibiotics, and toxins such as small molecule toxins or enzymatically active toxins of bacterial, fungal, plant or animal origin, including fragments and/or variants thereof, and the various antitumor or anticancer agents disclosed below. In some embodiments, the cytotoxic agent is a taxoid, vincas, taxanes, a maytansinoid or maytansinoid analog such as DM1 or DM4, a small drug, a tomaymycin or pyrrolobenzodiazepine derivative, a cryptophycin derivative, a leptomycin derivative, an auristatin or dolastatin analog, a prodrug, topoisomerase II inhibitors, a DNA alkylating agent, an anti-tubulin agent, a CC-1065 or CC-1065 analog.

The term "radioactive isotope" is intended to include radioactive isotopes suitable for treating cancer, such as $At^{211}$, $Bi^{212}$, $Er^{169}$, $I^{113}$, $I^{125}$, $Y^{90}$, $In^{111}$, $P^{32}$, $Re^{186}$, $Re^{188}$, $Sm^{153}$, $Sr^{89}$, and radioactive isotopes of Lu. Such radioisotopes generally emit mainly beta-radiation. In an embodiment the radioactive isotope is alpha-emitter isotope, more precisely Thorium 227 which emits alpha-radiation.

In some embodiments, the antigen binding proteins of the present invention are covalently attached, directly or via a cleavable or non-cleavable linker, to the at least one growth inhibitory agent. An antigen binding protein to which such the at least one growth inhibitory agent is attached may also be referred to as a conjugate. A cleavable linker facilitates release of the cytotoxic agent or growth inhibitory agent from the antigen binding protein in the cell. For example, an acid-labile linker, a peptidase-sensitive linker, an esterase labile linker, a photolabile linker or a disulfide-containing linker (See e.g. U.S. Pat. No. 5,208,020) may be used. The linker may be also a "non-cleavable linker" (for example SMCC linker) that might lead to better tolerance in some cases.

The preparation of such conjugates, for example immunoconjugates, is described in the application WO2004/091668 or Hudecz, F., Methods Mol. Biol. 298: 209-223 (2005) and Kirin et al., Inorg Chem. 44(15): 5405-5415 (2005), the contents of which are herein incorporated by reference in their entireties, and may by the skilled in the art be transferred to the preparation of antigen binding proteins of the present invention to which such a at least one growth inhibitory agent is attached.

Alternatively, a fusion protein comprising the antigen binding protein of the invention and a cytotoxic or growth inhibitory polypeptide may be made, by recombinant techniques or peptide synthesis. The length of DNA may comprise respective regions encoding the two portions of the conjugate either adjacent one another or separated by a region encoding a linker peptide which does not destroy the desired properties of the conjugate.

The antigen binding proteins of the present invention may also be used in Dependent Enzyme Mediated Prodrug Therapy by conjugating the polypeptide to a prodrug-activating enzyme which converts a prodrug (e.g. a peptidyl chemotherapeutic agent, see WO 81/01145) to an active anti-cancer drug (See, for example, WO 88/07378 and U.S. Pat. No. 4,975,278).

In some embodiments, the antigen binding protein specifically binds to a functional epitope comprising or consisting of amino acid positions 1, 3 and 4 of SEQ ID NO: 138. In some preferred embodiments, these antigen binding proteins specifically bind to a functional epitope comprising or consisting of amino acid positions 1, 3, 4 and 5, or 1, 3, 4 and 6 or 1, 3, 4, 5 and 6 or 1, 3, 4, 5, 6 and 7 of SEQ ID NO: 138.

In some embodiments, the antigen binding protein specifically binds to a functional epitope comprising or consisting of amino acid positions 4, 6 and 7 of SEQ ID NO: 138. In some preferred embodiments, these antigen binding proteins specifically bind to a functional epitope comprising or consisting of amino acid positions 1, 4, 6 and 7, or 3, 4, 6 and 7 or 1, 3, 4, 6 and 7 of SEQ ID NO: 138.

In some embodiments, the antigen binding protein specifically binds to a functional epitope comprising or consisting of amino acid positions 5 and 7 of SEQ ID NO: 138. In some preferred embodiments, these antigen binding proteins specifically bind to a functional epitope comprising or consisting of amino acid positions 5, 6 and 7, or 3, 4, 5, 6 and 7 of SEQ ID NO: 138.

In some embodiments, the antigen binding protein does not significantly bind to the similar peptides of the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010).

In some embodiments, the antigen binding protein does not significantly bind to the similar peptides of the group consisting of SEQ ID NO: 146 (SP-05-0001), SEQ ID NO: 147 (SP-05-0002), SEQ ID NO: 148 (SP-05-0003), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010).

The genes encoding the V regions and J regions comprised in $V_A$ and $V_B$ of the antigen binding proteins of the invention are listed in Table 2. The annotation was performed by GeneData 11.0.1 using the IMGT/GENE-DB (Version: 28 Nov. 2019) as reference database.

In some embodiments, $V_A$ comprises a V region encoded by TRAV14, in particular TRAV14/DV4, and a CDRa1 according to SEQ ID NO: 24 and a CDRa2 according to SEQ ID NO: 25.

In some embodiments, $V_B$ comprises a V region encoded by TRBV13, and a CDRb1 according to SEQ ID NO: 75 and a CDRb2 according to SEQ ID NO: 76.

In some embodiments, $V_B$ comprises a V region encoded by TRBV4-1, and a CDRb1 according to SEQ ID NO: 58 and a CDRb2 according to SEQ ID NO: 59.

In some embodiments, $V_B$ comprises a V region encoded by TRBV6-1, and a CDRb1 according to SEQ ID NO: 112 and a CDRb2 according to SEQ ID NO: 113.

The inventors have shown that the antigen binding proteins of the invention, if expressed in CD8+ T cells, are capable of activating said CD8+ T cells upon binding to CT45-IP presented on MHC by an antigen presenting cell.

Besides CD8+ T cells, also CD4+ T cells, referred to as T helper cells, are crucial for an orchestrated immune response engaging all kinds of different immune cells. For full activation of a T cell after encounter with its cognate peptide-MHC complex, usually the additional binding of the respective co-receptor is necessary. In the case of CD8+ T cells, this help is provided by the CD8 co-receptor, and in the case of CD4+ T cells this help is provided by the CD4 co-receptor. Only in rare cases a TCR, derived from a CD8+ T cell, when transferred to a CD4+ T cell, is able to elicit intracellular signaling which is strong enough to lead to activation of the CD4+ T cell.

The inventors have shown that some of the antigen binding proteins of the invention, if expressed in CD4+ T cells, in particular CD4+CD8− T cells, are capable of activating said CD4+CD8− T cells upon binding to CT45-IP presented on MHC by an antigen presenting cell (Example 3, data not shown).

In the context of the present invention, an antigen binding protein is considered "capable of activating a T cell" if, in a cytokine production assay as defined above, a T cell expressing the antigen binding protein (i.e., an effector cell) produces at least one intracellular cytokine upon co-culture with target cells presenting the CT45-IP antigenic peptide, in particular if the number of T cells expressing the antigen binding protein and producing at least one intracellular cytokine is at least 2%, at least 2.5%, preferably at least 3% per analysed population of T cells, such as CD4+ or CD8+ T cells.

Thus, in some embodiments, the antigen binding protein is capable of activating a CD8+ T cell, in particular a CD8+CD4− T cell, and/or a CD4+ T cell, in particular a CD4+CD8− T cell. In preferred embodiments, the antigen binding protein is capable of activating a CD4+ T cell, in particular a CD4+CD8− T cell. In other words, the antigen binding protein, preferably the TCR, is capable of activating a CD4+ T cell independently of CD8. In other words, the antigen binding protein, preferably the TCR, is capable of binding to a complex of the CT45 antigenic peptide and an MHC molecule in the absence of CD8. In most preferred embodiments, the antigen binding protein is capable of activating both a CD4+ T cell, in particular a CD4+CD8− T cell, and a CD8+ T cell, in particular a CD8+CD4− T cell. In preferred embodiments, the antigen binding protein is a TCR.

In the context of the present invention, an antigen binding protein is considered capable of activating a T cell population, if in a functional cytokine production assay as described above, cytokine production is detected in at least 2%, at least 2.5%, preferably at least 3% of said CD4+ or CD4− CD8+ T cell population. The secreted cytokines can be e.g. IFN-gamma and/or TNF-alpha.

Activation of CD4+ T cells via a CD8+ T cell-derived TCR can be enhanced by transferring the CD8 co-receptor together with the TCR into the CD4+ cell. The inventors have shown that co-transfection of CD4+ T cells with the herein described CT45-IP-specific TCRs and CD8 significantly enhances the killing of CT45-IP presenting tumor cells (Example 8, data not shown). Engaging CD4+ T cells alongside CD8+ T cells brings a lot of advantages for cellular immunotherapy. CD4+ T cells not only can elicit direct cytotoxicity against tumor cells but can also engage other immune cells, contributing to a long-lasting anti-tumor effect. This helper function is exerted by providing cytokines, chemokines and costimulatory molecules and comprises the support of cytotoxic CD8+ T cells, the formation of effector and memory T cells, the activation and maturation of macrophages/dendritic cells, the licencing of dendritic cells, which in turn effectively stimulates CD8+ T cells and drives CD8+ T cell effector and memory formation, the activation of innate immune cells such as NK cells, the formation of memory B cells and many other effects.

In some embodiments, the antigen binding protein has a mean expression of at least 5%, at least 10%, at least 20%, at least 30%, or at least 40%, in particular after transient expression. Mean expression of a TCR can be determined by TCR surface staining as described in the examples. Staining can be performed by techniques known in the art. For example, staining can be performed using a specific $V_B$ antibody (in case of a human TCR), or anti-mTCRB antibodies (in case of chimeric TCRs) or labelled CT45-IP:MHC multimers (e.g. tetramers or dextramers). Such stainings may be further combined with stainings to identify specific cell populations.

Antigen Binding Protein 1

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 14, CDRa3 comprises or consists of the amino acid sequence of SEQ ID NO: 16, CDRb1 comprises or consists of the amino acid sequence of SEQ ID NO: 19, and CDRb3 comprises or consists of the amino acid sequence of SEQ ID NO: 21, wherein the CDRa1, CDRa3, CDRb1 and/or CDRb3 sequences may comprise one, two or three amino acid mutations. An antigen binding protein comprising said CDR sequences is in the following also referred to as "antigen binding protein 1". In preferred embodiments of antigen binding protein 1, CDRa2 comprises or consists of the amino acid sequence of SEQ ID NO: 15, and CDRb2 comprises or consists of the amino acid sequence of SEQ ID NO: 20, wherein the CDRa2 and/or CDRb2 sequences may comprise one, two, three or four amino acid mutations. Antigen binding protein 1 specifically binds to a functional epitope comprising or consisting of 4, 5 or 6 amino acid positions selected from the group consisting of positions 1, 3, 4, 5, 6 and 7 of SEQ ID NO: 138. The $EC_{50}$ for inducing killing of CT45-IP:MHC complex presenting cells, such as CT45-IP loaded T2 cells, by T cells expressing antigen binding protein 1, measured e.g. in a luciferase release assay, is less than about 30 nM, less than about 25 nM, less than about 20 nM, less than about 15 nM or less than about 10 nM. Antigen binding protein 1 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 1, $V_A$ comprises or consists of the amino acid sequence of SEQ ID NO: 13 or an amino acid sequence having at least 70%, 75%, 80%, 85%, 90%, 95%, 98% or 99% identity to SEQ ID NO: 13 and $V_B$ comprises or consists of the amino acid sequence of SEQ ID NO: 18 or an amino acid sequence having at least 70%, 75%, 80%, 85%, 90%, 95%, 98% or 99% identity to SEQ ID NO: 18; wherein $V_A$ and $V_B$ comprise the CDR sequences as described above for antigen binding protein 1, wherein the CDR sequences may comprise one, two or three amino acid mutations, preferably no amino acid mutation. Preferably, the alpha chain variable region of antigen binding protein 1 is encoded by TRAV38-1 and/or the beta chain variable region of antigen binding protein 1 is encoded by TRBV7-9. In a preferred embodiment, the antigen binding protein 1 is capable of activating a CD8+ T cell, in particular a CD8+CD4− T cell, and/or a CD4+ T cell, in particular a CD4+CD8− T cell.

Antigen Binding Protein 2

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 24, CDRa3 comprises or consists of the amino acid sequence of SEQ ID NO: 133, CDRb1 comprises or consists of the amino acid sequence of SEQ ID NO: 75, and CDRb3 comprises or consists of the amino acid sequence of SEQ ID NO: 136, wherein the CDRa1, CDRa3, CDRb1 and/or CDRb3 sequences may comprise one, two or three amino acid mutations. An antigen binding protein comprising said CDR sequences is in the following also referred to as "antigen binding protein 2". In preferred embodiments of antigen binding protein 2, CDRa2 comprises or consists of the amino acid sequence of SEQ ID NO: 25, and CDRb2 comprises or consists of the amino acid sequence of SEQ ID NO: 76, wherein the CDRa2 and/or CDRb2 sequences may comprise one, two, three or four amino acid mutations. Antigen binding protein 2 specifically binds to a functional epitope comprising or consisting of 3, 4 or 5 amino acid positions selected from the group consisting of positions 3, 4, 5, 6 and 7 of SEQ ID NO: 138. The $EC_{50}$ for inducing killing of CT45-IP:MHC complex presenting cells, such as CT45-IP loaded T2 cells, by T cells expressing antigen binding protein 2, measured e.g. in a luciferase release assay, is less than about 30 nM, less than about 25 nM, less than about 20 nM, less than about 15 nM, less than about 10 nM or less than about 5 nM. Antigen binding protein 2 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 2, $V_A$ comprises or consists of the amino acid sequence of SEQ ID NO: 132 or an amino acid sequence having at least 70%, 75%, 80%, 85%, 90%, 95%, 98% or 99% identity to SEQ ID NO: 132 and $V_B$ comprises or consists of the amino acid sequence of SEQ ID NO: 135 or an amino acid sequence having at least 70%, 75%, 80%, 85%, 90%, 95%, 98% or 99% identity to SEQ ID NO: 135; wherein $V_A$ and $V_B$ comprise the CDR sequences as described above for antigen binding protein 2, wherein the CDR sequences may comprise one, two or three amino acid mutations, preferably no amino acid mutation. Preferably, the alpha chain variable region of antigen binding protein 2 is encoded by TRAV14/DV4 and/or the beta chain variable region of antigen binding protein 2 is encoded by TRBV13. In a preferred embodiment, the antigen binding protein 2 is capable of activating a CD8+ T cell, in particular a CD8+CD4− T cell, and/or a CD4+ T cell, in particular a CD4+CD8− T cell.

Antigen Binding Protein 3

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 24, CDRa3 comprises or consists of the amino acid sequence of SEQ ID NO: 63, CDRb1 comprises or consists of the amino acid sequence of SEQ ID NO: 66, and CDRb3 comprises or consists of the amino acid sequence of SEQ ID NO: 68, wherein the CDRa1, CDRa3, CDRb1 and/or CDRb3 sequences may comprise one, two or three amino acid mutations. An antigen binding protein comprising said CDR sequences is in the following also referred to as "antigen binding protein 3". In preferred embodiments of antigen binding protein 3, CDRa2 comprises or consists of the amino acid sequence of SEQ ID NO: 25, and CDRb2 comprises or consists of the amino acid sequence of SEQ ID NO: 67, wherein the CDRa2 and/or CDRb2 sequences may comprise one, two, three or four amino acid mutations. Antigen binding protein 3 specifically binds to a functional epitope comprising or consisting of 3, 4 or 5 amino acid positions selected from the group consisting of positions 3, 4, 5, 6 and 7 of SEQ ID NO: 138. The $EC_{50}$ for inducing killing of CT45-IP:MHC complex presenting cells, such as CT45-IP loaded T2 cells, by T cells expressing antigen binding protein 3, measured e.g. in a luciferase release assay, is less than about 15 nM, less than about 10 nM, less than about 5 nM, less than about 2.5 nM or less than about 1.5 nM. Antigen binding protein 3 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), preferably selected from the group consisting of SEQ ID NO: 146 (SP-05-0001), SEQ ID NO: 147 (SP-05-0002), SEQ ID NO: 149 (SP-05-0004), SEQ ID NO: 150 (SP-05-0005), SEQ ID NO: 151 (SP-05-

0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 3, $V_A$ comprises or consists of the amino acid sequence of SEQ ID NO: 62 or an amino acid sequence having at least 70%, 75%, 80%, 85%, 90%, 95%, 98% or 99% identity to SEQ ID NO: 62 and $V_B$ comprises or consists of the amino acid sequence of SEQ ID NO: 65 or an amino acid sequence having at least 70%, 75%, 80%, 85%, 90%, 95%, 98% or 99% identity to SEQ ID NO: 65; wherein $V_A$ and $V_B$ comprise the CDR sequences as described above for antigen binding protein 3, wherein the CDR sequences may comprise one, two or three amino acid mutations, preferably no amino acid mutation. Preferably, the alpha chain variable region of antigen binding protein 3 is encoded by TRAV14/DV4 and/or the beta chain variable region of antigen binding protein 3 is encoded by TRBV27. In a preferred embodiment, the antigen binding protein 3 is capable of activating a CD8+ T cell, in particular a CD8+ CD4− T cell, and/or a CD4+ T cell, in particular a CD4+ CD8− T cell.

Antigen Binding Protein 4

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 90, CDRa3 comprises or consists of the amino acid sequence of SEQ ID NO: 92, CDRb1 comprises or consists of the amino acid sequence of SEQ ID NO: 66, and CDRb3 comprises or consists of the amino acid sequence of SEQ ID NO: 96), wherein the CDRa1, CDRa3, CDRb1 and/or CDRb3 sequences may comprise one, two or three amino acid mutations. An antigen binding protein comprising said CDR sequences is in the following also referred to as "antigen binding protein 4". In preferred embodiments of antigen binding protein 4, CDRa2 comprises or consists of the amino acid sequence of SEQ ID NO: 91, and CDRb2 comprises or consists of the amino acid sequence of SEQ ID NO: 95, wherein the CDRa2 and/or CDRb2 sequences may comprise one, two, three or four amino acid mutations. Antigen binding protein 4 specifically binds to a functional epitope comprising or consisting of 3, 4 or 5 amino acid positions selected from the group consisting of positions 3, 4, 6, 7 and 8 of SEQ ID NO: 138. The $EC_{50}$ for inducing killing of CT45-IP:MHC complex presenting cells, such as CT45-IP loaded T2 cells, by T cells expressing antigen binding protein 4, measured e.g. in a luciferase release assay, is less than about 25 nM, less than about 20 nM, less than about 15 nM, less than about 10 nM, less than about 5 nM, less than about 2.5 nM or less than about 1.5 nM. Antigen binding protein 1 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), preferably selected from the group consisting of SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 154 (SP-05-0009) and SEQ ID NO: 155 (SP-05-0010). In preferred embodiments of antigen binding protein 4, $V_A$ comprises or consists of the amino acid sequence of SEQ ID NO: 89 or an amino acid sequence having at least 70%, 75%, 80%, 85%, 90%, 95%, 98% or 99% identity to SEQ ID NO: 89 and $V_B$ comprises or consists of the amino acid sequence of SEQ ID NO: 94 or an amino acid sequence having at least 70%, 75%, 80%, 85%, 90%, 95%, 98% or 99% identity to SEQ ID NO: 94; wherein $V_A$ and $V_B$ comprise the CDR sequences as described above for antigen binding protein 4, wherein the CDR sequences may comprise one, two or three amino acid mutations, preferably no amino acid mutation. Preferably, the alpha chain variable region of antigen binding protein 4 is encoded by TRAV3 and/or the beta chain variable region of antigen binding protein 4 is encoded by TRBV6-2. In a preferred embodiment, the antigen binding protein 4 is capable of activating a CD8+ T cell, in particular a CD8+ CD4− T cell, and/or a CD4+ T cell, in particular a CD4+ CD8− T cell.

Antigen Binding Protein 5

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 2, CDRa3 comprises or consists of the amino acid sequence of SEQ ID NO: 4, CDRb1 comprises or consists of the amino acid sequence of SEQ ID NO: 8, and CDRb3 comprises or consists of the amino acid sequence of SEQ ID NO: 10, wherein the CDRa1, CDRa3, CDRb1 and/or CDRb3 sequences may comprise one, two or three amino acid mutations. An antigen binding protein comprising said CDR sequences is in the following also referred to as "antigen binding protein 5". In preferred embodiments of antigen binding protein 5, CDRa2 comprises or consists of the amino acid sequence of SEQ ID NO: 3, and CDRb2 comprises or consists of the amino acid sequence of SEQ ID NO: 9, wherein the CDRa2 and/or CDRb2 sequences may comprise one, two, three or four amino acid mutations. Antigen binding protein 5 specifically binds to a functional epitope comprising or consisting of 2, 3 or 4 amino acid positions selected from the group consisting of positions 3, 6, 7 and 8 of SEQ ID NO: 138. The $EC_{50}$ for inducing killing of CT45-IP:MHC complex presenting cells, such as CT45-IP loaded T2 cells, by T cells expressing antigen binding protein 5, measured e.g. in a luciferase release assay, is less than about 25 nM, less than about 15 nM, less than about 10 nM, less than about 5 nM, less than about 2.5 nM, less than about 1.5 nM or less than about 1 nM. Antigen binding protein 5 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP 0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 5, $V_A$ comprises or consists of the amino acid sequence of SEQ ID NO: 1 or an amino acid sequence having at least 70%, 75%, 80%, 85%, 90%, 95%, 98% or 99% identity to SEQ ID NO: 1 and $V_B$ comprises or consists of the amino acid sequence of SEQ ID NO: 7 or an amino acid sequence having at least 70%, 75%, 80%, 85%, 90%, 95%, 98% or 99% identity to SEQ ID NO: 7; wherein $V_A$ and $V_B$ comprise the CDR sequences as described above for antigen binding protein 5, wherein the CDR sequences may comprise one, two or three amino acid mutations, preferably no amino acid mutation. Preferably, the alpha chain variable region of antigen binding protein 5 is encoded by TRAV35 and/or the beta chain variable region of antigen binding protein 5 is encoded by TRBV9. In a preferred embodiment, the antigen binding protein 5 is capable of activating a CD8+ T cell, in particular a CD8+CD4− T cell, and/or a CD4+ T cell, in particular a CD4+CD8− T cell.

Antigen Binding Protein 6

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 53, CDRa3 comprises or consists of the amino acid sequence of SEQ ID NO: 55, CDRb1 comprises or consists of the amino acid sequence of SEQ ID NO: 58, and CDRb3 comprises or consists of the amino acid sequence of SEQ ID NO: 60, wherein the CDRa1, CDRa3, CDRb1 and/or CDRb3 sequences may comprise one, two or three amino acid mutations. An antigen binding protein comprising said CDR sequences is in the following also referred to as "antigen binding protein 6". In preferred embodiments of antigen binding protein 6, CDRa2 comprises or consists of the amino acid sequence of SEQ ID NO: 54, and CDRb2 comprises or consists of the amino acid sequence of SEQ ID NO: 59, wherein the CDRa2 and/or CDRb2 sequences may comprise one, two, three or four amino acid mutations. Antigen binding protein 6 specifically binds to a functional epitope comprising or consisting of 2, 3 or 4 amino acid positions selected from the group consisting of positions 1, 3, 4 and 6 of SEQ ID NO: 138. The $EC_{50}$ for inducing killing of CT45-IP:MHC complex presenting cells, such as CT45-IP loaded T2 cells, by T cells expressing antigen binding protein 6, measured e.g. in a luciferase release assay, is less than about 30 nM, less than about 25 nM, less than about 20 nM, less than about 15 nM, less than about 10 nM or less than about 5 nM. Antigen binding protein 6 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), preferably selected from the group consisting of SEQ ID NO: 146 (SP-05-0001), SEQ ID NO: 147 (SP-05-0002), SEQ ID NO: 148 (SP-05-0003), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), more preferably selected from the group consisting of SEQ ID NO: 146 (SP-05-0001), SEQ ID NO: 147 (SP-05-0002), SEQ ID NO: 148 (SP-05-0003), SEQ ID NO: 150 (SP-05-0005), SEQ ID NO: 151 (SP-05-0006), SEQ ID NO: 152 (SP-05-0007), and SEQ ID NO: 155 (SP-05-0010). In preferred embodiments of antigen binding protein 6, $V_A$ comprises or consists of the amino acid sequence of SEQ ID NO: 52 or an amino acid sequence having at least 70%, 75%, 80%, 85%, 90%, 95%, 98% or 99% identity to SEQ ID NO: 52 and $V_B$ comprises or consists of the amino acid sequence of SEQ ID NO: 57 or an amino acid sequence having at least 70%, 75%, 80%, 85%, 90%, 95%, 98% or 99% identity to SEQ ID NO: 57; wherein $V_A$ and $V_B$ comprise the CDR sequences as described above for antigen binding protein 6, wherein the CDR sequences may comprise one, two or three amino acid mutations, preferably no amino acid mutation. Preferably, the alpha chain variable region of antigen binding protein 6 is encoded by TRAV12-3 and/or the beta chain variable region of antigen binding protein 6 is encoded by TRBV4-1. In a preferred embodiment, the antigen binding protein 6 is capable of activating a CD8+ T cell, in particular a CD8+ CD4− T cell, and/or a CD4+ T cell, in particular a CD4+ CD8− T cell.

Antigen Binding Protein 7

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 71, CDRa3 comprises or consists of the amino acid sequence of SEQ ID NO: 72, CDRb1 comprises or consists of the amino acid sequence of SEQ ID NO: 75, and CDRb3 comprises or consists of the amino acid sequence of SEQ ID NO: 77, wherein the CDRa1, CDRa3, CDRb1 and/or CDRb3 sequences may comprise one, two or three amino acid mutations. An antigen binding protein comprising said CDR sequences is in the following also referred to as "antigen binding protein 7". In preferred embodiments of antigen binding protein 7, CDRa2 comprises or consists of the amino acid sequence of SEQ ID NO: 15, and CDRb2 comprises or consists of the amino acid sequence of SEQ ID NO: 76, wherein the CDRa2 and/or CDRb2 sequences may comprise one, two, three or four amino acid mutations. Antigen binding protein 7 specifically binds to a functional epitope comprising or consisting of 3 or 4 amino acid positions selected from the group consisting of positions 1, 4, 6 and 7 of SEQ ID NO: 138. The $EC_{50}$ for inducing killing of CT45-IP:MHC complex presenting cells, such as CT45-IP loaded T2 cells, by T cells expressing antigen binding protein 7, measured e.g. in a luciferase release assay, is less than about 5 nM, less than about 2.5 nM, less than about 1.5 nM or less than about 1 nM. Antigen binding protein 7 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-

0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 7, $V_A$ comprises or consists of the amino acid sequence of SEQ ID NO: 70 or an amino acid sequence having at least 70%, 75%, 80%, 85%, 90%, 95%, 98% or 99% identity to SEQ ID NO: 70 and $V_B$ comprises or consists of the amino acid sequence of SEQ ID NO: 74 or an amino acid sequence having at least 70%, 75%, 80%, 85%, 90%, 95%, 98% or 99% identity to SEQ ID NO: 74; wherein $V_A$ and $V_B$ comprise the CDR sequences as described above for antigen binding protein 7, wherein the CDR sequences may comprise one, two or three amino acid mutations, preferably no amino acid mutation. Preferably, the alpha chain variable region of antigen binding protein 7 is encoded by TRAV38-2/DV8 and/or the beta chain variable region of antigen binding protein 7 is encoded by TRBV13. In a preferred embodiment, the antigen binding protein 7 is capable of activating a CD8+ T cell, in particular a CD8+CD4− T cell, and/or a CD4+ T cell, in particular a CD4+CD8− T cell.

Antigen Binding Protein 8

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 99), CDRa3 comprises or consists of the amino acid sequence of SEQ ID NO: 101, CDRb1 comprises or consists of the amino acid sequence of SEQ ID NO: 75, and CDRb3 comprises or consists of the amino acid sequence of SEQ ID NO: 104), wherein the CDRa1, CDRa3, CDRb1 and/or CDRb3 sequences may comprise one, two or three amino acid mutations. An antigen binding protein comprising said CDR sequences is in the following also referred to as "antigen binding protein 8". In preferred embodiments of antigen binding protein 8, CDRa2 comprises or consists of the amino acid sequence of SEQ ID NO: 100, and CDRb2 comprises or consists of the amino acid sequence of SEQ ID NO: 76, wherein the CDRa2 and/or CDRb2 sequences may comprise one, two, three or four amino acid mutations. Antigen binding protein 8 specifically binds to a functional epitope comprising or consisting of 1 or 2 amino acid positions selected from the group consisting of positions 5 and 7 of SEQ ID NO: 138. The $EC_{50}$ for inducing killing of CT45-IP:MHC complex presenting cells, such as CT45-IP loaded T2 cells, by T cells expressing antigen binding protein 8, measured e.g. in a luciferase release assay, is less than about 30 nM, less than about 25 nM, less than about 20 nM, less than about 15 nM, or less than about 10 nM. Antigen binding protein 8 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), preferably selected from the group consisting of SEQ ID NO: 146 (SP-05-0001), SEQ ID NO: 147 (SP-05-0002), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 8, $V_A$ comprises or consists of the amino acid sequence of SEQ ID NO: 98 or an amino acid sequence having at least 70%, 75%, 80%, 85%, 90%, 95%, 98% or 99% identity to SEQ ID NO: 98 and $V_B$ comprises or consists of the amino acid sequence of SEQ ID NO: 103 or an amino acid sequence having at least 70%, 75%, 80%, 85%, 90%, 95%, 98% or 99% identity to SEQ ID NO: 103; wherein $V_A$ and $V_B$ comprise the CDR sequences as described above for antigen binding protein 8, wherein the CDR sequences may comprise one, two or three amino acid mutations, preferably no amino acid mutation. Preferably, the alpha chain variable region of antigen binding protein 8 is encoded by TRAV19 and/or the beta chain variable region of antigen binding protein 8 is encoded by TRBV13. In a preferred embodiment, the antigen binding protein 8 is capable of activating a CD8+ T cell, in particular a CD8+CD4− T cell, and/or a CD4+ T cell, in particular a CD4+CD8− T cell.

Antigen Binding Protein 9

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 80, CDRa3 comprises or consists of the amino acid sequence of SEQ ID NO: 82, CDRb1 comprises or consists of the amino acid sequence of SEQ ID NO: 85, and CDRb3 comprises or consists of the amino acid sequence of SEQ ID NO: 87), wherein the CDRa1, CDRa3, CDRb1 and/or CDRb3 sequences may comprise one, two or three amino acid mutations. An antigen binding protein comprising said CDR sequences is in the following also referred to as "antigen binding protein 9". In preferred embodiments of antigen binding protein 9, CDRa2 comprises or consists of the amino acid sequence of SEQ ID NO: 81, and CDRb2 comprises or consists of the amino acid sequence of SEQ ID NO: 86, wherein the CDRa2 and/or CDRb2 sequences may comprise one, two, three or four amino acid mutations. Antigen binding protein 9 specifically binds to a functional epitope comprising or consisting of 5, 6 or 7 amino acid positions selected from the group consisting of positions 1, 3, 4, 5, 6, 7 and 8 of SEQ ID NO: 138. The $EC_{50}$ for inducing killing of CT45-IP:MHC complex presenting cells, such as CT45-IP loaded T2 cells, by T cells expressing antigen binding protein 9, measured e.g. in a luciferase release assay, is less than about 5 nM, less than about 2.5 nM, less than about 1.5 nM or less than about 1 nM. Antigen binding protein 9 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155

(SP-05-0010), preferably selected from the group consisting of SEQ ID NO: 146 (SP-05-0001), SEQ ID NO: 147 (SP-05-0002), SEQ ID NO: 148 (SP-05-0003), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 9, $V_A$ comprises or consists of the amino acid sequence of SEQ ID NO: 79 or an amino acid sequence having at least 70%, 75%, 80%, 85%, 90%, 95%, 98% or 99% identity to SEQ ID NO: 79 and $V_B$ comprises or consists of the amino acid sequence of SEQ ID NO: 84 or an amino acid sequence having at least 70%, 75%, 80%, 85%, 90%, 95%, 98% or 99% identity to SEQ ID NO: 84; wherein $V_A$ and $V_B$ comprise the CDR sequences as described above for antigen binding protein 9, wherein the CDR sequences may comprise one, two or three amino acid mutations, preferably no amino acid mutation. Preferably, the alpha chain variable region of antigen binding protein 9 is encoded by TRAV5 and/or the beta chain variable region of antigen binding protein 9 is encoded by TRBV2. In a preferred embodiment, the antigen binding protein 9 is capable of activating a CD8+ T cell, in particular a CD8+CD4− T cell, and/or a CD4+ T cell, in particular a CD4+CD8− T cell.

Antigen Binding Protein 10

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 107, CDRa3 comprises or consists of the amino acid sequence of SEQ ID NO: 109, CDRb1 comprises or consists of the amino acid sequence of SEQ ID NO: 112, and CDRb3 comprises or consists of the amino acid sequence of SEQ ID NO: 114, wherein the CDRa1, CDRa3, CDRb1 and/or CDRb3 sequences may comprise one, two or three amino acid mutations. An antigen binding protein comprising said CDR sequences is in the following also referred to as "antigen binding protein 10". In preferred embodiments of antigen binding protein 10, CDRa2 comprises or consists of the amino acid sequence of SEQ ID NO: 108, and CDRb2 comprises or consists of the amino acid sequence of SEQ ID NO: 113, wherein the CDRa2 and/or CDRb2 sequences may comprise one, two, three or four amino acid mutations. Antigen binding protein 10 specifically binds to a functional epitope comprising or consisting of 2 or 3 amino acid positions selected from the group consisting of positions 5, 6 and 7 of SEQ ID NO: 138. The $EC_{50}$ for inducing killing of CT45-IP:MHC complex presenting cells, such as CT45-IP loaded T2 cells, by T cells expressing antigen binding protein 10, measured e.g. in a luciferase release assay, is less than about 30 nM, less than about 25 nM, less than about 20 nM, less than about 15 nM or less than about 10 nM. Antigen binding protein 10 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 10, $V_A$ comprises or consists of the amino acid sequence of SEQ ID NO: 106 or an amino acid sequence having at least 70%, 75%, 80%, 85%, 90%, 95%, 98% or 99% identity to SEQ ID NO: 106 and $V_B$ comprises or consists of the amino acid sequence of SEQ ID NO: 111 or an amino acid sequence having at least 70%, 75%, 80%, 85%, 90%, 95%, 98% or 99% identity to SEQ ID NO: 111; wherein $V_A$ and $V_B$ comprise the CDR sequences as described above for antigen binding protein 10, wherein the CDR sequences may comprise one, two or three amino acid mutations, preferably no amino acid mutation. Preferably, the alpha chain variable region of antigen binding protein 10 is encoded by TRAV1-2 and/or the beta chain variable region of antigen binding protein 10 is encoded by TRBV6-1. In a preferred embodiment, the antigen binding protein 10 is capable of activating a CD8+ T cell, in particular a CD8+CD4− T cell, and/or a CD4+ T cell, in particular a CD4+CD8− T cell.

Antigen Binding Protein 11

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 125, CDRa3 comprises or consists of the amino acid sequence of SEQ ID NO: 127, CDRb1 comprises or consists of the amino acid sequence of SEQ ID NO: 112, and CDRb3 comprises or consists of the amino acid sequence of SEQ ID NO: 130, wherein the CDRa1, CDRa3, CDRb1 and/or CDRb3 sequences may comprise one, two or three amino acid mutations. An antigen binding protein comprising said CDR sequences is in the following also referred to as "antigen binding protein 11". In preferred embodiments of antigen binding protein 11, CDRa2 comprises or consists of the amino acid sequence of SEQ ID NO: 126, and CDRb2 comprises or consists of the amino acid sequence of SEQ ID NO: 113, wherein the CDRa2 and/or CDRb2 sequences may comprise one, two, three or four amino acid mutations. Antigen binding protein 11 specifically binds to a functional epitope comprising or consisting of 4, 5 or 6 amino acid positions selected from the group consisting of positions 1, 3, 4, 5, 6 and 8 of SEQ ID NO: 138. The $EC_{50}$ for inducing killing of CT45-IP:MHC complex presenting cells, such as CT45-IP loaded T2 cells, by T cells expressing antigen binding protein 11, measured e.g. in a luciferase release assay, is less than about 60 nM. Antigen binding protein 11 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 11, $V_A$ comprises or consists of the amino acid sequence of SEQ ID NO: 124 or an amino acid sequence having at least 70%, 75%, 80%, 85%, 90%, 95%, 98% or 99% identity to SEQ ID NO: 124 and $V_B$ comprises or consists of the amino acid sequence of SEQ ID NO: 129 or an amino acid sequence having at least 70%, 75%, 80%, 85%, 90%, 95%, 98% or 99% identity to SEQ ID NO: 129; wherein $V_A$ and $V_B$ comprise the CDR sequences as described above for antigen binding protein 11, wherein the CDR sequences may comprise one, two or three amino acid mutations, preferably no amino acid mutation. Preferably, the alpha chain variable region of antigen binding protein 11 is encoded by TRAV22 and/or the beta chain variable region of antigen binding protein 11 is encoded by TRBV6-1. In a preferred embodiment, the antigen binding protein 11 is capable of activating a CD8+ T cell, in particular a CD8+CD4− T cell, and/or a CD4+ T cell, in particular a CD4+CD8− T cell.

Antigen Binding Protein 12

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 117, CDRa3 comprises or consists of the amino acid sequence of SEQ ID NO: 119, CDRb1 comprises or consists of the amino acid sequence of SEQ ID NO: 58, and CDRb3 comprises or consists of the amino acid sequence of SEQ ID NO: 122, wherein the CDRa1, CDRa3, CDRb1 and/or CDRb3 sequences may comprise one, two or three amino acid mutations. An antigen binding protein comprising said CDR sequences is in the following also referred to as "antigen binding protein 12". In preferred embodiments of antigen binding protein 12, CDRa2 comprises or consists of the amino acid sequence of SEQ ID NO: 118, and CDRb2 comprises or consists of the amino acid sequence of SEQ ID NO: 59, wherein the CDRa2 and/or CDRb2 sequences may comprise one, two, three or four amino acid mutations. Antigen binding protein 12 specifically binds to a functional epitope comprising or consisting of 2, 3 or 4 amino acid positions selected from the group consisting of positions 3, 4, 6 and 7 of SEQ ID NO: 138. The $EC_{50}$ for inducing killing of CT45-IP:MHC complex presenting cells, such as CT45-IP loaded T2 cells, by T cells expressing antigen binding protein 12, measured e.g. in a luciferase release assay, is less than about 60 nM, or less than about 50 nM. Antigen binding protein 12 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 12, $V_A$ comprises or consists of the amino acid sequence of SEQ ID NO: 116 or an amino acid sequence having at least 70%, 75%, 80%, 85%, 90%, 95%, 98% or 99% identity to SEQ ID NO: 116 and $V_B$ comprises or consists of the amino acid sequence of SEQ ID NO: 121 or an amino acid sequence having at least 70%, 75%, 80%, 85%, 90%, 95%, 98% or 99% identity to SEQ ID NO: 121; wherein $V_A$ and $V_B$ comprise the CDR sequences as described above for antigen binding protein 12, wherein the CDR sequences may comprise one, two or three amino acid mutations, preferably no amino acid mutation. Preferably, the alpha chain variable region of antigen binding protein 12 is encoded by TRAV27 and/or the beta chain variable region of antigen binding protein 12 is encoded by TRBV4-1. In a preferred embodiment, the antigen binding protein 12 is capable of activating a CD8+ T cell, in particular a CD8+CD4− T cell, and/or a CD4+ T cell, in particular a CD4+CD8− T cell.

Antigen Binding Protein 13

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 24, CDRa3 comprises or consists of the amino acid sequence of SEQ ID NO: 35, CDRb1 comprises or consists of the amino acid sequence of SEQ ID NO: 38, and CDRb3 comprises or consists of the amino acid sequence of SEQ ID NO: 40, wherein the CDRa1, CDRa3, CDRb1 and/or CDRb3 sequences may comprise one, two or three amino acid mutations. An antigen binding protein comprising said CDR sequences is in the following also referred to as "antigen binding protein 13". In preferred embodiments of antigen binding protein 13, CDRa2 comprises or consists of the amino acid sequence of SEQ ID NO: 25, and CDRb2 comprises or consists of the amino acid sequence of SEQ ID NO: 39, wherein the CDRa2 and/or CDRb2 sequences may comprise one, two, three or four amino acid mutations. Antigen binding protein 13 specifically binds to a functional epitope comprising or consisting of 3, 4 or 5 amino acid positions selected from the group consisting of positions 1, 3, 4, 6 and 7 of SEQ ID NO: 138. The $EC_{50}$ for inducing killing of CT45-IP:MHC complex presenting cells, such as CT45-IP loaded T2 cells, by T cells expressing antigen binding protein 13, measured e.g. in a luciferase release assay, is less than about 50 nM, less than about 30 nM, less than about 25 nM, less than about 20 nM or less than about 15 nM. Antigen binding protein 13 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP 0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010). In preferred embodiments of antigen binding protein 13, $V_A$ comprises or consists of the amino acid sequence of SEQ ID NO: 34 or an amino acid sequence having at least 70%, 75%, 80%, 85%, 90%, 95%, 98% or 99% identity to SEQ ID NO: 34 and $V_B$ comprises or consists of the amino acid sequence of SEQ ID NO: 37 or an amino acid sequence having at least 70%, 75%, 80%, 85%, 90%, 95%, 98% or 99% identity to SEQ ID NO: 37; wherein $V_A$ and $V_B$ comprise the CDR sequences as described above for antigen binding protein 13, wherein the CDR sequences may comprise one, two or three amino acid mutations, preferably no amino acid mutation. Preferably, the alpha chain variable region of antigen binding protein 13 is encoded by TRAV14/DV4 and/or the beta chain variable region of antigen binding protein 13 is encoded by TRBV19. In a preferred embodiment, the antigen binding protein 13 is capable of activating a CD8+ T cell, in particular a CD8+ CD4− T cell, and/or a CD4+ T cell, in particular a CD4+ CD8− T cell.

Antigen Binding Protein 14

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 24, CDRa3 comprises or consists of the amino acid sequence of SEQ ID NO: 26, CDRb1 comprises or consists of the amino acid sequence of SEQ ID NO: 29, and CDRb3 comprises or consists of the amino acid sequence of SEQ ID NO: 31, wherein the CDRa1, CDRa3, CDRb1 and/or CDRb3 sequences may comprise one, two or three amino acid mutations. An antigen binding protein comprising said CDR sequences is in the following also referred to as "antigen binding protein 14". In preferred embodiments of antigen binding protein 14, CDRa2 comprises or consists of the amino acid sequence of SEQ ID NO: 25, and CDRb2 comprises or consists of the amino acid sequence of SEQ ID NO: 30, wherein the CDRa2 and/or CDRb2 sequences may comprise one, two, three or four amino acid mutations. Antigen binding protein 14 specifically binds to a functional epitope comprising or consisting of 2, 3 or 4 amino acid positions selected from the group consisting of positions 1, 3, 4 and 5 of SEQ ID NO: 138. The $EC_{50}$ for inducing killing of CT45-IP:MHC complex presenting cells, such as CT45-IP loaded T2 cells, by T cells expressing antigen binding protein 14, measured e.g. in a luciferase release assay, is less than about 50 nM, less than about 30 nM, less than about 25 nM or less than about 20 nM. Antigen binding protein 14 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP 0007), SEQ ID NO: 153 (SP-05-0008), SEQ ID NO: 154 (SP-05-0009) and SEQ ID NO: 155 (SP-05-0010). In preferred embodiments of antigen binding protein 14, $V_A$ comprises or consists of the amino acid sequence of SEQ ID NO: 23 or an amino acid sequence having at least 70%, 75%, 80%, 85%, 90%, 95%, 98% or 99% identity to SEQ ID NO: 23 and $V_B$ comprises or consists of the amino acid sequence of SEQ ID NO: 28 or an amino acid sequence having at least 70%, 75%, 80%, 85%, 90%, 95%, 98% or 99% identity to SEQ ID NO: 28; wherein $V_A$ and $V_B$ comprise the CDR sequences as described above for antigen binding protein 14, wherein the CDR sequences may comprise one, two or three amino acid mutations, preferably no amino acid mutation. Preferably, the alpha chain variable region of antigen binding protein 14 is encoded by TRAV14/DV4 and/or the beta chain variable region of antigen binding protein 14 is encoded by TRBV11-2. In a preferred embodiment, the antigen binding protein 14 is capable of activating a CD8+ T cell, in particular a CD8+CD4− T cell, and/or a CD4+ T cell, in particular a CD4+CD8− T cell.

Antigen Binding Protein 15

In some embodiments, the invention relates to an antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein CDRa1 comprises or consists of the amino acid sequence of SEQ ID NO: 43, CDRa3 comprises or consists of the amino acid sequence of SEQ ID NO: 45, CDRb1 comprises or consists of the amino acid sequence of SEQ ID NO: 48, and CDRb3 comprises or consists of the amino acid sequence of SEQ ID NO: 50, wherein the CDRa1, CDRa3, CDRb1 and/or CDRb3 sequences may comprise one, two or three amino acid mutations. An antigen binding protein comprising said CDR sequences is in the following also referred to as "antigen binding protein 15". In preferred embodiments of antigen binding protein 15, CDRa2 comprises or consists of the amino acid sequence of SEQ ID NO: 44, and CDRb2 comprises or consists of the amino acid sequence of SEQ ID NO: 49, wherein the CDRa2 and/or CDRb2 sequences may comprise one, two, three or four amino acid mutations. Antigen binding protein 15 specifically binds to a functional epitope comprising or consisting of 4, 5 or 6 amino acid positions selected from the group consisting of positions 1, 3, 4, 5, 6 and 7 of SEQ ID NO: 138. The $EC_{50}$ for inducing killing of CT45-IP:MHC complex presenting cells, such as CT45-IP loaded T2 cells, by T cells expressing antigen binding protein 15, measured e.g. in a luciferase release assay, is less than about 50 nM, less than about 30 nM, less than about 25 nM or less than about 20 nM. Antigen binding protein 15 does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), preferably selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 151 (SP-05-0006), SEQ ID NO: 152 (SP-05-0007), and SEQ ID NO: 155 (SP-05-0010). In preferred embodiments of antigen binding protein 15, $V_A$ comprises or consists of the amino acid sequence of SEQ ID NO: 42 or an amino acid sequence having at least 70%, 75%, 80%, 85%, 90%, 95%, 98% or 99% identity to SEQ ID NO: 42 and $V_B$ comprises or consists of the amino acid sequence of SEQ ID NO: 27 or an amino acid sequence having at least 70%, 75%, 80%, 85%, 90%, 95%, 98% or 99% identity to SEQ ID NO: 27; wherein $V_A$ and $V_B$ comprise the CDR sequences as described above for antigen binding protein 15, wherein the CDR sequences may comprise one, two or three amino acid mutations, preferably no amino acid mutation. Preferably, the alpha chain variable region of antigen binding protein 15 is encoded by TRAV21 and/or the beta chain variable region of antigen binding protein 15 is encoded by TRBV5-1. In a preferred embodiment, the antigen binding protein 15 is capable of activating a CD8+ T cell, in particular a CD8+CD4− T cell, and/or a CD4+ T cell, in particular a CD4+CD8− T cell.

The invention also includes particles displaying antigen binding proteins, in particular TCRs, and the inclusion of said particles within a library of particles. Such particles include but are not limited to phage, yeast, ribosomes, or mammalian cells. Method of producing such particles and libraries are known in the art (for example see WO2004/044004; WO01/48145, Chervin et al. (2008) J. Immuno. Methods 339.2: 175-184).

Nucleic Acids, Vectors and Recombinant Host Cells

The polypeptides of the antigen binding proteins of the invention can be encoded by nucleic acids and expressed in vivo, ex vivo or in vitro. Thus, in a second aspect, the invention relates to a nucleic acid or nucleic acids comprising or consisting of one or more sequences encoding the antigen binding protein of the first aspect of the invention.

The nucleic acid may be comprised in one nucleic acid molecule or may be separated into two or more nucleic acid molecules, wherein each nucleic acid molecule comprises at least one of the one or more sequences encoding the antigen binding protein of the first aspect of the invention. In some embodiments, one nucleic acid molecule encodes one part or monomer of an antigen binding protein of the invention (for example one of two chains of a TCR of the invention), and another nucleic acid molecule encodes another part or monomer of an antigen binding protein of the invention (for example the other of two chains of the TCR). In some embodiments, the nucleic acid encodes two or more antigen binding protein polypeptide chains, for example, at least two TCR chains. Nucleic acids encoding multiple antigen binding protein polypeptide chains can include a nucleic acid cleavage site between at least two chain sequences, can encode a transcription or translation start site, such as an internal ribosomal entry site (IRES) between two or more chain sequences, and/or can encode a proteolytic target site between two or more antigen binding protein chains. If two or more antigen binding protein polypeptide chains are encoded on one nucleic acid molecule, the two or more antigen binding protein polypeptide chains can be under the control of the same promoter or under the control of separate promoters.

The term "nucleic acid" refers in the context of this invention to single or double-stranded oligo- or polymers of deoxyribonucleotide or ribonucleotide bases or both. Nucleotide monomers are composed of a nucleobase, a five-carbon sugar (such as but not limited to ribose or 2′-deoxyribose), and one to three phosphate groups. Typically, a nucleic acid is formed through phosphodiester bonds between the individual nucleotide monomers, In the context of the present invention, the term nucleic acid includes but is not limited to ribonucleic acid (RNA) and deoxyribonucleic acid (DNA) molecules but also includes synthetic forms of nucleic acids comprising other linkages (e.g., peptide nucleic acids as described in Nielsen et al. (Science 254:1497-1500, 1991). Typically, nucleic acids are single- or double-stranded molecules and are composed of naturally occurring nucleotides. The depiction of a single strand of a nucleic acid also defines (at least partially) the sequence of the complementary strand. The nucleic acid may be single or double stranded or may contain portions of both double and single stranded sequences. Exemplified, double-stranded nucleic acid molecules can have 3′ or 5′ overhangs and as such are not required or assumed to be completely double-stranded over their entire length. The term nucleic acid comprises chromosomes or chromosomal segments, vectors (e.g., expression vectors), expression cassettes, naked DNA or RNA polymer, primers, probes, cDNA, genomic DNA, recombinant DNA, cRNA, mRNA, tRNA, microRNA (miRNA) or small interfering RNA (siRNA). A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

In preferred embodiments, the nucleic acid is an isolated nucleic acid. In preferred embodiments, the nucleic acid is a recombinant nucleic acid.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques.

Nucleic acid molecules of the disclosure can be obtained using standard molecular biology techniques, including but not limited to methods of amplification, and reverse transcription of RNA. Once DNA fragments encoding, for example, variable chains are obtained, these DNA fragments can be further manipulated by standard recombinant DNA techniques, for example to convert the variable region genes to full-length chain genes. In these manipulations, a variant-encoding DNA fragment is operatively linked to another DNA molecule, or to a fragment encoding another protein, such as a constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter. The isolated DNA encoding the variable region, e.g. the variable alpha region and/or variable beta region, can be converted to a full-length chain gene by operatively linking the variable-encoding DNA to another DNA molecule encoding constant regions. The sequences of human constant region genes, e.g. for TCRs or antibodies, are known in the art and DNA fragments encompassing these regions can be obtained by standard PCR amplification.

Typically, said nucleic acid comprises one or more DNA or RNA molecules, which may be included in one or more suitable vectors.

In a third aspect, the invention relates to a vector or a collection of vectors comprising the nucleic acid(s) of the second aspect of the invention. Preferably, the sequence encoding the antigen binding protein is operably linked to a promoter sequence. "Collection of vectors" herein refers to two or more vectors. If two or more antigen binding protein polypeptide chains are encoded on one vector, the two or more antigen binding protein polypeptide chains can be under the control of the same promoter or under the control of separate promoters.

The terms "vector", "cloning vector" and "expression vector" refers to a vehicle by which a DNA or RNA sequence (e.g. a foreign gene) can be introduced into a host cell, so as to transform the host and promote expression (e.g. transcription and translation) of the introduced sequence.

Various expression vectors can be employed to express the polynucleotides encoding the antigen binding proteins or functional fragments thereof. Both viral-based and non-viral expression vectors can be used to produce the antigen binding proteins or functional fragments thereof described herein in a mammalian host cell. Non-viral vectors and systems include plasmids, plasmid, cosmid, episome, artificial chromosome, phage or a viral vector.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of antibody heavy chain and the like.

For example, non-viral vectors useful for expression of polynucleotides and polypeptides described herein in mammalian (e.g. human or non-human) cells include all suitable vectors known in the art for expressing proteins. Other examples of plasmids and include replicating plasmids comprising an origin of replication, or integrative plasmids, such as for instance pUC, pcDNA, pBR, and the like.

The term "viral vector" refers to a nucleic acid vector construct that includes at least one element of viral origin and has the capacity to be packaged into a viral vector particle and encodes at least an exogenous nucleic acid. The vector and/or particle can be utilized for the purpose of transferring a nucleic acid of interest into cells either in vitro or in vivo. Numerous forms of viral vectors are known in the art. Useful viral vectors include vectors based on retroviruses, lentiviruses, adenoviruses, adeno-associated viruses, herpes viruses, vectors based on SV40, papilloma virus, Epstein Barr virus, vaccinia virus vectors, and Semliki Forest virus (SFV). Recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

The first polypeptide and the second polypeptide described herein can be present in the same vector or separate vectors, i.e. a collection of vectors.

In a fourth aspect, the invention relates to a host cell comprising the antigen binding protein of the first aspect of the invention, the nucleic acid of the second aspect of the invention or the vector of the third aspect of the invention. The host cell may be transfected, infected or transduced or transformed, in particular with a nucleic acid and/or a vector according to the invention.

The host cell can be a eukaryotic cell, e.g., plant, animal, fungi, or algae, or a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant antigen binding protein, for example a TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a lymphocyte, such as a T cell, a T cell progenitor or a NK cell. NK cells are naturally occurring lymphoid non-T cells that can rapidly kill virally infected cells and tumour cells. NK cells can be engineered to express a tumor-specific TCR for use as a cell therapy product in cancer therapy (Shimasaki et al., Nat Rev Drug Discov. 2020 March; 19(3):200-218). In preferred embodiments, the host cell is a T cell, for example a CD4 or CD8 positive T cell or a γδ T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precursor from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4-positive helper T cells, e.g., Th1 and Th2 cells, CD8-positive T cells (e.g., cytotoxic T cells), tumor infiltrating cells (TILs), memory T cells, naive T cells, γδ T cells, and the like.

In other preferred embodiments, the host cell is or a cell for recombinant expression, such as a Chinese Hamster Ovary (CHO) cell or a yeast cell.

The term "transformation" means the introduction of a "foreign" (i.e. extrinsic) gene, DNA or RNA sequence to a host cell, so that the host cell will express the introduced gene or sequence to produce a desired substance, typically the antigen-binding protein or functional fragment thereof described herein. A host cell that receives and expresses introduced DNA or RNA base been "transformed".

The nucleic acids of the invention may be used to produce a recombinant antigen binding protein of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, HEK cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene is defective (Urlaub G et al; 1980), rat YB2/3HL.P2.G11.16Ag.20 cell (ATCC CRL1662), and the like. In some embodiments, the YB2/0 cell may be preferred, since ADCC activity of chimeric or humanized antibodies is enhanced when expressed in this cell. In preferred embodiments the host cells described above are used as expression system.

In particular, for expression of some of the antigen binding proteins of the invention, in particular the antigen binding proteins comprising two polypeptides that are not linked, the expression vector may be either of a type in which a gene encoding a first polypeptide, such as a TCR alpha chain and a gene encoding a second polypeptide, such as such as a TCR beta chain exists on separate vectors or of a type in which both genes exist on the same vector (tandem type). In respect of easiness of construction of antigen binding protein expression vector, easiness of introduction into animal cells, and balance between the expression levels of two polypeptides, such as TCR alpha and beta chains, in animal cells, an expression vector of the tandem type is preferred as described in context of humanized antibodies (shitara K et al. J Immunol Methods. 1994 Jan. 3; 167(1-2):271-8). Examples of tandem type expression vectors as described in context of the humanized antibodies include pKANTEX93 (WO 97/10354), pEE18 and the like.

In one embodiment, such recombinant host cells can be used for the production of at least one antigen binding protein of the invention.

Pharmaceutical Compositions

In a fifth aspect, the invention relates to a pharmaceutical composition comprising the antigen binding protein of the first aspect of the invention, the nucleic acid of the second aspect of the invention, the vector of the third aspect of the invention or the host cell of the fourth aspect of the invention and optionally a pharmaceutically acceptable carrier.

Antigen binding proteins of the present invention have been shown to be capable of effecting cytotoxicity against cells presenting the CT45-IP antigenic peptide. Since this peptide is specifically presented by tumor cells, the antigen binding proteins of the present invention are useful for destroying tumor cells in a patient. An immune response in a patient can be induced by direct administration of the described antigen binding proteins to the patient, ideally in combination with an agent enhancing the immunogenicity (i.e. an adjuvant). The immune response originating from such a therapeutic vaccination can be expected to be highly specific against tumor cells because the peptide KIFEM-LEGV (SEQ ID NO: 138) is not presented or over-presented on normal tissues in comparable copy numbers, preventing the risk of undesired autoimmune reactions against normal tissue cells in the patient.

The invention also relates to an antigen binding protein according to the invention, for use as a medicament. The invention also relates to a pharmaceutical composition of the invention for use as a medicament.

The terms "pharmaceutical composition" or "therapeutic composition" as used herein refer to a compound or composition capable of inducing a desired therapeutic effect when properly administered to a subject.

In some embodiments, the subject may also be referred to as patient.

Such therapeutic or pharmaceutical compositions may comprise a therapeutically effective amount of an antigen binding protein of the invention or an antigen binding protein further comprising a therapeutic agent, in admixture with a pharmaceutically or physiologically acceptable formulation agent selected for suitability with the mode of administration.

In some embodiments, antigen binding protein of the present invention will be supplied as part of a sterile, pharmaceutical composition which will normally include a pharmaceutically acceptable carrier.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier refers to a non-toxic solid, semi-solid or liquid filler, diluent, encapsulating material or formulation auxiliary of any type.

A "pharmaceutically acceptable carrier" and may include solvents, bulking agents, stabilizing agents, dispersion media, coatings, antibacterial and antifungal agents, isotonic and absorption delaying agents, and the like which are physiologically compatible. In one embodiment the carrier is an aqueous carrier. In some embodiments, the aqueous carrier is capable of imparting improved properties when combined with an antigen binding protein described herein, for example, improved solubility, efficacy, and/or improved immunotherapy.

Further examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The form of the pharmaceutical compositions, the route of administration, the dosage and the regimen naturally depend upon the condition to be treated, the severity of the illness, the age, weight, and gender of the patient, etc. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

Preferably, the pharmaceutical composition is administered by injection, e.g., intravenously. When the pharmaceutical composition comprises a host cell expressing the antigen binding protein of the invention, preferably a TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMALYTE A (Baxter, Deerfield, Ill.), about 5% dextrose in water, or Ringer's lactate. In an embodiment, the pharmaceutically acceptable carrier is supplemented with human serum albumen.

Empirical considerations, such as the biological half-life, generally will contribute to the determination of the dosage. Frequency of administration may be determined and adjusted over the course of therapy and is based on reducing the number of cancer cells, maintaining the reduction of cancer cells, reducing the proliferation of cancer cells, or killing the cancer cells. Alternatively, sustained continuous release formulations of the antigen binding protein may be appropriate. Various formulations and devices for achieving sustained release are known in the art.

In one embodiment, dosages for the antigen binding proteins may be determined empirically in individuals who have been given one or more administration(s). Individuals are given incremental dosages of the antigen binding protein. To assess efficacy of the antigen binding protein, a marker of the cancer cell state can be followed. These include direct measurements of cancer cell proliferation and cell death by FACS, other imaging techniques; an improvement in health as assessed by such measurements, or an increase in quality of life as measured by accepted tests or prolongation of survival. It will be apparent to one of skill in the art that the dosage will vary depending on the individual, the stage of the disease, and the past and concurrent treatments being used.

The doses used for the administration can be adapted as a function of various parameters, and in particular as a function of the mode of administration used, of the relevant pathology, or alternatively of the desired duration of treatment.

Pharmaceutical compositions, vectors, nucleic acids and cells of the invention may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure Methods of Producing Antigen Binding Proteins In a sixth aspect, the invention relates to a method of producing the antigen binding protein according to the first aspect of the invention, comprising the steps of (a) providing a host cell, (b) providing a genetic construct comprising a coding sequence encoding the antigen binding protein of any of the first aspect of the invention, (c) introducing the genetic construct into the host cell, and (d) expressing the genetic construct by the host cell.

In one embodiment, the method further comprises the isolation and purification of the antigen binding protein from the host cell and, optionally, reconstitution of the antigen binding protein in a host cell, preferably a lymphocyte, more preferably a T cell or NK cell, most preferably T cell. The skilled person is entirely capable of selecting suitable host cells for expressing an antigen binding protein.

An antigen binding protein of the invention may be produced by any technique known in the art, such as, without limitation, any chemical, biological, genetic or enzymatic technique, either alone or in combination.

Antigen binding proteins of the invention are suitably separated from the culture medium by antibody purification procedures such as, for example, protein A-sepharose, hydroxylapatite chromatography, gel electrophoresis, dialysis, or affinity chromatography.

In one embodiment, recovering the expressed antigen binding proteins or polypeptides herein refers to performing a protein A chromatography, a Kappa select chromatography, and/or a size exclusion chromatography, preferably a protein A chromatography and/or a size exclusion chromatography, more preferably a protein A chromatography and a size exclusion chromatography.

Knowing the amino acid sequence of the desired sequence, one skilled in the art can produce the antigen binding proteins of the present invention, by standard techniques for production of polypeptides. For instance, they can be synthesized using well-known solid phase method, in particular using a commercially available peptide synthesis apparatus (such as that made by Applied Biosystems, Foster City, Calif.) and following the manufacturer's instructions. Alternatively, antibodies, and antigen binding proteins of the invention can be produced by recombinant DNA and gene transfection techniques well known in the art (see Morrison S L. et al. (1984) and patent documents U.S. Pat. Nos. 5,202,238; and 5,204,244). For example, fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Methods for producing humanized antibodies based on conventional recombinant DNA and gene transfection techniques are well known in the art (See, e.g., Riechmann L. et al. 1988; Neuberger M S. et al. 1985) and can be easily applied to the production of the antigen binding proteins of the invention.

In one example, vectors for the expression of the recombinant antigen binding proteins of the invention were designed as monocistronic, for instance, controlled by HCMV-derived promoter elements, pUC19-derivatives. Plasmid DNA was amplified, for example, in E. coli according to standard culture methods and subsequently purified using commercially-available kits (Macherey & Nagel). Purified plasmid DNA was used for transient transfection of, for example, CHO-S cells according to instructions of the manufacturer (ExpiCHO™ system; Thermo Fisher Scientific). Transfected CHO-cells were cultured, for instance, for 6-14 days at, for example, 32° C. to 37° C. and received one to two feeds of ExpiCHO™ Feed solution.

Conditioned cell supernatant was cleared by, for example, filtration (0.22 µm) utilizing, for instance, Sartoclear Dynamics® Lab Filter Aid (Sartorius). Bispecific antigen binding proteins were purified using, for example, an Akta Pure 25 L FPLC system (GE Lifesciences) equipped to perform affinity and size-exclusion chromatography in line. Affinity chromatography was performed on, for example, protein A or L columns (GE Lifesciences) following standard affinity chromatographic protocols. For instance, size exclusion chromatography was performed directly after elution (pH 2.8) from the affinity column to obtain highly pure monomeric protein using, for example, Superdex 200 pg 16/600 columns (GE Lifesciences) following standard protocols. Protein concentrations were determined on, for example, a NanoDrop system (Thermo Scientific) using calculated extinction coefficients according to predicted protein sequences. Concentration was adjusted, if needed, by using Vivaspin devices (Sartorius). Finally, purified molecules were stored in, for example, phosphate-buffered saline at concentrations of about 1 mg/mL at temperatures of 2-8° C.

Quality of purified bispecific antigen binding proteins was determined by, for example, HPLC-SEC on MabPac SEC-1 columns (5 µm, 7.8×300 mm) running in, for example, 50 mM sodium-phosphate pH 6.8 containing 300 mM NaCl within a Vanquish UHPLC-System.

Therapeutic Methods and Uses

In a seventh aspect, the invention relates to the antigen binding protein of the first aspect of the invention, the nucleic acid of the second aspect of the invention, the vector of the third aspect of the invention, the host cell of the fourth aspect of the invention, or the pharmaceutical composition of the fourth aspect of the invention for use in medicine.

In an eighth aspect, the invention relates to the antigen binding protein of the first aspect of the invention, the nucleic acid of the second aspect of the invention, the vector of the third aspect of the invention, the host cell of the fourth aspect of the invention, or the pharmaceutical composition of the fourth aspect of the invention for use in a method of treatment and/or diagnosis of a proliferative disease.

The antigen binding proteins of the invention are in particular for use in immune therapy, preferably adoptive cell therapy, more preferably adoptive T cell therapy, for the prevention and/or treatment of a proliferative disease. The administration of the compounds of the invention can, for example, involve the infusion of lymphocytes, preferably NK cells or T cells, more preferably T cells of the invention into said patient. Preferably, such lymphocytes are autologous lymphocytes of the patient and in vitro transduced with a nucleic acid or antigen binding protein of the present invention.

In preferred embodiments, the proliferative disease is cancer, in particular a CT45 expressing cancer.

In the context of the present invention, a cancer is considered to be a "CT45 expressing cancer" (also referred to as CT45 "positive" cancer), if the related peptide, such as, for example the CT45-IP peptide, is presented in >98% of all cancers according to the guidelines by the NCI. In all other indications named here a biopsy can be performed as it is standard in the treatment of these cancers and the peptide can be identified according to the XPresident® and related methods (according to WO 03/100432; WO 2005/076009; WO 2011/128448; WO 2016/107740, U.S. Pat. Nos. 7,811,828, 9,791,444, and US 2016/0187351, the contents of each are hereby incorporated by reference in their entirety). In one embodiment, the cancer is readily assayed (i.e. diagnosed) for instance by using an antigen binding protein of the invention. Methods to identify an antigen expressing cancer using an antigen binding protein are known to the skilled in the art. It is to be understood that the terms "cancer" and "carcinoma" are not used interchangeably herein since a carcinoma is a specific type of cancer emerging in the skin or in tissues that line or cover body organs.

In one embodiment, the CT45 expressing cancer is selected from the group consisting of lung cancer, NSCLC, gall bladder cancer, bile duct cancer, lymph node cancer, ovarian cancer, esophageal cancer, liver cancer, uterus cancer and melanoma.

In one embodiment, the cancer is a cancer where a CT45-antigen is overexpressed, mutated, and/or a CT45 antigenic peptide is presented. Such a cancer is readily assayed (i.e. diagnosed) for instance by using an antigen binding protein of the invention. Methods to identify an antigen expressing cancer using an antigen-binding protein are known to the skilled in the art.

In another aspect, the invention relates to a method of treatment of a proliferative disease comprising administering to a subject in need thereof a therapeutically effective amount of the antigen binding protein, the nucleic acid or vector, the host cell or the pharmaceutical composition according to the invention as defined herein above.

In a particular embodiment, the invention relates to a method of treatment of a subject who has a proliferative disease comprising administering to said subject lymphocytes, preferably NK cells or T cells, more preferably T cells expressing the antigen binding protein of the invention on the cell surface.

The terms "subject" or "individual" are used interchangeably and may be, for example, a human or a non-human mammal, preferably, a human.

In the context of the invention, the terms "treating" or "treatment", include both therapeutic treatment (i.e. on a subject having a given disease) and/or preventive or prophylactic treatment (i.e. on a subject susceptible of developing a given disease). Therapeutic treatment and means reversing, alleviating and/or inhibiting the progress of one or more symptoms of a disorder or condition. Prophylactic treatment means preventing the occurrence of one or more symptoms of a disorder or condition. Therefore, treatment does not only refer to a treatment that leads to a complete cure of the disease, but also to treatments that slow down the progression of the disease, prevent or delay the occurrence of the disease and/or prolong the survival of the subject.

In one embodiment, a "disease" or "disorder" is any condition that would benefit from treatment with the antigen binding protein of the invention. In one embodiment, this includes chronic and acute disorders or diseases including those pathological conditions which predisposes the subject to the disorder in question. The term "in need of treatment" refers to a subject having already the disorder as well as those in which the disorder is to be prevented.

"Proliferative diseases", such as cancer, involve the unregulated and/or inappropriate proliferation of cells.

In one embodiment, the method of treatment comprises immune therapy, in particular adoptive autologous or heterologous cell therapy, preferably T-cell therapy.

In a preferred embodiment, the antigen binding protein is or comprises a TCR or a functional fragment thereof.

It is preferred that the antigen binding protein is expressed on the surface of a host cell.

In one embodiment, the method of treatment comprises administration of a host cell expressing the antigen binding protein, wherein the host cell is a T cell, T cell progenitor or NK cell, preferably a T cell.

In one embodiment, the host cell, preferably a T cell, T cell progenitor or NK cell, more preferably a T cell, is autologous.

In one embodiment, the host cell, preferably a T cell, T cell progenitor or NK cell, more preferably a T cell, is allogeneic.

In one embodiment, the antigen binding protein is conjugated to a therapeutically active agent, preferably a therapeutically active agent selected from the group consisting of a radionuclide, a chemotherapeutic agent and a toxin.

In one embodiment, the method of treatment further comprises administering at least one chemotherapeutic agent to the subject in need of treatment.

In one embodiment, the method of treatment further comprises administering radiation therapy to the subject in need of treatment.

In a related aspect, the invention relates to a method of eliciting an immune response in a patient who has a proliferative disease, in particular a cancer that presents a peptide comprising or consisting of the amino acid sequence of KIFEMLEGV (SEQ ID NO: 138) in a complex with an MHC protein, comprising administering to the patient an antigen binding protein of the present disclosure, wherein said cancer is selected from the group of cancers consisting of lung cancer, NSCLC, gall bladder cancer, bile duct cancer, lymph node cancer, ovarian cancer, esophageal cancer, liver cancer, uterus cancer and melanoma. In one embodiment, the immune response referred to in said method is a cytotoxic T cell response.

In yet another aspect, the invention relates to the use of an antigen binding protein, the nucleic acid or vector, the host cell or the pharmaceutical composition according to the invention for the manufacture of a medicament for the treatment of a proliferative disease in a subject.

In yet another aspect, the invention relates to the use of the antigen binding protein, the nucleic acid or vector, the host cell or the pharmaceutical composition according to the invention for treating a disease in a subject.

Among the texts providing guidance for cancer therapy is Cancer, Principles and Practice of Oncology, 4th Edition, DeVita et al, Eds. J. B. Lippincott Co., Philadelphia, Pa. (1993). An appropriate therapeutic approach is chosen according to the particular type of cancer, and other factors such as the general condition of the patient, as is recognized in the pertinent field. An antigen binding protein of the present invention can be used by itself or can be added to a therapy regimen using other anti-neoplastic agents in treating a cancer patient.

Accordingly, in some embodiments, the antigen binding protein can be administered concurrently with, before, or after a variety of drugs and treatments widely employed in cancer treatment such as, for example, chemotherapeutic agents, non-chemotherapeutic, anti-neoplastic agents, and/or radiation.

"Diagnosis" herein refers to a medical diagnosis and refers to determining which disease or condition explains a person's symptoms and signs.

By a "therapeutically effective amount" of the antigen binding protein or pharmaceutical composition thereof is meant a sufficient amount of the antigen binding protein to treat said proliferative disease, at a reasonable benefit/risk ratio applicable to any medical treatment. It will be understood, however, that the total daily usage of the antigen binding proteins, the nucleic acid or vector, the host cell or the pharmaceutical composition of the present invention will be decided by the attending physician within the scope of sound medical judgment. The specific therapeutically effective dose level for any particular patient will depend upon a variety of factors including the disorder being treated and the severity of the disorder; activity of the specific antigen binding protein employed; the specific composition employed, the age, body weight, general health, sex and diet of the patient; the time of administration, route of administration, and rate of excretion of the specific polypeptide employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

In one embodiment, efficacy of the treatment with an antigen binding protein of the invention is assayed in vivo, for instance in a mouse model of cancer and by measuring, for example, changes in tumor volume between treated and control groups.

The antigen binding protein of the invention, the nucleic acid of the invention or the vector of the invention, the host cell of the invention or the pharmaceutical composition of the invention can be administered by any feasible method.

As herein disclosed, in some embodiments host cells as defined herein above are used in the herein described medical uses or treatment methods. In such embodiments, the host cell is preferably a lymphocyte, such as an NK cell, a T cell or T cell progenitor, preferably a CD4 and/or CD8 positive T cell or a γδ T cell, most preferably a CD4 and/or CD8 positive T cell, most preferably a CD4 and/or CD8 positive T cell.

Accordingly, the host cell of the present invention, preferably the T cells, may be used as active ingredients of a therapeutic composition. Thus, the invention also provides a method of killing target cells in a patient whose target cells aberrantly express a polypeptide comprising the peptide KIFEMLEGV (SEQ ID NO: 138), the method comprising administering to the patient an effective number of host cells, preferably T cells. In the context of this method the host cells, once administered to the subject, preferably elicit an immune response.

In an aspect, the TCR-elicited immune response or T cell response may refer to the proliferation and activation of effector functions induced by a peptide, such as KIFEMLEGV (SEQ ID NO: 138), in vitro, ex vivo or in vivo. For MHC class I restricted cytotoxic T cells, for example, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, for example, granzymes or perforins induced by peptide, or degranulation.

In the context of the present invention, when a T cell is used as a medicament, usually, T cells are collected from a subject by apheresis. Then the T cells are genetically engineered to express the antigen binding protein of the present invention on their cell surface, the genetically engineered T cells are then expanded and then re-infused into the subject.

In this example, the antigen binding protein is preferably a membrane bound antigen binding protein, more preferably a TCR.

Accordingly, the host cell has been transfected, infected or transformed with a nucleic acid and/or a vector according to the invention, as described herein above in the section 'nucleic acids, vectors and recombinant host cells'.

When the host cell is transfected to express the antigen binding protein of the invention, preferably the cell comprises an expression vector capable of expressing the antigen binding protein. The host cell may then be referred to as activated host cell.

Protocols for this so-called adoptive transfer of T cells are well known in the art. Reviews can be found in: Gattioni et al. and Morgan et al. (Gattinoni, L. et al., Nat. Rev. Immunol. 6 (2006): 383-393; Morgan, R. A. et al., Science 314 (2006): 126-129).

For purposes of the invention, the amount or dose of the antigen binding protein of the first aspect of the invention, the nucleic acid of the second aspect of the invention, the vector of the third aspect of the invention, the host cell of the fourth aspect of the invention, or the pharmaceutical composition of the fifth aspect of the invention administered may be sufficient to effect, e.g., a therapeutic or prophylactic response, in the subject or animal over a reasonable time frame. For example, the dose of the antigen binding protein, the nucleic acid, the vector, the host cell, or the pharmaceutical composition according to the invention should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the antigen binding protein, nucleic acid, vector, host cell, or pharmaceutical composition according to the invention and the condition of the animal (e.g., human), as well as the body weight of the animal (e.g., human) to be treated.

A number of other methods may be used for generating T cells in vitro. For example, autologous tumor-infiltrating lymphocytes can be used in the generation of CTL. Plebanski et al. (Plebanski, M. et al., Eur. J Immunol 25 (1995): 1783-1787) made use of autologous peripheral blood lymphocytes (PLBs) in the preparation of T cells. Also, B cells can be used in the production of autologous T cells.

Allogeneic cells may also be used in the preparation of T cells and a method is described in detail in U.S. Pat. No. 6,805,861, incorporated herein by reference.

Host cells expressing the antigen binding protein of the invention directed against the peptides KIFEMLEGV (SEQ ID NO: 138) are useful in therapy. Thus, a further aspect of the invention provides activated host cells obtainable by the foregoing methods of the invention.

Activated host cells, which are produced by the above method, may specifically recognize a cell that aberrantly expresses a polypeptide that comprises the peptide KIFEMLEGV (SEQ ID NO: 138).

By "aberrantly expressed" the inventors also mean that the polypeptide is overexpressed compared to levels of expression in normal (healthy) tissues or that the gene is silent in the tissue from which the tumor is derived but, in the tumor, it is expressed. By "overexpressed" the inventors mean that the polypeptide is present at a level at least 1.2-fold of that present in normal tissue; preferably at least 2-fold, and more preferably at least 5-fold or 10-fold the level present in normal tissue.

In an aspect, the host cell, in particular the T cell, recognizes the cell by interacting through its antigen binding protein, in particular its TCR, with the CT45-IP:MHC complex (for example, binding). The host cells are useful in a method of killing target cells in a patient whose target cells aberrantly express a polypeptide comprising the peptide KIFEMLEGV (SEQ ID NO: 138) wherein the patient is administered an effective number of the activated host cells. The T cells that are administered to the patient may be derived from the patient and activated as described above (i.e. they are autologous T cells). Alternatively, the T cells are not from the patient but are from another individual (i.e. they are heterologous T cells). In such instances, it is preferred if the individual is a healthy individual. By "healthy individual" the inventors mean that the individual is generally in good health, preferably has a competent immune system and, more preferably, is not suffering from any disease that can be readily tested for and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel, J. et al., Clin Cancer Res 12 (2006): 4163-4170).

Diagnostic Use

CT45 is expressed on the surface of cancers defined herein above. The CT45 antigenic peptide constitutes a cancer marker and, therefore, has the potential to be used to indicate the effectiveness of an anti-cancer therapy or detecting recurrence of the disease.

Thus, in another aspect, the invention provides the antigen binding protein of the first aspect, the nucleic acid of the second aspect, the vector of the third aspect, the host cell of the fourth aspect, or the pharmaceutical composition of the fifth aspect for use as a diagnostic agent, in particular for use as an in vivo diagnostic agent. In preferred embodiments, the diagnostic agent is for the diagnosis of a proliferative disease. In more preferred embodiments, the diagnostic agent is for the diagnosis of a cancer that presents a peptide comprising or consisting of the amino acid sequence of KIFEMLEGV (SEQ ID NO: 138) in a complex with an MHC protein, preferably wherein said cancer is selected from the group of cancers consisting of lung cancer, NSCLC, gall bladder cancer, bile duct cancer, lymph node cancer, ovarian cancer, esophageal cancer, liver cancer, uterus cancer and melanoma.

In an embodiment, the antigen binding protein of the invention is used as component of an assay in the context of a therapy targeting CT45 expressing tumours, in order to determine susceptibility of the patient to the therapeutic agent, monitor the effectiveness of the anti-cancer therapy or detect recurrence of the disease after treatment.

Thus, a further object of the invention relates to an antigen binding protein according to the invention for use for in vivo detecting CT45 expression in a subject, or for use for ex vivo or in vitro detecting CT45 expression in biological sample of a subject. Said detection may be intended in particular for
a) diagnosing the presence of a cancer in a subject, or
b) determining susceptibility of a patient having cancer to a therapeutic agent targeting CT45, or
c) monitoring effectiveness of anti-CT45 cancer therapy or detecting cancer relapse after anti-CT45 cancer therapy, in particular for therapy with an antigen binding protein according to the invention; by detecting presentation of the CT45 antigenic peptide on tumor cells.

In an embodiment, the antigen binding protein is intended for an in vitro or ex vivo use.

In still another aspect, the invention relates to an in-vitro method of detecting cancer in a biological sample comprising the steps of (a) contacting the biological sample with the antigen binding protein of the first aspect of the invention, and (b) detecting binding of the antigen binding protein to the biological sample.

Kits

Finally, the invention also provides kits comprising at least one antigen binding protein of the invention.

In one embodiment, the kit comprises
a) at least one antigen binding protein of the invention as defined herein above in the section "antigen binding proteins", a nucleic acid encoding said antigen binding protein, a vector comprising said nucleic acid, or a host cell comprising said antigen binding protein, nucleic acid and/or vector,
b) optionally packaging material, and
c) optionally a label or packaging insert contained within said packaging material indicting that said antigen binding protein is effective for treating cancer or for use for the treatment of cancer.

In preferred embodiments, the kit comprises a nucleic acid encoding the antigen binding protein of the invention, or a vector comprising this nucleic acid. The kit may further comprise instructions for regulatable expression of the antigen binding protein on the surface of a cell, preferably a T cell, T cell progenitor or NK cell, more preferably a T cell.

The kits of the present disclosure may further include any other reagents useful for regulatable expression of the antigen binding protein on the surface of a cell, preferably a T cell, T cell progenitor or NK cell, more preferably a T cell, such as transfection/transduction reagents useful for introducing the nucleic acid or expression vector into the cell.

It can also be preferred that the kit comprises a host cell comprising a nucleic acid encoding the antigen binding protein of the invention, or a vector comprising this nucleic acid, i.e. a host cell that is capable of expressing the antigen binding protein of the invention.

Components of the kits may be present in separate containers, or multiple components may be present in a single container. A suitable container includes a single tube, one or more wells of a plate (e.g., a 96-well plate, a 384-well plate, etc.), or the like.

In a related embodiment, the at least one antigen binding proteins of the invention is contained in a single and/or multi-chambered pre-filled syringes (e.g., liquid syringes and lyosyringes).

In one embodiment, the invention encompasses kits for producing a single-dose administration unit.

Accordingly, in one embodiment, the at least one antigen binding proteins of the invention as mentioned in a) of the kit of the invention is a dried antigen binding protein of the invention contained in a first container. The kit then further contains a second container having an aqueous formulation.

Accordingly, in one embodiment, the kit comprises
a) a first container comprising at least one dried antigen binding protein of the invention as defined herein above in the section "Antigen binding proteins",
b) a second container comprising an aqueous formulation;
c) optionally packaging material, and
d) optionally a label or packaging insert contained within said packaging material indicting that said antigen binding protein is for effective for treating cancer or for use for the treatment of cancer.

The aqueous formulation is typically an aqueous solution comprising pharmaceutically acceptable carriers as defined herein above in the section "pharmaceutical compositions".

In a related embodiment, the "first container" and the "second" container refer to the chambers of a multi-chambered pre-filled syringes (e.g., lyosyringes).

Throughout the instant application, the term "and/or" is a grammatical conjunction that is to be interpreted as encompassing that one or more of the cases it connects may occur. For example, the wording "such native sequence proteins can be prepared using standard recombinant and/or synthetic methods" indicates that native sequence proteins can be prepared using standard recombinant and synthetic methods or native sequence proteins can be prepared using standard recombinant methods or native sequence proteins can be prepared using synthetic methods.

Furthermore, throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Furthermore, the indefinite article "a" or "an" does not exclude a plurality. The mere fact that certain measures are recited in mutually different dependent claims does not indicate that a combination of these measures cannot be used to advantage.

The invention will now be described in more details with reference to the following figures and examples. All literature and patent documents cited herein are hereby incorporated by reference. While the invention has been illustrated and described in detail in the foregoing description, the examples are to be considered illustrative or exemplary and not restrictive.

EXAMPLES

Figure 1:
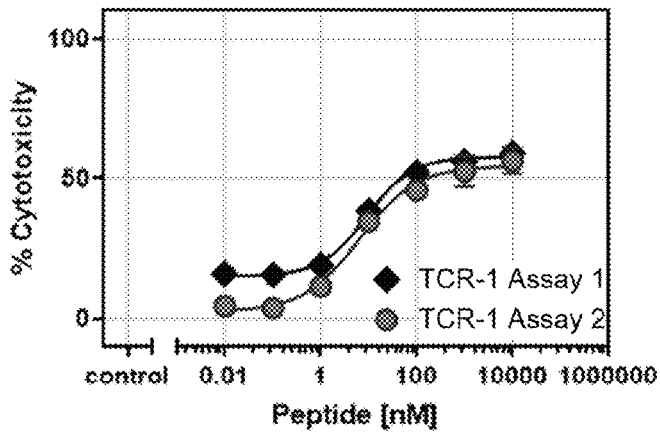
FIG. 1: Functional avidity ($EC_{50}$) measured by killing efficiency of CT45-IP peptide-loaded T2 cells by TCR-transfected T cells. Constitutively luciferase-expressing T2-cells were loaded with titrated amounts of CT45-IP peptide and then co-cultivated with CD8+ T cells transfected with specific TCRs. Killing was analyzed by measuring luciferase activity in the supernatant which is released by dying T2 cells. The assay was repeated twice with cells of two different donors (indicated by filled circles and diamond-shaped symbols). The functional avidity was assessed by calculating the half maximal killing efficiency of the tested TCRs.
Figure 1:
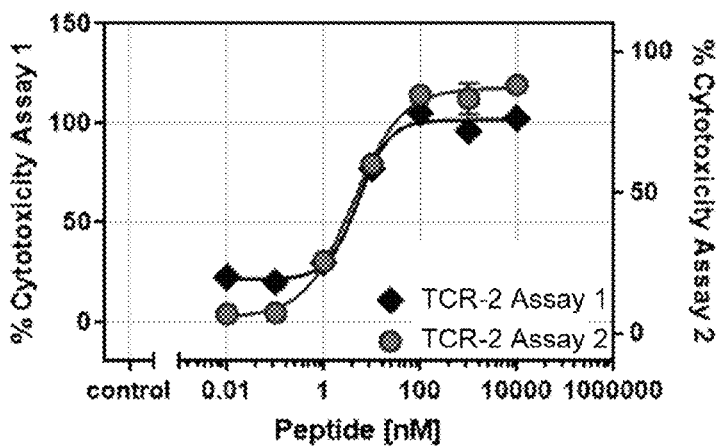
Figure 1:
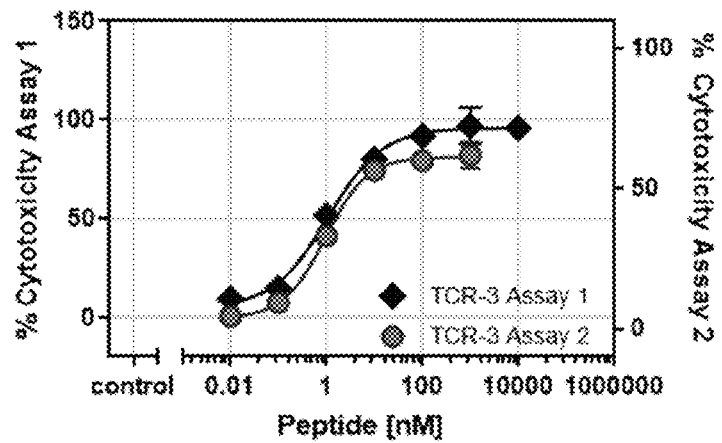
Figure 1:
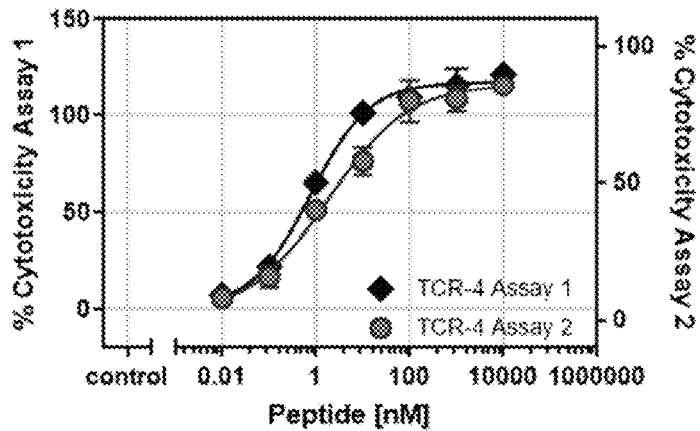
Figure 1:
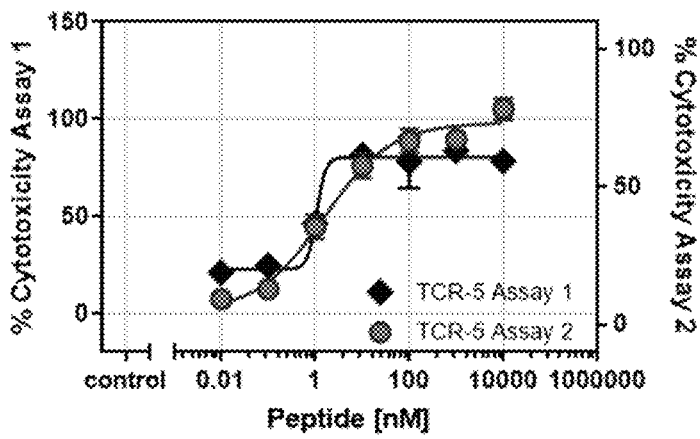
Figure 1:
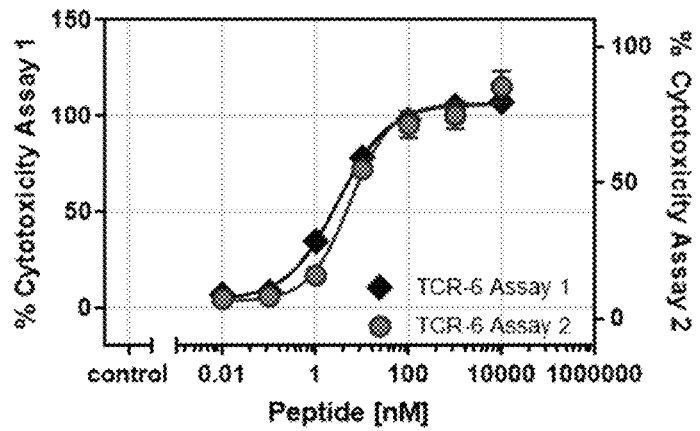
Figure 1:
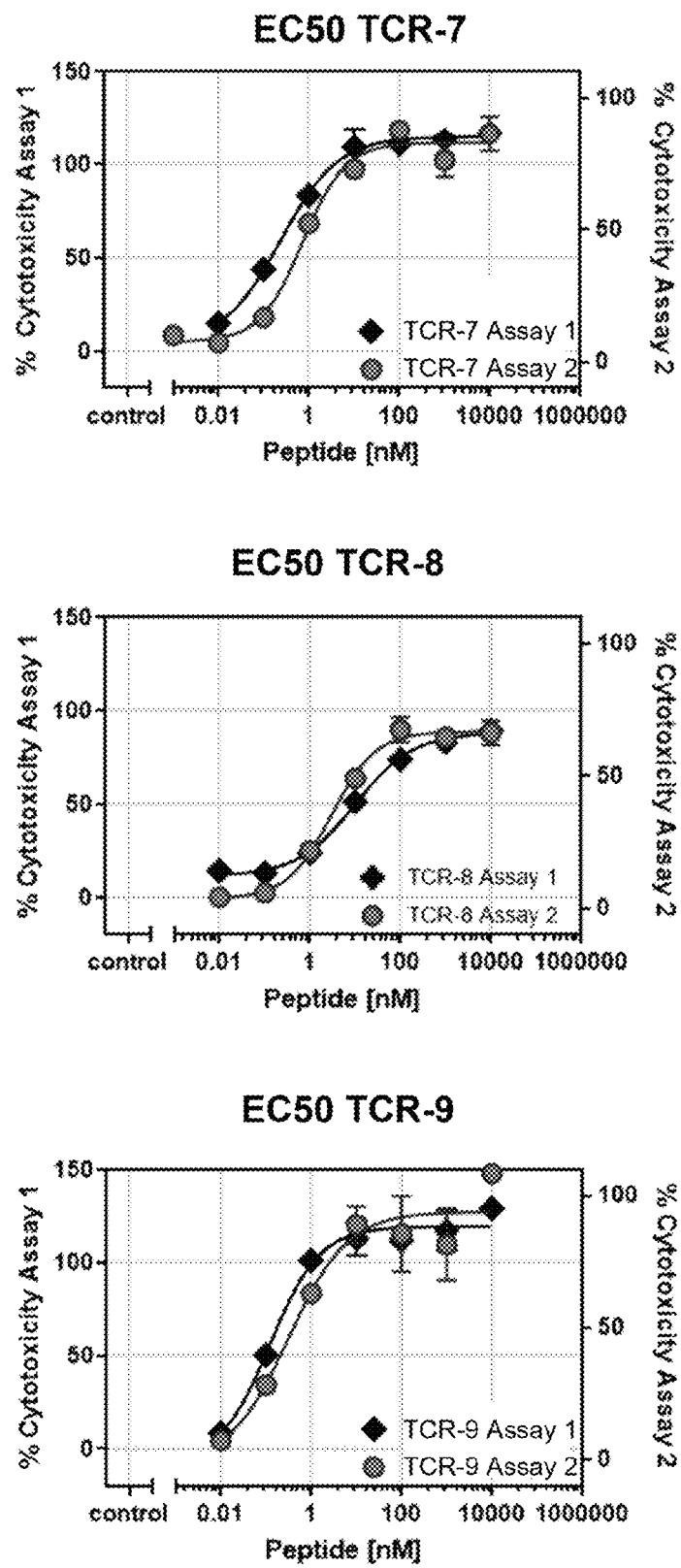
Figure 1:
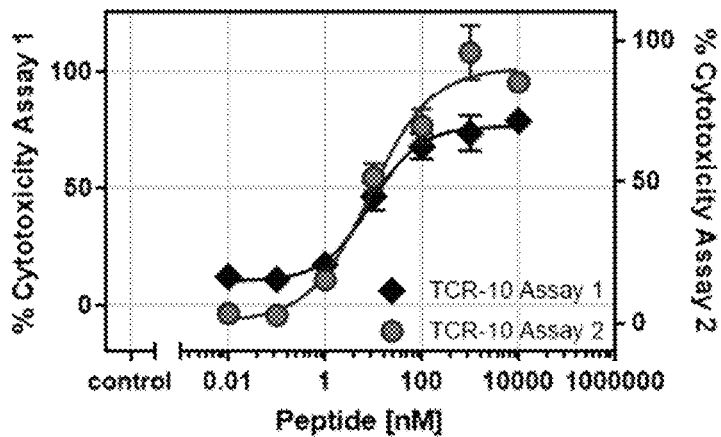
Figure 1:
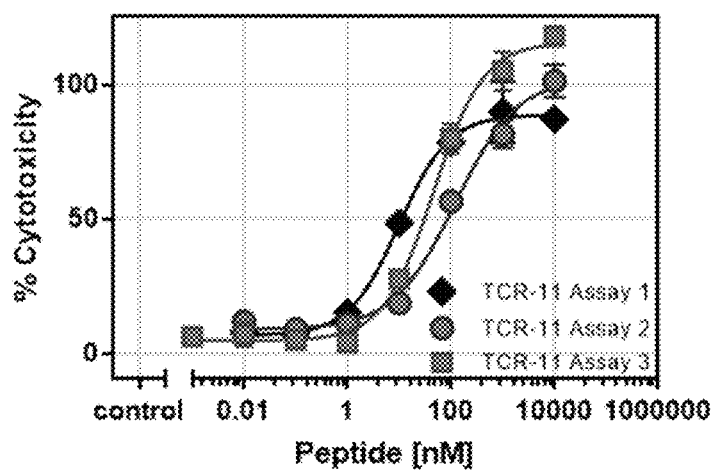
Figure 1:
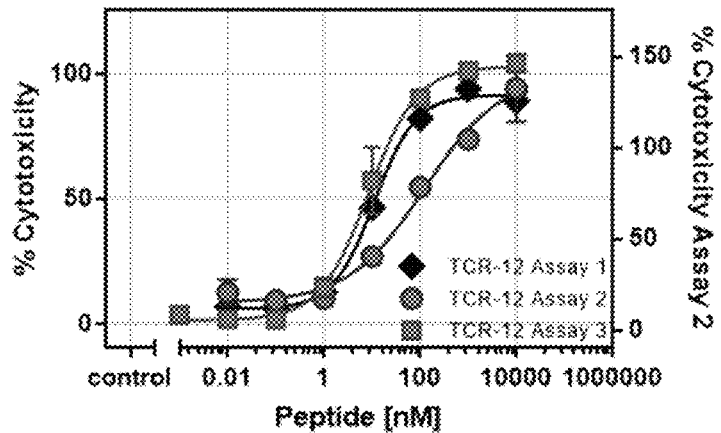
Figure 1:
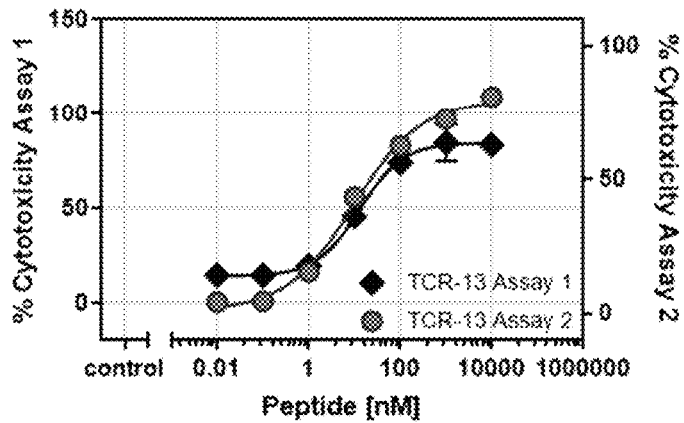
Figure 1:
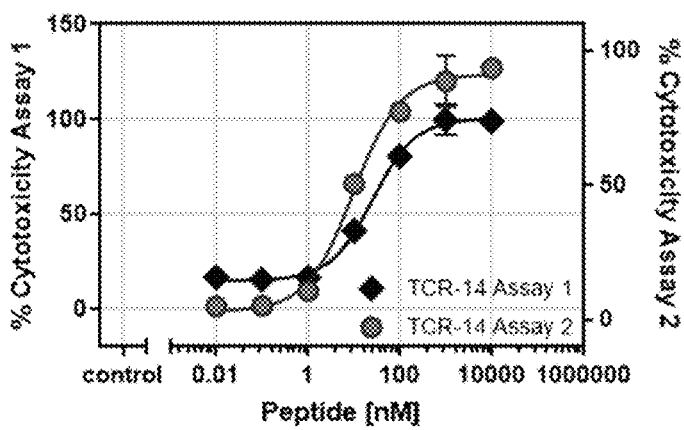
Figure 1:
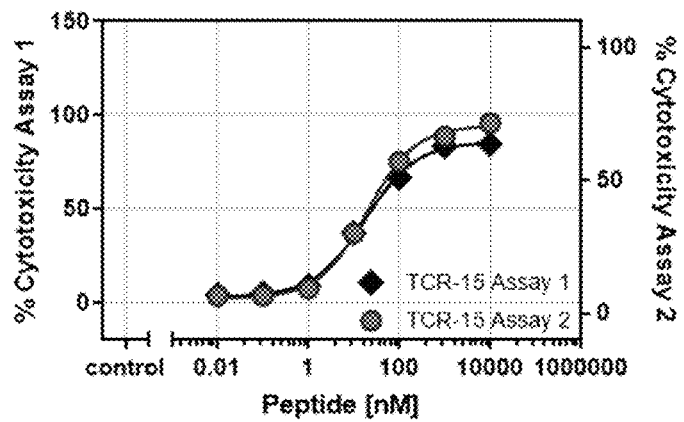

Material and Methods
TCR-Identification

The alpha and beta TCR chain sequences were isolated from T cells of healthy donors. To ensure enrichment of peptide-specific T cells, the cells were either repeatedly stimulated with artificial antigen-presenting cells coated with CT45-IP-MHC and CD28 (Priming) as described in Walter et al., 2003 J Immunol., November 15; 171(10): 4974-8 and subsequently, single-cell sorted using CT45-IP-HLA-A*02 tetramers or alternatively stimulated with CT45-IP-loaded T2 cells. After sufficient expansion, the cells were sorted using CT45-IP-HLA-A*02 tetramers.

The TCR nucleotide sequences were obtained via standard methods such as 5' RACE and Sanger sequencing as described e.g. in Molecular Cloning, Laboratory Manual, Fourth Edition by Green and Sambrook. The genes encoding the V regions and J regions of the TCRs are listed in Table 2. The annotation was performed by GeneData 11.0.1 using the IMGT/GENE-DB (Version: 28 Nov. 2019) as reference database. The TCR amino acid sequences are listed in Table 3.

TABLE 2

Identified TCRs

| ID | Valpha | Jalpha | Vbeta | Jbeta |
| --- | --- | --- | --- | --- |
| TCR-1 | TRAV38-1 | TRAJ22 | TRBV7-9 | TRBJ2-7 |
| TCR-2 | TRAV14/DV4 | TRAJ52 | TRBV13 | TRBJ1-1 |
| TCR-3 | TRAV14/DV4 | TRAJ33 | TRBV27 | TRBJ1-5 |
| TCR-4 | TRAV3 | TRAJ30 | TRBV6-2 | TRBJ2-1 |
| TCR-5 | TRAV35 | TRAJ26 | TRBV9 | TRBJ2-7 |
| TCR-6 | TRAV12-3 | TRAJ7 | TRBV4-1 | TRBJ2-1 |
| TCR-7 | TRAV38-2/DV8 | TRAJ32 | TRBV13 | TRBJ2-1 |
| TCR-8 | TRAV19 | TRAJ40 | TRBV13 | TRBJ2-1 |
| TCR-9 | TRAV5 | TRAJ17 | TRBV2 | TRBJ2-1 |
| TCR-10 | TRAV1-2 | TRAJ44 | TRBV6-1 | TRBJ2-1 |
| TCR-11 | TRAV22 | TRAJ44 | TRBV6-1 | TRBJ2-7 |
| TCR-12 | TRAV27 | TRAJ50 | TRBV4-1 | TRBJ1-2 |
| TCR-13 | TRAV14/DV4 | TRAJ5 | TRBV19 | TRBJ2-1 |
| TCR-14 | TRAV14/DV4 | TRAJ22 | TRBV11-2 | TRBJ1-6 |
| TCR-15 | TRAV21 | TRAJ37 | TRBV5-1 | TRBJ2-7 |

TABLE 3

TCR amino acid sequences

| SEQ ID NO: | TCR | Chain | Region/ Domian | Sequence |
|---|---|---|---|---|
| 1 | TCR-5 | alpha | variable domain | QQLNQSPQSMFIQEGEDVSMNCTSSSIFNTWLWYKQDPGEGP VLLIALYKAGELTSNGRLTAQFGITRKDSFLNISASIPSDVGIYFCAG GYNYGQNFVFGPGTRLSVLP |
| 2 | TCR-5 | alpha | CDR1 | SIFNT |
| 3 | TCR-5 | alpha | CDR2 | LYKAGEL |
| 4 | TCR-5 | alpha | CDR3 | AGGYNYGQNFV |
| 5 | TCR-5 | alpha | constant domain | YIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 6 | TCR-5 | alpha | full-length | QQLNQSPQSMFIQEGEDVSMNCTSSSIFNTWLWYKQDPGEGP VLLIALYKAGELTSNGRLTAQFGITRKDSFLNISASIPSDVGIYFCAG GYNYGQNFVFGPGTRLSVLPYIQNPDPAVYQLRDSKSSDKSVCLF TDFDSQTNVSQSKDSDVYITDKTVLDMRSMDFKSNSAVAWSNK SDFACANAFNNSIIPEDTFFPSPESSCDVKLVEKSFETDTNLNFQN LSVIGFRILLLKVAGFNLLMTLRLWSS |
| 7 | TCR-5 | beta | variable domain | GVTQTPKHLITATGQRVTLRCSPRSGDLSVYWYQQSLDQGLQFLI QYYNGEERAKGNILERFSAQQFPDLHSELNLSSLELGDSALYFCAS SAGLAGGYEQYFGPGTRLTVT |
| 8 | TCR-5 | beta | CDR1 | SGDLS |
| 9 | TCR-5 | beta | CDR2 | YYNGEE |
| 10 | TCR-5 | beta | CDR3 | ASSAGLAGGY EQY |
| 11 | TCR-5 | beta | constant domain | EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 12 | TCR-5 | beta | full-length | GVTQTPKHLITATGQRVTLRCSPRSGDLSVYWYQQSLDQGLQFLI QYYNGEERAKGNILERFSAQQFPDLHSELNLSSLELGDSALYFCAS SAGLAGGYEQYFGPGTRLTVTEDLKNVFPPEVAVFEPSEAEISHT QKATLVCLATGFYPDHVELSWWVNGKEVHSGVSTDPQPLKEQP ALNDSRYCLSSRLRVSATFWQNPRNHFRCQVQFYGLSENDEWT QDRAKPVTQIVSAEAWGRADCGFTSESYQQGVLSATILYEILLGK ATLYAVLVSALVLMAMVKRKDSRG |
| 13 | TCR-1 | alpha | variable domain | QTVTQSQPEM SVQEAETVTL SCTYDTSENN YYLFWYKQPP SRQMILVIRQ EAYKQQNATE NRFSVNFQKA AKSFSLKISD SQLGDTAMYF CAPLGLVAGS ARQLTFGSGT QLTVLP |
| 14 | TCR-1 | alpha | CDR1 | TSENNYY |
| 15 | TCR-1 | alpha | CDR2 | QEAYKQQN |
| 16 | TCR-1 | alpha | CDR3 | APLGLVAGSA RQLT |
| 750 | TCR-1 | alpha | constant domain | DIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 17 | TCR-1 | alpha | full-length | QTVTQSQPEM SVQEAETVTL SCTYDTSENN YYLFWYKQPP SRQMILVIRQ EAYKQQNATE NRFSVNFQKA AKSFSLKISD SQLGDTAMYF CAPLGLVAGS ARQLTFGSGT QLTVLP DIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 18 | TCR-1 | beta | variable domain | GVSQDPRHKI TKRGQNVTFR CDPISEHNRL YWYRQTLGQG PEFLTYFQNE AQLEKSRLLS DRFSAERPKG SFSTLEIQRT EQGDSAMYLC ASSTDITSYE QYFGPGTRLT VT |
| 19 | TCR-1 | beta | CDR1 | SEHNR |

TABLE 3-continued

TCR amino acid sequences

| SEQ ID NO: | TCR | Chain | Region/Domian | Sequence |
|---|---|---|---|---|
| 20 | TCR-1 | beta | CDR2 | FQNEAQ |
| 21 | TCR-1 | beta | CDR3 | ASSTDITSYE QY |
| 11 | TCR-1 | beta | constant domain | EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 22 | TCR-1 | beta | full-length | GVSQDPRHKI TKRGQNVTFR CDPISEHNRL YWYRQTLGQG PEFLTYFQNE AQLEKSRLLS DRFSAERPKG SFSTLEIQRT EQGDSAMYLC ASSTDITSYE QYFGPGTRLT VT EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 23 | TCR-14 | alpha | variable domain | QKITQTQPGM FVQEKEAVTL DCTYDTSDQS YGLFWYKQPS SGEMIFLIYQ GSYDEQNATE GRYSLNFQKA RKSANLVISA SQLGDSAMYF CAINGLPGSA RQLTFGSGTQ LTVLP |
| 24 | TCR-14 | alpha | CDR1 | TSDQSYG |
| 25 | TCR-14 | alpha | CDR2 | QGSYDEQN |
| 26 | TCR-14 | alpha | CDR3 | AINGLPGSAR QLT |
| 750 | TCR-14 | alpha | constant domain | DIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 27 | TCR-14 | alpha | full-length | QKITQTQPGM FVQEKEAVTL DCTYDTSDQS YGLFWYKQPS SGEMIFLIYQ GSYDEQNATE GRYSLNFQKA RKSANLVISA SQLGDSAMYF CAINGLPGSA RQLTFGSGTQ LTVLP DIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLLKVAGFNLLMTL RLWSS |
| 28 | TCR-14 | beta | variable domain | GVAQSPRYKI IEKRQSVAFW CNPISGHATL YWYQQILGQG PKLLIQFQNN GVVDDSQLPK DRFSAERLKG VDSTLKIQPA KLEDSAVYLC ASSRFVATGT SPLHFGNGTR LTVT |
| 29 | TCR-14 | beta | CDR1 | SGHAT |
| 30 | TCR-14 | beta | CDR2 | FQNNGV |
| 31 | TCR-14 | beta | CDR3 | ASSRFVATGT SPLH |
| 32 | TCR-14 | beta | constant domain | EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |
| 33 | TCR-14 | beta | full-length | GVAQSPRYKI IEKRQSVAFW CNPISGHATL YWYQQILGQG PKLLIQFQNN GVVDDSQLPK DRFSAERLKG VDSTLKIQPA KLEDSAVYLC ASSRFVATGT SPLHFGNGTR LTVT EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |
| 34 | TCR-13 | alpha | variable domain | QKITQTQPGM FVQEKEAVTL DCTYDTSDQS YGLFWYKQPS SGEMIFLIYQ GSYDEQNATE GRYSLNFQKA RKSANLVISA SQLGDSAMYF CAMSDPIMDT GRRALTFGSG TRLQVQP |
| 24 | TCR-13 | alpha | CDR1 | TSDQSYG |

TABLE 3-continued

TCR amino acid sequences

| SEQ ID NO: | TCR | Chain | Region/ Domian | Sequence |
|---|---|---|---|---|
| 25 | TCR-13 | alpha | CDR2 | QGSYDEQN |
| 35 | TCR-13 | alpha | CDR3 | AMSDPIMDTG RRALT |
| 751 | TCR-13 | alpha | constant domain | NIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 36 | TCR-13 | alpha | full-length | QKITQTQPGM FVQEKEAVTL DCTYDTSDQS YGLFWYKQPS SGEMIFLIYQ GSYDEQNATE GRYSLNFQKA RKSANLVISA SQLGDSAMYF CAMSDPIM DT GRRALTFGSG TRLQVQP NIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 37 | TCR-13 | beta | variable domain | GITQSPKYLF RKEGQNVTLS CEQNLNHDAM YWYRQDPGQG LRLIYYSQIV NDFQKGDIAE GYSVSREKKE SFPLTVTSAQ KNPTAFYLCA SKSRGPNLAD TQYFGPGTRL TVL |
| 38 | TCR-13 | beta | CDR1 | LNHDA |
| 39 | TCR-13 | beta | CDR2 | SQIVND |
| 40 | TCR-13 | beta | CDR3 | ASKSRGPNLA DTQY |
| 11 | TCR-13 | beta | constant domain | EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 41 | TCR-13 | beta | full-length | GITQSPKYLF RKEGQNVTLS CEQNLNHDAM YWYRQDPGQG LRLIYYSQIV NDFQKGDIAE GYSVSREKKE SFPLTVTSAQ KNPTAFYLCA SKSRGPNLAD TQYFGPGTRL TVL EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 42 | TCR-15 | alpha | variable domain | KQEVTQIPAA LSVPEGENLV LNCSFTDSAI YNLQWFRQDP GKGLTSLLLI QSSQREQTSG RLNASLDKSS GRSTLYIAAS QPGDSATYLC AVLLTGKLIF GQGTTLQVKP |
| 43 | TCR-15 | alpha | CDR1 | DSAIYN |
| 44 | TCR-15 | alpha | CDR2 | IQSSQRE |
| 45 | TCR-15 | alpha | CDR3 | AVLLTGKLI |
| 750 | TCR-15 | alpha | constant domain | DIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 46 | TCR-15 | alpha | full-length | KQEVTQIPAA LSVPEGENLV LNCSFTDSAI YNLQWFRQDP GKGLTSLLLI QSSQREQTSG RLNASLDKSS GRSTLYIAAS QPGDSATYLC AVLLTGKLIF GQGTTLQVKP DIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 47 | TCR-15 | beta | variable domain | GVTQTPRYLI KTRGQQVTLS CSPISGHRSV SWYQQTPGQG LQFLFEYFSE TQRNKGNFPG RFSGRQFSNS RSEMNVSTLE LGDSALYLCA SSGGPGPSGE QYFGPGTRLT VT |
| 48 | TCR-15 | beta | CDR1 | SGHRS |
| 49 | TCR-15 | beta | CDR2 | YFSETQ |
| 50 | TCR-15 | beta | CDR3 | ASSGGPGPSG EQY |

TABLE 3-continued

TCR amino acid sequences

| SEQ ID NO: | TCR | Chain | Region/ Domian | Sequence |
|---|---|---|---|---|
| 11 | TCR-15 | beta | constant domain | EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 51 | TCR-15 | beta | full-length | GVTQTPRYLI KTRGQQVTLS CSPISGHRSV SWYQQTPGQG LQFLFEYFSE TQRNKGNFPG RFSGRQFSNS RSEMNVSTLE LGDSALYLCA SSGGPGPSGE QYFGPGTRLT VT EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 52 | TCR-6 | alpha | variable domain | QQKEVEQDPG PLSVPEGAIV SLNCTYSNSA FQYFMWYRQY SRKGPELLMY TYSSGNKEDG RFTAQVDKSS KYISLFIRDS QPSDSATYLC AMSGNSGARD YGNNRLAFGK GNQVVVIP |
| 53 | TCR-6 | alpha | CDR1 | NSAFQY |
| 54 | TCR-6 | alpha | CDR2 | TYSSGN |
| 55 | TCR-6 | alpha | CDR3 | AMSGNSGARD YGNNRLA |
| 751 | TCR-6 | alpha | constant domain | NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 56 | TCR-6 | alpha | full-length | QQKEVEQDPG PLSVPEGAIV SLNCTYSNSA FQYFMWYRQY SRKGPELLMY TYSSGNKEDG RFTAQVDKSS KYISLFIRDS QPSDSATYLC AMSGNSGARD YGNNRLAFGK GNQVVVIP NIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 57 | TCR-6 | beta | variable domain | EVTQTPKHLV MGMTNKKSLK CEQHMGHRAM YWYKQKAKKP PELMFVYSYE KLSINESVPS RFSPECPNSS LLNLHLHALQ PEDSALYLCA SATWEEAGPY NEQFFGPGTR LTVL |
| 58 | TCR-6 | beta | CDR1 | MGHRA |
| 59 | TCR-6 | beta | CDR2 | YSYEKL |
| 60 | TCR-6 | beta | CDR3 | ASATWEEAGP YNEQF |
| 11 | TCR-6 | beta | constant domain | EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 61 | TCR-6 | beta | full-length | EVTQTPKHLV MGMTNKKSLK CEQHMGHRAM YWYKQKAKKP PELMFVYSYE KLSINESVPS RFSPECPNSS LLNLHLHALQ PEDSALYLCA SATWEEAGPY NEQFFGPGTR LTVL EDLKNVFPPEVAVFEPSEAEISHTQKATLVCLATGFYPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSESYQQGVLSATILYEILLGKATLYAVLVSALVLMAMVKRKD SRG |
| 62 | TCR-3 | alpha | variable domain | QKITQTQPGM FVQEKEAVTL DCTYDTSDQS YGLFWYKQPS SGEMIFLIYQ GSYDEQNATE GRYSLNFQKA RKSANLVISA SQLGDSAMYF CGYSNYQLIW GAGTKLIIKP |
| 24 | TCR-3 | alpha | CDR1 | TSDQSYG |
| 25 | TCR-3 | alpha | CDR2 | QGSYDEQN |
| 63 | TCR-3 | alpha | CDR3 | GYSNYQLI |

TABLE 3-continued

TCR amino acid sequences

| SEQ ID NO: | TCR | Chain | Region/ Domian | Sequence |
|---|---|---|---|---|
| 750 | TCR-3 | alpha | constant domain | DIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 64 | TCR-3 | alpha | full-length | QKITQTQPGM FVQEKEAVTL DCTYDTSDQS YGLFWYKQPS SGEMIFLIYQ GSYDEQNATE GRYSLNFQKA RKSANLVISA SQLGDSAMYF CGYSNYQLIW GAGTKLIIKP DIQNPDPAVYQLRDSKSSDKSVCLFTDFDSQTNVSQSKDSDVYIT DKWLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 65 | TCR-3 | beta | variable domain | QVTQNPRYLI TVTGKKLTVT CSQNMNHEYM SWYRQDPGLG LRQIYYSMNV EVTDKGDVPE GYKVSRKEKR NFPLILESPS PNQTSLYFCA SREGTGGYQP QHFGDGTRLS IL |
| 66 | TCR-3 | beta | CDR1 | MNHEY |
| 67 | TCR-3 | beta | CDR2 | SMNVEV |
| 68 | TCR-3 | beta | CDR3 | ASREGTGGYQ PQH |
| 32 | TCR-3 | beta | constant domain | EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |
| 69 | TCR-3 | beta | full-length | QVTQNPRYLI TVTGKKLTVT CSQNMNHEYM SWYRQDPGLG LRQIYYSMNV EVTDKGDVPE GYKVSRKEKR NFPLILESPS PNQTSLYFCA SREGTGGYQP QHFGDGTRLS IL EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |
| 70 | TCR-7 | alpha | variable domain | QTVTQSQPEM SVQEAETVTL SCTYDTSESD YYLFWYKQPP SRQMILVIRQ EAYKQQNATE NRFSVNFQKA AKSFSLKISD SQLGDAAMYF CTFRYGGATN KLIFGTGTLL AVQP |
| 71 | TCR-7 | alpha | CDR1 | TSESDYY |
| 15 | TCR-7 | alpha | CDR2 | QEAYKQQN |
| 72 | TCR-7 | alpha | CDR3 | TFRYGGATNK LI |
| 751 | TCR-7 | alpha | constant domain | NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 73 | TCR-7 | alpha | full-length | QTVTQSQPEM SVQEAETVTL SCTYDTSESD YYLFWYKQPP SRQMILVIRQ EAYKQQNATE NRFSVNFQKA AKSFSLKISD SQLGDAAMYF CTFRYGGATN KLIFGTGTLL AVQP NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 74 | TCR-7 | beta | variable domain | GVIQSPRHLI KEKRETATLK CYPIPRHDTV YWYQQGPGQD PQFLISFYEK MQSDKGSIPD RFSAQQFSDY HSELNMSSLE LGDSALYFCA SRGGWAETPD TQYFGPGTRL TVL |
| 75 | TCR-7 | beta | CDR1 | PRHDT |
| 76 | TCR-7 | beta | CDR2 | FYEKMQ |
| 77 | TCR-7 | beta | CDR3 | ASRGGWAETP DTQY |
| 11 | TCR-7 | beta | constant domain | EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI |

TABLE 3-continued

TCR amino acid sequences

| SEQ ID NO: | TCR | Chain | Region/ Domian | Sequence |
|---|---|---|---|---|
| | | | | VSAEAWGRAD CGFTSESYQQ GVLSATILYE ILLGKATLYA VLVSALVLMA MVKRKDSRG |
| 78 | TCR-7 | beta | full-length | GVIQSPRHLI KEKRETATLK CYPIPRHDTV YWYQQGPGQD PQFLISFYEK MQSDKGSIPD RFSAQQFSDY HSELNMSSLE LGDSALYFCA SRGGWAETPD TQYFGPGTRL TVL EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 79 | TCR-9 | alpha | variable domain | EDVEQSLFLS VREGDSSVIN CTYTDSSSTY LYWYKQEPGA GLQLLTYIFS NMDMKQDQRL TVLLNKKDKH LSLRIADTQT GDSAIYFCAE KETAGNKLTF GGGTRVLVKP |
| 80 | TCR-9 | alpha | CDR1 | DSSSTY |
| 81 | TCR-9 | alpha | CDR2 | IFSNMDM |
| 82 | TCR-9 | alpha | CDR3 | AEKETAGNKL T |
| 751 | TCR-9 | alpha | constant domain | NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 83 | TCR-9 | alpha | full-length | EDVEQSLFLS VREGDSSVIN CTYTDSSSTY LYWYKQEPGA GLQLLTYIFS NMDMKQDQRL TVLLNKKDKH LSLRIADTQT GDSAIYFCAE KETAGNKLTF GGGTRVLVKP NIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLLKVAGFNLLMTL RLWSS |
| 84 | TCR-9 | beta | variable domain | EPEVTQTPSH QVTQMGQEVI LRCVPISNHL YFYWYRQILG QKVEFLVSFY NNEISEKSEI FDDQFSVERP DGSNFTLKIR STKLEDSAMY FCASTVQSPR TNEQFFGPGT RLTVL |
| 85 | TCR-9 | beta | CDR1 | SNHLY |
| 86 | TCR-9 | beta | CDR2 | FYNNEI |
| 87 | TCR-9 | beta | CDR3 | ASTVQSPRTN EQF |
| 11 | TCR-9 | beta | constant domain | EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 88 | TCR-9 | beta | full-length | EPEVTQTPSH QVTQMGQEVI LRCVPISNHL YFYWYRQILG QKVEFLVSFY NNEISEKSEI FDDQFSVERP DGSNFTLKIR STKLEDSAMY FCASTVQSPR TNEQFFGPGT RLTVL EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 89 | TCR-4 | alpha | variable domain | QSVAQPEDQV NVAEGNPLIV KCTYSVSGNP YLFWYVQYPN RGLQFLLKYI TGDNLVKGSY GFEAEFNKSQ TSFHLKKPSA LVSDSALYFC AAPRDDKIIF GKGTRLHILP |
| 90 | TCR-4 | alpha | CDR1 | VSGNPY |
| 91 | TCR-4 | alpha | CDR2 | YITGDNLV |
| 92 | TCR-4 | alpha | CDR3 | AAPRDDKII |
| 751 | TCR-4 | alpha | constant domain | NIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLLKVAGFNLLMTL RLWSS |

TABLE 3-continued

TCR amino acid sequences

| SEQ ID NO: | TCR | Chain | Region/Domian | Sequence |
|---|---|---|---|---|
| 93 | TCR-4 | alpha | full-length | QSVAQPEDQV NVAEGNPLIV KCTYSVSGNP YLFWYVQYPN RGLQFLLKYI TGDNLVKGSY GFEAEFNKSQTSFHLKKPSA LVSDSALYFC AAPRDDKIIF GKGTRLHILP NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 94 | TCR-4 | beta | variable domain | GVTQTPKFRV LKTGQSMTLL CAQDMNHEYM YWYRQDPGMG LRLIHYSVGE GTTAKGEVPD GYNVSRLKKQ NFLLGLESAA PSQTSVYFCA SSYLRTGGNE QFFGPGTRLT VL |
| 66 | TCR-4 | beta | CDR1 | MNHEY |
| 95 | TCR-4 | beta | CDR2 | SVGEGT |
| 96 | TCR-4 | beta | CDR3 | ASSYLRTGGN EQF |
| 11 | TCR-4 | beta | constant domain | EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 97 | TCR-4 | beta | full-length | GVTQTPKFRV LKTGQSMTLL CAQDMNHEYM YWYRQDPGMG LRLIHYSVGE GTTAKGEVPD GYNVSRLKKQ NFLLGLESAA PSQTSVYFCA SSYLRTGGNE QFFGPGTRLT VL EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 98 | TCR-8 | alpha | variable domain | QKVTQAQTEI SVVEKEDVTL DCVYETRDTT YYLFWYKQPP SGELVFLIRR NSFDEQNEIS GRYSWNFQKS TSSFNFTITA SQVVDSAVYF CALSGRGSGT YKYIFGTGTR LKVLA |
| 99 | TCR-8 | alpha | CDR1 | TRDTTYY |
| 100 | TCR-8 | alpha | CDR2 | RNSFDEQN |
| 101 | TCR-8 | alpha | CDR3 | ALSGRGSGTY KYI |
| 751 | TCR-8 | alpha | constant domain | NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 102 | TCR-8 | alpha | full-length | QKVTQAQTEI SVVEKEDVTL DCVYETRDTT YYLFWYKQPP SGELVFLIRR NSFDEQNEIS GRYSWNFQKS TSSFNFTITA SQVVDSAVYF CALSGRGSGT YKYIFGTGTR LKVLA NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 103 | TCR-8 | beta | variable domain | GVIQSPRHLI KEKRETATLK CYPIPRHDTV YWYQQGPGQD PQFLISFYEK MQSDKGSIPD RFSAQQFSDY HSELNMSSLE LGDSALYFCA SSAGTSYNEQ FFGPGTRLTV L |
| 75 | TCR-8 | beta | CDR1 | PRHDT |
| 76 | TCR-8 | beta | CDR2 | FYEKMQ |
| 104 | TCR-8 | beta | CDR3 | ASSAGTSYNE QF |
| 11 | TCR-8 | beta | constant domain | EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |

TABLE 3-continued

TCR amino acid sequences

| SEQ ID NO: | TCR | Chain | Region/ Domian | Sequence |
|---|---|---|---|---|
| 105 | TCR-8 | beta | full-length | GVIQSPRHLI KEKRETATLK CYPIPRHDTV YWYQQGPGQD PQFLISFYEK MQSDKGSIPD RFSAQQFSDY HSELNMSSLE LGDSALYFCA SSAGTSYNEQ FFGPGTRLIV L EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 106 | TCR-10 | alpha | variable domain | QNIDQPTEMT ATEGAIVQIN CTYQTSGFNG LFWYQQHAGE APTFLSYNVL DGLEEKGRFS SFLSRSKGYS YLLLKELQMK DSASYLCAVP APYTGTASKL TFGTGTRLQV TL |
| 107 | TCR-10 | alpha | CDR1 | TSGFNG |
| 108 | TCR-10 | alpha | CDR2 | NVLDGL |
| 109 | TCR-10 | alpha | CDR3 | AVPAPYTGTA SKLT |
| 750 | TCR-10 | alpha | constant domain | DIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 110 | TCR-10 | alpha | full-length | QNIDQPTEMT ATEGAIVQIN CTYQTSGFNG LFWYQQHAGE APTFLSYNVL DGLEEKGRFS SFLSRSKGYS YLLLKELQMK DSASYLCAVP APYTGTASKL TFGTGTRLQV TL DIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 111 | TCR-10 | beta | variable domain | GVTQTPKFQV LKTGQSMTLQ CAQDMNHNSM YWYRQDPGMG LRLIYYSASE GTTDKGEVPN GYNVSRLNKR EFSLRLESAA PSQTSVYFCA SSEGYSTYNE QFFGPGTRLT VL |
| 112 | TCR-10 | beta | CDR1 | MNHNS |
| 113 | TCR-10 | beta | CDR2 | SASEGT |
| 114 | TCR-10 | beta | CDR3 | ASSEGYSTYN EQF |
| 11 | TCR-10 | beta | constant domain | EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 115 | TCR-10 | beta | full-length | GVTQTPKFQV LKTGQSMTLQ CAQDMNHNSM YWYRQDPGMG LRLIYYSASE GTTDKGEVPN GYNVSRLNKR EFSLRLESAA PSQTSVYFCA SSEGYSTYNE QFFGPGTRLT VL EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 116 | TCR-12 | alpha | variable domain | QLLEQSPQFL SIQEGENLTV YCNSSSVFSS LQWYRQEPGE GPVLLVTVVT GGEVKKLKRL TFQFGDARKD SSLHITAAQP GDTGLYLCAG GLSDSYDKVI FGPGTSLSVI P |
| 117 | TCR-12 | alpha | CDR1 | SVFSS |
| 118 | TCR-12 | alpha | CDR2 | VVTGGEV |
| 119 | TCR-12 | alpha | CDR3 | AGGLSDSYDK VI |
| 751 | TCR-12 | alpha | constant domain | NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |

TABLE 3-continued

TCR amino acid sequences

| SEQ ID NO: | TCR | Chain | Region/ Domian | Sequence |
|---|---|---|---|---|
| 120 | TCR-12 | alpha | full-length | QLLEQSPQFL SIQEGENLTV YCNSSSVFSS LQWYRQEPGE GPVLLVTVVT GGEVKKLKRL TFQFGDARKD SSLHITAAQP GDTGLYLCAG GLSDSYDKVI FGPGTSLSVI P NIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 121 | TCR-12 | beta | variable domain | EVTQTPKHLV MGMTNKKSLK CEQHMGHRAM YWYKQKAKKP PELMFVYSYE KLSINESVPS RFSPECPNSS LLNLHLHALQ PEDSALYLCA SSQGVGQEYG YTFGSGTRLT VV |
| 58 | TCR-12 | beta | CDR1 | MGHRA |
| 59 | TCR-12 | beta | CDR2 | YSYEKL |
| 122 | TCR-12 | beta | CDR3 | ASSQGVGQEY GYT |
| 32 | TCR-12 | beta | constant domain | EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |
| 123 | TCR-12 | beta | full-length | EVTQTPKHLV MGMTNKKSLK CEQHMGHRAM YWYKQKAKKP PELMFVYSYE KLSINESVPS RFSPECPNSS LLNLHLHALQ PEDSALYLCA SSQGVGQEYG YTFGSGTRLT VV EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |
| 124 | TCR-11 | alpha | variable domain | IQVEQSPPDL ILQEGANSTL RCNFSDSVNN LQWFHQNPWG QLINLFYIPS GTKQNGRLSA TTVATERYSL LYISSSQTTD SGVYFCAVNT GTASKLTFGT GTRLQVTL |
| 125 | TCR-11 | alpha | CDR1 | DSVNN |
| 126 | TCR-11 | alpha | CDR2 | IPSGT |
| 127 | TCR-11 | alpha | CDR3 | AVNTGTASKL T |
| 750 | TCR-11 | alpha | constant domain | DIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 128 | TCR-11 | alpha | full-length | IQVEQSPPDL ILQEGANSTL RCNFSDSVNN LQWFHQNPWG QLINLFYIPS GTKQNGRLSA TTVATERYSL LYISSSQTTD SGVYFCAVNT GTASKLTFGT GTRLQVTL DIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 129 | TCR-11 | beta | variable domain | GVTQTPKFQV LKTGQSMTLQ CAQDMNHNSM YWYRQDPGMG LRLIYYSASE GTTDKGEVPN GYNVSRLNKR EFSLRLESAA PSQTSVYFCA SSPRGQGRSY EQYFGPGTRL TVT |
| 112 | TCR-11 | beta | CDR1 | MNHNS |
| 113 | TCR-11 | beta | CDR2 | SASEGT |
| 130 | TCR-11 | beta | CDR3 | ASSPRGQGRS YEQY |
| 11 | TCR-11 | beta | constant domain | EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |

TABLE 3-continued

TCR amino acid sequences

| SEQ ID NO: | TCR | Chain | Region/ Domian | Sequence |
|---|---|---|---|---|
| 131 | TCR-11 | beta | full-length | GVTQTPKFQV LKTGQSMTLQ CAQDMNHNSM YWYRQDPGMG LRLIYYSASE GTTDKGEVPN GYNVSRLNKR EFSLRLESAA PSQTSVYFCA SSPRGQGRSY EQYFGPGTRL TVT EDLKNVFPPE VAVFEPSEAE ISHTQKATLV CLATGFYPDH VELSWWVNGK EVHSGVSTDP QPLKEQPALN DSRYCLSSRL RVSATFWQNP RNHFRCQVQF YGLSENDEWT QDRAKPVTQI VSAEAWGRAD CGFTSESYQQ GVLSATILYE ILLGKATLYA VLVSALVLMA MVKRKDSRG |
| 132 | TCR-2 | alpha | variable domain | QKITQTQPGM FVQEKEAVTL DCTYDTSDQS YGLFWYKQPS SGEMIFLIYQ GSYDEQNATE GRYSLNFQKA RKSANLVISA SQLGDSAMYF CAMREGSDAG GTSYGKLTFG QGTILTVHP |
| 24 | TCR-2 | alpha | CDR1 | TSDQSYG |
| 25 | TCR-2 | alpha | CDR2 | QGSYDEQN |
| 133 | TCR-2 | alpha | CDR3 | AMREGSDAGG TSYGKLT |
| 751 | TCR-2 | alpha | constant domain | NIQNPDPAVYQLRDSKSSDKSVCLFTDFDSQTNVSQSKDSDVYIT DKTVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 134 | TCR-2 | alpha | full-length | QKITQTQPGM FVQEKEAVTL DCTYDTSDQS YGLFWYKQPS SGEMIFLIYQ GSYDEQNATE GRYSLNFQKA RKSANLVISA SQLGDSAMYF CAMREGSDAG GTSYGKLTFG QGTILIVHP NIQNPDPAVYQLRDSKSSDKSVCLFTDFDSQTNVSQSKDSDVYIT DKIVLDMRSMDFKSNSAVAWSNKSDFACANAFNNSIIPEDTFFP SPESSCDVKLVEKSFETDTNLNFQNLSVIGFRILLLKVAGFNLLMTL RLWSS |
| 135 | TCR-2 | beta | variable domain | GVIQSPRHLI KEKRETATLK CYPIPRHDTV YWYQQGPGQD PQFLISFYEK MQSDKGSIPD RFSAQQFSDY HSELNMSSLE LGDSALYFCA SSPSTGRLNT EAFFGQGTRL TVV |
| 75 | TCR-2 | beta | CDR1 | PRHDT |
| 76 | TCR-2 | beta | CDR2 | FYEKMQ |
| 136 | TCR-2 | beta | CDR3 | ASSPSTGRLN TEAF |
| 32 | TCR-2 | beta | constant domain | EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |
| 137 | TCR-2 | beta | full-length | GVIQSPRHLI KEKRETATLK CYPIPRHDTV YWYQQGPGQD PQFLISFYEK MQSDKGSIPD RFSAQQFSDY HSELNMSSLE LGDSALYFCA SSPSTGRLNT EAFFGQGTRL TVV EDLNKVFPPEVAVFEPSEAEISHTQKATLVCLATGFFPDHVELSW WVNGKEVHSGVSTDPQPLKEQPALNDSRYCLSSRLRVSATFWQ NPRNHFRCQVQFYGLSENDEWTQDRAKPVTQIVSAEAWGRAD CGFTSVSYQQGVLSATILYEILLGKATLYAVLVSALVLMAMVKRKD F |

Re-Expression of TCRs

The human constant chain domains were exchanged by their murine counterparts with additional mutations in the transmembrane domain to enhance hydrophobicity. Both modifications are described in Jin et al., JCI Insight. 2018; 3(8):e99488.

In order to assess their functional characteristics, the identified TCRs were re-expressed in primary T cells of healthy donors using TCR mRNA electroporation technique. In brief, a T7 transcription was performed on DNA templates of the TCR alpha and beta chain nucleotide sequence. The resulting TCR mRNA was used for electroporation of pre-activated T cells for transient expression of the exogenous TCR which was validated in co-culture experiments.

Co-Culture Assays (Assessment of Functional Avidity, Specificity, and TCR-Motif)

The functional characteristics of the TCRs were assessed in co-culture experiments with T2 cells. CD8+ T cells were pre-stimulated and electroporated with TCR mRNA. At the day of co-culture, luciferase-transduced T2 cells were either loaded with peptide CT45-IP (SEQ ID NO: 138) at different concentrations (assessment of functional avidity, $EC_{50}$), with sequence similar peptides (SEQ ID NO: 146-155) at a concentration of 10 µM or with alanine-substitution variants of the CT45-IP peptide (SEQ ID NO: 139-145) at a concentration range of 10-30 fold above the average $EC_{50}$ of the respective TCR (TCR-motif determination). As control the irrelevant peptide NYESO1-001 (SEQ ID NO: 188) at a concentration of 10 µM and unloaded T2 cells were used. In brief, T2 cells were incubated for 2 hours with the respective amount of peptide and subsequently washed and harvested.

Cells electroporated with the model TCR 1G4-a95Ly as well as mock-electroporated T cells without exogenous TCR served as control. T cells and peptide-loaded T2 cells were seeded at a ratio of 1:1 and incubated for 24 h until supernatant harvest. Supernatants were subjected to an analysis for the presence of luciferase, released by apoptotic/necrotic T2 cells, killed by peptide-specific T cells. By adding specific substrate, the amount of luciferase present in the supernatant was determined by measuring the chemiluminescent signal in a microplate reader.

Test for Functionality in CD4+ T Cells

CD3+ T cells were stimulated and electroporated with TCR mRNA. After overnight incubation, the TCR-transfected T cells were co-cultivated at a 1:1 ratio with T2 cells loaded either with 10 µM CT45-IP (SEQ ID NO: 138) or 10 µM irrelevant NYESO1-001 (SEQ ID NO: 188) peptide. Directly after start of co-culture a cytokine secretion blocking reagent was added and incubated for 5 h at 37° C. Afterwards, the T cells were stained with fluorescently labeled antibodies for different surface markers such as CD4 and CD8. After fixation and permeabilization, the cells were stained for intracellular cytokines (TNF-α and IFN-γ) and analyzed on a flow cytometer (data not shown).

Lentiviral Co-Transduction of the Co-Stimulatory Molecule CD8

In order to engage CD4 T cells in the immune response after transduction with the MHC class I-restricted TCRs, a co-transduction with the co-stimulatory molecule CD8 was conducted. For that purpose, a lentiviral vector encoding the TCR chains as well as the CD8 molecule was used for transduction of pre-stimulated CD3+ T cells. The T cells were activated using plate-coated CD3 and anti-CD28 together with addition of IL-2 for 24 h. Pre-titrated concentrated lentiviral supernatant was added to the cells together with an adjuvant for transduction enhancement of lentivirus particles, e.g., Lentiboost® reagent (Sirion Biotech). The T cells were expanded over the course of 10 days using increasing volumes of media and decreasing concentration of IL-2 while transferring the cells consecutively into larger cell culture flasks. Transduction efficiency and resting state of T cells was checked prior to freezing of cells via flow cytometry. Subsequently, the effect of CD8 co-transfection on the killing efficiency against CT45-IP presenting tumor cells was analyzed in a live-cell monitoring killing assay (data not shown).

TCR Surface-Staining

A surface marker staining was performed with electroporated and pre-activated CD8+ T cells. To this end, anti-CD8, CD3 and/or mTCRB antibodies were used as well as TCR staining with fluorescently labeled Dextramers (dextramer backbone with conjugated CT45-IP-HLA-A*02 or irrelevant NYESO1-001-HLA-A*02). After 30 minutes cells were washed, fixed and subsequently analyzed by flow cytometry. Gates, to define dextramer-positive cells, were set according to the signal of cells stained with irrelevant peptide-MHC dextramer.

Live-Cell Monitoring Killing Assays

Proliferation of tumor cell lines expressing red fluorescent protein (RFP) was monitored using a live cell imaging system by quantifying red object counts over time. The cell lines NCIH1703 and A375 were co-cultivated with T cells expressing TCRs of the invention at an E:T ratio of 9:1, 3:1 or 1:1 or without T cells and monitored over a period of 48 h. As positive control, target cells were loaded with 10 µM of peptide CT45-IP. Decline of tumor cell line proliferation over time is an indicator for tumor cell killing.

Example 1: Functional Avidity

All fifteen identified CT45-IP-specific TCRs show high functional avidity as measured by peptide titration experiments which is expressed as half maximal killing capacity $EC_{50}$ shown in FIG. 1. The measured $EC_{50}$ values range from 0.15 nM to 59.5 nM. In particular the $EC_{50}$ values are 7.78 nM (TCR-1); 4.69 nM (TCR-2); 1.02 nM (TCR-3); 1.31 nM (TCR-4); 1.32 nM (TCR-5); 3.25 nM (TCR-6); 0.48 nM (TCR-7); 6.52 nM (TCR-8); 0.15 nM (TCR-9); 8.75 nM (TCR-10); 59.50 nM (TCR-11); 47.47 nM (TCR-12); 11.38 nM (TCR-13); 17.69 nM (TCR-14); 18.60 nM (TCR-15).

Example 2: Specificity and TCR-Motif

Figure 2:
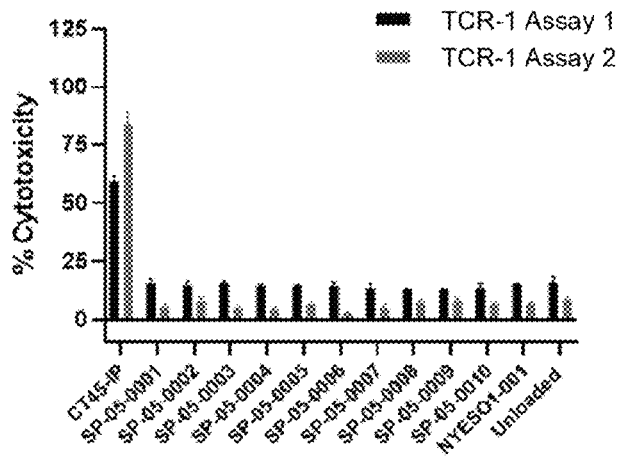
FIG. 2: Cross-reactivity check for sequence similar-peptides. Constitutively luciferase-expressing T2-cells were loaded with CT45-IP peptide, 10 different sequence-similar peptides, the irrelevant peptide control NYESO1-001 at a concentration of 10 µM per peptide or not loaded, respectively. Those T2 cell were then co-cultivated with CD8+ T cells transfected with specific TCRs. Killing was analyzed by measuring luciferase activity in the supernatant which is released by dying T2 cells. The assay was repeated twice with cells of two different donors (black bars=assay 1, donor 1; red bars=assay 2, donor 2).
Figure 2:
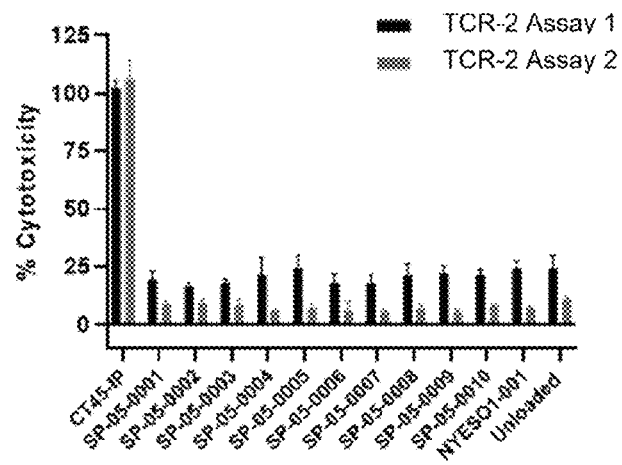
Figure 2:
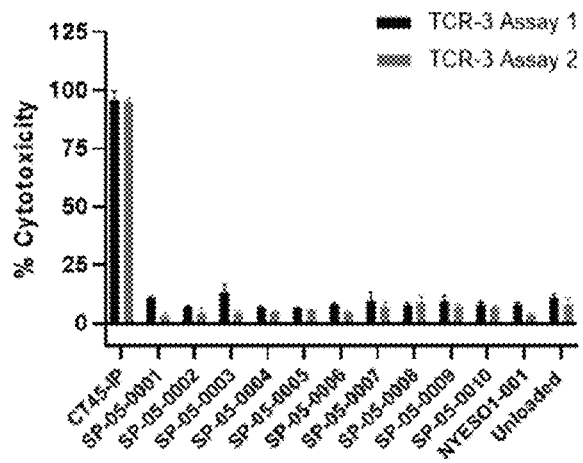
Figure 2:
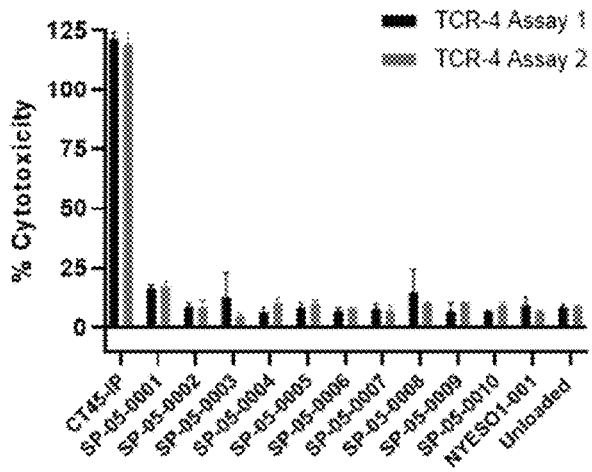
Figure 2:
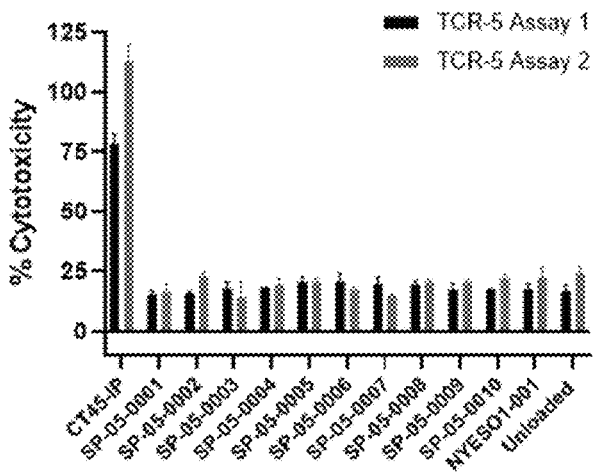
Figure 2:
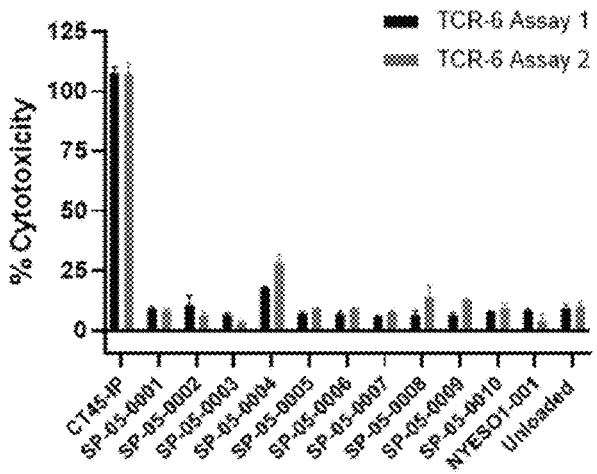
Figure 2:
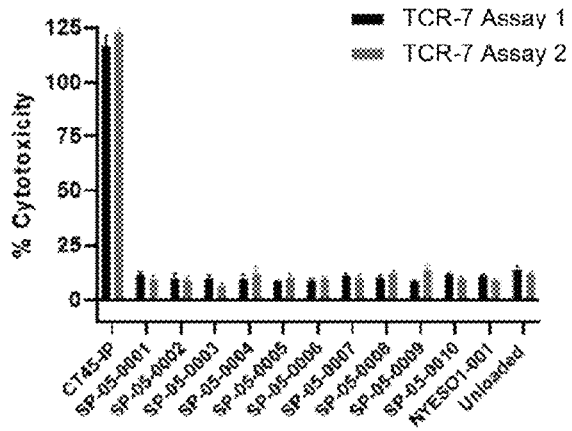
Figure 2:
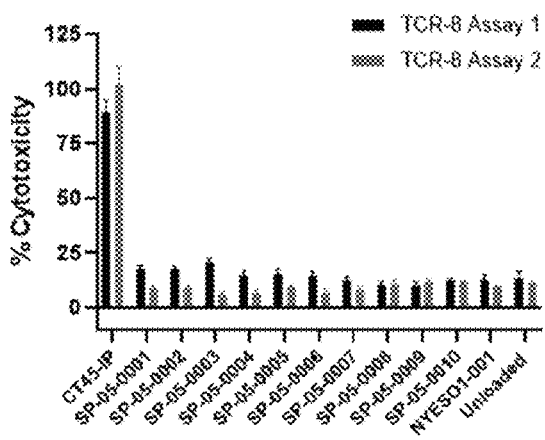
Figure 2:
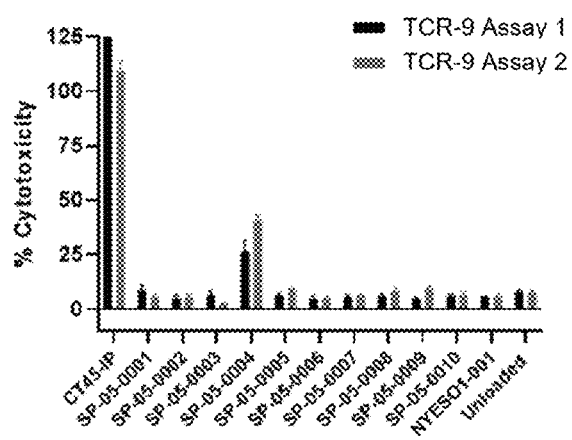
Figure 2:
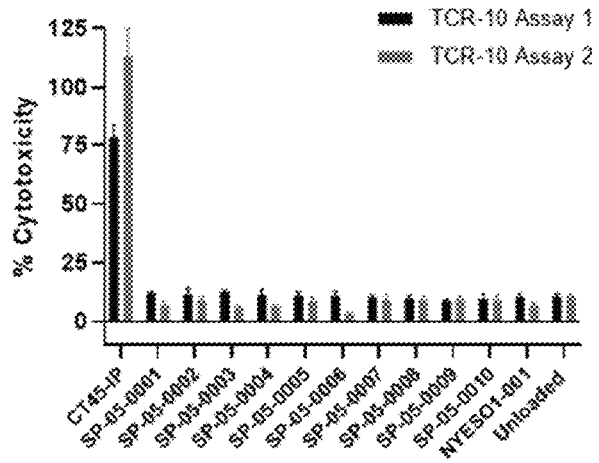
Figure 2:
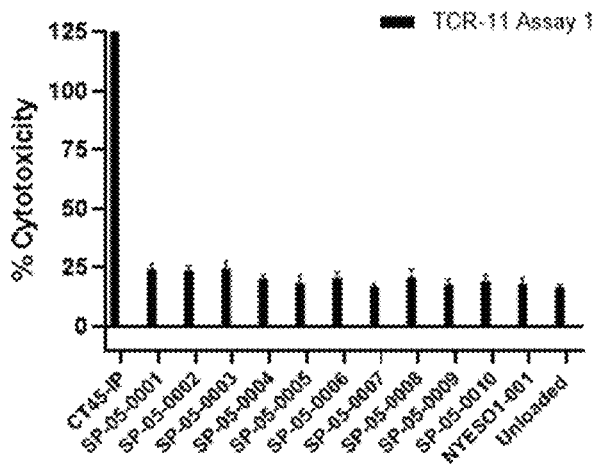
Figure 2:
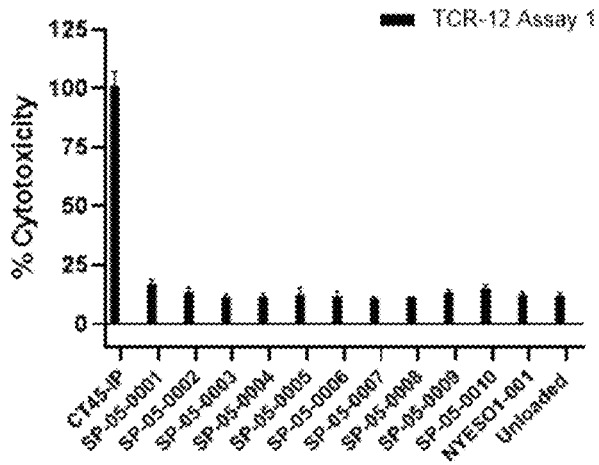
Figure 2:
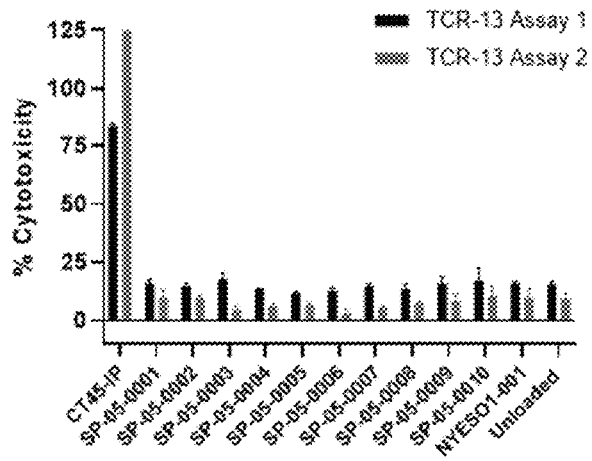
Figure 2:
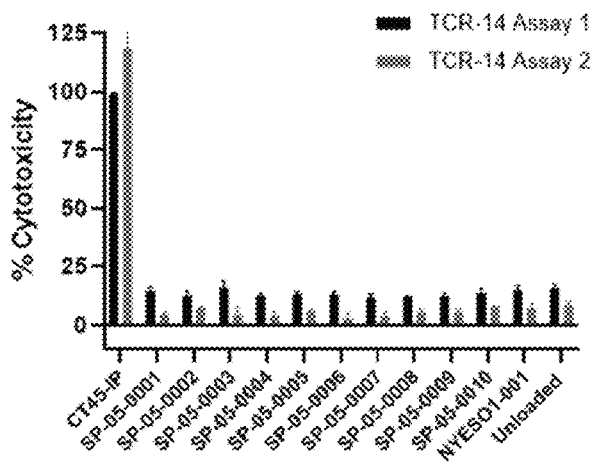
Figure 2:
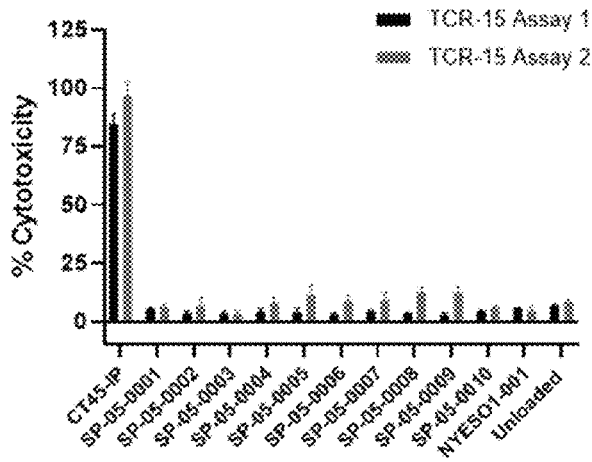

The herein described TCRs were tested for their specificity profiles by testing their ability to recognize 10 CT45-IP sequence-similar peptides (SEQ ID NOs: 146-155). Loading with CT45-IP and CT45-IP sequence-similar peptides occurred at a very high concentration of 10 µM, to detect low signals. TCRs showed no binding to another peptide except CT45-IP. Minor binding signals were detected for TCR-9 and TCR-6 to peptide SP-05-0004 (SEQ ID NO: 149) as depicted in FIG. 2. The TCR characterization also involved the determination of the TCR binding motif to CT45-IP peptide as listed in Table 4. For this purpose, CT45-IP alanine exchange peptide variants (SEQ ID NO: 139-145) were tested in co-culture experiments with all fifteen TCRs. Alanine exchange peptides were tested at a concentration range of 10-30 fold above the average $EC_{50}$ of the respective TCR. A relevant position is indicated by a number (referring to the position of the amino acid in the peptide), a non-relevant position is represented by a hyphen, and a position that was not tested is marked by an x.

TABLE 4

| Consensus motif | |
| --- | --- |
| ID | Consensus motif |
| TCR-1 | 1x34567-x |
| TCR-2 | -x3(4)567-x |
| TCR-3 | -x34567-x |
| TCR-4 | -x34-678x |
| TCR-5 | -x3--67(8)x |
| TCR-6 | 1x34-6--x |
| TCR-7 | 1x-4-67-x |
| TCR-8 | -x---5-7-x |
| TCR-9 | 1x34567(8)x |
| TCR-10 | -x--567-x |
| TCR-11 | 1x3456-8x |
| TCR-12 | -x34-67-x |
| TCR-13 | 1x34-67-x |
| TCR-14 | 1x345---x |
| TCR-15 | 1x34567-x |

Example 3: CD4-Functionality

A test for functionality in CD4+ T cells was performed as described above. Among the fifteen tested TCRs, the inventors identified TCRs, which show functionality in CD8+ T cells as well as CD4+ T cells (data not shown).

Example 4: Surface Expression

Figure 3:
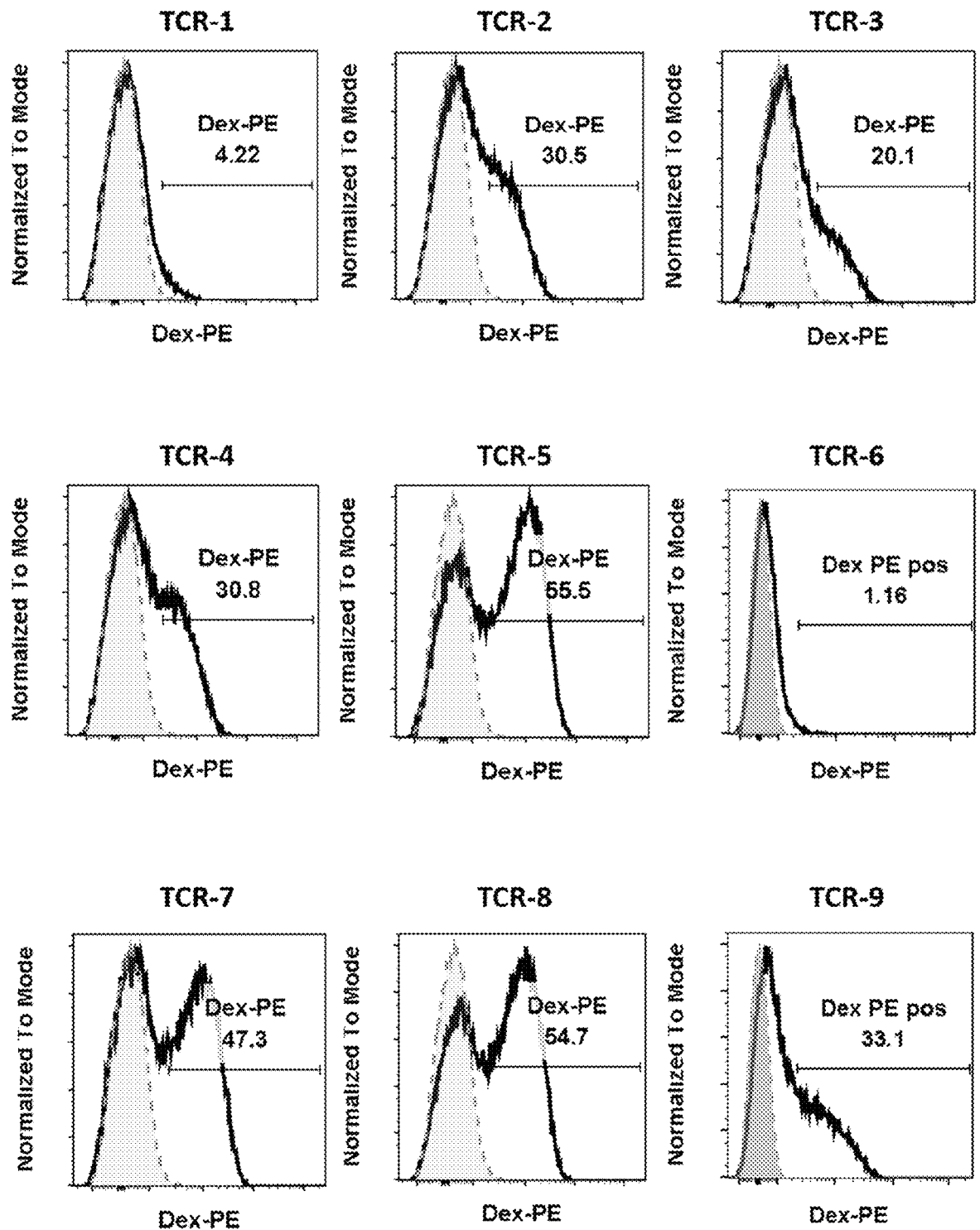
FIG. 3: TCR surface-staining. Flow-cytometric assessment of TCR expression measured by pHLA-Dextramer-binding. Histograms show TCR-mRNA electroporated T cells (black line) and the Mock-TCR control (light grey dotted line) after staining with CT45-IP-HLA-A2*02 dextramers. Percent positive events are indicated in the plots. The Mock-TCR control is used as reference for the dextramer-negative area.

The surface expression of the herein described TCRs was measured by CT45-IP-HLA-A2*02 dextramer staining and is shown in FIG. 3. The surface expression varied from 0.53% (TCR-11) to 55.5% (TCR-5) positive events after gating on CD3+ T cells after TCR mRNA electroporation. In particular, surface expression was 8.9% (TCR-1); 39.1% (TCR-2); 27.2% (TCR-3); 39.1% (TCR-4); 61.1% (TCR-5); 2.9% (TCR-6); 53.3% (TCR-7); 60.7% (TCR-8); 44.0% (TCR-9); 52.8% (TCR-10); 6.6% (TCR-11); 20.1% (TCR-12); 53.1% (TCR-13); 11.6% (TCR-14); 22.6% (TCR-15).

Example 5: Efficacy Against Tumor Cell Lines

Figure 4:
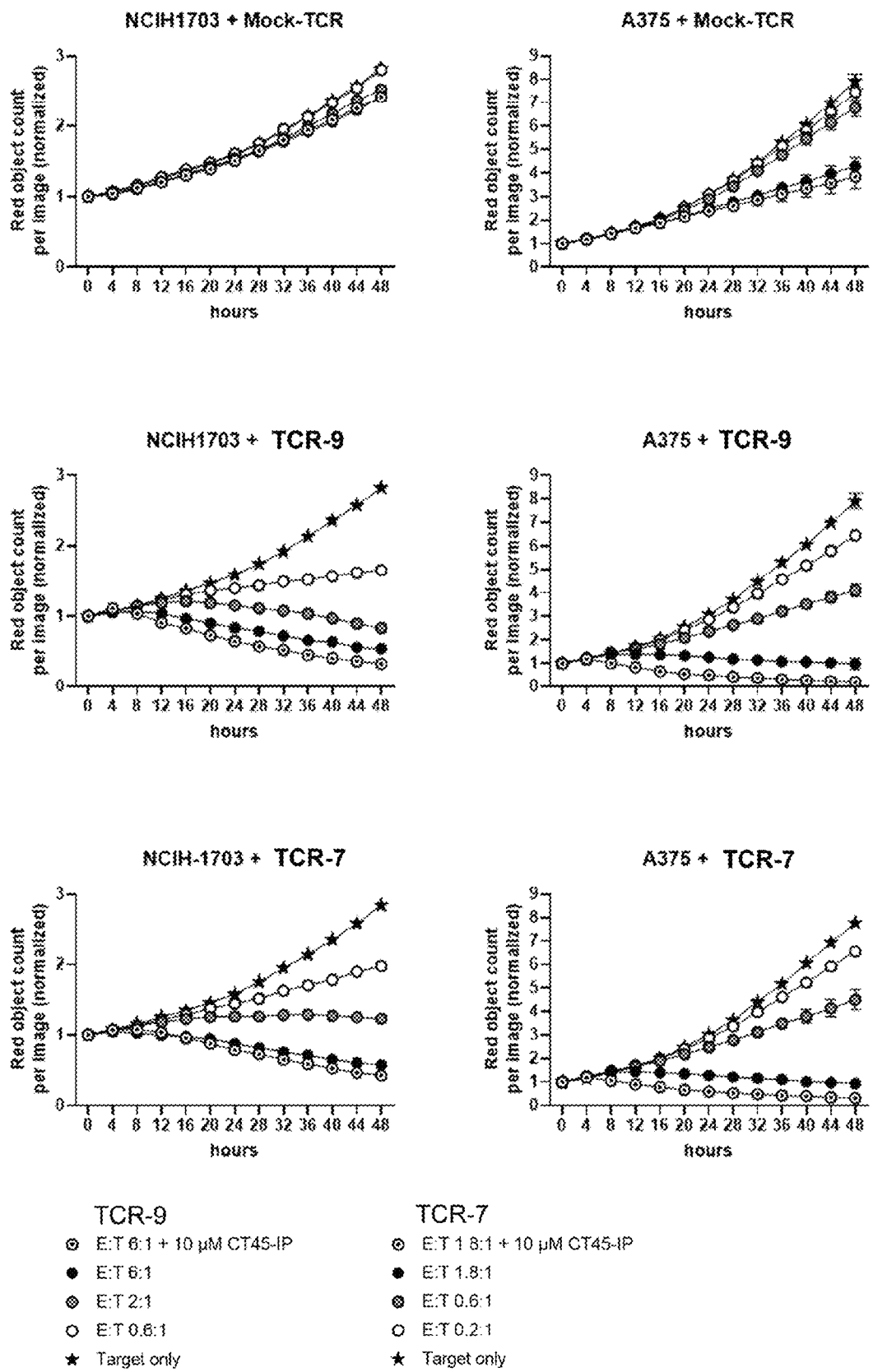
FIG. 4: Tumor cell line efficacy. Live cell monitoring of tumor cell lines expressing RFP which are co-cultivated with or without T cells expressing our TCRs of interest. Red counts representing the tumor cells were quantified over a period of 48 h and normalized to time point 0 h. Plots on the left side show tumor cell line NCIH1703 and plots on the right side show proliferation of cell line A375. CD8+ T cell electroporated with Mock-TCR (negative control, top), TCR-9 (middle) and TCR-7 (below) are shown. Target cells additionally loaded with 10 µM CT45-IP peptide as positive control were used (circle with spot in the middle) as well as target cells without effector cells (asterisk) and different E:T ratios of effector cells expressing the TCR of interest (circles in different shades of grey).

Two tumor cell lines, the A375 with ~30 copies per cell and the NCIH1703 with ~150 copies per cell of CT45-IP were co-cultivated with CD8+ T cells expressing TCR-9, TCR-7 or Mock-TCR (FIG. 4). The efficacy of those TCRs for killing the two cell lines was assessed in a live cell monitoring experiment. While Mock-TCR does not lead to significant reduction of tumor cell proliferation, TCR-9 and TCR-7 efficiently kill the tumor cell lines loaded with CT45-IP peptide at an E:T ratio of 6:1 (TCR-9) or 1.8:1 (TCR-7) (NCIH1703 & A375), without additional peptide loading at an E:T ratio of 6:1 (TCR-9) or 1.8:1 (TCR-7) (NCIH1703 & A375), and at an E:T ratio of 2:1 (TCR-9) or 0.6:1 (TCR-7) and 0.6:1 (TCR-9) or 0.2:1 (TCR-7) (NICIH1703) as measured by the normalized red object count of <2.

Example 6: Safety Window

Co-culture assays were performed using T2 cells loaded with a titration series of peptide CT45-IP and SP-05-0004, respectively. The safety window was determined as $EC_{50}$ SP 0004 divided by $EC_{50}$ CT45-IP (data not shown).

Example 7: CT45-IP Presentation

The detection frequency of the CT45-IP antigenic peptide was analysed in primary and cultured tumor samples. A summary of the results is shown in Table 5. In the table, an expression of >0% is indicated as +, an expression of 10% is indicated as ++ and an expression of 30% is indicated as +++. The tumor entities in which presentation was detected are bile duct cancer (CCC), liver cancer (HCC), skin cancer (MEL, due to cell line identifications), lymph node cancer (NHL), non-small cell lung cancer (NSCLC), ovarian cancer (OC), esophageal cancer (OSCAR) and uterus cancer (UEC).

TABLE 5

| Target presentation | |
| --- | --- |
| Entity | Target detection frequency (%) |
| CCC | + |
| HCC | + |
| MEL | +++ |
| NHL | + |
| NSCLC | + |
| OC | ++ |
| OSCAR | ++ |
| UEC | + |

Example 8: Efficacy of CD4+ T Cells Co-Transduced with a CT45-IP-Specific TCR and CD8 Against Tumor Cells Tumor cells presenting CT45-IP were co-cultivated with CD4+ T cells or CD3+ T cells co-transduced with the herein described CT45-IP-specific TCRs and CD8. The killing efficacy of the T cells was assessed in a live cell monitoring experiment. Upon co-transduction with CT45-IP-specific TCR and CD8, efficient killing of the tumor cell lines as measured by the normalized red object count of <2 was observed (data not shown).

Items

1. An antigen binding protein specifically binding to a CT45 antigenic peptide that is in a complex with a major histocompatibility complex (MHC) protein, wherein the CT45 antigenic peptide comprises or consists of the amino acid sequence of SEQ ID NO: 138 (KIFEMLEGV) and wherein the antigen binding protein comprises a first polypeptide comprising a variable domain $V_A$ comprising complementarity determining regions (CDR) CDRa1, CDRa2 and CDRa3 and a second polypeptide comprising a variable domain $V_B$ comprising CDRb1, CDRb2 and CDRb3, wherein
   1) CDRa1 comprises or consists of the amino acid sequence of SEQ ID NO: 14, CDRa3 comprises or consists of the amino acid sequence of SEQ ID NO: 16, CDRb1 comprises or consists of the amino acid sequence of SEQ ID NO: 19, and CDRb3 comprises or consists of the amino acid sequence of SEQ ID NO: 21,
   2) CDRa1 comprises or consists of the amino acid sequence of SEQ ID NO: 24, CDRa3 comprises or consists of the amino acid sequence of SEQ ID NO: 133, CDRb1 comprises or consists of the amino acid sequence of SEQ ID NO: 75, and CDRb3 comprises or consists of the amino acid sequence of SEQ ID NO: 136,
   3) CDRa1 comprises or consists of the amino acid sequence of SEQ ID NO: 24, CDRa3 comprises or consists of the amino acid sequence of SEQ ID NO: 63, CDRb1 comprises or consists of the amino acid sequence of SEQ ID NO: 66, and CDRb3 comprises or consists of the amino acid sequence of SEQ ID NO: 68,
   4) CDRa1 comprises or consists of the amino acid sequence of SEQ ID NO: 90, CDRa3 comprises or consists of the amino acid sequence of SEQ ID NO: 92, CDRb1 comprises or consists of the amino acid sequence of SEQ ID NO: 66, and CDRb3 comprises or consists of the amino acid sequence of SEQ ID NO: 96,
   5) CDRa1 comprises or consists of the amino acid sequence of SEQ ID NO: 2, CDRa3 comprises or consists of the amino acid sequence of SEQ ID NO: 4, CDRb1 comprises or consists of the amino acid sequence of SEQ ID NO: 8, and CDRb3 comprises or consists of the amino acid sequence of SEQ ID NO: 10, 6) CDRa1 comprises or consists of the amino acid sequence of SEQ ID NO: 53, CDRa3 comprises or consists of the amino acid sequence of SEQ ID NO: 55, CDRb1 comprises or consists of the amino acid sequence of SEQ ID NO: 58, and CDRb3 comprises or consists of the amino acid sequence of SEQ ID NO: 60,
7) CDRa1 comprises or consists of the amino acid sequence of SEQ ID NO: 71, CDRa3 comprises or consists of the amino acid sequence of SEQ ID NO: 72, CDRb1 comprises or consists of the amino acid sequence of SEQ ID NO: 75, and CDRb3 comprises or consists of the amino acid sequence of SEQ ID NO: 77,
8) CDRa1 comprises or consists of the amino acid sequence of SEQ ID NO: 99, CDRa3 comprises or consists of the amino acid sequence of SEQ ID NO: 101, CDRb1 comprises or consists of the amino acid sequence of SEQ ID NO: 75, and CDRb3 comprises or consists of the amino acid sequence of SEQ ID NO: 104,
9) CDRa1 comprises or consists of the amino acid sequence of SEQ ID NO: 80, CDRa3 comprises or consists of the amino acid sequence of SEQ ID NO: 82, CDRb1 comprises or consists of the amino acid sequence of SEQ ID NO: 85, and CDRb3 comprises or consists of the amino acid sequence of SEQ ID NO: 87,
10) CDRa1 comprises or consists of the amino acid sequence of SEQ ID NO: 107, CDRa3 comprises or consists of the amino acid sequence of SEQ ID NO: 109, CDRb1 comprises or consists of the amino acid sequence of SEQ ID NO: 112, and CDRb3 comprises or consists of the amino acid sequence of SEQ ID NO: 114,
11) CDRa1 comprises or consists of the amino acid sequence of SEQ ID NO: 125, CDRa3 comprises or consists of the amino acid sequence of SEQ ID NO: 127, CDRb1 comprises or consists of the amino acid sequence of SEQ ID NO: 112, and CDRb3 comprises or consists of the amino acid sequence of SEQ ID NO: 130, or
12) CDRa1 comprises or consists of the amino acid sequence of SEQ ID NO: 117, CDRa3 comprises or consists of the amino acid sequence of SEQ ID NO: 119, CDRb1 comprises or consists of the amino acid sequence of SEQ ID NO: 58, and CDRb3 comprises or consists of the amino acid sequence of SEQ ID NO: 122,
13) CDRa1 comprises or consists of the amino acid sequence of SEQ ID NO: 24, CDRa3 comprises or consists of the amino acid sequence of SEQ ID NO: 35, CDRb1 comprises or consists of the amino acid sequence of SEQ ID NO: 38, and CDRb3 comprises or consists of the amino acid sequence of SEQ ID NO: 40,
14) CDRa1 comprises or consists of the amino acid sequence of SEQ ID NO: 24, CDRa3 comprises or consists of the amino acid sequence of SEQ ID NO: 26, CDRb1 comprises or consists of the amino acid sequence of SEQ ID NO: 29, and CDRb3 comprises or consists of the amino acid sequence of SEQ ID NO: 31, or
15) CDRa1 comprises or consists of the amino acid sequence of SEQ ID NO: 43, CDRa3 comprises or consists of the amino acid sequence of SEQ ID NO: 45, CDRb1 comprises or consists of the amino acid sequence of SEQ ID NO: 48, and CDRb3 comprises or consists of the amino acid sequence of SEQ ID NO: 50,
wherein the antigen binding protein comprises said CDRa1, CDRa3, CDRb1 and CDRb3 sequence(s) with not more than one, two or three amino acid mutations, wherein each of CDRa1, CDRa3, CDRb1 and/or CDRb3 may comprise one, two or three amino acid mutations.

2. The antigen binding protein of item 1, wherein
1) CDRa2 comprises or consists of the amino acid sequence of SEQ ID NO: 15, and CDRb2 comprises or consists of the amino acid sequence of SEQ ID NO: 20,
2) CDRa2 comprises or consists of the amino acid sequence of SEQ ID NO: 25, and CDRb2 comprises or consists of the amino acid sequence of SEQ ID NO: 76,
3) CDRa2 comprises or consists of the amino acid sequence of SEQ ID NO: 25, and CDRb2 comprises or consists of the amino acid sequence of SEQ ID NO: 67,
4) CDRa2 comprises or consists of the amino acid sequence of SEQ ID NO: 91, and CDRb2 comprises or consists of the amino acid sequence of SEQ ID NO: 95,
5) CDRa2 comprises or consists of the amino acid sequence of SEQ ID NO: 3, and CDRb2 comprises or consists of the amino acid sequence of SEQ ID NO: 9,
6) CDRa2 comprises or consists of the amino acid sequence of SEQ ID NO: 54, and CDRb2 comprises or consists of the amino acid sequence of SEQ ID NO: 59,
7) CDRa2 comprises or consists of the amino acid sequence of SEQ ID NO: 15, and CDRb2 comprises or consists of the amino acid sequence of SEQ ID NO: 76,
8) CDRa2 comprises or consists of the amino acid sequence of SEQ ID NO: 100, and CDRb2 comprises or consists of the amino acid sequence of SEQ ID NO: 76,
9) CDRa2 comprises or consists of the amino acid sequence of SEQ ID NO: 81, and CDRb2 comprises or consists of the amino acid sequence of SEQ ID NO: 86,
10) CDRa2 comprises or consists of the amino acid sequence of SEQ ID NO: 108, and CDRb2 comprises or consists of the amino acid sequence of SEQ ID NO: 113,
11) CDRa2 comprises or consists of the amino acid sequence of SEQ ID NO: 126, and CDRb2 comprises or consists of the amino acid sequence of SEQ ID NO: 113, or
12) CDRa2 comprises or consists of the amino acid sequence of SEQ ID NO: 118, and CDRb2 comprises or consists of the amino acid sequence of SEQ ID NO: 59,
13) CDRa2 comprises or consists of the amino acid sequence of SEQ ID NO: 25, and CDRb2 comprises or consists of the amino acid sequence of SEQ ID NO: 39,
14) CDRa2 comprises or consists of the amino acid sequence of SEQ ID NO: 25, and CDRb2 comprises or consists of the amino acid sequence of SEQ ID NO: 30, or
15) CDRa2 comprises or consists of the amino acid sequence of SEQ ID NO: 44, and CDRb2 comprises or consists of the amino acid sequence of SEQ ID NO: 49,
wherein the antigen binding protein comprises said CDRa2 and CDRb2 sequence(s) with not more than one, two, three or four amino acid mutations, wherein each of CDRa2 and/or CDRb2 may comprise one, two, three or four amino acid mutations.
3. The antigen binding protein of item 1 or 2, wherein the antigen binding protein specifically binds to a complex of the CT45 antigenic peptide and an MHC protein.
4. The antigen binding protein of any one of items 1 to 3, wherein the MHC protein is an HLA protein, more particularly HLA-A, even more particularly HLA-A*02.
5. The antigen binding protein of any one of items 1 to 4, wherein the $EC_{50}$ of CT45-IP for inducing killing of CT45-IP:MHC complex presenting cells by T cells expressing the antigen binding protein is less than about 60 nM, less than about 50 nM, less than about 30 nM, less than about 25 nM, less than about 20 nM, less than about 15 nM, less than about 10 nM, less than about 5 nM, less than about 2.5 nM, less than about 1.5 nM or less than about 1 nM.
6. The antigen binding protein of any one of items 1 to 5, wherein the antigen binding protein specifically binds to a functional epitope comprising or consisting of 2, 3 or 4 amino acid positions selected from the group consisting of positions 3, 4, 5, 6 and 7 of SEQ ID NO: 138.
7. The antigen binding protein of any one of items 1 to 6, wherein the antigen binding protein does not significantly bind to at least 1, at least 2, at least 3, at least 4, at least 5, or all similar peptides selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), preferably from the group consisting of SEQ ID NO: 146 (SP-05-0001), SEQ ID NO: 147 (SP-05-0002), SEQ ID NO: 148 (SP-05-0003), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010), more preferably from the group consisting of SEQ ID NO: 147 (SP-05-0002), SEQ ID NO: 151 (SP-05-0006), SEQ ID NO: 152 (SP-05-0007) and SEQ ID NO: 155 (SP-05-0010).
8. The antigen binding protein of any one of items 1 to 7, wherein the first and the second polypeptide are comprised on two polypeptide chains, preferably wherein $V_A$ is comprised in a first polypeptide chain and $V_B$ is comprised in a second polypeptide chain.
9. The antigen binding protein of any one of items 1 to 7, wherein the antigen binding protein is a single chain antigen binding protein, preferably a single chain TCR, or a single chain bispecific antigen binding protein, preferably a single chain bispecific TCR.
10. The antigen binding protein of any one of items 1 to 9, wherein the antigen binding protein is monovalent or multivalent, e.g. tetra-, tri- or bivalent.
11. The antigen binding protein of any one of items 1 to 10, wherein the antigen binding protein is monospecific or multispecific, e.g. tetra-, tri- or bispecific.
12. The antigen binding protein of any one of items 1 to 11, wherein the antigen binding protein is a soluble protein.
13. The antigen binding protein of any one of items 1 to 12, wherein the antigen binding protein is a TCR.
14. The antigen binding protein of item 13, wherein the TCR is selected from the group consisting of an α/β TCR, a γ/δ TCR, a single chain TCR, a membrane-bound TCR, a soluble TCR, a monovalent, bivalent or multivalent TCR, a monospecific, bispecific or multispecific TCR, a functional fragment of a TCR, and a fusion protein or chimeric protein comprising a functional fragment of a TCR.
15. The antigen binding protein of item 13, wherein the TCR is an α/β TCR or a γ/δ TCR, preferably an α/β TCR.
16. The antigen binding protein of any one of items 1 to 15, further comprising one or more of the following:
    (i) one or more further antigen binding sites;
    (ii) a transmembrane domain, optionally including a cytoplasmic signaling region;
    (iii) a diagnostic agent;
    (iv) a therapeutic agent.
17. The antigen binding protein of item 16, wherein the one or more further antigen binding sites comprise an antibody-derived antigen binding site, preferably comprising or consisting of $V_L$ and $V_H$.
18. The antigen binding protein of any one of items 1 to 17, wherein $V_A$ comprises or consists of an amino acid sequence selected from the group consisting of SEQ ID NO: 13, 132, 62, 89, 1, 52, 70, 98, 79, 106, 124, 116, 34, 23, and 42, or an amino acid sequence having at least 70%, 75%, 80%, 85%, 90%, 95%, 98% or 99% identity to SEQ ID NO: 13, 132, 62, 89, 1, 52, 70, 98, 79, 106, 124, 116, 34, 23, or 42 and comprising the CDRa1, CDRa2 and CDRa3 according to item 1 or 2; and wherein $V_B$ comprises or consists of an amino acid sequence selected from the group consisting of SEQ ID NO: 18, 135, 65, 94, 7, 57, 74, 103, 84, 111, 129, 121, 37, 28 and 47 or an amino acid sequence having at least 70%, 75%, 80%, 85%, 90%, 95%, 98% or 99% identity to SEQ ID NO: 18, 135, 65, 94, 7, 57, 74, 103, 84, 111, 129, 121, 37, 28 or 47 and comprising the CDRb1, CDRb2 and CDRb3 according to item 1 or 2, wherein the CDRa1, CDRa2, CDRa3, CDRb1, CDRb2 and/or CDRb3 sequences may comprise one, two or three amino acid mutations, preferably amino acid substitutions.
19. The antigen binding protein of any one of items 1 to 18, wherein $V_A$ and $V_B$ are TCR variable domains, preferably TCR alpha, beta, gamma or delta variable domains, more preferably wherein $V_A$ is a TCR alpha or gamma, preferably alpha, variable domain, and $V_B$ is a TCR beta or delta, preferably beta, variable domain.
20. The antigen binding protein of any one of items 1 to 19, further comprising a constant domain, wherein the constant domain comprises or consists of an amino acid sequence selected from the group consisting of SEQ ID NO: 5, 750, 751, 156, 11, 32, and 157, preferably selected from the group consisting of SEQ ID NO: 5, 750, 751, 11 and 32, or an amino acid sequence having at least 70%, 75%, 80%, 85%, 90%, 95%, 98% or 99% identity to SEQ ID NO: 5, 750, 751, 156, 11, 32 or 157.
21. The antigen binding protein of any one of items 1 to 20, wherein the first polypeptide is a TCR alpha chain and the second polypeptide is a TCR beta chain or the first polypeptide is a TCR gamma chain and the second polypeptide is a TCR delta chain preferably wherein the first polypeptide is a TCR alpha chain and the second polypeptide is a TCR beta chain.
22. The antigen binding protein of any one of items 1 to 21, wherein the first polypeptide comprises or consists of an amino acid sequence selected from the group consisting of SEQ ID NO: 17, 134, 64, 93, 6, 56, 73, 102, 83, 110, 128, 120, 36, 27, 46 and 158-172, preferably selected from the group consisting of SEQ ID NO: 17, 134, 64, 93, 6, 56, 73, 102, 83, 110, 128, 120, 36, 27, 46 or an amino acid sequence having at least 70%, 75%, 80%, 85%, 90%, 95%, 98% or 99% identity to SEQ ID NO: 17, 134, 64, 93, 6, 56, 73, 102, 83, 110, 128, 120, 36, 27, 46 or 158-172, and the second polypeptide comprises or consists of an amino acid sequence selected from the group consisting of SEQ ID NO: 22, 137, 69, 97, 12, 61, 78, 105, 88, 115, 131, 123, 41, 33, 51 and 173-187, preferably selected from the group consisting of SEQ ID NO: 22, 137, 69, 97, 12, 61, 78, 105, 88, 115, 131, 123, 41, 33, 51, or an amino acid sequence having at least 70%, 75%, 80%, 85%, 90%, 95%, 98% or 99% identity to SEQ ID NO: 22, 137, 69, 97, 12, 61, 78, 105, 88, 115, 131, 123, 41, 33, 51 or 173-187.

23. The antigen binding protein of any one of items 1 to 22, wherein the antigen binding protein specifically binds to a functional epitope comprising or consisting of
   i. amino acid positions 1, 3 and 4 of SEQ ID NO: 138, preferably amino acid positions 1, 3, 4 and 5, or 1, 3, 4 and 6 or 1, 3, 4, 5 and 6 or 1, 3, 4, 5, 6 and 7 of SEQ ID NO: 138;
   ii. amino acid positions 4, 6 and 7 of SEQ ID NO: 138, preferably amino acid positions 1, 4, 6 and 7, or 3, 4, 6 and 7 or 1, 3, 4, 6 and 7 of SEQ ID NO: 138; or
   iii. amino acid positions 5 and 7 of SEQ ID NO: 138, preferably amino acid positions 5, 6 and 7, or 3, 4, 5, 6 and 7 of SEQ ID NO: 138.

24. The antigen binding protein of any one of items 1 to 23, wherein the antigen binding protein does not significantly bind to the similar peptides of the group consisting of
   i. SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010); or
   ii. SEQ ID NO: 146 (SP-05-0001), SEQ ID NO: 147 (SP-05-0002), SEQ ID NO: 148 (SP-05-0003), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010).

25. The antigen binding protein of any one of items 1 to 24, wherein the antigen binding protein has a mean expression of at least 5%, at least 10%, at least 20%, at least 30%, or at least 40%.

26. The antigen binding protein of any one of items 1 to 25, wherein $V_A$ comprises a V segment encoded by TRAV14, in particular TRAV14/DV4, and a CDRa1 according to SEQ ID NO: 24 and a CDRa2 according to SEQ ID NO: 25.

27. The antigen binding protein of any one of items 1 to 26, wherein $V_B$ comprises
   i. a V segment encoded by TRBV13, and a CDRb1 according to SEQ ID NO: 75 and a CDRb2 according to SEQ ID NO: 76;
   ii. a V region encoded by TRBV4-1, and a CDRb1 according to SEQ ID NO: 58 and a CDRb2 according to SEQ ID NO: 59, or
   iii. a V region encoded by TRBV6-1, and a CDRb1 according to SEQ ID NO: 112 and a CDRb2 according to SEQ ID NO: 113.

28. The antigen binding protein of any one of items 1 to 27, wherein the antigen binding protein is capable of activating
   a CD4+ T cell, in particular a CD4+CD8− T cell, and/or
   a CD8+ T cell, in particular a CD8+CD4-T cell, and wherein the antigen binding protein is preferably a TCR, more preferably an α/β TCR or γ/δ TCR.

29. A nucleic acid or nucleic acids comprising one or more sequences encoding the antigen binding protein of any one of items 1 to 28.

30. A vector or a collection of vectors comprising the nucleic acid(s) of item 29.

31. A host cell comprising the antigen binding protein of any one of items 1 to 28, or the nucleic acid(s) of item 29, or the vector or collection of vectors of item 30.

32. The host cell of item 31, wherein the host cell is
   a lymphocyte, preferably a T cell, a T cell progenitor or an NK cell, more preferably a CD4 or CD8 positive T cell; or
   a cell for recombinant expression, such as a Chinese Hamster Ovary (CHO) cell or a yeast cell.

33. A pharmaceutical composition comprising the antigen binding protein of any one of items 1 to 28, the nucleic acid(s) of item 29, the vector or collection of vectors of item 30, or the host cell of item 31 or 32 and optionally a pharmaceutically acceptable carrier.

34. The antigen binding protein of any one of items 1 to 28, the nucleic acid(s) of item 29, the vector or collection of vectors of item 30, the host cell of item 31 or 32, or the pharmaceutical composition of item 33 for use in medicine.

35. The antigen binding protein of any one of items 1 to 28, the nucleic acid(s) of item 29, the vector or collection of vectors of item 30, the host cell of item 31 or 32, or the pharmaceutical composition of item 33 for use in a method of treatment and/or diagnosis of a proliferative disease, in particular cancer.

36. A method of treatment of a proliferative disease, in particular cancer, comprising administering to a subject in need thereof a therapeutically effective amount of the antigen binding protein of any one of items 1 to 28, the nucleic acid(s) of item 29, the vector or collection of vectors of item 30, the host cell of item 31 or 32, or the pharmaceutical composition of item 33.

37. The antigen binding protein, nucleic acid(s), vector or collection of vectors, host cell or pharmaceutical composition for use of item 35 or the method of treatment of item 36, wherein the cancer is a CT45 expressing cancer, more particularly selected from the group of cancers consisting of lung cancer, NSCLC, gall bladder cancer, bile duct cancer, lymph node cancer, ovarian cancer, esophageal cancer, liver cancer, uterus cancer and melanoma.

38. The antigen binding protein, nucleic acid(s), vector or collection of vectors, host cell or pharmaceutical composition for use of item 35 or 37 or the method of treatment of item 36 or 37, wherein the method of treatment comprises immune therapy, in particular adoptive autologous or heterologous T-cell therapy.

39. The antigen binding protein, nucleic acid(s), vector or collection of vectors, host cell or pharmaceutical composition for use of any one of items 35, 37 or 38 or the method of treatment of any one of items 36 to 38, wherein the antigen binding protein is a TCR.

40. The antigen binding protein, nucleic acid(s), vector or collection of vectors, host cell or pharmaceutical composition for use of any one of items 35 or 37 to 39 or the method of treatment of any one of items 36 to 39, wherein the antigen binding protein is expressed on the surface of a host cell.

41. The antigen binding protein, nucleic acid(s), vector or collection of vectors, host cell or pharmaceutical composition for use of any one of items 35 or 37 to 40 or the method of treatment of any one of items 36 to 40, wherein the method of treatment comprises administration of a host cell expressing the antigen binding protein, wherein the host cell is a T cell, a T cell progenitor or an NK cell, preferably a T cell.

42. The antigen binding protein, nucleic acid(s), vector or collection of vectors, host cell or pharmaceutical composition for use of item 40 or the method of treatment of item 40, wherein the host cell, preferably the T cell, T cell progenitor or NK cell, more preferably the T cell, is autologous.

43. The antigen binding protein, nucleic acid(s), vector or collection of vectors, host cell or pharmaceutical composition for use of item 40 or the method of treatment of item 40, wherein the host cell, preferably the T cell, T cell progenitor or NK cell, more preferably the T cell, is allogeneic.

44. The antigen binding protein, nucleic acid(s), vector or collection of vectors, host cell or pharmaceutical composition for use of any one of items 35 or 37 to 43 or the method of treatment of any one of items 36 to 43, wherein the antigen binding protein is conjugated to a therapeutically active agent.

45. The antigen binding protein, nucleic acid(s), vector or collection of vectors, host cell or pharmaceutical composition for use of any one of items 44 or the method of treatment of any one of items 44, wherein the therapeutically active agent is selected from the group consisting of a radionuclide, a chemotherapeutic agent and a toxin.

46. The antigen binding protein, nucleic acid(s), vector or collection of vectors, host cell or pharmaceutical composition for use of any one of items 35 or 37 to 45 or the method of treatment of any one of items 36 to 45, wherein the method of treatment further comprises administering at least one chemotherapeutic agent to the subject in need of treatment.

47. The antigen binding protein, nucleic acid(s), vector or collection of vectors, host cell or pharmaceutical composition for use of any one of items 35 or 37 to 46 or the method of treatment of any one of items 36 to 46, wherein the method of treatment further comprises administering radiation therapy to the subject in need of treatment.

48. A method of treating cancer in a subject in need thereof, comprising:
    a) isolating a cell from said subject;
    b) transforming the cell with a vector or collection of vectors encoding the antigen binding protein of any one of items 1 to 28 to produce a transformed cell;
    c) expanding the transformed cell to produce a plurality of transformed cells; and
    d) administering the plurality of transformed cells to said subject.

49. A method of treating cancer in a subject in need thereof, comprising:
    a) isolating a cell from a healthy donor;
    b) transforming the cell with a vector or collection of vectors encoding the antigen binding protein of any one of items 1 to 28 to produce a transformed cell;
    c) expanding the transformed cell to produce a plurality of transformed cells; and
    d) administering the plurality of transformed cells to said subject.

50. The method of item 48 or 49, wherein the transformed cell is a lymphocyte, preferably an NK cell or T cell or T cell progenitor, more preferably a T cell.

51. Use of the antigen binding protein of any one of items 1 to 28 for the manufacture of a medicament for the treatment of a proliferative disease.

52. An in-vitro method of detecting cancer, in particular cancer expressing CT45, in a biological sample comprising:
    a) contacting the biological sample with the antigen binding protein of any one of items 1 to 28, and
    b) detecting binding of the antigen binding protein to the biological sample.

53. A method of producing the antigen binding protein according to any one of items 1 to 28, comprising
    a) providing a host cell,
    b) providing a genetic construct comprising a nucleic acid or nucleic acids encoding the antigen binding protein of any of items 1 to 28,
    c) introducing the genetic construct into the host cell, and
    d) expressing the genetic construct by the host cell.

54. The method of item 53, further comprising the isolation and purification of the antigen binding protein from the host cell and, optionally, reconstitution of the antigen binding protein in a T cell.

55. The method of item 53 or 54, further comprising cell surface presentation of said antigen binding protein.

56. The method of any one of items 53 to 55, wherein the genetic construct is an expression construct comprising a promoter sequence operably linked to the nucleic acid encoding the antigen binding protein.

57. The method according to any one of items 53 to 56, wherein the genetic construct is introduced into the host cell by retroviral transfection.

The invention claimed is:

1. An antigen binding protein comprising
   a first polypeptide comprising a variable domain $V_A$ comprising
   a complementarity determining region (CDR) a1 comprising SEQ ID NO: 80,
   a CDRa2 comprising SEQ ID NO: 81, and
   a CDRa3 comprising SEQ ID NO: 82, and
   a second polypeptide comprising a variable domain $V_B$ comprising
   a CDRb1 comprising SEQ ID NO: 85,
   a CDRb2 comprising SEQ ID NO: 86, and
   a CDRb3 comprising SEQ ID NO: 87.

2. The antigen binding protein of claim 1, wherein the antigen binding protein is a T Cell Receptor (TCR) selected from the group consisting of an α/β TCR, a γ/δ TCR, a single chain TCR, a membrane-bound TCR, a soluble TCR, a monovalent, bivalent or multivalent TCR, a monospecific, bispecific or multispecific TCR, a functional fragment of a TCR, and a fusion protein or chimeric protein comprising a functional fragment of a TCR.

3. The antigen binding protein of claim 1,
   wherein $V_A$ comprises an amino acid sequence having at least 90% identity to SEQ ID NO: 79; and
   wherein $V_B$ comprises an amino acid sequence having at least 90% identity to SEQ ID NO: 84.

4. The antigen binding protein of claim 1, wherein the first polypeptide further comprises a constant domain comprising, an amino acid sequence having at least 90% identity to SEQ ID NO: 751, and the second polypeptide further comprises a constant domain having an amino acid comprising at least 90% identity to SEQ ID NO: 11.

5. The antigen binding protein of claim 1, wherein
the first polypeptide comprises an amino acid sequence having at least 90% identity to SEQ ID NO: 83, and
the second polypeptide comprises an amino acid sequence having at least 90% identity to SEQ ID NO: 88%.

6. The antigen binding protein of claim 1, wherein the antigen binding protein does not significantly bind to at least one peptide selected from the group consisting of SEQ ID NO: 146 (SP-05-0001), SEQ ID NO: 147 (SP-05-0002), SEQ ID NO: 148 (SP-05-0003), SEQ ID NO: 149 (SP-05-0004), SEQ ID NO: 150 (SP-05-0005), SEQ ID NO: 151 (SP-05-0006), SEQ ID NO: 152 (SP-05-0007), SEQ ID NO: 153 (SP-05-0008), SEQ ID NO: 154 (SP-05-0009) and SEQ ID NO: 155 (SP-05-0010).

7. A pharmaceutical composition comprising the antigen binding protein of claim 1.

8. The antigen binding protein of claim 1, wherein
the CDRa1 consists of SEQ ID NO: 80,
the CDRa2 comprises SEQ ID NO: 81,
the CDRa3 consists of SEQ ID NO: 82,
the CDRb1 consists of SEQ ID NO: 85,
the CDRb2 comprises SEQ ID NO: 86, and
the CDRb3 consists of SEQ ID NO: 87.

9. The antigen binding protein of claim 1, wherein
the CDRa1 consists of SEQ ID NO: 80,
the CDRa2 consists of SEQ ID NO: 81,
the CDRa3 consists of SEQ ID NO: 82,
the CDRb1 consists of SEQ ID NO: 85,
the CDRb2 consists of SEQ ID NO: 86, and
the CDRb3 consists of SEQ ID NO: 87.

10. The antigen binding protein of claim 4, wherein the first polypeptide comprises a constant domain comprising SEQ ID NO: 751 and the second polypeptide comprises a constant domain comprising SEQ ID NO: 11.

11. The antigen binding protein of claim 1, wherein the antigen binding protein binds to a peptide consisting of SEQ ID NO: 138 (KIFEMLEGV) in a complex with an MHC protein.

12. The antigen binding protein of claim 11, wherein the antigen binding protein binds to a peptide consisting of SEQ ID NO: 138 (KIFEMLEGV) in a complex with an HLA-A*02 protein.

13. The antigen binding protein of claim 1,
wherein $V_A$ comprises an amino acid sequence having at least 95% identity to SEQ ID NO: 79; and
wherein $V_B$ comprises an amino acid sequence having at least 95% identity to SEQ ID NO: 84.

14. The antigen binding protein of claim 1, wherein
the first polypeptide comprises a constant domain comprising an amino acid sequence having at least 95% identity to SEQ ID NO: 751 and
the second polypeptide comprises a constant domain comprising an amino acid sequence having at least 95% identity to SEQ ID NO: 11.

15. The antigen binding protein of claim 1, wherein
the first polypeptide comprises an amino acid sequence having at least 95% identity to SEQ ID NO: 83, and
the second polypeptide comprises an amino acid sequence having at least 95% identity to SEQ ID NO: 88.

16. The antigen binding protein of claim 1,
wherein $V_A$ comprises an amino acid sequence having at least 98% identity to SEQ ID NO: 79; and
wherein $V_B$ comprises an amino acid sequence having at least 98% identity to SEQ ID NO: 84.

17. The antigen binding protein of claim 1, wherein
the first polypeptide comprises an amino acid sequence having at least 98% identity to SEQ ID NO: 83, and
the second polypeptide comprises an amino acid sequence having at least 98% identity to SEQ ID NO: 88.

18. The antigen binding protein of claim 3, wherein the antigen binding protein binds to a peptide consisting of SEQ ID NO: 138 (KIFEMLEGV) in a complex with an MHC protein.

19. The antigen binding protein of claim 18, wherein the antigen binding protein binds to a peptide consisting of SEQ ID NO: 138 (KIFEMLEGV) in a complex with an HLA-A*02 protein.

20. The antigen binding protein of claim 13, wherein the antigen binding protein binds to a peptide consisting of SEQ ID NO: 138 (KIFEMLEGV) in a complex with an MHC protein.

21. The antigen binding protein of claim 20, wherein the antigen binding protein binds to a peptide consisting of SEQ ID NO: 138 (KIFEMLEGV) in a complex with an HLA-A*02 protein.

22. The antigen binding protein of claim 16, wherein the antigen binding protein binds to a peptide consisting of SEQ ID NO: 138 (KIFEMLEGV) in a complex with an MHC protein.

23. The antigen binding protein of claim 22, wherein the antigen binding protein binds to a peptide consisting of SEQ ID NO: 138 (KIFEMLEGV) in a complex with an HLA-A*02 protein.

24. The antigen binding protein of claim 5, wherein the antigen binding protein binds to a peptide consisting of SEQ ID NO: 138 (KIFEMLEGV) in a complex with an MHC protein.

25. The antigen binding protein of claim 24, wherein the antigen binding protein binds to a peptide consisting of SEQ ID NO: 138 (KIFEMLEGV) in a complex with an HLA-A*02 protein.

26. The antigen binding protein of claim 15, wherein the antigen binding protein binds to a peptide consisting of SEQ ID NO: 138 (KIFEMLEGV) in a complex with an MHC protein.

27. The antigen binding protein of claim 26, wherein the antigen binding protein binds to a peptide consisting of SEQ ID NO: 138 (KIFEMLEGV) in a complex with an HLA-A*02 protein.

28. The antigen binding protein of claim 17, wherein the antigen binding protein binds to a peptide consisting of SEQ ID NO: 138 (KIFEMLEGV) in a complex with an MHC protein.

29. The antigen binding protein of claim 28, wherein the antigen binding protein binds to a peptide consisting of SEQ ID NO: 138 (KIFEMLEGV) in a complex with an HLA-A*02 protein.

30. The antigen binding protein of claim 3, wherein the antigen binding protein is a TCR.

31. The antigen binding protein of claim 5, wherein the antigen binding protein is a TCR.

32. The antigen binding protein of claim 13, wherein the antigen binding protein is a TCR.

33. The antigen binding protein of claim 15, wherein the antigen binding protein is a TCR.

34. The antigen binding protein of claim 16, wherein the antigen binding protein is a TCR.

35. The antigen binding protein of claim 17, wherein the antigen binding protein is a TCR.

36. The antigen binding protein of claim 18, wherein the antigen binding protein is a TCR.

37. The antigen binding protein of claim 19, wherein the antigen binding protein is a TCR.

38. The antigen binding protein of claim 20, wherein the antigen binding protein is a TCR.

39. The antigen binding protein of claim 21, wherein the antigen binding protein is a TCR.

40. The antigen binding protein of claim 22, wherein the antigen binding protein is a TCR.

41. The antigen binding protein of claim 23, wherein the antigen binding protein is a TCR.

42. The antigen binding protein of claim 24, wherein the antigen binding protein is a TCR.

43. The antigen binding protein of claim 25, wherein the antigen binding protein is a TCR.

44. The antigen binding protein of claim 26, wherein the antigen binding protein is a TCR.

45. The antigen binding protein of claim 27, wherein the antigen binding protein is a TCR.

46. The antigen binding protein of claim 28, wherein the antigen binding protein is a TCR.

47. The antigen binding protein of claim 29, wherein the antigen binding protein is a TCR.

48. An antigen binding protein comprising
- a first polypeptide comprising a variable domain $V_A$ comprising SEQ ID NO: 79 and
- a second polypeptide comprising a variable domain $V_B$ comprising SEQ ID NO: 84.

49. An antigen binding protein comprising
- a first polypeptide comprising SEQ ID NO: 83 and
- a second polypeptide comprising SEQ ID NO: 88.

50. The antigen binding protein of claim 48, wherein the antigen binding protein binds to a peptide consisting of SEQ ID NO: 138 (KIFEMLEGV) in a complex with an MHC protein.

51. The antigen binding protein of claim 50, wherein the antigen binding protein binds to a peptide consisting of SEQ ID NO: 138 (KIFEMLEGV) in a complex with an HLA-A*02 protein.

52. The antigen binding protein of claim 49, wherein the antigen binding protein binds to a peptide consisting of SEQ ID NO: 138 (KIFEMLEGV) in a complex with an MHC protein.

53. The antigen binding protein of claim 52, wherein the antigen binding protein binds to a peptide consisting of SEQ ID NO: 138 (KIFEMLEGV) in a complex with an HLA-A*02 protein.

54. The antigen binding protein of claim 48, wherein the antigen binding protein is a TCR.

55. The antigen binding protein of claim 49, wherein the antigen binding protein is a TCR.

56. The antigen binding protein of claim 50, wherein the antigen binding protein is a TCR.

57. The antigen binding protein of claim 51, wherein the antigen binding protein is a TCR.

58. The antigen binding protein of claim 52, wherein the antigen binding protein is a TCR.

59. The antigen binding protein of claim 53, wherein the antigen binding protein is a TCR.

60. A method of treating a CT45-expressing proliferative disease comprising administering to a subject in need thereof a T cell comprising the antigen binding protein of claim 1.

61. The method of claim 60, wherein said CT45-expressing proliferative disease is cancer.

62. The method of claim 61, wherein said cancer is selected from the group consisting of lung cancer, NSCLC, gall bladder cancer, bile duct cancer, lymph node cancer, ovarian cancer, esophageal cancer, liver cancer, uterus cancer and melanoma.

63. A method of treatment of a CT45-expressing proliferative disease comprising administering to a subject in need thereof a T cell comprising the antigen binding protein of claim 3.

64. The method of claim 63, wherein said CT45-expressing proliferative disease is cancer and said cancer is selected from the group consisting of lung cancer, NSCLC, gall bladder cancer, bile duct cancer, lymph node cancer, ovarian cancer, esophageal cancer, liver cancer, uterus cancer and melanoma.

* * * * *

SEQUENCE LISTING

```
Sequence total quantity: 751
SEQ ID NO: 1           moltype = AA  length = 110
FEATURE                Location/Qualifiers
source                 1..110
                       mol_type = protein
                       organism = Homo sapiens
SEQUENCE: 1
QQLNQSPQSM FIQEGEDVSM NCTSSSIFNT WLWYKQDPGE GPVLLIALYK AGELTSNGRL   60
TAQFGITRKD SFLNISASIP SDVGIYFCAG GYNYGQNFVF GPGTRLSVLP              110
```

```
SEQ ID NO: 2              moltype = AA   length = 5
FEATURE                   Location/Qualifiers
source                    1..5
                          mol_type = protein
                          organism = Homo sapiens
SEQUENCE: 2
SIFNT                                                                       5

SEQ ID NO: 3              moltype = AA   length = 7
FEATURE                   Location/Qualifiers
source                    1..7
                          mol_type = protein
                          organism = Homo sapiens
SEQUENCE: 3
LYKAGEL                                                                     7

SEQ ID NO: 4              moltype = AA   length = 11
FEATURE                   Location/Qualifiers
source                    1..11
                          mol_type = protein
                          organism = Homo sapiens
SEQUENCE: 4
AGGYNYGQNF V                                                               11

SEQ ID NO: 5              moltype = AA   length = 141
FEATURE                   Location/Qualifiers
source                    1..141
                          mol_type = protein
                          organism = Homo sapiens
SEQUENCE: 5
YIQNPDPAVY QLRDSKSSDK SVCLFTDFDS QTNVSQSKDS DVYITDKTVL DMRSMDFKSN          60
SAVAWSNKSD FACANAFNNS IIPEDTFFPS PESSCDVKLV EKSFETDTNL NFQNLSVIGF         120
RILLLKVAGF NLLMTLRLWS S                                                  141

SEQ ID NO: 6              moltype = AA   length = 251
FEATURE                   Location/Qualifiers
source                    1..251
                          mol_type = protein
                          organism = Homo sapiens
SEQUENCE: 6
QQLNQSPQSM FIQEGEDVSM NCTSSSIFNT WLWYKQDPGE GPVLLIALYK AGELTSNGRL          60
TAQFGITRKD SFLNISASIP SDVGIYFCAG GYNYGQNFVF GPGTRLSVLP YIQNPDPAVY         120
QLRDSKSSDK SVCLFTDFDS QTNVSQSKDS DVYITDKTVL DMRSMDFKSN SAVAWSNKSD         180
FACANAFNNS IIPEDTFFPS PESSCDVKLV EKSFETDTNL NFQNLSVIGF RILLLKVAGF         240
NLLMTLRLWS S                                                             251

SEQ ID NO: 7              moltype = AA   length = 112
FEATURE                   Location/Qualifiers
source                    1..112
                          mol_type = protein
                          organism = Homo sapiens
SEQUENCE: 7
GVTQTPKHLI TATGQRVTLR CSPRSGDLSV YWYQQSLDQG LQFLIQYYNG EERAKGNILE          60
RFSAQQFPDL HSELNLSSLE LGDSALYFCA SSAGLAGGYE QYFGPGTRLT VT                 112

SEQ ID NO: 8              moltype = AA   length = 5
FEATURE                   Location/Qualifiers
source                    1..5
                          mol_type = protein
                          organism = Homo sapiens
SEQUENCE: 8
SGDLS                                                                       5

SEQ ID NO: 9              moltype = AA   length = 6
FEATURE                   Location/Qualifiers
source                    1..6
                          mol_type = protein
                          organism = Homo sapiens
SEQUENCE: 9
YYNGEE                                                                      6

SEQ ID NO: 10             moltype = AA   length = 13
FEATURE                   Location/Qualifiers
source                    1..13
                          mol_type = protein
                          organism = Homo sapiens
SEQUENCE: 10
ASSAGLAGGY EQY                                                             13
```

```
SEQ ID NO: 11             moltype = AA   length = 179
FEATURE                   Location/Qualifiers
source                    1..179
                          mol_type = protein
                          organism = Homo sapiens
SEQUENCE: 11
EDLKNVFPPE VAVFEPSEAE ISHTQKATLV CLATGFYPDH VELSWWVNGK EVHSGVSTDP      60
QPLKEQPALN DSRYCLSSRL RVSATFWQNP RNHFRCQVQF YGLSENDEWT QDRAKPVTQI     120
VSAEAWGRAD CGFTSESYQQ GVLSATILYE ILLGKATLYA VLVSALVLMA MVKRKDSRG     179

SEQ ID NO: 12             moltype = AA   length = 291
FEATURE                   Location/Qualifiers
source                    1..291
                          mol_type = protein
                          organism = Homo sapiens
SEQUENCE: 12
GVTQTPKHLI TATGQRVTLR CSPRSGDLSV YWYQQSLDQG LQFLIQYYNG EERAKGNILE      60
RFSAQQFPDL HSELNLSSLE LGDSALYFCA SSAGLAGGYE QYFGPGTRLT VTEDLKNVFP     120
PEVAVFEPSE AEISHTQKAT LVCLATGFYP DHVELSWWVN GKEVHSGVST DPQPLKEQPA     180
LNDSRYCLSS RLRVSATFWQ NPRNHFRCQV QFYGLSENDE WTQDRAKPVT QIVSAEAWGR     240
ADCGFTSESY QQGVLSATIL YEILLGKATL YAVLVSALVL MAMVKRKDSR G              291

SEQ ID NO: 13             moltype = AA   length = 116
FEATURE                   Location/Qualifiers
source                    1..116
                          mol_type = protein
                          organism = Homo sapiens
SEQUENCE: 13
QTVTQSQPEM SVQEAETVTL SCTYDTSENN YYLFWYKQPP SRQMILVIRQ EAYKQQNATE      60
NRFSVNFQKA AKSFSLKISD SQLGDTAMYF CAPLGLVAGS ARQLTFGSGT QLTVLP         116

SEQ ID NO: 14             moltype = AA   length = 7
FEATURE                   Location/Qualifiers
source                    1..7
                          mol_type = protein
                          organism = Homo sapiens
SEQUENCE: 14
TSENNYY                                                                 7

SEQ ID NO: 15             moltype = AA   length = 8
FEATURE                   Location/Qualifiers
source                    1..8
                          mol_type = protein
                          organism = Homo sapiens
SEQUENCE: 15
QEAYKQQN                                                                8

SEQ ID NO: 16             moltype = AA   length = 14
FEATURE                   Location/Qualifiers
source                    1..14
                          mol_type = protein
                          organism = Homo sapiens
SEQUENCE: 16
APLGLVAGSA RQLT                                                        14

SEQ ID NO: 17             moltype = AA   length = 257
FEATURE                   Location/Qualifiers
source                    1..257
                          mol_type = protein
                          organism = Homo sapiens
SEQUENCE: 17
QTVTQSQPEM SVQEAETVTL SCTYDTSENN YYLFWYKQPP SRQMILVIRQ EAYKQQNATE      60
NRFSVNFQKA AKSFSLKISD SQLGDTAMYF CAPLGLVAGS ARQLTFGSGT QLTVLPDIQN     120
PDPAVYQLRD SKSSDKSVCL FTDFDSQTNV SQSKDSDVYI TDKTVLDMRS MDFKSNSAVA     180
WSNKSDFACA NAFNNSIIPE DTFFPSPESS CDVKLVEKSF ETDTNLNFQN LSVIGFRILL     240
LKVAGFNLLM TLRLWSS                                                    257

SEQ ID NO: 18             moltype = AA   length = 112
FEATURE                   Location/Qualifiers
source                    1..112
                          mol_type = protein
                          organism = Homo sapiens
SEQUENCE: 18
GVSQDPRHKI TKRGQNVTFR CDPISEHNRL YWYRQTLGQG PEFLTYFQNE AQLEKSRLLS      60
DRFSAERPKG SFSTLEIQRT EQGDSAMYLC ASSTDITSYE QYFGPGTRLT VT             112

SEQ ID NO: 19             moltype = AA   length = 5
FEATURE                   Location/Qualifiers
source                    1..5
```

```
                         mol_type = protein
                         organism = Homo sapiens
SEQUENCE: 19
SEHNR                                                                  5

SEQ ID NO: 20            moltype = AA   length = 6
FEATURE                  Location/Qualifiers
source                   1..6
                         mol_type = protein
                         organism = Homo sapiens
SEQUENCE: 20
FQNEAQ                                                                 6

SEQ ID NO: 21            moltype = AA   length = 12
FEATURE                  Location/Qualifiers
source                   1..12
                         mol_type = protein
                         organism = Homo sapiens
SEQUENCE: 21
ASSTDITSYE QY                                                         12

SEQ ID NO: 22            moltype = AA   length = 291
FEATURE                  Location/Qualifiers
source                   1..291
                         mol_type = protein
                         organism = Homo sapiens
SEQUENCE: 22
GVSQDPRHKI TKRGQNVTFR CDPISEHNRL YWYRQTLGQG PEFLTYFQNE AQLEKSRLLS      60
DRFSAERPKG SFSTLEIQRT EQGDSAMYLC ASSTDITSYE QYFGPGTRLT VTEDLKNVFP     120
PEVAVFEPSE AEISHTQKAT LVCLATGFYP DHVELSWWVN GKEVHSGVST DPQPLKEQPA     180
LNDSRYCLSS RLRVSATFWQ NPRNHFRCQV QFYGLSENDE WTQDRAKPVT QIVSAEAWGR     240
ADCGFTSESY QQGVLSATIL YEILLGKATL YAVLVSALVL MAMVKRKDSR G             291

SEQ ID NO: 23            moltype = AA   length = 115
FEATURE                  Location/Qualifiers
source                   1..115
                         mol_type = protein
                         organism = Homo sapiens
SEQUENCE: 23
QKITQTQPGM FVQEKEAVTL DCTYDTSDQS YGLFWYKQPS SGEMIFLIYQ GSYDEQNATE      60
GRYSLNFQKA RKSANLVISA SQLGDSAMYF CAINGLPGSA RQLTFGSGTQ LTVLP         115

SEQ ID NO: 24            moltype = AA   length = 7
FEATURE                  Location/Qualifiers
source                   1..7
                         mol_type = protein
                         organism = Homo sapiens
SEQUENCE: 24
TSDQSYG                                                                7

SEQ ID NO: 25            moltype = AA   length = 8
FEATURE                  Location/Qualifiers
source                   1..8
                         mol_type = protein
                         organism = Homo sapiens
SEQUENCE: 25
QGSYDEQN                                                               8

SEQ ID NO: 26            moltype = AA   length = 13
FEATURE                  Location/Qualifiers
source                   1..13
                         mol_type = protein
                         organism = Homo sapiens
SEQUENCE: 26
AINGLPGSAR QLT                                                        13

SEQ ID NO: 27            moltype = AA   length = 256
FEATURE                  Location/Qualifiers
source                   1..256
                         mol_type = protein
                         organism = Homo sapiens
SEQUENCE: 27
QKITQTQPGM FVQEKEAVTL DCTYDTSDQS YGLFWYKQPS SGEMIFLIYQ GSYDEQNATE      60
GRYSLNFQKA RKSANLVISA SQLGDSAMYF CAINGLPGSA RQLTFGSGTQ LTVLPDIQNP    120
DPAVYQLRDS KSSDKSVCLF TDFDSQTNVS QSKDSDVYIT DKTVLDMRSM DFKSNSAVAW    180
SNKSDFACAN AFNNSIIPED TFFPSPESSC DVKLVEKSFE TDTNLNFQNL SVIGFRILLL    240
KVAGFNLLMT LRLWSS                                                    256

SEQ ID NO: 28            moltype = AA   length = 114
```

-continued

```
FEATURE                 Location/Qualifiers
source                  1..114
                        mol_type = protein
                        organism = Homo sapiens
SEQUENCE: 28
GVAQSPRYKI IEKRQSVAFW CNPISGHATL YWYQQILGQG PKLLIQFQNN GVVDDSQLPK    60
DRFSAERLKG VDSTLKIQPA KLEDSAVYLC ASSRFVATGT SPLHFGNGTR LTVT         114

SEQ ID NO: 29           moltype = AA  length = 5
FEATURE                 Location/Qualifiers
source                  1..5
                        mol_type = protein
                        organism = Homo sapiens
SEQUENCE: 29
SGHAT                                                                 5

SEQ ID NO: 30           moltype = AA  length = 6
FEATURE                 Location/Qualifiers
source                  1..6
                        mol_type = protein
                        organism = Homo sapiens
SEQUENCE: 30
FQNNGV                                                                6

SEQ ID NO: 31           moltype = AA  length = 14
FEATURE                 Location/Qualifiers
source                  1..14
                        mol_type = protein
                        organism = Homo sapiens
SEQUENCE: 31
ASSRFVATGT SPLH                                                      14

SEQ ID NO: 32           moltype = AA  length = 177
FEATURE                 Location/Qualifiers
source                  1..177
                        mol_type = protein
                        organism = Homo sapiens
SEQUENCE: 32
EDLNKVFPPE VAVFEPSEAE ISHTQKATLV CLATGFFPDH VELSWWVNGK EVHSGVSTDP    60
QPLKEQPALN DSRYCLSSRL RVSATFWQNP RNHFRCQVQF YGLSENDEWT QDRAKPVTQI   120
VSAEAWGRAD CGFTSVSYQQ GVLSATILYE ILLGKATLYA VLVSALVLMA MVKRKDF      177

SEQ ID NO: 33           moltype = AA  length = 291
FEATURE                 Location/Qualifiers
source                  1..291
                        mol_type = protein
                        organism = Homo sapiens
SEQUENCE: 33
GVAQSPRYKI IEKRQSVAFW CNPISGHATL YWYQQILGQG PKLLIQFQNN GVVDDSQLPK    60
DRFSAERLKG VDSTLKIQPA KLEDSAVYLC ASSRFVATGT SPLHFGNGTR LTVTEDLNKV   120
FPPEVAVFEP SEAEISHTQK ATLVCLATGF FPDHVELSWW VNGKEVHSGV STDPQPLKEQ   180
PALNDSRYCL SSRLRVSATF WQNPRNHFRC QVQFYGLSEN DEWTQDRAKP VTQIVSAEAW   240
GRADCGFTSV SYQQGVLSAT ILYEILLGKA TLYAVLVSAL VLMAMVKRKD F            291

SEQ ID NO: 34           moltype = AA  length = 117
FEATURE                 Location/Qualifiers
source                  1..117
                        mol_type = protein
                        organism = Homo sapiens
SEQUENCE: 34
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMSDPIMDT GRRALTFGSG TRLQVQP      117

SEQ ID NO: 35           moltype = AA  length = 15
FEATURE                 Location/Qualifiers
source                  1..15
                        mol_type = protein
                        organism = Homo sapiens
SEQUENCE: 35
AMSDPIMDTG RRALT                                                     15

SEQ ID NO: 36           moltype = AA  length = 258
FEATURE                 Location/Qualifiers
source                  1..258
                        mol_type = protein
                        organism = Homo sapiens
SEQUENCE: 36
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMSDPIMDT GRRALTFGSG TRLQVQPNIQ   120
```

```
NPDPAVYQLR DSKSSDKSVC LFTDFDSQTN VSQSKDSDVY ITDKTVLDMR SMDFKSNSAV    180
AWSNKSDFAC ANAFNNSIIP EDTFFPSPES SCDVKLVEKS FETDTNLNFQ NLSVIGFRIL    240
LLKVAGFNLL MTLRLWSS                                                  258

SEQ ID NO: 37           moltype = AA   length = 113
FEATURE                 Location/Qualifiers
source                  1..113
                        mol_type = protein
                        organism = Homo sapiens
SEQUENCE: 37
GITQSPKYLF RKEGQNVTLS CEQNLNHDAM YWYRQDPGQG LRLIYYSQIV NDFQKGDIAE    60
GYSVSREKKE SFPLTVTSAQ KNPTAFYLCA SKSRGPNLAD TQYFGPGTRL TVL           113

SEQ ID NO: 38           moltype = AA   length = 5
FEATURE                 Location/Qualifiers
source                  1..5
                        mol_type = protein
                        organism = Homo sapiens
SEQUENCE: 38
LNHDA                                                                5

SEQ ID NO: 39           moltype = AA   length = 6
FEATURE                 Location/Qualifiers
source                  1..6
                        mol_type = protein
                        organism = Homo sapiens
SEQUENCE: 39
SQIVND                                                               6

SEQ ID NO: 40           moltype = AA   length = 14
FEATURE                 Location/Qualifiers
source                  1..14
                        mol_type = protein
                        organism = Homo sapiens
SEQUENCE: 40
ASKSRGPNLA DTQY                                                      14

SEQ ID NO: 41           moltype = AA   length = 292
FEATURE                 Location/Qualifiers
source                  1..292
                        mol_type = protein
                        organism = Homo sapiens
SEQUENCE: 41
GITQSPKYLF RKEGQNVTLS CEQNLNHDAM YWYRQDPGQG LRLIYYSQIV NDFQKGDIAE    60
GYSVSREKKE SFPLTVTSAQ KNPTAFYLCA SKSRGPNLAD TQYFGPGTRL TVLEDLKNVF    120
PPEVAVFEPS EAEISHTQKA TLVCLATGFY PDHVELSWWV NGKEVHSGVS TDPQPLKEQP    180
ALNDSRYCLS SRLRVSATFW QNPRNHFRCQ VQFYGLSEND EWTQDRAKPV TQIVSAEAWG    240
RADCGFTSES YQQGVLSATI LYEILLGKAT LYAVLVSALV LMAMVKRKDS RG            292

SEQ ID NO: 42           moltype = AA   length = 110
FEATURE                 Location/Qualifiers
source                  1..110
                        mol_type = protein
                        organism = Homo sapiens
SEQUENCE: 42
KQEVTQIPAA LSVPEGENLV LNCSFTDSAI YNLQWFRQDP GKGLTSLLLI QSSQREQTSG    60
RLNASLDKSS GRSTLYIAAS QPGDSATYLC AVLLTGKLIF GQGTTLQVKP              110

SEQ ID NO: 43           moltype = AA   length = 6
FEATURE                 Location/Qualifiers
source                  1..6
                        mol_type = protein
                        organism = Homo sapiens
SEQUENCE: 43
DSAIYN                                                               6

SEQ ID NO: 44           moltype = AA   length = 7
FEATURE                 Location/Qualifiers
source                  1..7
                        mol_type = protein
                        organism = Homo sapiens
SEQUENCE: 44
IQSSQRE                                                              7

SEQ ID NO: 45           moltype = AA   length = 9
FEATURE                 Location/Qualifiers
source                  1..9
                        mol_type = protein
                        organism = Homo sapiens
```

```
SEQUENCE: 45
AVLLTGKLI                                                                           9

SEQ ID NO: 46           moltype = AA   length = 251
FEATURE                 Location/Qualifiers
source                  1..251
                        mol_type = protein
                        organism = Homo sapiens
SEQUENCE: 46
KQEVTQIPAA LSVPEGENLV LNCSFTDSAI YNLQWFRQDP GKGLTSLLLI QSSQREQTSG    60
RLNASLDKSS GRSTLYIAAS QPGDSATYLC AVLLTGKLIF GQGTTLQVKP DIQNPDDPAVY  120
QLRDSKSSDK SVCLFTDFDS QTNVSQSKDS DVYITDKTVL DMRSMDFKSN SAVAWSNKSD   180
FACANAFNNS IIPEDTFFPS PESSCDVKLV EKSFETDTNL NFQNLSVIGF RILLLKVAGF   240
NLLMTLRLWS S                                                       251

SEQ ID NO: 47           moltype = AA   length = 112
FEATURE                 Location/Qualifiers
source                  1..112
                        mol_type = protein
                        organism = Homo sapiens
SEQUENCE: 47
GVTQTPRYLI KTRGQQVTLS CSPISGHRSV SWYQQTPGQG LQFLFEYFSE TQRNKGNFPG    60
RFSGRQFSNS RSEMNVSTLE LGDSALYLCA SSGGPGPSGE QYFGPGTRLT VT           112

SEQ ID NO: 48           moltype = AA   length = 5
FEATURE                 Location/Qualifiers
source                  1..5
                        mol_type = protein
                        organism = Homo sapiens
SEQUENCE: 48
SGHRS                                                                               5

SEQ ID NO: 49           moltype = AA   length = 6
FEATURE                 Location/Qualifiers
source                  1..6
                        mol_type = protein
                        organism = Homo sapiens
SEQUENCE: 49
YFSETQ                                                                              6

SEQ ID NO: 50           moltype = AA   length = 13
FEATURE                 Location/Qualifiers
source                  1..13
                        mol_type = protein
                        organism = Homo sapiens
SEQUENCE: 50
ASSGGPGPSG EQY                                                                     13

SEQ ID NO: 51           moltype = AA   length = 291
FEATURE                 Location/Qualifiers
source                  1..291
                        mol_type = protein
                        organism = Homo sapiens
SEQUENCE: 51
GVTQTPRYLI KTRGQQVTLS CSPISGHRSV SWYQQTPGQG LQFLFEYFSE TQRNKGNFPG    60
RFSGRQFSNS RSEMNVSTLE LGDSALYLCA SSGGPGPSGE QYFGPGTRLT VTEDLKNVFP   120
PEVAVFEPSE AEISHTQKAT LVCLATGFYP DHVELSWWVN GKEVHSGVST DPQPLKEQPA   180
LNDSRYCLSS RLRVSATFWQ NPRNHFRCQV QFYGLSENDE WTQDRAKPVT QIVSAEAWGR   240
ADCGFTSESY QQGVLSATIL YEILLGKATL YAVLVSALVL MAMVKRKDSR G            291

SEQ ID NO: 52           moltype = AA   length = 118
FEATURE                 Location/Qualifiers
source                  1..118
                        mol_type = protein
                        organism = Homo sapiens
SEQUENCE: 52
QQKEVEQDPG PLSVPEGAIV SLNCTYSNSA FQYFMWYRQY SRKGPELLMY TYSSGNKEDG    60
RFTAQVDKSS KYISLFIRDS QPSDSATYLC AMSGNSGARD YGNNRLAFGK GNQVVVIP    118

SEQ ID NO: 53           moltype = AA   length = 6
FEATURE                 Location/Qualifiers
source                  1..6
                        mol_type = protein
                        organism = Homo sapiens
SEQUENCE: 53
NSAFQY                                                                              6

SEQ ID NO: 54           moltype = AA   length = 6
FEATURE                 Location/Qualifiers
```

```
source                  1..6
                        mol_type = protein
                        organism = Homo sapiens
SEQUENCE: 54
TYSSGN                                                                    6

SEQ ID NO: 55           moltype = AA   length = 17
FEATURE                 Location/Qualifiers
source                  1..17
                        mol_type = protein
                        organism = Homo sapiens
SEQUENCE: 55
AMSGNSGARD YGNNRLA                                                       17

SEQ ID NO: 56           moltype = AA   length = 259
FEATURE                 Location/Qualifiers
source                  1..259
                        mol_type = protein
                        organism = Homo sapiens
SEQUENCE: 56
QQKEVEQDPG PLSVPEGAIV SLNCTYSNSA FQYFMWYRQY SRKGPELLMY TYSSGNKEDG         60
RFTAQVDKSS KYISLFIRDS QPSDSATYLC AMSGNSGARD YGNNRLAFGK GNQVVVIPNI        120
QNPDPAVYQL RDKSSDKSV  CLFTDFDSQT NVSQSKDSDV YITDKTVLDM RSMDFKSNSA        180
VAWSNKSDFA CANAFNNSII PEDTFFPSPE SSCDVKLVEK SFETDTNLNF QNLSVIGFRI        240
LLLKVAGFNL LMTLRLWSS                                                    259

SEQ ID NO: 57           moltype = AA   length = 114
FEATURE                 Location/Qualifiers
source                  1..114
                        mol_type = protein
                        organism = Homo sapiens
SEQUENCE: 57
EVTQTPKHLV MGMTNKKSLK CEQHMGHRAM YWYKQKAKKP PELMFVYSYE KLSINESVPS         60
RFSPECPNSS LLNLHLHALQ PEDSALYLCA SATWEEAGPY NEQFFGPGTR LTVL              114

SEQ ID NO: 58           moltype = AA   length = 5
FEATURE                 Location/Qualifiers
source                  1..5
                        mol_type = protein
                        organism = Homo sapiens
SEQUENCE: 58
MGHRA                                                                     5

SEQ ID NO: 59           moltype = AA   length = 6
FEATURE                 Location/Qualifiers
source                  1..6
                        mol_type = protein
                        organism = Homo sapiens
SEQUENCE: 59
YSYEKL                                                                    6

SEQ ID NO: 60           moltype = AA   length = 15
FEATURE                 Location/Qualifiers
source                  1..15
                        mol_type = protein
                        organism = Homo sapiens
SEQUENCE: 60
ASATWEEAGP YNEQF                                                         15

SEQ ID NO: 61           moltype = AA   length = 293
FEATURE                 Location/Qualifiers
source                  1..293
                        mol_type = protein
                        organism = Homo sapiens
SEQUENCE: 61
EVTQTPKHLV MGMTNKKSLK CEQHMGHRAM YWYKQKAKKP PELMFVYSYE KLSINESVPS         60
RFSPECPNSS LLNLHLHALQ PEDSALYLCA SATWEEAGPY NEQFFGPGTR LTVLEDLKNV        120
FPPEVAVFEP SEAEISHTQK ATLVCLATGF YPDHVELSWW VNGKEVHSGV STDPQPLKEQ        180
PALNDSRYCL SSRLRVSATF WQNPRNHFRC QVQFYGLSEN DEWTQDRAKP VTQIVSAEAW        240
GRADCGFTSE SYQQGVLSAT ILYEILLGKA TLYAVLVSAL VLMAMVKRKD SRG               293

SEQ ID NO: 62           moltype = AA   length = 110
FEATURE                 Location/Qualifiers
source                  1..110
                        mol_type = protein
                        organism = Homo sapiens
SEQUENCE: 62
QKITQTQPGM FVQEKEAVTL DCTYDTSDQS YGLFWYKQPS SGEMIFLIYQ GSYDEQNATE         60
GRYSLNFQKA RKSANLVISA SQLGDSAMYF CGYSNYQLIW GAGTKLIIKP                  110
```

```
SEQ ID NO: 63              moltype = AA  length = 8
FEATURE                    Location/Qualifiers
source                     1..8
                           mol_type = protein
                           organism = Homo sapiens
SEQUENCE: 63
GYSNYQLI                                                                  8

SEQ ID NO: 64              moltype = AA  length = 251
FEATURE                    Location/Qualifiers
source                     1..251
                           mol_type = protein
                           organism = Homo sapiens
SEQUENCE: 64
QKITQTQPGM FVQEKEAVTL DCTYDTSDQS YGLFWYKQPS SGEMIFLIYQ GSYDEQNATE        60
GRYSLNFQKA RKSANLVISA SQLGDSAMYF CGYSNYQLIW GAGTKLIIKP DIQNPDDPAVY      120
QLRDSKSSDK SVCLFTDFDS QTNVSQSKDS DVYITDKTVL DMRSMDFKSN SAVAWSNKSD       180
FACANAFNNS IIPEDTFFPS PESSCDVKLV EKSFETDTNL NFQNLSVIGF RILLLKVAGF       240
NLLMTLRLWS S                                                            251

SEQ ID NO: 65              moltype = AA  length = 112
FEATURE                    Location/Qualifiers
source                     1..112
                           mol_type = protein
                           organism = Homo sapiens
SEQUENCE: 65
QVTQNPRYLI TVTGKKLTVT CSQNMNHEYM SWYRQDPGLG LRQIYYSMNV EVTDKGDVPE        60
GYKVSRKEKR NFPLILESPS PNQTSLYFCA SREGTGGYQP QHFGDGTRLS IL               112

SEQ ID NO: 66              moltype = AA  length = 5
FEATURE                    Location/Qualifiers
source                     1..5
                           mol_type = protein
                           organism = Homo sapiens
SEQUENCE: 66
MNHEY                                                                     5

SEQ ID NO: 67              moltype = AA  length = 6
FEATURE                    Location/Qualifiers
source                     1..6
                           mol_type = protein
                           organism = Homo sapiens
SEQUENCE: 67
SMNVEV                                                                    6

SEQ ID NO: 68              moltype = AA  length = 13
FEATURE                    Location/Qualifiers
source                     1..13
                           mol_type = protein
                           organism = Homo sapiens
SEQUENCE: 68
ASREGTGGYQ PQH                                                           13

SEQ ID NO: 69              moltype = AA  length = 289
FEATURE                    Location/Qualifiers
source                     1..289
                           mol_type = protein
                           organism = Homo sapiens
SEQUENCE: 69
QVTQNPRYLI TVTGKKLTVT CSQNMNHEYM SWYRQDPGLG LRQIYYSMNV EVTDKGDVPE        60
GYKVSRKEKR NFPLILESPS PNQTSLYFCA SREGTGGYQP QHFGDGTRLS ILEDLNKVFP       120
PEVAVFEPSE AEISHTQKAT LVCLATGFFP DHVELSWWVN GKEVHSGVST DPQPLKEQPA       180
LNDSRYCLSS RLRVSATFWQ NPRNHFRCQV QFYGLSENDE WTQDRAKPVT QIVSAEAWGR       240
ADCGFTSVSY QQGVLSATIL YEILLGKATL YAVLVSALVL MAMVKRKDF                   289

SEQ ID NO: 70              moltype = AA  length = 114
FEATURE                    Location/Qualifiers
source                     1..114
                           mol_type = protein
                           organism = Homo sapiens
SEQUENCE: 70
QTVTQSQPEM SVQEAETVTL SCTYDTSESD YYLFWYKQPP SRQMILVIRQ EAYKQQNATE        60
NRFSVNFQKA AKSFSLKISD SQLGDAAMYF CTFRYGGATN KLIFGTGTLL AVQP             114

SEQ ID NO: 71              moltype = AA  length = 7
FEATURE                    Location/Qualifiers
source                     1..7
                           mol_type = protein
```

```
SEQUENCE: 71
TSESDYY                                                                  7

SEQ ID NO: 72           moltype = AA   length = 12
FEATURE                 Location/Qualifiers
source                  1..12
                        mol_type = protein
                        organism = Homo sapiens
SEQUENCE: 72
TFRYGGATNK LI                                                            12

SEQ ID NO: 73           moltype = AA   length = 255
FEATURE                 Location/Qualifiers
source                  1..255
                        mol_type = protein
                        organism = Homo sapiens
SEQUENCE: 73
QTVTQSQPEM SVQEAETVTL SCTYDTSESD YYLFWYKQPP SRQMILVIRQ EAYKQQNATE        60
NRFSVNFQKA AKSFSLKISD SQLGDAAMYF CTFRYGGATN KLIFGTGTLL AVQPNIQNPD        120
PAVYQLRDSK SSDKSVCLFT DFDSQTNVSQ SKDSDVYITD KTVLDMRSMD FKSNSAVAWS        180
NKSDFACANA FNNSIIPEDT FFPSPESSCD VKLVEKSFET DTNLNFQNLS VIGFRILLLK        240
VAGFNLLMTL RLWSS                                                         255

SEQ ID NO: 74           moltype = AA   length = 113
FEATURE                 Location/Qualifiers
source                  1..113
                        mol_type = protein
                        organism = Homo sapiens
SEQUENCE: 74
GVIQSPRHLI KEKRETATLK CYPIPRHDTV YWYQQGPGQD PQFLISFYEK MQSDKGSIPD        60
RFSAQQFSDY HSELNMSSLE LGDSALYFCA SRGGWAETPD TQYFGPGTRL TVL               113

SEQ ID NO: 75           moltype = AA   length = 5
FEATURE                 Location/Qualifiers
source                  1..5
                        mol_type = protein
                        organism = Homo sapiens
SEQUENCE: 75
PRHDT                                                                    5

SEQ ID NO: 76           moltype = AA   length = 6
FEATURE                 Location/Qualifiers
source                  1..6
                        mol_type = protein
                        organism = Homo sapiens
SEQUENCE: 76
FYEKMQ                                                                   6

SEQ ID NO: 77           moltype = AA   length = 14
FEATURE                 Location/Qualifiers
source                  1..14
                        mol_type = protein
                        organism = Homo sapiens
SEQUENCE: 77
ASRGGWAETP DTQY                                                          14

SEQ ID NO: 78           moltype = AA   length = 292
FEATURE                 Location/Qualifiers
source                  1..292
                        mol_type = protein
                        organism = Homo sapiens
SEQUENCE: 78
GVIQSPRHLI KEKRETATLK CYPIPRHDTV YWYQQGPGQD PQFLISFYEK MQSDKGSIPD        60
RFSAQQFSDY HSELNMSSLE LGDSALYFCA SRGGWAETPD TQYFGPGTRL TVLEDLKNVF        120
PPEVAVFEPS EAEISHTQKA TLVCLATGFY PDHVELSWWV NGKEVHSGVS TDPQPLKEQP        180
ALNDSRYCLS SRLRVSATFW QNPRNHFRCQ VQFYGLSEND EWTQDRAKPV TQIVSAEAWG        240
RADCGFTSES YQQGVLSATI LYEILLGKAT LYAVLVSALV LMAMVKRKDS RG                292

SEQ ID NO: 79           moltype = AA   length = 110
FEATURE                 Location/Qualifiers
source                  1..110
                        mol_type = protein
                        organism = Homo sapiens
SEQUENCE: 79
EDVEQSLFLS VREGDSSVIN CTYTDSSSTY LYWYKQEPGA GLQLLTYIFS NMDMKQDQRL        60
TVLLNKKDKH LSLRIADTQT GDSAIYFCAE KETAGNKLTF GGGTRVLVKP                   110

SEQ ID NO: 80           moltype = AA   length = 6
```

```
FEATURE                 Location/Qualifiers
source                  1..6
                        mol_type = protein
                        organism = Homo sapiens
SEQUENCE: 80
DSSSTY                                                                       6

SEQ ID NO: 81           moltype = AA   length = 7
FEATURE                 Location/Qualifiers
source                  1..7
                        mol_type = protein
                        organism = Homo sapiens
SEQUENCE: 81
IFSNMDM                                                                      7

SEQ ID NO: 82           moltype = AA   length = 11
FEATURE                 Location/Qualifiers
source                  1..11
                        mol_type = protein
                        organism = Homo sapiens
SEQUENCE: 82
AEKETAGNKL T                                                                11

SEQ ID NO: 83           moltype = AA   length = 251
FEATURE                 Location/Qualifiers
source                  1..251
                        mol_type = protein
                        organism = Homo sapiens
SEQUENCE: 83
EDVEQSLFLS VREGDSSVIN CTYTDSSSTY LYWYKQEPGA GLQLLTYIFS NMDMKQDQRL            60
TVLLNKKDKH LSLRIADTQT GDSAIYFCAE KETAGNKLTF GGGTRVLVKP NIQNPDPAVY           120
QLRDSKSSDK SVCLFTDFDS QTNVSQSKDS DVYITDKTVL DMRSMDFKSN SAVAWSNKSD           180
FACANAFNNS IIPEDTFFPS PESSCDVKLV EKSFETDTNL NFQNLSVIGF RILLLKVAGF           240
NLLMTLRLWS S                                                               251

SEQ ID NO: 84           moltype = AA   length = 115
FEATURE                 Location/Qualifiers
source                  1..115
                        mol_type = protein
                        organism = Homo sapiens
SEQUENCE: 84
EPEVTQTPSH QVTQMGQEVI LRCVPISNHL YFYWYRQILG QKVEFLVSFY NNEISEKSEI            60
FDDQFSVERP DGSNFTLKIR STKLEDSAMY FCASTVQSPR TNEQFFGPGT RLTVL                115

SEQ ID NO: 85           moltype = AA   length = 5
FEATURE                 Location/Qualifiers
source                  1..5
                        mol_type = protein
                        organism = Homo sapiens
SEQUENCE: 85
SNHLY                                                                        5

SEQ ID NO: 86           moltype = AA   length = 6
FEATURE                 Location/Qualifiers
source                  1..6
                        mol_type = protein
                        organism = Homo sapiens
SEQUENCE: 86
FYNNEI                                                                       6

SEQ ID NO: 87           moltype = AA   length = 13
FEATURE                 Location/Qualifiers
source                  1..13
                        mol_type = protein
                        organism = Homo sapiens
SEQUENCE: 87
ASTVQSPRTN EQF                                                              13

SEQ ID NO: 88           moltype = AA   length = 294
FEATURE                 Location/Qualifiers
source                  1..294
                        mol_type = protein
                        organism = Homo sapiens
SEQUENCE: 88
EPEVTQTPSH QVTQMGQEVI LRCVPISNHL YFYWYRQILG QKVEFLVSFY NNEISEKSEI            60
FDDQFSVERP DGSNFTLKIR STKLEDSAMY FCASTVQSPR TNEQFFGPGT RLTVLEDLKN           120
VFPPEVAVFE PSEAEISHTQ KATLVCLATG FYPDHVELSW WVNGKEVHSG VSTDPQPLKE           180
QPALNDSRYC LSSRLRVSAT FWQNPRNHFR CQVQFYGLSE NDEWTQDRAK PVTQIVSAEA           240
WGRADCGFTS ESYQQGVLSA TILYEILLGK ATLYAVLVSA LVLMAMVKRK DSRG                294
```

```
SEQ ID NO: 89          moltype = AA   length = 110
FEATURE                Location/Qualifiers
source                 1..110
                       mol_type = protein
                       organism = Homo sapiens
SEQUENCE: 89
QSVAQPEDQV NVAEGNPLTV KCTYSVSGNP YLFWYVQYPN RGLQFLLKYI TGDNLVKGSY    60
GFEAEFNKSQ TSFHLKKPSA LVSDSALYFC AAPRDDKIIF GKGTRLHILP              110

SEQ ID NO: 90          moltype = AA   length = 6
FEATURE                Location/Qualifiers
source                 1..6
                       mol_type = protein
                       organism = Homo sapiens
SEQUENCE: 90
VSGNPY                                                                6

SEQ ID NO: 91          moltype = AA   length = 8
FEATURE                Location/Qualifiers
source                 1..8
                       mol_type = protein
                       organism = Homo sapiens
SEQUENCE: 91
YITGDNLV                                                              8

SEQ ID NO: 92          moltype = AA   length = 9
FEATURE                Location/Qualifiers
source                 1..9
                       mol_type = protein
                       organism = Homo sapiens
SEQUENCE: 92
AAPRDDKII                                                             9

SEQ ID NO: 93          moltype = AA   length = 251
FEATURE                Location/Qualifiers
source                 1..251
                       mol_type = protein
                       organism = Homo sapiens
SEQUENCE: 93
QSVAQPEDQV NVAEGNPLTV KCTYSVSGNP YLFWYVQYPN RGLQFLLKYI TGDNLVKGSY    60
GFEAEFNKSQ TSFHLKKPSA LVSDSALYFC AAPRDDKIIF GKGTRLHILP NIQNPDPAVY   120
QLRDSKSSDK SVCLFTDFDS QTNVSQSKDS DVYITDKTVL DMRSMDFKSN SAVAWSNKSD   180
FACANAFNNS IIPEDTFFPS PESSCDVKLV EKSFETDTNL NFQNLSVIGF RILLLKVAGF   240
NLLMTLRLWS S                                                        251

SEQ ID NO: 94          moltype = AA   length = 112
FEATURE                Location/Qualifiers
source                 1..112
                       mol_type = protein
                       organism = Homo sapiens
SEQUENCE: 94
GVTQTPKFRV LKTGQSMTLL CAQDMNHEYM YWYRQDPGMG LRLIHYSVGE GTTAKGEVPD    60
GYNVSRLKKQ NFLLGLESAA PSQTSVYFCA SSYLRTGGNE QFFGPGTRLT VL           112

SEQ ID NO: 95          moltype = AA   length = 6
FEATURE                Location/Qualifiers
source                 1..6
                       mol_type = protein
                       organism = Homo sapiens
SEQUENCE: 95
SVGEGT                                                                6

SEQ ID NO: 96          moltype = AA   length = 13
FEATURE                Location/Qualifiers
source                 1..13
                       mol_type = protein
                       organism = Homo sapiens
SEQUENCE: 96
ASSYLRTGGN EQF                                                       13

SEQ ID NO: 97          moltype = AA   length = 291
FEATURE                Location/Qualifiers
source                 1..291
                       mol_type = protein
                       organism = Homo sapiens
SEQUENCE: 97
GVTQTPKFRV LKTGQSMTLL CAQDMNHEYM YWYRQDPGMG LRLIHYSVGE GTTAKGEVPD    60
GYNVSRLKKQ NFLLGLESAA PSQTSVYFCA SSYLRTGGNE QFFGPGTRLT VLEDLKNVFP   120
```

```
PEVAVFEPSE AEISHTQKAT LVCLATGFYP DHVELSWWVN GKEVHSGVST DPQPLKEQPA    180
LNDSRYCLSS RLRVSATFWQ NPRNHFRCQV QFYGLSENDE WTQDRAKPVT QIVSAEAWGR    240
ADCGFTSESY QQGVLSATIL YEILLGKATL YAVLVSALVL MAMVKRKDSR G             291

SEQ ID NO: 98            moltype = AA   length = 115
FEATURE                  Location/Qualifiers
source                   1..115
                         mol_type = protein
                         organism = Homo sapiens
SEQUENCE: 98
QKVTQAQTEI SVVEKEDVTL DCVYETRDTT YYLFWYKQPP SGELVFLIRR NSFDEQNEIS    60
GRYSWNFQKS TSSFNFTITA SQVVDSAVYF CALSGRGSGT YKYIFGTGTR LKVLA         115

SEQ ID NO: 99            moltype = AA   length = 7
FEATURE                  Location/Qualifiers
source                   1..7
                         mol_type = protein
                         organism = Homo sapiens
SEQUENCE: 99
TRDTTYY                                                              7

SEQ ID NO: 100           moltype = AA   length = 8
FEATURE                  Location/Qualifiers
source                   1..8
                         mol_type = protein
                         organism = Homo sapiens
SEQUENCE: 100
RNSFDEQN                                                             8

SEQ ID NO: 101           moltype = AA   length = 13
FEATURE                  Location/Qualifiers
source                   1..13
                         mol_type = protein
                         organism = Homo sapiens
SEQUENCE: 101
ALSGRGSGTY KYI                                                       13

SEQ ID NO: 102           moltype = AA   length = 256
FEATURE                  Location/Qualifiers
source                   1..256
                         mol_type = protein
                         organism = Homo sapiens
SEQUENCE: 102
QKVTQAQTEI SVVEKEDVTL DCVYETRDTT YYLFWYKQPP SGELVFLIRR NSFDEQNEIS    60
GRYSWNFQKS TSSFNFTITA SQVVDSAVYF CALSGRGSGT YKYIFGTGTR LKVLANIQNP    120
DPAVYQLRDS KSSDKSVCLF TDFDSQTNVS QSKDSDVYIT DKTVLDMRSM DFKSNSAVAW    180
SNKSDFACAN AFNNSIIPED TFFPSPESSC DVKLVEKSFE TDTNLNFQNL SVIGFRILLL    240
KVAGFNLLMT LRLWSS                                                    256

SEQ ID NO: 103           moltype = AA   length = 111
FEATURE                  Location/Qualifiers
source                   1..111
                         mol_type = protein
                         organism = Homo sapiens
SEQUENCE: 103
GVIQSPRHLI KEKRETATLK CYPIPRHDTV YWYQQGPGQD PQFLISFYEK MQSDKGSIPD    60
RFSAQQFSDY HSELNMSSLE LGDSALYFCA SSAGTSYNEQ FFGPGTRLTV L             111

SEQ ID NO: 104           moltype = AA   length = 12
FEATURE                  Location/Qualifiers
source                   1..12
                         mol_type = protein
                         organism = Homo sapiens
SEQUENCE: 104
ASSAGTSYNE QF                                                        12

SEQ ID NO: 105           moltype = AA   length = 290
FEATURE                  Location/Qualifiers
source                   1..290
                         mol_type = protein
                         organism = Homo sapiens
SEQUENCE: 105
GVIQSPRHLI KEKRETATLK CYPIPRHDTV YWYQQGPGQD PQFLISFYEK MQSDKGSIPD    60
RFSAQQFSDY HSELNMSSLE LGDSALYFCA SSAGTSYNEQ FFGPGTRLTV LEDLKNVFPP    120
EVAVFEPSEA EISHTQKATL VCLATGFYPD HVELSWWVNG KEVHSGVSTD PQPLKEQPAL    180
NDSRYCLSSR LRVSATFWQN PRNHFRCQVQ FYGLSENDEW TQDRAKPVTQ IVSAEAWGRA    240
DCGFTSESYQ QGVLSATILY EILLGKATLY AVLVSALVLM AMVKRKDSRG               290

SEQ ID NO: 106           moltype = AA   length = 112
```

```
FEATURE                 Location/Qualifiers
source                  1..112
                        mol_type = protein
                        organism = Homo sapiens
SEQUENCE: 106
QNIDQPTEMT ATEGAIVQIN CTYQTSGFNG LFWYQQHAGE APTFLSYNVL DGLEEKGRFS    60
SFLSRSKGYS YLLLKELQMK DSASYLCAVP APYTGTASKL TFGTGTRLQV TL           112

SEQ ID NO: 107          moltype = AA   length = 6
FEATURE                 Location/Qualifiers
source                  1..6
                        mol_type = protein
                        organism = Homo sapiens
SEQUENCE: 107
TSGFNG                                                                6

SEQ ID NO: 108          moltype = AA   length = 6
FEATURE                 Location/Qualifiers
source                  1..6
                        mol_type = protein
                        organism = Homo sapiens
SEQUENCE: 108
NVLDGL                                                                6

SEQ ID NO: 109          moltype = AA   length = 14
FEATURE                 Location/Qualifiers
source                  1..14
                        mol_type = protein
                        organism = Homo sapiens
SEQUENCE: 109
AVPAPYTGTA SKLT                                                      14

SEQ ID NO: 110          moltype = AA   length = 253
FEATURE                 Location/Qualifiers
source                  1..253
                        mol_type = protein
                        organism = Homo sapiens
SEQUENCE: 110
QNIDQPTEMT ATEGAIVQIN CTYQTSGFNG LFWYQQHAGE APTFLSYNVL DGLEEKGRFS    60
SFLSRSKGYS YLLLKELQMK DSASYLCAVP APYTGTASKL TFGTGTRLQV TLDIQNPDPA   120
VYQLRDSKSS DKSVCLFTDF DSQTNVSQSK DSDVYITDKT VLDMRSMDFK SNSAVAWSNK   180
SDFACANAFN NSIIPEDTFF PSPESSCDVK LVEKSFETDT NLNFQNLSVI GFRILLLKVA   240
GFNLLMTLRL WSS                                                     253

SEQ ID NO: 111          moltype = AA   length = 112
FEATURE                 Location/Qualifiers
source                  1..112
                        mol_type = protein
                        organism = Homo sapiens
SEQUENCE: 111
GVTQTPKFQV LKTGQSMTLQ CAQDMNHNSM YWYRQDPGMG LRLIYYSASE GTTDKGEVPN    60
GYNVSRLNKR EFSLRLESAA PSQTSVYFCA SSEGYSTYNE QFFGPGTRLT VL           112

SEQ ID NO: 112          moltype = AA   length = 5
FEATURE                 Location/Qualifiers
source                  1..5
                        mol_type = protein
                        organism = Homo sapiens
SEQUENCE: 112
MNHNS                                                                 5

SEQ ID NO: 113          moltype = AA   length = 6
FEATURE                 Location/Qualifiers
source                  1..6
                        mol_type = protein
                        organism = Homo sapiens
SEQUENCE: 113
SASEGT                                                                6

SEQ ID NO: 114          moltype = AA   length = 13
FEATURE                 Location/Qualifiers
source                  1..13
                        mol_type = protein
                        organism = Homo sapiens
SEQUENCE: 114
ASSEGYSTYN EQF                                                       13

SEQ ID NO: 115          moltype = AA   length = 291
FEATURE                 Location/Qualifiers
```

```
source                    1..291
                          mol_type = protein
                          organism = Homo sapiens
SEQUENCE: 115
GVTQTPKFQV LKTGQSMTLQ CAQDMNHNSM YWYRQDPGMG LRLIYYSASE GTTDKGEVPN   60
GYNVSRLNKR EFSLRLESAA PSQTSVYFCA SSEGYSTYNE QFFGPGTRLT VLEDLKNVFP  120
PEVAVFEPSE AEISHTQKAT LVCLATGFYP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSESY QQGVLSATIL YEILLGKATL YAVLVSALVL MAMVKRKDSR G          291

SEQ ID NO: 116            moltype = AA   length = 111
FEATURE                   Location/Qualifiers
source                    1..111
                          mol_type = protein
                          organism = Homo sapiens
SEQUENCE: 116
QLLEQSPQFL SIQEGENLTV YCNSSSVFSS LQWYRQEPGE GPVLLVTVVT GGEVKKLKRL   60
TFQFGDARKD SSLHITAAQP GDTGLYLCAG GLSDSYDKVI FGPGTSLSVI P           111

SEQ ID NO: 117            moltype = AA   length = 5
FEATURE                   Location/Qualifiers
source                    1..5
                          mol_type = protein
                          organism = Homo sapiens
SEQUENCE: 117
SVFSS                                                                5

SEQ ID NO: 118            moltype = AA   length = 7
FEATURE                   Location/Qualifiers
source                    1..7
                          mol_type = protein
                          organism = Homo sapiens
SEQUENCE: 118
VVTGGEV                                                              7

SEQ ID NO: 119            moltype = AA   length = 12
FEATURE                   Location/Qualifiers
source                    1..12
                          mol_type = protein
                          organism = Homo sapiens
SEQUENCE: 119
AGGLSDSYDK VI                                                       12

SEQ ID NO: 120            moltype = AA   length = 252
FEATURE                   Location/Qualifiers
source                    1..252
                          mol_type = protein
                          organism = Homo sapiens
SEQUENCE: 120
QLLEQSPQFL SIQEGENLTV YCNSSSVFSS LQWYRQEPGE GPVLLVTVVT GGEVKKLKRL   60
TFQFGDARKD SSLHITAAQP GDTGLYLCAG GLSDSYDKVI FGPGTSLSVI PNIQNPDPAV  120
YQLRDSKSSD KSVCLFTDFD SQTNVSQSKD SDVYITDKTV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 121            moltype = AA   length = 112
FEATURE                   Location/Qualifiers
source                    1..112
                          mol_type = protein
                          organism = Homo sapiens
SEQUENCE: 121
EVTQTPKHLV MGMTNKKSLK CEQHMGHRAM YWYKQKAKKP PELMFVYSYE KLSINESVPS   60
RFSPECPNSS LLNLHLHALQ PEDSALYLCA SSQGVGQEYG YTFGSGTRLT VV          112

SEQ ID NO: 122            moltype = AA   length = 13
FEATURE                   Location/Qualifiers
source                    1..13
                          mol_type = protein
                          organism = Homo sapiens
SEQUENCE: 122
ASSQGVGQEY GYT                                                      13

SEQ ID NO: 123            moltype = AA   length = 289
FEATURE                   Location/Qualifiers
source                    1..289
                          mol_type = protein
                          organism = Homo sapiens
SEQUENCE: 123
EVTQTPKHLV MGMTNKKSLK CEQHMGHRAM YWYKQKAKKP PELMFVYSYE KLSINESVPS   60
```

```
RFSPECPNSS LLNLHLHALQ PEDSALYLCA SSQGVGQEYG YTFGSGTRLT VVEDLNKVFP    120
PEVAVFEPSE AEISHTQKAT LVCLATGFFP DHVELSWWVN GKEVHSGVST DPQPLKEQPA    180
LNDSRYCLSS RLRVSATFWQ NPRNHFRCQV QFYGLSENDE WTQDRAKPVT QIVSAEAWGR    240
ADCGFTSVSY QQGVLSATIL YEILLGKATL YAVLVSALVL MAMVKRKDF               289

SEQ ID NO: 124           moltype = AA   length = 108
FEATURE                  Location/Qualifiers
source                   1..108
                         mol_type = protein
                         organism = Homo sapiens
SEQUENCE: 124
IQVEQSPPDL ILQEGANSTL RCNFSDSVNN LQWFHQNPWG QLINLFYIPS GTKQNGRLSA    60
TTVATERYSL LYISSSQTTD SGVYFCAVNT GTASKLTFGT GTRLQVTL                108

SEQ ID NO: 125           moltype = AA   length = 5
FEATURE                  Location/Qualifiers
source                   1..5
                         mol_type = protein
                         organism = Homo sapiens
SEQUENCE: 125
DSVNN                                                                5

SEQ ID NO: 126           moltype = AA   length = 5
FEATURE                  Location/Qualifiers
source                   1..5
                         mol_type = protein
                         organism = Homo sapiens
SEQUENCE: 126
IPSGT                                                                5

SEQ ID NO: 127           moltype = AA   length = 11
FEATURE                  Location/Qualifiers
source                   1..11
                         mol_type = protein
                         organism = Homo sapiens
SEQUENCE: 127
AVNTGTASKL T                                                         11

SEQ ID NO: 128           moltype = AA   length = 249
FEATURE                  Location/Qualifiers
source                   1..249
                         mol_type = protein
                         organism = Homo sapiens
SEQUENCE: 128
IQVEQSPPDL ILQEGANSTL RCNFSDSVNN LQWFHQNPWG QLINLFYIPS GTKQNGRLSA    60
TTVATERYSL LYISSSQTTD SGVYFCAVNT GTASKLTFGT GTRLQVTLDI QNPDPAVYQL    120
RDSKSSDKSV CLFTDFDSQT NVSQSKDSDV YITDKTVLDM RSMDFKSNSA VAWSNKSDFA    180
CANAFNNSII PEDTFFPSPE SSCDVKLVEK SFETDTNLNF QNLSVIGFRI LLLKVAGFNL    240
LMTLRLWSS                                                           249

SEQ ID NO: 129           moltype = AA   length = 113
FEATURE                  Location/Qualifiers
source                   1..113
                         mol_type = protein
                         organism = Homo sapiens
SEQUENCE: 129
GVTQTPKFQV LKTGQSMTLQ CAQDMNHNSM YWYRQDPGMG LRLIYYSASE GTTDKGEVPN    60
GYNVSRLNKR EFSLRLESAA PSQTSVYFCA SSPRGQGRSY EQYFGPGTRL TVT           113

SEQ ID NO: 130           moltype = AA   length = 14
FEATURE                  Location/Qualifiers
source                   1..14
                         mol_type = protein
                         organism = Homo sapiens
SEQUENCE: 130
ASSPRGQGRS YEQY                                                      14

SEQ ID NO: 131           moltype = AA   length = 292
FEATURE                  Location/Qualifiers
source                   1..292
                         mol_type = protein
                         organism = Homo sapiens
SEQUENCE: 131
GVTQTPKFQV LKTGQSMTLQ CAQDMNHNSM YWYRQDPGMG LRLIYYSASE GTTDKGEVPN    60
GYNVSRLNKR EFSLRLESAA PSQTSVYFCA SSPRGQGRSY EQYFGPGTRL TVTEDLKNVF    120
PPEVAVFEPS EAEISHTQKA TLVCLATGFY PDHVELSWWV NGKEVHSGVS TDPQPLKEQP    180
ALNDSRYCLS SRLRVSATFW QNPRNHFRCQ VQFYGLSEND EWTQDRAKPV TQIVSAEAWG    240
RADCGFTSES YQQGVLSATI LYEILLGKAT LYAVLVSALV LMAMVKRKDS RG            292
```

-continued

```
SEQ ID NO: 132           moltype = AA   length = 119
FEATURE                  Location/Qualifiers
source                   1..119
                         mol_type = protein
                         organism = Homo sapiens
SEQUENCE: 132
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMREGSDAG GTSYGKLTFG QGTILTVHP    119

SEQ ID NO: 133           moltype = AA   length = 17
FEATURE                  Location/Qualifiers
source                   1..17
                         mol_type = protein
                         organism = Homo sapiens
SEQUENCE: 133
AMREGSDAGG TSYGKLT                                                   17

SEQ ID NO: 134           moltype = AA   length = 260
FEATURE                  Location/Qualifiers
source                   1..260
                         mol_type = protein
                         organism = Homo sapiens
SEQUENCE: 134
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMREGSDAG GTSYGKLTFG QGTILTVHPN   120
IQNPDPAVYQ LRDSKSSDKS VCLFTDFDSQ TNVSQSKDSD VYITDKTVLD MRSMDFKSNS   180
AVAWSNKSDF ACANAFNNSI IPEDTFFPSP ESSCDVKLVE KSFETDTNLN FQNLSVIGFR   240
ILLLKVAGFN LLMTLRLWSS                                               260

SEQ ID NO: 135           moltype = AA   length = 113
FEATURE                  Location/Qualifiers
source                   1..113
                         mol_type = protein
                         organism = Homo sapiens
SEQUENCE: 135
GVIQSPRHLI KEKRETATLK CYPIPRHDTV YWYQQGPGQD PQFLISFYEK MQSDKGSIPD    60
RFSAQQFSDY HSELNMSSLE LGDSALYFCA SSPSTGRLNT EAFFGQGTRL TVV          113

SEQ ID NO: 136           moltype = AA   length = 14
FEATURE                  Location/Qualifiers
source                   1..14
                         mol_type = protein
                         organism = Homo sapiens
SEQUENCE: 136
ASSPSTGRLN TEAF                                                      14

SEQ ID NO: 137           moltype = AA   length = 290
FEATURE                  Location/Qualifiers
source                   1..290
                         mol_type = protein
                         organism = Homo sapiens
SEQUENCE: 137
GVIQSPRHLI KEKRETATLK CYPIPRHDTV YWYQQGPGQD PQFLISFYEK MQSDKGSIPD    60
RFSAQQFSDY HSELNMSSLE LGDSALYFCA SSPSTGRLNT EAFFGQGTRL TVVEDLNKVF   120
PPEVAVFEPS EAEISHTQKA TLVCLATGFF PDHVELSWWV NGKEVHSGVS TDPQPLKEQP   180
ALNDSRYCLS SRLRVSATFW QNPRNHFRCQ VQFYGLSEND EWTQDRAKPV TQIVSAEAWG   240
RADCGFTSVS YQQGVLSATI LYEILLGKAT LYAVLVSALV LMAMVKRKDF              290

SEQ ID NO: 138           moltype = AA   length = 9
FEATURE                  Location/Qualifiers
source                   1..9
                         mol_type = protein
                         organism = Homo sapiens
SEQUENCE: 138
KIFEMLEGV                                                             9

SEQ ID NO: 139           moltype = AA   length = 9
FEATURE                  Location/Qualifiers
source                   1..9
                         mol_type = protein
                         organism = synthetic construct
SEQUENCE: 139
AIFEMLEGV                                                             9

SEQ ID NO: 140           moltype = AA   length = 9
FEATURE                  Location/Qualifiers
source                   1..9
                         mol_type = protein
                         organism = synthetic construct
```

```
SEQUENCE: 140
KIAEMLEGV                                                                                  9

SEQ ID NO: 141           moltype = AA  length = 9
FEATURE                  Location/Qualifiers
source                   1..9
                         mol_type = protein
                         organism = synthetic construct
SEQUENCE: 141
KIFAMLEGV                                                                                  9

SEQ ID NO: 142           moltype = AA  length = 9
FEATURE                  Location/Qualifiers
source                   1..9
                         mol_type = protein
                         organism = synthetic construct
SEQUENCE: 142
KIFEALEGV                                                                                  9

SEQ ID NO: 143           moltype = AA  length = 9
FEATURE                  Location/Qualifiers
source                   1..9
                         mol_type = protein
                         organism = synthetic construct
SEQUENCE: 143
KIFEMAEGV                                                                                  9

SEQ ID NO: 144           moltype = AA  length = 9
FEATURE                  Location/Qualifiers
source                   1..9
                         mol_type = protein
                         organism = synthetic construct
SEQUENCE: 144
KIFEMLAGV                                                                                  9

SEQ ID NO: 145           moltype = AA  length = 9
FEATURE                  Location/Qualifiers
source                   1..9
                         mol_type = protein
                         organism = synthetic construct
SEQUENCE: 145
KIFEMLEAV                                                                                  9

SEQ ID NO: 146           moltype = AA  length = 9
FEATURE                  Location/Qualifiers
source                   1..9
                         mol_type = protein
                         organism = Homo sapiens
SEQUENCE: 146
HIMEHLEGV                                                                                  9

SEQ ID NO: 147           moltype = AA  length = 9
FEATURE                  Location/Qualifiers
source                   1..9
                         mol_type = protein
                         organism = Homo sapiens
SEQUENCE: 147
KIFSGLLKV                                                                                  9

SEQ ID NO: 148           moltype = AA  length = 9
FEATURE                  Location/Qualifiers
source                   1..9
                         mol_type = protein
                         organism = Homo sapiens
SEQUENCE: 148
KVTEMLVNV                                                                                  9

SEQ ID NO: 149           moltype = AA  length = 9
FEATURE                  Location/Qualifiers
source                   1..9
                         mol_type = protein
                         organism = Homo sapiens
SEQUENCE: 149
KIWEWLVGV                                                                                  9

SEQ ID NO: 150           moltype = AA  length = 9
FEATURE                  Location/Qualifiers
source                   1..9
                         mol_type = protein
```

```
                        organism = Homo sapiens
SEQUENCE: 150
KIEEFLEAV                                                               9

SEQ ID NO: 151          moltype = AA   length = 9
FEATURE                 Location/Qualifiers
source                  1..9
                        mol_type = protein
                        organism = Homo sapiens
SEQUENCE: 151
KIAELLENV                                                               9

SEQ ID NO: 152          moltype = AA   length = 9
FEATURE                 Location/Qualifiers
source                  1..9
                        mol_type = protein
                        organism = Homo sapiens
SEQUENCE: 152
KIFPALCTV                                                               9

SEQ ID NO: 153          moltype = AA   length = 9
FEATURE                 Location/Qualifiers
source                  1..9
                        mol_type = protein
                        organism = Homo sapiens
SEQUENCE: 153
KILDELEKV                                                               9

SEQ ID NO: 154          moltype = AA   length = 9
FEATURE                 Location/Qualifiers
source                  1..9
                        mol_type = protein
                        organism = Homo sapiens
SEQUENCE: 154
KIIDLLPKV                                                               9

SEQ ID NO: 155          moltype = AA   length = 9
FEATURE                 Location/Qualifiers
source                  1..9
                        mol_type = protein
                        organism = Homo sapiens
SEQUENCE: 155
RIFETVNSV                                                               9

SEQ ID NO: 156          moltype = AA   length = 137
FEATURE                 Location/Qualifiers
source                  1..137
                        mol_type = protein
                        organism = Mus musculus
SEQUENCE: 156
NIQNPEPAVY QLKDPRSQDS TLCLFTDFDS QINVPKTMES GTFITDKTVL DMKAMDSKSN        60
GAIAWSNQTS FTCQDIFKET NATYPSSDVP CDATLTEKSF ETDMNLNFQN LLVIVLRILL       120
LKVAGFNLLM TLRLWSS                                                     137

SEQ ID NO: 157          moltype = AA   length = 173
FEATURE                 Location/Qualifiers
source                  1..173
                        mol_type = protein
                        organism = Mus musculus
SEQUENCE: 157
EDLRNVTPPK VSLFEPSKAE IANKQKATLV CLARGFFPDH VELSWWVNGK EVHSGVSTDP        60
QAYKESNYSY CLSSRLRVSA TFWHNPRNHF RCQVQFHGLS EEDKWPEGSP KPVTQNISAE       120
AWGRADCGIT SASYQQGVLS ATILYEILLG KATLYAVLVS TLVVMAMVKR KNS              173

SEQ ID NO: 158          moltype = AA   length = 247
FEATURE                 Location/Qualifiers
source                  1..247
                        mol_type = protein
                        organism = synthetic construct
SEQUENCE: 158
QQLNQSPQSM FIQEGEDVSM NCTSSSIFNT WLWYKQDPGE GPVLLIALYK AGELTSNGRL        60
TAQFGITRKD SFLNISASIP SDVGIYFCAG GYNYGQNFVF GPGTRLSVLP NIQNPEPAVY       120
QLKDPRSQDS TLCLFTDFDS QINVPKTMES GTFITDKTVL DMKAMDSKSN GAIAWSNQTS       180
FTCQDIFKET NATYPSSDVP CDATLTEKSF ETDMNLNFQN LLVIVLRILL LKVAGFNLLM       240
TLRLWSS                                                                247

SEQ ID NO: 159          moltype = AA   length = 253
FEATURE                 Location/Qualifiers
source                  1..253
```

```
                          mol_type = protein
                          organism = synthetic construct
SEQUENCE: 159
QTVTQSQPEM SVQEAETVTL SCTYDTSENN YYLFWYKQPP SRQMILVIRQ EAYKQQNATE     60
NRFSVNFQKA AKSFSLKISD SQLGDTAMYF CAPLGLVAGS ARQLTFGSGT QLTVLPNIQN    120
PEPAVYQLKD PRSQDSTLCL FTDFDSQINV PKTMESGTFI TDKTVLDMKA MDSKSNGAIA    180
WSNQTSFTCQ DIFKETNATY PSSDVPCDAT LTEKSFETDM NLNFQNLLVI VLRILLLKVA    240
GFNLLMTLRL WSS                                                      253

SEQ ID NO: 160            moltype = AA  length = 252
FEATURE                   Location/Qualifiers
source                    1..252
                          mol_type = protein
                          organism = synthetic construct
SEQUENCE: 160
QKITQTQPGM FVQEKEAVTL DCTYDTSDQS YGLFWYKQPS SGEMIFLIYQ GSYDEQNATE     60
GRYSLNFQKA RKSANLVISA SQLGDSAMYF CAINGLPGSA RQLTFGSGTQ LTVLPNIQNP    120
EPAVYQLKDP RSQDSTLCLF TDFDSQINVP KTMESGTFIT DKTVLDMKAM DSKSNGAIAW    180
SNQTSFTCQD IFKETNATYP SSDVPCDATL TEKSFETDMN LNFQNLLVIV LRILLLKVAG    240
FNLLMTLRLW SS                                                       252

SEQ ID NO: 161            moltype = AA  length = 254
FEATURE                   Location/Qualifiers
source                    1..254
                          mol_type = protein
                          organism = synthetic construct
SEQUENCE: 161
QKITQTQPGM FVQEKEAVTL DCTYDTSDQS YGLFWYKQPS SGEMIFLIYQ GSYDEQNATE     60
GRYSLNFQKA RKSANLVISA SQLGDSAMYF CAMSDPIMDT GRRALTFGSG TRLQVQPNIQ    120
NPEPAVYQLK DPRSQDSTLC LFTDFDSQIN VPKTMESGTF ITDKTVLDMK AMDSKSNGAI    180
AWSNQTSFTC QDIFKETNAT YPSSDVPCDA TLTEKSFETD MNLNFQNLLV IVLRILLLKV    240
AGFNLLMTLR LWSS                                                     254

SEQ ID NO: 162            moltype = AA  length = 247
FEATURE                   Location/Qualifiers
source                    1..247
                          mol_type = protein
                          organism = synthetic construct
SEQUENCE: 162
KQEVTQIPAA LSVPEGENLV LNCSFTDSAI YNLQWFRQDP GKGLTSLLLI QSSQREQTSG     60
RLNASLDKSS GRSTLYIAAS QPGDSATYLC AVLLTGKLIF GQGTTLQVKP NIQNPEPAVY    120
QLKDPRSQDS TLCLFTDFDS QINVPKTMES GTFITDKTVL DMKAMDSKSN GAIAWSNQTS    180
FTCQDIFKET NATYPSSDVP CDATLTEKSF ETDMNLNFQN LLVIVLRILL LKVAGFNLLM    240
TLRLWSS                                                             247

SEQ ID NO: 163            moltype = AA  length = 255
FEATURE                   Location/Qualifiers
source                    1..255
                          mol_type = protein
                          organism = synthetic construct
SEQUENCE: 163
QQKEVEQDPG PLSVPEGAIV SLNCTYSNSA FQYFMWYRQY SRKGPELLMY TYSSGNKEDG     60
RFTAQVDKSS KYISLFIRDS QPSDSATYLC AMSGNSGARD YGNNRLAFGK GNQVVVIPNI    120
QNPEPAVYQL KDPRSQDSTL CLFTDFDSQI NVPKTMESGT FITDKTVLDM KAMDSKSNGA    180
IAWSNQTSFT CQDIFKETNA TYPSSDVPCD ATLTEKSFET DMNLNFQNLL VIVLRILLLK    240
VAGFNLLMTL RLWSS                                                    255

SEQ ID NO: 164            moltype = AA  length = 247
FEATURE                   Location/Qualifiers
source                    1..247
                          mol_type = protein
                          organism = synthetic construct
SEQUENCE: 164
QKITQTQPGM FVQEKEAVTL DCTYDTSDQS YGLFWYKQPS SGEMIFLIYQ GSYDEQNATE     60
GRYSLNFQKA RKSANLVISA SQLGDSAMYF CGYSNYQLIW GAGTKLIIKP NIQNPEPAVY    120
QLKDPRSQDS TLCLFTDFDS QINVPKTMES GTFITDKTVL DMKAMDSKSN GAIAWSNQTS    180
FTCQDIFKET NATYPSSDVP CDATLTEKSF ETDMNLNFQN LLVIVLRILL LKVAGFNLLM    240
TLRLWSS                                                             247

SEQ ID NO: 165            moltype = AA  length = 251
FEATURE                   Location/Qualifiers
source                    1..251
                          mol_type = protein
                          organism = synthetic construct
SEQUENCE: 165
QTVTQSQPEM SVQEAETVTL SCTYDTSESD YYLFWYKQPP SRQMILVIRQ EAYKQQNATE     60
NRFSVNFQKA AKSFSLKISD SQLGDAAMYF CTFRYGGATN KLIFGTGTLL AVQPNIQNPE    120
PAVYQLKDPR SQDSTLCLFT DFDSQINVPK TMESGTFITD KTVLDMKAMD SKSNGAIAWS    180
NQTSFTCQDI FKETNATYPS SDVPCDATLT EKSFETDMNL NFQNLLVIVL RILLLKVAGF    240
```

```
NLLMTLRLWS S                                                                 251

SEQ ID NO: 166              moltype = AA  length = 247
FEATURE                     Location/Qualifiers
source                      1..247
                            mol_type = protein
                            organism = synthetic construct
SEQUENCE: 166
EDVEQSLFLS VREGDSSVIN CTYTDSSSTY LYWYKQEPGA GLQLLTYIFS NMDMKQDQRL             60
TVLLNKKDKH LSLRIADTQT GDSAIYFCAE KETAGNKLTF GGGTRVLVKP NIQNPEPAVY            120
QLKDPRSQDS TLCLFTDFDS QINVPKTMES GTFITDKTVL DMKAMDSKSN GAIAWSNQTS            180
FTCQDIFKET NATYPSSDVP CDATLTEKSF ETDMNLNFQN LLVIVLRILL LKVAGFNLLM            240
TLRLWSS                                                                     247

SEQ ID NO: 167              moltype = AA  length = 247
FEATURE                     Location/Qualifiers
source                      1..247
                            mol_type = protein
                            organism = synthetic construct
SEQUENCE: 167
QSVAQPEDQV NVAEGNPLTV KCTYSVSGNP YLFWYVQYPN RGLQFLLKYI TGDNLVKGSY             60
GFEAEFNKSQ TSFHLKKPSA LVSDSALYFC AAPRDDKIIF GKGTRLHILP NIQNPEPAVY            120
QLKDPRSQDS TLCLFTDFDS QINVPKTMES GTFITDKTVL DMKAMDSKSN GAIAWSNQTS            180
FTCQDIFKET NATYPSSDVP CDATLTEKSF ETDMNLNFQN LLVIVLRILL LKVAGFNLLM            240
TLRLWSS                                                                     247

SEQ ID NO: 168              moltype = AA  length = 252
FEATURE                     Location/Qualifiers
source                      1..252
                            mol_type = protein
                            organism = synthetic construct
SEQUENCE: 168
QKVTQAQTEI SVVEKEDVTL DCVYETRDTT YYLFWYKQPP SGELVFLIRR NSFDEQNEIS             60
GRYSWNFQKS TSSFNFTITA SQVVDSAVYF CALSGRGSST YKYIFGTGTR LKVLANIQNP            120
EPAVYQLKDP RSQDSTLCLF TDFDSQINVP KTMESGTFIT DKTVLDMKAM DSKSNGAIAW            180
SNQTSFTCQD IFKETNATYP SSDVPCDATL TEKSFETDMN LNFQNLLVIV LRILLLKVAG            240
FNLLMTLRLW SS                                                               252

SEQ ID NO: 169              moltype = AA  length = 249
FEATURE                     Location/Qualifiers
source                      1..249
                            mol_type = protein
                            organism = synthetic construct
SEQUENCE: 169
QNIDQPTEMT ATEGAIVQIN CTYQTSGFNG LFWYQQHAGE APTFLSYNVL DGLEEKGRFS             60
SFLSRSKGYS YLLLKELQMK DSASYLCAVP APYTGTASKL TFGTGTRLQV TLNIQNPEPA            120
VYQLKDPRSQ DSTLCLFTDF DSQINVPKTM ESGTFITDKT VLDMKAMDSK SNGAIAWSNQ            180
TSFTCQDIFK ETNATYPSSD VPCDATLTEK SFETDMNLNF QNLLVIVLRI LLLKVAGFNL            240
LMTLRLWSS                                                                   249

SEQ ID NO: 170              moltype = AA  length = 248
FEATURE                     Location/Qualifiers
source                      1..248
                            mol_type = protein
                            organism = synthetic construct
SEQUENCE: 170
QLLEQSPQFL SIQEGENLTV YCNSSSVFSS LQWYRQEPGE GPVLLVTVVT GGEVKKLKRL             60
TFQFGDARKD SSLHITAAQP GDTGLYLCAG GLSDSYDKVI FGPGTSLSVI PNIQNPEPAV            120
YQLKDPRSQD STLCLFTDFD SQINVPKTME SGTFITDKTV LDMKAMDSKS NGAIAWSNQT            180
SFTCQDIFKE TNATYPSSDV PCDATLTEKS FETDMNLNFQ NLLVIVLRIL LLKVAGFNLL            240
MTLRLWSS                                                                    248

SEQ ID NO: 171              moltype = AA  length = 245
FEATURE                     Location/Qualifiers
source                      1..245
                            mol_type = protein
                            organism = synthetic construct
SEQUENCE: 171
IQVEQSPPDL ILQEGANSTL RCNFSDSVNN LQWFHQNPWG QLINLFYIPS GTKQNGRLSA             60
TTVATERYSL LYISSSQTTD SGVYFCAVNT GTASKLTFGT GTRLQVTLNI QNPEPAVYQL            120
KDPRSQDSTL CLFTDFDSQI NVPKTMESGT FITDKTVLDM KAMDSKSNGA IAWSNQTSFT            180
CQDIFKETNA TYPSSDVPCD ATLTEKSFET DMNLNFQNLL VIVLRILLLK VAGFNLLMTL            240
RLWSS                                                                       245

SEQ ID NO: 172              moltype = AA  length = 256
FEATURE                     Location/Qualifiers
source                      1..256
                            mol_type = protein
                            organism = synthetic construct
```

```
SEQUENCE: 172
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMREGSDAG GTSYGKLTFG QGTILTVHPN   120
IQNPEPAVYQ LKDPRSQDST LCLFTDFDSQ INVPKTMESG TFITDKTVLD MKAMDSKSNG   180
AIAWSNQTSF TCQDIFKETN ATYPSSDVPC DATLTEKSFE TDMNLNFQNL LVIVLRILLL   240
KVAGFNLLMT LRLWSS                                                  256

SEQ ID NO: 173          moltype = AA  length = 285
FEATURE                 Location/Qualifiers
source                  1..285
                        mol_type = protein
                        organism = synthetic construct
SEQUENCE: 173
GVTQTPKHLI TATGQRVTLR CSPRSGDLSV YWYQQSLDQG LQFLIQYYNG EERAKGNILE    60
RFSAQQFPDL HSELNLSSLE LGDSALYFCA SSAGLAGGYE QYFGPGTRLT VTEDLRNVTP   120
PKVSLFEPSK AEIANKQKAT LVCLARGFFP DHVELSWWVN GKEVHSGVST DPQAYKESNY   180
SYCLSSRLRV SATFWHNPRN HFRCQVQFHG LSEEDKWPEG SPKPVTQNIS AEAWGRADCG   240
ITSASYQQGV LSATILYEIL LGKATLYAVL VSTLVVMAMV KRKNS                  285

SEQ ID NO: 174          moltype = AA  length = 285
FEATURE                 Location/Qualifiers
source                  1..285
                        mol_type = protein
                        organism = synthetic construct
SEQUENCE: 174
GVSQDPRHKI TKRGQNVTFR CDPISEHNRL YWYRQTLGQG PEFLTYFQNE AQLEKSRLLS    60
DRFSAERPKG SFSTLEIQRT EQGDSAMYLC ASSTDITSYE QYFGPGTRLT VTEDLRNVTP   120
PKVSLFEPSK AEIANKQKAT LVCLARGFFP DHVELSWWVN GKEVHSGVST DPQAYKESNY   180
SYCLSSRLRV SATFWHNPRN HFRCQVQFHG LSEEDKWPEG SPKPVTQNIS AEAWGRADCG   240
ITSASYQQGV LSATILYEIL LGKATLYAVL VSTLVVMAMV KRKNS                  285

SEQ ID NO: 175          moltype = AA  length = 287
FEATURE                 Location/Qualifiers
source                  1..287
                        mol_type = protein
                        organism = synthetic construct
SEQUENCE: 175
GVAQSPRYKI IEKRQSVAFW CNPISGHATL YWYQQILGQG PKLLIQFQNN GVVDDSQLPK    60
DRFSAERLKG VDSTLKIQPA KLEDSAVYLC ASSRFVATGT SPLHFGNGTR LTVTEDLRNV   120
TPPKVSLFEP SKAEIANKQK ATLVCLARGF FPDHVELSWW VNGKEVHSGV STDPQAYKES   180
NYSYCLSSRL RVSATFWHNP RNHFRCQVQF HGLSEEDKWP EGSPKPVTQN ISAEAWGRAD   240
CGITSASYQQ GVLSATILYE ILLGKATLYA VLVSTLVVMA MVKRKNS                287

SEQ ID NO: 176          moltype = AA  length = 286
FEATURE                 Location/Qualifiers
source                  1..286
                        mol_type = protein
                        organism = synthetic construct
SEQUENCE: 176
GITQSPKYLF RKEGQNVTLS CEQNLNHDAM YWYRQDPGQG LRLIYYSQIV NDFQKGDIAE    60
GYSVSREKKE SFPLTVTSAQ KNPTAFYLCA SKSRGPNLAD TQYFGPGTRL TVLEDLRNVT   120
PPKVSLFEPS KAEIANKQKA TLVCLARGFF PDHVELSWWV NGKEVHSGVS TDPQAYKESN   180
YSYCLSSRLR VSATFWHNPR NHFRCQVQFH GLSEEDKWPE GSPKPVTQNI SAEAWGRADC   240
GITSASYQQG VLSATILYEI LLGKATLYAV LVSTLVVMAM VKRKNS                 286

SEQ ID NO: 177          moltype = AA  length = 285
FEATURE                 Location/Qualifiers
source                  1..285
                        mol_type = protein
                        organism = synthetic construct
SEQUENCE: 177
GVTQTPRYLI KTRGQQVTLS CSPISGHRSV SWYQQTPGQG LQFLFEYFSE TQRNKGNFPG    60
RFSGRQFSNS RSEMNVSTLE LGDSALYLCA SSGGPGPSGE QYFGPGTRLT VTEDLRNVTP   120
PKVSLFEPSK AEIANKQKAT LVCLARGFFP DHVELSWWVN GKEVHSGVST DPQAYKESNY   180
SYCLSSRLRV SATFWHNPRN HFRCQVQFHG LSEEDKWPEG SPKPVTQNIS AEAWGRADCG   240
ITSASYQQGV LSATILYEIL LGKATLYAVL VSTLVVMAMV KRKNS                  285

SEQ ID NO: 178          moltype = AA  length = 287
FEATURE                 Location/Qualifiers
source                  1..287
                        mol_type = protein
                        organism = synthetic construct
SEQUENCE: 178
EVTQTPKHLV MGMTNKKSLK CEQHMGHRAM YWYKQKAKKP PELMFVYSYE KLSINESVPS    60
RFSPECPNSS LLNLHLHALQ PEDSALYLCA SATWEEAGPY NEQFFGPGTR LTVLEDLRNV   120
TPPKVSLFEP SKAEIANKQK ATLVCLARGF FPDHVELSWW VNGKEVHSGV STDPQAYKES   180
NYSYCLSSRL RVSATFWHNP RNHFRCQVQF HGLSEEDKWP EGSPKPVTQN ISAEAWGRAD   240
CGITSASYQQ GVLSATILYE ILLGKATLYA VLVSTLVVMA MVKRKNS                287
```

```
SEQ ID NO: 179          moltype = AA   length = 285
FEATURE                 Location/Qualifiers
source                  1..285
                        mol_type = protein
                        organism = synthetic construct
SEQUENCE: 179
QVTQNPRYLI TVTGKKLTVT CSQNMNHEYM SWYRQDPGLG LRQIYYSMNV EVTDKGDVPE   60
GYKVSRKEKR NFPLILESPS PNQTSLYFCA SREGTGGYQP QHFGDGTRLS ILEDLRNVTP  120
PKVSLFEPSK AEIANKQKAT LVCLARGFFP DHVELSWWVN GKEVHSGVST DPQAYKESNY  180
SYCLSSRLRV SATFWHNPRN HFRCQVQFHG LSEEDKWPEG SPKPVTQNIS AEAWGRADCG  240
ITSASYQQGV LSATILYEIL LGKATLYAVL VSTLVVMAMV KRKNS                  285

SEQ ID NO: 180          moltype = AA   length = 286
FEATURE                 Location/Qualifiers
source                  1..286
                        mol_type = protein
                        organism = synthetic construct
SEQUENCE: 180
GVIQSPRHLI KEKRETATLK CYPIPRHDTV YWYQQGPGQD PQFLISFYEK MQSDKGSIPD   60
RFSAQQFSDY HSELNMSSLE LGDSALYFCA SRGGWAETPD TQYFGPGTRL TVLEDLRNVT  120
PPKVSLFEPS KAEIANKQKA TLVCLARGFF PDHVELSWWV NGKEVHSGVS TDPQAYKESN  180
YSYCLSSRLR VSATFWHNPR NHFRCQVQFH GLSEEDKWPE GSPKPVTQNI SAEAWGRADC  240
GITSASYQQG VLSATILYEI LLGKATLYAV LVSTLVVMAM VKRKNS                 286

SEQ ID NO: 181          moltype = AA   length = 288
FEATURE                 Location/Qualifiers
source                  1..288
                        mol_type = protein
                        organism = synthetic construct
SEQUENCE: 181
EPEVTQTPSH QVTQMGQEVI LRCVPISNHL YFYWYRQILG QKVEFLVSFY NNEISEKSEI   60
FDDQFSVERP DGSNFTLKIR STKLEDSAMY FCASTVQSPR TNEQFFGPGT RLTVLEDLRN  120
VTPPKVSLFE PSKAEIANKQ KATLVCLARG FFPDHVELSW WVNGKEVHSG VSTDPQAYKE  180
SNYSYCLSSR LRVSATFWHN PRNHFRCQVQ FHGLSEEDKW PEGSPKPVTQ NISAEAWGRA  240
DCGITSASYQ QGVLSATILY EILLGKATLY AVLVSTLVVM AMVKRKNS                288

SEQ ID NO: 182          moltype = AA   length = 285
FEATURE                 Location/Qualifiers
source                  1..285
                        mol_type = protein
                        organism = synthetic construct
SEQUENCE: 182
GVTQTPKFRV LKTGQSMTLL CAQDMNHEYM YWYRQDPGMG LRLIHYSVGE GTTAKGEVPD   60
GYNVSRLKKQ NFLLGLESAA PSQTSVYFCA SSYLRTGGNE QFFGPGTRLT VLEDLRNVTP  120
PKVSLFEPSK AEIANKQKAT LVCLARGFFP DHVELSWWVN GKEVHSGVST DPQAYKESNY  180
SYCLSSRLRV SATFWHNPRN HFRCQVQFHG LSEEDKWPEG SPKPVTQNIS AEAWGRADCG  240
ITSASYQQGV LSATILYEIL LGKATLYAVL VSTLVVMAMV KRKNS                  285

SEQ ID NO: 183          moltype = AA   length = 284
FEATURE                 Location/Qualifiers
source                  1..284
                        mol_type = protein
                        organism = synthetic construct
SEQUENCE: 183
GVIQSPRHLI KEKRETATLK CYPIPRHDTV YWYQQGPGQD PQFLISFYEK MQSDKGSIPD   60
RFSAQQFSDY HSELNMSSLE LGDSALYFCA SSAGTSYNEQ FFGPGTRLTV LEDLRNVTPP  120
KVSLFEPSKA EIANKQKATL VCLARGFFPD HVELSWWVNG KEVHSGVSTD PQAYKESNYS  180
YCLSSRLRVS ATFWHNPRNH FRCQVQFHGL SEEDKWPEGS PKPVTQNISA EAWGRADCGI  240
TSASYQQGVL SATILYEILL GKATLYAVLV STLVVMAMVK RKNS                   284

SEQ ID NO: 184          moltype = AA   length = 285
FEATURE                 Location/Qualifiers
source                  1..285
                        mol_type = protein
                        organism = synthetic construct
SEQUENCE: 184
GVTQTPKFQV LKTGQSMTLQ CAQDMNHNSM YWYRQDPGMG LRLIYYSASE GTTDKGEVPN   60
GYNVSRLNKR EFSLRLESAA PSQTSVYFCA SSEGYSTYNE QFFGPGTRLT VLEDLRNVTP  120
PKVSLFEPSK AEIANKQKAT LVCLARGFFP DHVELSWWVN GKEVHSGVST DPQAYKESNY  180
SYCLSSRLRV SATFWHNPRN HFRCQVQFHG LSEEDKWPEG SPKPVTQNIS AEAWGRADCG  240
ITSASYQQGV LSATILYEIL LGKATLYAVL VSTLVVMAMV KRKNS                  285

SEQ ID NO: 185          moltype = AA   length = 285
FEATURE                 Location/Qualifiers
source                  1..285
                        mol_type = protein
                        organism = synthetic construct
SEQUENCE: 185
EVTQTPKHLV MGMTNKKSLK CEQHMGHRAM YWYKQKAKKP PELMFVYSYE KLSINESVPS   60
```

```
RFSPECPNSS LLNLHLHALQ PEDSALYLCA SSQGVGQEYG YTFGSGTRLT VVEDLRNVTP    120
PKVSLFEPSK AEIANKQKAT LVCLARGFFP DHVELSWWVN GKEVHSGVST DPQAYKESNY    180
SYCLSSRLRV SATFWHNPRN HFRCQVQFHG LSEEDKWPEG SPKPVTQNIS AEAWGRADCG    240
ITSASYQQGV LSATILYEIL LGKATLYAVL VSTLVVMAMV KRKNS                    285

SEQ ID NO: 186          moltype = AA   length = 286
FEATURE                 Location/Qualifiers
source                  1..286
                        mol_type = protein
                        organism = synthetic construct
SEQUENCE: 186
GVTQTPKFQV LKTGQSMTLQ CAQDMNHNSM YWYRQDPGMG LRLIYYSASE GTTDKGEVPN    60
GYNVSRLNKR EFSLRLESAA PSQTSVYFCA SSPRGQGRSY EQYFGPGTRL TVTEDLRNVT    120
PPKVSLFEPS KAEIANKQKA TLVCLARGFF PDHVELSWWV NGKEVHSGVS TDPQAYKESN    180
YSYCLSSRLR VSATFWHNPR NHFRCQVQFH GLSEEDKWPE GSPKPVTQNI SAEAWGRADC    240
GITSASYQQG VLSATILYEI LLGKATLYAV LVSTLVVMAM VKRKNS                   286

SEQ ID NO: 187          moltype = AA   length = 286
FEATURE                 Location/Qualifiers
source                  1..286
                        mol_type = protein
                        organism = synthetic construct
SEQUENCE: 187
GVIQSPRHLI KEKRETATLK CYPIPRHDTV YWYQQGPGQD PQFLISFYEK MQSDKGSIPD    60
RFSAQQFSDY HSELNMSSLE LGDSALYFCA SSPSTGRLNT EAFFGQGTRL TVVEDLRNVT    120
PPKVSLFEPS KAEIANKQKA TLVCLARGFF PDHVELSWWV NGKEVHSGVS TDPQAYKESN    180
YSYCLSSRLR VSATFWHNPR NHFRCQVQFH GLSEEDKWPE GSPKPVTQNI SAEAWGRADC    240
GITSASYQQG VLSATILYEI LLGKATLYAV LVSTLVVMAM VKRKNS                   286

SEQ ID NO: 188          moltype = AA   length = 9
FEATURE                 Location/Qualifiers
source                  1..9
                        mol_type = protein
                        organism = Homo sapiens
SEQUENCE: 188
SLLMWITQV                                                            9

SEQ ID NO: 189          moltype = AA   length = 105
FEATURE                 Location/Qualifiers
source                  1..105
                        mol_type = protein
                        organism = Homo sapiens
SEQUENCE: 189
QTVTQSQPEM SVQEAETVTL SCTYDTSENN YYLFWYKQPP SRQMILVIRQ EAYKQQNATE    60
NRFSVNFQKA AKSFSLKISD SQLGDTAMYF CAPLGLVAGS ARQLT                    105

SEQ ID NO: 190          moltype = AA   length = 108
FEATURE                 Location/Qualifiers
source                  1..108
                        mol_type = protein
                        organism = Homo sapiens
SEQUENCE: 190
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMREGSDAG GTSYGKLT                 108

SEQ ID NO: 191          moltype = AA   length = 99
FEATURE                 Location/Qualifiers
source                  1..99
                        mol_type = protein
                        organism = Homo sapiens
SEQUENCE: 191
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CGYSNYQLI                           99

SEQ ID NO: 192          moltype = AA   length = 99
FEATURE                 Location/Qualifiers
source                  1..99
                        mol_type = protein
                        organism = Homo sapiens
SEQUENCE: 192
QSVAQPEDQV NVAEGNPLTV KCTYSVSGNP YLFWYVQYPN RGLQFLLKYI TGDNLVKGSY    60
GFEAEFNKSQ TSFHLKKPSA LVSDSALYFC AAPRDDKII                           99

SEQ ID NO: 193          moltype = AA   length = 99
FEATURE                 Location/Qualifiers
source                  1..99
                        mol_type = protein
                        organism = Homo sapiens
SEQUENCE: 193
```

```
QQLNQSPQSM FIQEGEDVSM NCTSSSIFNT WLWYKQDPGE GPVLLIALYK AGELTSNGRL    60
TAQFGITRKD SFLNISASIP SDVGIYFCAG GYNYGQNFV                          99

SEQ ID NO: 194          moltype = AA  length = 107
FEATURE                 Location/Qualifiers
source                  1..107
                        mol_type = protein
                        organism = Homo sapiens
SEQUENCE: 194
QQKEVEQDPG PLSVPEGAIV SLNCTYSNSA FQYFMWYRQY SRKGPELLMY TYSSGNKEDG    60
RFTAQVDKSS KYISLFIRDS QPSDSATYLC AMSGNSGARD YGNNRLA                 107

SEQ ID NO: 195          moltype = AA  length = 103
FEATURE                 Location/Qualifiers
source                  1..103
                        mol_type = protein
                        organism = Homo sapiens
SEQUENCE: 195
QTVTQSQPEM SVQEAETVTL SCTYDTSESD YYLFWYKQPP SRQMILVIRQ EAYKQQNATE    60
NRFSVNFQKA AKSFSLKISD SQLGDAAMYF CTFRYGGATN KLI                     103

SEQ ID NO: 196          moltype = AA  length = 104
FEATURE                 Location/Qualifiers
source                  1..104
                        mol_type = protein
                        organism = Homo sapiens
SEQUENCE: 196
QKVTQAQTEI SVVEKEDVTL DCVYETRDTT YYLFWYKQPP SGELVFLIRR NSFDEQNEIS    60
GRYSWNFQKS TSSFNFTITA SQVVDSAVYF CALSGRGSGT YKYI                    104

SEQ ID NO: 197          moltype = AA  length = 99
FEATURE                 Location/Qualifiers
source                  1..99
                        mol_type = protein
                        organism = Homo sapiens
SEQUENCE: 197
EDVEQSLFLS VREGDSSVIN CTYTDSSSTY LYWYKQEPGA GLQLLTYIFS NMDMKQDQRL    60
TVLLNKKDKH LSLRIADTQT GDSAIYFCAE KETAGNKLT                          99

SEQ ID NO: 198          moltype = AA  length = 101
FEATURE                 Location/Qualifiers
source                  1..101
                        mol_type = protein
                        organism = Homo sapiens
SEQUENCE: 198
QNIDQPTEMT ATEGAIVQIN CTYQTSGFNG LFWYQQHAGE APTFLSYNVL DGLEEKGRFS    60
SFLSRSKGYS YLLLKELQMK DSASYLCAVP APYTGTASKL T                       101

SEQ ID NO: 199          moltype = AA  length = 97
FEATURE                 Location/Qualifiers
source                  1..97
                        mol_type = protein
                        organism = Homo sapiens
SEQUENCE: 199
IQVEQSPPDL ILQEGANSTL RCNFSDSVNN LQWFHQNPWG QLINLFYIPS GTKQNGRLSA    60
TTVATERYSL LYISSSQTTD SGVYFCAVNT GTASKLT                            97

SEQ ID NO: 200          moltype = AA  length = 100
FEATURE                 Location/Qualifiers
source                  1..100
                        mol_type = protein
                        organism = Homo sapiens
SEQUENCE: 200
QLLEQSPQFL SIQEGENLTV YCNSSSVFSS LQWYRQEPGE GPVLLVTVVT GGEVKKLKRL    60
TFQFGDARKD SSLHITAAQP GDTGLYLCAG GLSDSYDKVI                         100

SEQ ID NO: 201          moltype = AA  length = 106
FEATURE                 Location/Qualifiers
source                  1..106
                        mol_type = protein
                        organism = Homo sapiens
SEQUENCE: 201
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMSDPIMDT GRRALT                  106

SEQ ID NO: 202          moltype = AA  length = 104
FEATURE                 Location/Qualifiers
source                  1..104
                        mol_type = protein
```

```
                              organism = Homo sapiens
SEQUENCE: 202
QKITQTQPGM FVQEKEAVTL DCTYDTSDQS YGLFWYKQPS SGEMIFLIYQ GSYDEQNATE    60
GRYSLNFQKA RKSANLVISA SQLGDSAMYF CAINGLPGSA RQLT                    104

SEQ ID NO: 203            moltype = AA  length = 99
FEATURE                   Location/Qualifiers
source                    1..99
                          mol_type = protein
                          organism = Homo sapiens
SEQUENCE: 203
KQEVTQIPAA LSVPEGENLV LNCSFTDSAI YNLQWFRQDP GKGLTSLLLI QSSQREQTSG    60
RLNASLDKSS GRSTLYIAAS QPGDSATYLC AVLLTGKLI                          99

SEQ ID NO: 204            moltype = AA  length = 116
FEATURE                   Location/Qualifiers
source                    1..116
                          mol_type = protein
                          organism = Homo sapiens
SEQUENCE: 204
QTVTQSQPKM SVQEAETVTL SCTYDTSENN YYLFWYKQPP SRQMILVIRQ EAYKQQNATE    60
NRFSVNFQKA AKSFSLKISD SQLGDTAMYF CAPLGLVAGS ARQLTFGSGT QLTVLP       116

SEQ ID NO: 205            moltype = AA  length = 119
FEATURE                   Location/Qualifiers
source                    1..119
                          mol_type = protein
                          organism = Homo sapiens
SEQUENCE: 205
QKITQTQPGM FVQEKEAVTL DCTWDTSDQS YGLFWYKQPS SGEMIFLIYQ GSYDEQNATE    60
GRYSLNFQKA RKSANLVISA SQLGDSAMYF CAMREGSDAG GTSYGKLTFG QGTILTVHP    119

SEQ ID NO: 206            moltype = AA  length = 110
FEATURE                   Location/Qualifiers
source                    1..110
                          mol_type = protein
                          organism = Homo sapiens
SEQUENCE: 206
QKITQTQPAM FVQEKEAVTL DCTYDTSDQS YGLFWYKQPS SGEMIFLIYQ GSYDEQNATE    60
GRYSLNFQKA RKSANLVISA SQLGDSAMYF CGYSNYQLIW GAGTKLIIKP              110

SEQ ID NO: 207            moltype = AA  length = 110
FEATURE                   Location/Qualifiers
source                    1..110
                          mol_type = protein
                          organism = Homo sapiens
SEQUENCE: 207
QSVAQPEDQV NVAEGQPLTV KCTYSVSGNP YLFWYVQYPN RGLQFLLKYI TGDNLVKGSY    60
GFEAEFNKSQ TSFHLKKPSA LVSDSALYFC AAPRDDKIIF GKGTRLHILP              110

SEQ ID NO: 208            moltype = AA  length = 110
FEATURE                   Location/Qualifiers
source                    1..110
                          mol_type = protein
                          organism = Homo sapiens
SEQUENCE: 208
QQLNQSPQTM FIQEGEDVSM NCTSSSIFNT WLWYKQDPGE GPVLLIALYK AGELTSNGRL    60
TAQFGITRKD SFLNISASIP SDVGIYFCAG GYNYGQNFVF GPGTRLSVLP              110

SEQ ID NO: 209            moltype = AA  length = 118
FEATURE                   Location/Qualifiers
source                    1..118
                          mol_type = protein
                          organism = Homo sapiens
SEQUENCE: 209
QQKEVEQDPG PLSVPEGAIV SLNCTYTNSA FQYFMWYRQY SRKGPELLMY TYSSGNKEDG    60
RFTAQVDKSS KYISLFIRDS QPSDSATYLC AMSGNSGARD YGNNRLAFGK GNQVVVIP     118

SEQ ID NO: 210            moltype = AA  length = 114
FEATURE                   Location/Qualifiers
source                    1..114
                          mol_type = protein
                          organism = Homo sapiens
SEQUENCE: 210
QTVTQSQPEM SVQEAETFTL SCTYDTSESD YYLFWYKQPP SRQMILVIRQ EAYKQQNATE    60
NRFSVNFQKA AKSFSLKISD SQLGDAAMYF CTFRYGGATN KLIFGTGTLL AVQP         114

SEQ ID NO: 211            moltype = AA  length = 115
FEATURE                   Location/Qualifiers
```

```
source                  1..115
                        mol_type = protein
                        organism = Homo sapiens
SEQUENCE: 211
QKVTQAQTEI SWVEKEDVTL DCVYETRDTT YYLFWYKQPP SGELVFLIRR NSFDEQNEIS       60
GRYSWNFQKS TSSFNFTITA SQVVDSAVYF CALSGRGSGT YKYIFGTGTR LKVLA           115

SEQ ID NO: 212          moltype = AA  length = 110
FEATURE                 Location/Qualifiers
source                  1..110
                        mol_type = protein
                        organism = Homo sapiens
SEQUENCE: 212
EDVEQSLFIS VREGDSSVIN CTYTDSSSTY LYWYKQEPGA GLQLLTYIFS NMDMKQDQRL       60
TVLLNKKDKH LSLRIADTQT GDSAIYFCAE KETAGNKLTF GGGTRVLVKP                 110

SEQ ID NO: 213          moltype = AA  length = 112
FEATURE                 Location/Qualifiers
source                  1..112
                        mol_type = protein
                        organism = Homo sapiens
SEQUENCE: 213
QNIDQPTEMT GTEGAIVQIN CTYQTSGFNG LFWYQQHAGE APTFLSYNVL DGLEEKGRFS       60
SFLSRSKGYS YLLLKELQMK DSASYLCAVP APYTGTASKL TFGTGTRLQV TL               112

SEQ ID NO: 214          moltype = AA  length = 108
FEATURE                 Location/Qualifiers
source                  1..108
                        mol_type = protein
                        organism = Homo sapiens
SEQUENCE: 214
IQVEQSPPDL ILNEGANSTL RCNFSDSVNN LQWFHQNPWG QLINLFYIPS GTKQNGRLSA       60
TTVATERYSL LYISSSQTTD SGVYFCAVNT GTASKLTFGT GTRLQVTL                   108

SEQ ID NO: 215          moltype = AA  length = 111
FEATURE                 Location/Qualifiers
source                  1..111
                        mol_type = protein
                        organism = Homo sapiens
SEQUENCE: 215
QLLENSPQFL SIQEGENLTV YCNSSSVFSS LQWYRQEPGE GPVLLVTVVT GGEVKKLKRL       60
TFQFGDARKD SSLHITAAQP GDTGLYLCAG GLSDSYDKVI FGPGTSLSVI P               111

SEQ ID NO: 216          moltype = AA  length = 117
FEATURE                 Location/Qualifiers
source                  1..117
                        mol_type = protein
                        organism = Homo sapiens
SEQUENCE: 216
QKITQTQPGM FVQEKEAVSL DCTYDTSDQS YGLFWYKQPS SGEMIFLIYQ GSYDEQNATE       60
GRYSLNFQKA RKSANLVISA SQLGDSAMYF CAMSDPIMDT GRRALTFGSG TRLQVQP         117

SEQ ID NO: 217          moltype = AA  length = 115
FEATURE                 Location/Qualifiers
source                  1..115
                        mol_type = protein
                        organism = Homo sapiens
SEQUENCE: 217
QKITQTQPGM FVQEKEAVTL DCTYNTSDQS YGLFWYKQPS SGEMIFLIYQ GSYDEQNATE       60
GRYSLNFQKA RKSANLVISA SQLGDSAMYF CAINGLPGSA RQLTFGSGTQ LTVLP           115

SEQ ID NO: 218          moltype = AA  length = 110
FEATURE                 Location/Qualifiers
source                  1..110
                        mol_type = protein
                        organism = Homo sapiens
SEQUENCE: 218
KQEVTQIPAA ISVPEGENLV LNCSFTDSAI YNLQWFRQDP GKGLTSLLLI QSSQREQTSG       60
RLNASLDKSS GRSTLYIAAS QPGDSATYLC AVLLTGKLIF GQGTTLQVKP                 110

SEQ ID NO: 219          moltype = AA  length = 116
FEATURE                 Location/Qualifiers
source                  1..116
                        mol_type = protein
                        organism = Homo sapiens
SEQUENCE: 219
QTVTNSQPEM SVQEAETVTL SCTYDTSENN YYLFWYKQPP SRQMILVIRQ EAYKQQNATE       60
NRFSVNFQKA AKSFSLKISD SQLGDTAMYF CAPLGLVAGS ARQLTFGSGT QLTVLP          116
```

```
SEQ ID NO: 220          moltype = AA   length = 119
FEATURE                 Location/Qualifiers
source                  1..119
                        mol_type = protein
                        organism = Homo sapiens
SEQUENCE: 220
QKITQSQPGM FVQEKEAVTL DCTYDTSDQS YGLFWYKQPS SGEMIFLIYQ GSYDEQNATE     60
GRYSLNFQKA RKSANLVISA SQLGDSAMYF CAMREGSDAG GTSYGKLTFG QGTILTVHP      119

SEQ ID NO: 221          moltype = AA   length = 110
FEATURE                 Location/Qualifiers
source                  1..110
                        mol_type = protein
                        organism = Homo sapiens
SEQUENCE: 221
QKITQTQPGM FVQEKEGVTL DCTYDTSDQS YGLFWYKQPS SGEMIFLIYQ GSYDEQNATE     60
GRYSLNFQKA RKSANLVISA SQLGDSAMYF CGYSNYQLIW GAGTKLIIKP                110

SEQ ID NO: 222          moltype = AA   length = 110
FEATURE                 Location/Qualifiers
source                  1..110
                        mol_type = protein
                        organism = Homo sapiens
SEQUENCE: 222
QSVANPEDQV NVAEGNPLTV KCTYSVSGNP YLFWYVQYPN RGLQFLLKYI TGDNLVKGSY     60
GFEAEFNKSQ TSFHLKKPSA LVSDSALYFC AAPRDDKIIF GKGTRLHILP                110

SEQ ID NO: 223          moltype = AA   length = 110
FEATURE                 Location/Qualifiers
source                  1..110
                        mol_type = protein
                        organism = Homo sapiens
SEQUENCE: 223
QQLNQSPQSM FIQEGERVSM NCTSSSIFNT WLWYKQDPGE GPVLLIALYK AGELTSNGRL     60
TAQFGITRKD SFLNISASIP SDVGIYFCAG GYNYGQNFVF GPGTRLSVLP                110

SEQ ID NO: 224          moltype = AA   length = 118
FEATURE                 Location/Qualifiers
source                  1..118
                        mol_type = protein
                        organism = Homo sapiens
SEQUENCE: 224
QQKEVEQRPG PLSVPEGAIV SLNCTYSNSA FQYFMWYRQY SRKGPELLMY TYSSGNKEDG     60
RFTAQVDKSS KYISLFIRDS QPSDSATYLC AMSGNSGARD YGNNRLAFGK GNQVVVIP       118

SEQ ID NO: 225          moltype = AA   length = 114
FEATURE                 Location/Qualifiers
source                  1..114
                        mol_type = protein
                        organism = Homo sapiens
SEQUENCE: 225
QTVTQTQPEM SVQEAETVTL SCTYDTSESD YYLFWYKQPP SRQMILVIRQ EAYKQQNATE     60
NRFSVNFQKA AKSFSLKISD SQLGDAAMYF CTFRYGGATN KLIFGTGTLL AVQP           114

SEQ ID NO: 226          moltype = AA   length = 115
FEATURE                 Location/Qualifiers
source                  1..115
                        mol_type = protein
                        organism = Homo sapiens
SEQUENCE: 226
QKVTQAQTEL SVVEKEDVTL DCVYETRDTT YYLFWYKQPP SGELVFLIRR NSFDEQNEIS     60
GRYSWNFQKS TSSFNFTITA SQVVDSAVYF CALSGRGSGT YKYIFGTGTR LKVLA          115

SEQ ID NO: 227          moltype = AA   length = 110
FEATURE                 Location/Qualifiers
source                  1..110
                        mol_type = protein
                        organism = Homo sapiens
SEQUENCE: 227
EDVEQSLFLS VREGDTSVIN CTYTDSSSTY LYWYKQEPGA GLQLLTYIFS NMDMKQDQRL     60
TVLLNKKDKH LSLRIADTQT GDSAIYFCAE KETAGNKLTF GGGTRVLVKP                110

SEQ ID NO: 228          moltype = AA   length = 112
FEATURE                 Location/Qualifiers
source                  1..112
                        mol_type = protein
                        organism = Homo sapiens
SEQUENCE: 228
QNIDQPSEMT ATEGAIVQIN CTYQTSGFNG LFWYQQHAGE APTFLSYNVL DGLEEKGRFS     60
```

```
SFLSRSKGYS YLLLKELQMK DSASYLCAVP APYTGTASKL TFGTGTRLQV TL            112

SEQ ID NO: 229          moltype = AA   length = 108
FEATURE                 Location/Qualifiers
source                  1..108
                        mol_type = protein
                        organism = Homo sapiens
SEQUENCE: 229
IQVEQSPPDL ILNEGANSTL RCNFSDSVNN LQWFHQNPWG QLINLFYIPS GTKQNGRLSA    60
TTVATERYSL LYISSSQTTD SGVYFCAVNT GTASKLTFGT GTRLQVTL                108

SEQ ID NO: 230          moltype = AA   length = 111
FEATURE                 Location/Qualifiers
source                  1..111
                        mol_type = protein
                        organism = Homo sapiens
SEQUENCE: 230
QLLEQSPQFL SIQEGENLTV YCQSSSVFSS LQWYRQEPGE GPVLLVTVVT GGEVKKLKRL    60
TFQFGDARKD SSLHITAAQP GDTGLYLCAG GLSDSYDKVI FGPGTSLSVI P             111

SEQ ID NO: 231          moltype = AA   length = 117
FEATURE                 Location/Qualifiers
source                  1..117
                        mol_type = protein
                        organism = Homo sapiens
SEQUENCE: 231
QKLTQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMSDPIMDT GRRALTFGSG TRLQVQP       117

SEQ ID NO: 232          moltype = AA   length = 115
FEATURE                 Location/Qualifiers
source                  1..115
                        mol_type = protein
                        organism = Homo sapiens
SEQUENCE: 232
QKITQTQPGM FVQEKEAVSL DCTYDTSDQS YGLFWYKQPS SGEMIFLIYQ GSYDEQNATE    60
GRYSLNFQKA RKSANLVISA SQLGDSAMYF CAINGLPGSA RQLTFGSGTQ LTVLP         115

SEQ ID NO: 233          moltype = AA   length = 110
FEATURE                 Location/Qualifiers
source                  1..110
                        mol_type = protein
                        organism = Homo sapiens
SEQUENCE: 233
KQEVTQIPGA LSVPEGENLV LNCSFTDSAI YNLQWFRQDP GKGLTSLLLI QSSQREQTSG    60
RLNASLDKSS GRSTLYIAAS QPGDSATYLC AVLLTGKLIF GQGTTLQVKP               110

SEQ ID NO: 234          moltype = AA   length = 116
FEATURE                 Location/Qualifiers
source                  1..116
                        mol_type = protein
                        organism = Homo sapiens
SEQUENCE: 234
QTVTQSQPEM SVQEAETVTL SCTYDTSENN YYLFWYKQPP SRQMILVIRQ EAYKQQNATE    60
NRFSVNLQKA AKSFSLKISD SQLGDTAMYF CAPLGLVAGS ARQLTFGSGT QLTVLP        116

SEQ ID NO: 235          moltype = AA   length = 119
FEATURE                 Location/Qualifiers
source                  1..119
                        mol_type = protein
                        organism = Homo sapiens
SEQUENCE: 235
QKITQTQPGM FVQEKEAVTL DCTYDTSDQS YGLFWYKQPS SGEMIFLIYQ GSYDEQNATE    60
GRYSLNFNKA RKSANLVISA SQLGDSAMYF CAMREGSDAG GTSYGKLTFG QGTILTVHP     119

SEQ ID NO: 236          moltype = AA   length = 110
FEATURE                 Location/Qualifiers
source                  1..110
                        mol_type = protein
                        organism = Homo sapiens
SEQUENCE: 236
QKITQTQPGM FVQEKEAVTL DCTYDTSDQS YGLFWYKQPS SGEMIFLIYQ GSYDEQNATE    60
GKYSLNFQKA RKSANLVISA SQLGDSAMYF CGYSNYQLIW GAGTKLIIKP               110

SEQ ID NO: 237          moltype = AA   length = 110
FEATURE                 Location/Qualifiers
source                  1..110
                        mol_type = protein
                        organism = Homo sapiens
```

```
SEQUENCE: 237
QSVAQPEDQV NVAEGNPLTV KCTYSVSGNP YLFWYVQYPN RGLQFLLKYI TGDNLVKGSY    60
GFEAEFNRSQ TSFHLKKPSA LVSDSALYFC AAPRDDKIIF GKGTRLHILP              110

SEQ ID NO: 238          moltype = AA   length = 110
FEATURE                 Location/Qualifiers
source                  1..110
                        mol_type = protein
                        organism = Homo sapiens
SEQUENCE: 238
QQLNQSPQSM FIQEGEDVSM NCTSSSIFNT WLWYKQDPGE GPVLLIALYK AGELTSNGRL    60
TAQFGITRKD SFLNITASIP SDVGIYFCAG GYNYGQNFVF GPGTRLSVLP              110

SEQ ID NO: 239          moltype = AA   length = 118
FEATURE                 Location/Qualifiers
source                  1..118
                        mol_type = protein
                        organism = Homo sapiens
SEQUENCE: 239
QQKEVEQDPG PLSVPEGAIV SLNCTYSNSA FQYFMWYRQY SRKGPELLMY TYSSGNKEDG    60
RFTAQVDKSS KYISLFIRDS NPSDSATYLC AMSGNSGARD YGNNRLAFGK GNQVVVIP     118

SEQ ID NO: 240          moltype = AA   length = 114
FEATURE                 Location/Qualifiers
source                  1..114
                        mol_type = protein
                        organism = Homo sapiens
SEQUENCE: 240
QTVTQSQPEM SVQEAETVTL SCTYDTSESD YYLFWYKQPP SRQMILVIRQ EAYKQQNATE    60
NRFSVNFQKA AKSFSLKLSD SQLGDAAMYF CTFRYGGATN KLIFGTGTLL AVQP         114

SEQ ID NO: 241          moltype = AA   length = 115
FEATURE                 Location/Qualifiers
source                  1..115
                        mol_type = protein
                        organism = Homo sapiens
SEQUENCE: 241
QKVTQAQTEI SVVEKEDVTL DCVYETRDTT YYLFWYKQPP SGELVFLIRR NSFDEQNEIS    60
GRYSWNFQKS TSSFQFTITA SQVVDSAVYF CALSGRGSGT YKYIFGTGTR LKVLA        115

SEQ ID NO: 242          moltype = AA   length = 110
FEATURE                 Location/Qualifiers
source                  1..110
                        mol_type = protein
                        organism = Homo sapiens
SEQUENCE: 242
EDVEQSLFLS VREGDSSVIN CTYTDSSSTY LYWYKQEPGA GLQLLTYIFS NMDMKQDQRL    60
TVLLNKKDKH LSLRIADSQT GDSAIYFCAE KETAGNKLTF GGGTRVLVKP              110

SEQ ID NO: 243          moltype = AA   length = 112
FEATURE                 Location/Qualifiers
source                  1..112
                        mol_type = protein
                        organism = Homo sapiens
SEQUENCE: 243
QNIDQPTEMT ATEGAIVQIN CTYQTSGFNG LFWYQQHAGE APTFLSYNVL DGLEEKGRFS    60
SFLSRSKGYS YLLIKELQMK DSASYLCAVP APYTGTASKL TFGTGTRLQV TL           112

SEQ ID NO: 244          moltype = AA   length = 108
FEATURE                 Location/Qualifiers
source                  1..108
                        mol_type = protein
                        organism = Homo sapiens
SEQUENCE: 244
IQVEQSPPDL ILQEGANSTL RCNFSDSVNN LQWFHQNPWG QLINLFYIPS GTKQNGRLTA    60
TTVATERYSL LYISSSQTTD SGVYFCAVNT GTASKLTFGT GTRLQVTL                108

SEQ ID NO: 245          moltype = AA   length = 111
FEATURE                 Location/Qualifiers
source                  1..111
                        mol_type = protein
                        organism = Homo sapiens
SEQUENCE: 245
QLLEQSPQFL SIQEGENLTV YCNSSSVFSS LQWYRQEPGE GPVLLVTVVT GGEVKKLKRL    60
TFQFGDARKD SSLHITAAQP GDTALYLCAG GLSDSYDKVI FGPGTSLSVI P            111

SEQ ID NO: 246          moltype = AA   length = 117
FEATURE                 Location/Qualifiers
source                  1..117
```

```
                              mol_type = protein
                              organism = Homo sapiens
SEQUENCE: 246
QKITQTQPGM FVQEKEAVTL DCTYDTSDQS YGLFWYKQPS SGEMIFLIYQ GSYDEQNATE    60
GRYSLNFQKA RKSAQLVISA SQLGDSAMYF CAMSDPIMDT GRRALTFGSG TRLQVQP      117

SEQ ID NO: 247            moltype = AA  length = 115
FEATURE                   Location/Qualifiers
source                    1..115
                          mol_type = protein
                          organism = Homo sapiens
SEQUENCE: 247
QKITQTQPGM FVQEKEAVTL DCTYDTSDQS YGLFWYKQPS SGEMIFLIYQ GSYDEQNATE    60
GRYSLNFQKA RKSANIVISA SQLGDSAMYF CAINGLPGSA RQLTFGSGTQ LTVLP        115

SEQ ID NO: 248            moltype = AA  length = 110
FEATURE                   Location/Qualifiers
source                    1..110
                          mol_type = protein
                          organism = Homo sapiens
SEQUENCE: 248
KQEVTQIPAA LSVPEGENLV LNCSFTDSAI YNLQWFRQDP GKGLTSLLLI QSSQREQTSG    60
RLNASLDKSS GRSTLYIAGS QPGDSATYLC AVLLTGKLIF GQGTTLQVKP             110

SEQ ID NO: 249            moltype = AA  length = 105
FEATURE                   Location/Qualifiers
source                    1..105
                          mol_type = protein
                          organism = Homo sapiens
SEQUENCE: 249
QTVTQSQPKM SVQEAETVTL SCTYDTSENN YYLFWYKQPP SRQMILVIRQ EAYKQQNATE    60
NRFSVNFQKA AKSFSLKISD SQLGDTAMYF CAPLGLVAGS ARQLT                  105

SEQ ID NO: 250            moltype = AA  length = 108
FEATURE                   Location/Qualifiers
source                    1..108
                          mol_type = protein
                          organism = Homo sapiens
SEQUENCE: 250
QKITQTQPGM FVQEKEAVTL DCTWDTSDQS YGLFWYKQPS SGEMIFLIYQ GSYDEQNATE    60
GRYSLNFQKA RKSANLVISA SQLGDSAMYF CAMREGSDAG GTSYGKLT               108

SEQ ID NO: 251            moltype = AA  length = 99
FEATURE                   Location/Qualifiers
source                    1..99
                          mol_type = protein
                          organism = Homo sapiens
SEQUENCE: 251
QKITQTQPAM FVQEKEAVTL DCTYDTSDQS YGLFWYKQPS SGEMIFLIYQ GSYDEQNATE    60
GRYSLNFQKA RKSANLVISA SQLGDSAMYF CGYSNYQLI                          99

SEQ ID NO: 252            moltype = AA  length = 99
FEATURE                   Location/Qualifiers
source                    1..99
                          mol_type = protein
                          organism = Homo sapiens
SEQUENCE: 252
QSVAQPEDQV NVAEGQPLTV KCTYSVSGNP YLFWYVQYPN RGLQFLLKYI TGDNLVKGSY    60
GFEAEFNKSQ TSFHLKKPSA LVSDSALYFC AAPRDDKII                          99

SEQ ID NO: 253            moltype = AA  length = 99
FEATURE                   Location/Qualifiers
source                    1..99
                          mol_type = protein
                          organism = Homo sapiens
SEQUENCE: 253
QQLNQSPQTM FIQEGEDVSM NCTSSSIFNT WLWYKQDPGE GPVLLIALYK AGELTSNGRL    60
TAQFGITRKD SFLNISASIP SDVGIYFCAG GYNYGQNFV                          99

SEQ ID NO: 254            moltype = AA  length = 107
FEATURE                   Location/Qualifiers
source                    1..107
                          mol_type = protein
                          organism = Homo sapiens
SEQUENCE: 254
QQKEVEQDPG PLSVPEGAIV SLNCTYTNSA FQYFMWYRQY SRKGPELLMY TYSSGNKEDG    60
RFTAQVDKSS KYISLFIRDS QPSDSATYLC AMSGNSGARD YGNNRLA                107

SEQ ID NO: 255            moltype = AA  length = 103
```

```
FEATURE                 Location/Qualifiers
source                  1..103
                        mol_type = protein
                        organism = Homo sapiens
SEQUENCE: 255
QTVTQSQPEM SVQEAETFTL SCTYDTSESD YYLFWYKQPP SRQMILVIRQ EAYKQQNATE    60
NRFSVNFQKA AKSFSLKISD SQLGDAAMYF CTFRYGGATN KLI                     103

SEQ ID NO: 256          moltype = AA   length = 104
FEATURE                 Location/Qualifiers
source                  1..104
                        mol_type = protein
                        organism = Homo sapiens
SEQUENCE: 256
QKVTQAQTEI SWVEKEDVTL DCVYETRDTT YYLFWYKQPP SGELVFLIRR NSFDEQNEIS    60
GRYSWNFQKS TSSFNFTITA SQVVDSAVYF CALSGRGSGT YKYI                    104

SEQ ID NO: 257          moltype = AA   length = 99
FEATURE                 Location/Qualifiers
source                  1..99
                        mol_type = protein
                        organism = Homo sapiens
SEQUENCE: 257
EDVEQSLFIS VREGDSSVIN CTYTDSSSTY LYWYKQEPGA GLQLLTYIFS NMDMKQDQRL    60
TVLLNKKDKH LSLRIADTQT GDSAIYFCAE KETAGNKLT                          99

SEQ ID NO: 258          moltype = AA   length = 101
FEATURE                 Location/Qualifiers
source                  1..101
                        mol_type = protein
                        organism = Homo sapiens
SEQUENCE: 258
QNIDQPTEMT GTEGAIVQIN CTYQTSGFNG LFWYQQHAGE APTFLSYNVL DGLEEKGRFS    60
SFLSRSKGYS YLLLKELQMK DSASYLCAVP APYTGTASKL T                       101

SEQ ID NO: 259          moltype = AA   length = 97
FEATURE                 Location/Qualifiers
source                  1..97
                        mol_type = protein
                        organism = Homo sapiens
SEQUENCE: 259
IQVEQSPPDL ILNEGANSTL RCNFSDSVNN LQWFHQNPWG QLINLFYIPS GTKQNGRLSA    60
TTVATERYSL LYISSSQTTD SGVYFCAVNT GTASKLT                            97

SEQ ID NO: 260          moltype = AA   length = 100
FEATURE                 Location/Qualifiers
source                  1..100
                        mol_type = protein
                        organism = Homo sapiens
SEQUENCE: 260
QLLENSPQFL SIQEGENLTV YCNSSSVFSS LQWYRQEPGE GPVLLVTVVT GGEVKKLKRL    60
TFQFGDARKD SSLHITAAQP GDTGLYLCAG GLSDSYDKVI                         100

SEQ ID NO: 261          moltype = AA   length = 106
FEATURE                 Location/Qualifiers
source                  1..106
                        mol_type = protein
                        organism = Homo sapiens
SEQUENCE: 261
QKITQTQPGM FVQEKEAVSL DCTYDTSDQS YGLFWYKQPS SGEMIFLIYQ GSYDEQNATE    60
GRYSLNFQKA RKSANLVISA SQLGDSAMYF CAMSDPIMDT GRRALT                  106

SEQ ID NO: 262          moltype = AA   length = 104
FEATURE                 Location/Qualifiers
source                  1..104
                        mol_type = protein
                        organism = Homo sapiens
SEQUENCE: 262
QKITQTQPGM FVQEKEAVTL DCTYNTSDQS YGLFWYKQPS SGEMIFLIYQ GSYDEQNATE    60
GRYSLNFQKA RKSANLVISA SQLGDSAMYF CAINGLPGSA RQLT                    104

SEQ ID NO: 263          moltype = AA   length = 99
FEATURE                 Location/Qualifiers
source                  1..99
                        mol_type = protein
                        organism = Homo sapiens
SEQUENCE: 263
KQEVTQIPAA ISVPEGENLV LNCSFTDSAI YNLQWFRQDP GKGLTSLLLI QSSQREQTSG    60
RLNASLDKSS GRSTLYIAAS QPGDSATYLC AVLLTGKLI                          99
```

```
SEQ ID NO: 264          moltype = AA   length = 105
FEATURE                 Location/Qualifiers
source                  1..105
                        mol_type = protein
                        organism = Homo sapiens
SEQUENCE: 264
QTVTNSQPEM SVQEAETVTL SCTYDTSENN YYLFWYKQPP SRQMILVIRQ EAYKQQNATE    60
NRFSVNFQKA AKSFSLKISD SQLGDTAMYF CAPLGLVAGS ARQLT                   105

SEQ ID NO: 265          moltype = AA   length = 108
FEATURE                 Location/Qualifiers
source                  1..108
                        mol_type = protein
                        organism = Homo sapiens
SEQUENCE: 265
QKITQSQPGM FVQEKEAVTL DCTYDTSDQS YGLFWYKQPS SGEMIFLIYQ GSYDEQNATE    60
GRYSLNFQKA RKSANLVISA SQLGDSAMYF CAMREGSDAG GTSYGKLT                108

SEQ ID NO: 266          moltype = AA   length = 99
FEATURE                 Location/Qualifiers
source                  1..99
                        mol_type = protein
                        organism = Homo sapiens
SEQUENCE: 266
QKITQTQPGM FVQEKEGVTL DCTYDTSDQS YGLFWYKQPS SGEMIFLIYQ GSYDEQNATE    60
GRYSLNFQKA RKSANLVISA SQLGDSAMYF CGYSNYQLI                           99

SEQ ID NO: 267          moltype = AA   length = 99
FEATURE                 Location/Qualifiers
source                  1..99
                        mol_type = protein
                        organism = Homo sapiens
SEQUENCE: 267
QSVANPEDQV NVAEGNPLTV KCTYSVSGNP YLFWYVQYPN RGLQFLLKYI TGDNLVKGSY    60
GFEAEFNKSQ TSFHLKKPSA LVSDSALYFC AAPRDDKII                           99

SEQ ID NO: 268          moltype = AA   length = 99
FEATURE                 Location/Qualifiers
source                  1..99
                        mol_type = protein
                        organism = Homo sapiens
SEQUENCE: 268
QQLNQSPQSM FIQEGERVSM NCTSSSIFNT WLWYKQDPGE GPVLLIALYK AGELTSNGRL    60
TAQFGITRKD SFLNISASIP SDVGIYFCAG GYNYGQNFV                           99

SEQ ID NO: 269          moltype = AA   length = 107
FEATURE                 Location/Qualifiers
source                  1..107
                        mol_type = protein
                        organism = Homo sapiens
SEQUENCE: 269
QQKEVEQRPG PLSVPEGAIV SLNCTYSNSA FQYFMWYRQY SRKGPELLMY TYSSGNKEDG    60
RFTAQVDKSS KYISLFIRDS QPSDSATYLC AMSGNSGARD YGNNRLA                 107

SEQ ID NO: 270          moltype = AA   length = 103
FEATURE                 Location/Qualifiers
source                  1..103
                        mol_type = protein
                        organism = Homo sapiens
SEQUENCE: 270
QTVTQTQPEM SVQEAETVTL SCTYDTSESD YYLFWYKQPP SRQMILVIRQ EAYKQQNATE    60
NRFSVNFQKA AKSFSLKISD SQLGDAAMYF CTFRYGGATN KLI                     103

SEQ ID NO: 271          moltype = AA   length = 104
FEATURE                 Location/Qualifiers
source                  1..104
                        mol_type = protein
                        organism = Homo sapiens
SEQUENCE: 271
QKVTQAQTEL SVVEKEDVTL DCVYETRDTT YYLFWYKQPP SGELVFLIRR NSFDEQNEIS    60
GRYSWNFQKS TSSFNFTITA SQVVDSAVYF CALSGRGSGT YKYI                    104

SEQ ID NO: 272          moltype = AA   length = 99
FEATURE                 Location/Qualifiers
source                  1..99
                        mol_type = protein
                        organism = Homo sapiens
SEQUENCE: 272
```

```
EDVEQSLFLS VREGDTSVIN CTYTDSSSTY LYWYKQEPGA GLQLLTYIFS NMDMKQDQRL    60
TVLLNKKDKH LSLRIADTQT GDSAIYFCAE KETAGNKLT                          99

SEQ ID NO: 273          moltype = AA  length = 101
FEATURE                 Location/Qualifiers
source                  1..101
                        mol_type = protein
                        organism = Homo sapiens
SEQUENCE: 273
QNIDQPSEMT ATEGAIVQIN CTYQTSGFNG LFWYQQHAGE APTFLSYNVL DGLEEKGRFS    60
SFLSRSKGYS YLLLKELQMK DSASYLCAVP APYTGTASKL T                       101

SEQ ID NO: 274          moltype = AA  length = 97
FEATURE                 Location/Qualifiers
source                  1..97
                        mol_type = protein
                        organism = Homo sapiens
SEQUENCE: 274
IQVEQSPPDL ILNEGANSTL RCNFSDSVNN LQWFHQNPWG QLINLFYIPS GTKQNGRLSA    60
TTVATERYSL LYISSSQTTD SGVYFCAVNT GTASKLT                            97

SEQ ID NO: 275          moltype = AA  length = 100
FEATURE                 Location/Qualifiers
source                  1..100
                        mol_type = protein
                        organism = Homo sapiens
SEQUENCE: 275
QLLEQSPQFL SIQEGENLTV YCQSSSVFSS LQWYRQEPGE GPVLLVTVVT GGEVKKLKRL    60
TFQFGDARKD SSLHITAAQP GDTGLYLCAG GLSDSYDKVI                         100

SEQ ID NO: 276          moltype = AA  length = 106
FEATURE                 Location/Qualifiers
source                  1..106
                        mol_type = protein
                        organism = Homo sapiens
SEQUENCE: 276
QKLTQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMSDPIMDT GRRALT                  106

SEQ ID NO: 277          moltype = AA  length = 104
FEATURE                 Location/Qualifiers
source                  1..104
                        mol_type = protein
                        organism = Homo sapiens
SEQUENCE: 277
QKITQTQPGM FVQEKEAVSL DCTYDTSDQS YGLFWYKQPS SGEMIFLIYQ GSYDEQNATE    60
GRYSLNFQKA RKSANLVISA SQLGDSAMYF CAINGLPGSA RQLT                    104

SEQ ID NO: 278          moltype = AA  length = 99
FEATURE                 Location/Qualifiers
source                  1..99
                        mol_type = protein
                        organism = Homo sapiens
SEQUENCE: 278
KQEVTQIPGA LSVPEGENLV LNCSFTDSAI YNLQWFRQDP GKGLTSLLLI QSSQREQTSG    60
RLNASLDKSS GRSTLYIAAS QPGDSATYLC AVLLTGKLI                          99

SEQ ID NO: 279          moltype = AA  length = 105
FEATURE                 Location/Qualifiers
source                  1..105
                        mol_type = protein
                        organism = Homo sapiens
SEQUENCE: 279
QTVTQSQPEM SVQEAETVTL SCTYDTSENN YYLFWYKQPP SRQMILVIRQ EAYKQQNATE    60
NRFSVNLQKA AKSFSLKISD SQLGDTAMYF CAPLGLVAGS ARQLT                   105

SEQ ID NO: 280          moltype = AA  length = 108
FEATURE                 Location/Qualifiers
source                  1..108
                        mol_type = protein
                        organism = Homo sapiens
SEQUENCE: 280
QKITQTQPGM FVQEKEAVTL DCTYDTSDQS YGLFWYKQPS SGEMIFLIYQ GSYDEQNATE    60
GRYSLNFNKA RKSANLVISA SQLGDSAMYF CAMREGSDAG GTSYGKLT                108

SEQ ID NO: 281          moltype = AA  length = 99
FEATURE                 Location/Qualifiers
source                  1..99
                        mol_type = protein
```

```
                             organism = Homo sapiens
SEQUENCE: 281
QKITQTQPGM FVQEKEAVTL DCTYDTSDQS YGLFWYKQPS SGEMIFLIYQ GSYDEQNATE      60
GKYSLNFQKA RKSANLVISA SQLGDSAMYF CGYSNYQLI                             99

SEQ ID NO: 282           moltype = AA   length = 99
FEATURE                  Location/Qualifiers
source                   1..99
                         mol_type = protein
                         organism = Homo sapiens
SEQUENCE: 282
QSVAQPEDQV NVAEGNPLTV KCTYSVSGNP YLFWYVQYPN RGLQFLLKYI TGDNLVKGSY      60
GFEAEFNRSQ TSFHLKKPSA LVSDSALYFC AAPRDDKII                             99

SEQ ID NO: 283           moltype = AA   length = 99
FEATURE                  Location/Qualifiers
source                   1..99
                         mol_type = protein
                         organism = Homo sapiens
SEQUENCE: 283
QQLNQSPQSM FIQEGEDVSM NCTSSSIFNT WLWYKQDPGE GPVLLIALYK AGELTSNGRL      60
TAQFGITRKD SFLNITASIP SDVGIYFCAG GYNYGQNFV                             99

SEQ ID NO: 284           moltype = AA   length = 107
FEATURE                  Location/Qualifiers
source                   1..107
                         mol_type = protein
                         organism = Homo sapiens
SEQUENCE: 284
QQKEVEQDPG PLSVPEGAIV SLNCTYSNSA FQYFMWYRQY SRKGPELLMY TYSSGNKEDG      60
RFTAQVDKSS KYISLFIRDS NPSDSATYLC AMSGNSGARD YGNNRLA                   107

SEQ ID NO: 285           moltype = AA   length = 103
FEATURE                  Location/Qualifiers
source                   1..103
                         mol_type = protein
                         organism = Homo sapiens
SEQUENCE: 285
QTVTQSQPEM SVQEAETVTL SCTYDTSESD YYLFWYKQPP SRQMILVIRQ EAYKQQNATE      60
NRFSVNFQKA AKSFSLKLSD SQLGDAAMYF CTFRYGGATN KLI                       103

SEQ ID NO: 286           moltype = AA   length = 104
FEATURE                  Location/Qualifiers
source                   1..104
                         mol_type = protein
                         organism = Homo sapiens
SEQUENCE: 286
QKVTQAQTEI SVVEKEDVTL DCVYETRDTT YYLFWYKQPP SGELVFLIRR NSFDEQNEIS      60
GRYSWNFQKS TSSFQFTITA SQVVDSAVYF CALSGRGSGT YKYI                      104

SEQ ID NO: 287           moltype = AA   length = 99
FEATURE                  Location/Qualifiers
source                   1..99
                         mol_type = protein
                         organism = Homo sapiens
SEQUENCE: 287
EDVEQSLFLS VREGDSSVIN CTYTDSSSTY LYWYKQEPGA GLQLLTYIFS NMDMKQDQRL      60
TVLLNKKDKH LSLRIADSQT GDSAIYFCAE KETAGNKLT                             99

SEQ ID NO: 288           moltype = AA   length = 101
FEATURE                  Location/Qualifiers
source                   1..101
                         mol_type = protein
                         organism = Homo sapiens
SEQUENCE: 288
QNIDQPTEMT ATEGAIVQIN CTYQTSGFNG LFWYQQHAGE APTFLSYNVL DGLEEKGRFS      60
SFLSRSKGYS YLLIKELQMK DSASYLCAVP APYTGTASKL T                         101

SEQ ID NO: 289           moltype = AA   length = 97
FEATURE                  Location/Qualifiers
source                   1..97
                         mol_type = protein
                         organism = Homo sapiens
SEQUENCE: 289
IQVEQSPPDL ILQEGANSTL RCNFSDSVNN LQWFHQNPWG QLINLFYIPS GTKQNGRLTA      60
TTVATERYSL LYISSSQTTD SGVYFCAVNT GTASKLT                               97

SEQ ID NO: 290           moltype = AA   length = 100
FEATURE                  Location/Qualifiers
```

```
source                      1..100
                            mol_type = protein
                            organism = Homo sapiens
SEQUENCE: 290
QLLEQSPQFL SIQEGENLTV YCNSSSVFSS LQWYRQEPGE GPVLLVTVVT GGEVKKLKRL    60
TFQFGDARKD SSLHITAAQP GDTALYLCAG GLSDSYDKVI                         100

SEQ ID NO: 291              moltype = AA  length = 106
FEATURE                     Location/Qualifiers
source                      1..106
                            mol_type = protein
                            organism = Homo sapiens
SEQUENCE: 291
QKITQTQPGM FVQEKEAVTL DCTYDTSDQS YGLFWYKQPS SGEMIFLIYQ GSYDEQNATE    60
GRYSLNFQKA RKSAQLVISA SQLGDSAMYF CAMSDPIMDT GRRALT                  106

SEQ ID NO: 292              moltype = AA  length = 104
FEATURE                     Location/Qualifiers
source                      1..104
                            mol_type = protein
                            organism = Homo sapiens
SEQUENCE: 292
QKITQTQPGM FVQEKEAVTL DCTYDTSDQS YGLFWYKQPS SGEMIFLIYQ GSYDEQNATE    60
GRYSLNFQKA RKSANIVISA SQLGDSAMYF CAINGLPGSA RQLT                    104

SEQ ID NO: 293              moltype = AA  length = 99
FEATURE                     Location/Qualifiers
source                      1..99
                            mol_type = protein
                            organism = Homo sapiens
SEQUENCE: 293
KQEVTQIPAA LSVPEGENLV LNCSFTDSAI YNLQWFRQDP GKGLTSLLLI QSSQREQTSG    60
RLNASLDKSS GRSTLYIAGS QPGDSATYLC AVLLTGKLI                           99

SEQ ID NO: 294              moltype = AA  length = 257
FEATURE                     Location/Qualifiers
source                      1..257
                            mol_type = protein
                            organism = Homo sapiens
SEQUENCE: 294
QTVTQSQPKM SVQEAETVTL SCTYDTSENN YYLFWYKQPP SRQMILVIRQ EAYKQQNATE    60
NRFSVNFQKA AKSFSLKISD SQLGDTAMYF CAPLGLVAGS ARQLTFGSGT QLTVLPDIQN   120
PDPAVYQLRD SKSSDKSVCL FTDFDSQTNV SQSKDSDVYI TDKTVLDMRS MDFKSNSAVA   180
WSNKSDFACA NAFNNSIIPE DTFFPSPESS CDVKLVEKSF ETDTNLNFQN LSVIGFRILL   240
LKVAGFNLLM TLRLWSS                                                  257

SEQ ID NO: 295              moltype = AA  length = 260
FEATURE                     Location/Qualifiers
source                      1..260
                            mol_type = protein
                            organism = Homo sapiens
SEQUENCE: 295
QKITQTQPGM FVQEKEAVTL DCTWDTSDQS YGLFWYKQPS SGEMIFLIYQ GSYDEQNATE    60
GRYSLNFQKA RKSANLVISA SQLGDSAMYF CAMREGSDAG GTSYGKLTFG QGTILTVHPN   120
IQNPDPAVYQ LRDSKSSDKS VCLFTDFDSQ TNVSQSKDSD VYITDKTVLD MRSMDFKSNS   180
AVAWSNKSDF ACANAFNNSI IPEDTFFPSP ESSCDVKLVE KSFETDTNLN FQNLSVIGFR   240
ILLLKVAGFN LLMTLRLWSS                                               260

SEQ ID NO: 296              moltype = AA  length = 251
FEATURE                     Location/Qualifiers
source                      1..251
                            mol_type = protein
                            organism = Homo sapiens
SEQUENCE: 296
QKITQTQPAM FVQEKEAVTL DCTYDTSDQS YGLFWYKQPS SGEMIFLIYQ GSYDEQNATE    60
GRYSLNFQKA RKSANLVISA SQLGDSAMYF CGYSNYQLIW GAGTKLIIKP DIQNPDPAVY   120
QLRDSKSSDK SVCLFTDFDS QTNVSQSKDS DVYITDKTVL DMRSMDFKSN SAVAWSNKSD   180
FACANAFNNS IIPEDTFFPS PESSCDVKLV EKSFETDTNL NFQNLSVIGF RILLLKVAGF   240
NLLMTLRLWS S                                                        251

SEQ ID NO: 297              moltype = AA  length = 251
FEATURE                     Location/Qualifiers
source                      1..251
                            mol_type = protein
                            organism = Homo sapiens
SEQUENCE: 297
QSVAQPEDQV NVAEGQPLTV KCTYSVSGNP YLFWYVQYPN RGLQFLLKYI TGDNLVKGSY    60
GFEAEFNKSQ TSFHLKKPSA LVSDSALYFC AAPRDDKIIF GKGTRLHILP NIQNPDPAVY   120
QLRDSKSSDK SVCLFTDFDS QTNVSQSKDS DVYITDKTVL DMRSMDFKSN SAVAWSNKSD   180
```

```
FACANAFNNS IIPEDTFFPS PESSCDVKLV EKSFETDTNL NFQNLSVIGF RILLLKVAGF    240
NLLMTLRLWS S                                                        251

SEQ ID NO: 298          moltype = AA  length = 251
FEATURE                 Location/Qualifiers
source                  1..251
                        mol_type = protein
                        organism = Homo sapiens
SEQUENCE: 298
QQLNQSPQTM FIQEGEDVSM NCTSSSIFNT WLWYKQDPGE GPVLLIALYK AGELTSNGRL    60
TAQFGITRKD SFLNISASIP SDVGIYFCAG GYNYGQNFVF GPGTRLSVLP YIQNPDDAVY    120
QLRDSKSSDK SVCLFTDFDS QTNVSQSKDS DVYITDKTVL DMRSMDFKSN SAVAWSNKSD    180
FACANAFNNS IIPEDTFFPS PESSCDVKLV EKSFETDTNL NFQNLSVIGF RILLLKVAGF    240
NLLMTLRLWS S                                                        251

SEQ ID NO: 299          moltype = AA  length = 259
FEATURE                 Location/Qualifiers
source                  1..259
                        mol_type = protein
                        organism = Homo sapiens
SEQUENCE: 299
QQKEVEQDPG PLSVPEGAIV SLNCTYTNSA FQYFMWYRQY SRKGPELLMY TYSSGNKEDG    60
RFTAQVDKSS KYISLFIRDS QPSDSATYLC AMSGNSGARD YGNNRLAFGK GNQVVVIPNI    120
QNPDPAVYQL RDSKSSDKSV CLFTDFDSQT NVSQSKDSDV YITDKTVLDM RSMDFKSNSA    180
VAWSNKSDFA CANAFNNSII PEDTFFPSPE SSCDVKLVEK SFETDTNLNF QNLSVIGFRI    240
LLLKVAGFNL LMTLRLWSS                                                259

SEQ ID NO: 300          moltype = AA  length = 255
FEATURE                 Location/Qualifiers
source                  1..255
                        mol_type = protein
                        organism = Homo sapiens
SEQUENCE: 300
QTVTQSQPEM SVQEAETFTL SCTYDTSESD YYLFWYKQPP SRQMILVIRQ EAYKQQNATE    60
NRFSVNFQKA AKSFSLKISD SQLGDAAMYF CTFRYGGATN KLIFGTGTLL AVQPNIQNPD    120
PAVYQLRDSK SSDKSVCLFT DFDSQTNVSQ SKDSDVYITD KTVLDMRSMD FKSNSAVAWS    180
NKSDFACANA FNNSIIPEDT FFPSPESSCD VKLVEKSFET DTNLNFQNLS VIGFRILLLK    240
VAGFNLLMTL RLWSS                                                    255

SEQ ID NO: 301          moltype = AA  length = 256
FEATURE                 Location/Qualifiers
source                  1..256
                        mol_type = protein
                        organism = Homo sapiens
SEQUENCE: 301
QKVTQAQTEI SWVEKEDVTL DCVYETRDTT YYLFWYKQPP SGELVFLIRR NSFDEQNEIS    60
GRYSWNFQKS TSSFNFTITA SQVVDSAVYF CALSGRGSGT YKYIFGTGTR LKVLANIQNP    120
DPAVYQLRDS KSSDKSVCLF TDFDSQTNVS QSKDSDVYIT DKTVLDMRSM DFKSNSAVAW    180
SNKSDFACAN AFNNSIIPED TFFPSPESSC DVKLVEKSFE TDTNLNFQNL SVIGFRILLL    240
KVAGFNLLMT LRLWSS                                                   256

SEQ ID NO: 302          moltype = AA  length = 251
FEATURE                 Location/Qualifiers
source                  1..251
                        mol_type = protein
                        organism = Homo sapiens
SEQUENCE: 302
EDVEQSLFIS VREGDSSVIN CTYTDSSSTY LYWYKQEPGA GLQLLTYIFS NMDMKQDQRL    60
TVLLNKKDKH LSLRIADTQT GDSAIYFCAE KETAGNKLTF GGGTRVLVKP NIQNPDDAVY    120
QLRDSKSSDK SVCLFTDFDS QTNVSQSKDS DVYITDKTVL DMRSMDFKSN SAVAWSNKSD    180
FACANAFNNS IIPEDTFFPS PESSCDVKLV EKSFETDTNL NFQNLSVIGF RILLLKVAGF    240
NLLMTLRLWS S                                                        251

SEQ ID NO: 303          moltype = AA  length = 253
FEATURE                 Location/Qualifiers
source                  1..253
                        mol_type = protein
                        organism = Homo sapiens
SEQUENCE: 303
QNIDQPTEMT GTEGAIVQIN CTYQTSGFNG LFWYQQHAGE APTFLSYNVL DGLEEKGRFS    60
SFLSRSKGYS YLLLKELQMK DSASYLCAVP APYTGTASKL TFGTGTRLQV TLDIQNPDPA    120
VYQLRDSKSS DKSVCLFTDF DSQTNVSQSK DSDVYITDKT VLDMRSMDFK SNSAVAWSNK    180
SDFACANAFN NSIIPEDTFF PSPESSCDVK LVEKSFETDT NLNFQNLSVI GFRILLLKVA    240
GFNLLMTLRL WSS                                                      253

SEQ ID NO: 304          moltype = AA  length = 249
FEATURE                 Location/Qualifiers
source                  1..249
                        mol_type = protein
```

```
                             organism = Homo sapiens
SEQUENCE: 304
IQVEQSPPDL ILNEGANSTL RCNFSDSVNN LQWFHQNPWG QLINLFYIPS GTKQNGRLSA       60
TTVATERYSL LYISSSQTTD SGVYFCAVNT GTASKLTFGT GTRLQVTLDI QNPDPAVYQL      120
RDSKSSDKSV CLFTDFDSQT NVSQSKDSDV YITDKTVLDM RSMDFKSNSA VAWSNKSDFA      180
CANAFNNSII PEDTFFPSPE SSCDVKLVEK SFETDTNLNF QNLSVIGFRI LLLKVAGFNL      240
LMTLRLWSS                                                              249

SEQ ID NO: 305           moltype = AA  length = 252
FEATURE                  Location/Qualifiers
source                   1..252
                         mol_type = protein
                         organism = Homo sapiens
SEQUENCE: 305
QLLENSPQFL SIQEGENLTV YCNSSSVFSS LQWYRQEPGE GPVLLVTVVT GGEVKKLKRL       60
TFQFGDARKD SSLHITAAQP GDTGLYLCAG GLSDSYDKVI FGPGTSLSVI PNIQNPDPAV      120
YQLRDSKSSD KSVCLFTDFD SQTNVSQSKD SDVYITDKTV LDMRSMDFKS NSAVAWSNKS      180
DFACANAFNN SIIPEDTFFP SPESSCDVKL VEKSFETDTN LNFQNLSVIG FRILLLKVAG      240
FNLLMTLRLW SS                                                          252

SEQ ID NO: 306           moltype = AA  length = 258
FEATURE                  Location/Qualifiers
source                   1..258
                         mol_type = protein
                         organism = Homo sapiens
SEQUENCE: 306
QKITQTQPGM FVQEKEAVSL DCTYDTSDQS YGLFWYKQPS SGEMIFLIYQ GSYDEQNATE       60
GRYSLNFQKA RKSANLVISA SQLGDSAMYF CAMSDPIMDT GRRALTFGSG TRLQVQPNIQ      120
NPDPAVYQLR DSKSSDKSVC LFTDFDSQTN VSQSKDSDVY ITDKTVLDMR SMDFKSNSAV      180
AWSNKSDFAC ANAFNNSIIP EDTFFPSPES SCDVKLVEKS FETDTNLNFQ NLSVIGFRIL      240
LLKVAGFNLL MTLRLWSS                                                    258

SEQ ID NO: 307           moltype = AA  length = 256
FEATURE                  Location/Qualifiers
source                   1..256
                         mol_type = protein
                         organism = Homo sapiens
SEQUENCE: 307
QKITQTQPGM FVQEKEAVTL DCTYNTSDQS YGLFWYKQPS SGEMIFLIYQ GSYDEQNATE       60
GRYSLNFQKA RKSANLVISA SQLGDSAMYF CAINGLPGSA RQLTFGSGTQ LTVLPDIQNP      120
DPAVYQLRDS KSSDKSVCLF TDFDSQTNVS QSKDSDVYIT DKTVLDMRSM DFKSNSAVAW      180
SNKSDFACAN AFNNSIIPED TFFPSPESSC DVKLVEKSFE TDTNLNFQNL SVIGFRILLL      240
KVAGFNLLMT LRLWSS                                                      256

SEQ ID NO: 308           moltype = AA  length = 205
FEATURE                  Location/Qualifiers
source                   1..205
                         mol_type = protein
                         organism = Homo sapiens
SEQUENCE: 308
KQEVTQIPAA ISVPEGENLV LNCSFTDSAI YNLQWFRQDP GKGLTSLLLI QSSQREQTSG       60
RLNASLDKSS GRSTLYIAAS QPGDSATYLC AVLLTGKLIF GQGTTLQVKP NIQKPDAVY       120
QLRDSKSSDK SVCLFTDFDS QTNVSQSKDS DVYITDKTVL DMRSMDFKSN SAVAWSNKSD      180
FACANAFNNS IIPEDTFFPS PESSC                                            205

SEQ ID NO: 309           moltype = AA  length = 257
FEATURE                  Location/Qualifiers
source                   1..257
                         mol_type = protein
                         organism = Homo sapiens
SEQUENCE: 309
QTVTNSQPEM SVQEAETVTL SCTYDTSENN YYLFWYKQPP SRQMILVIRQ EAYKQQNATE       60
NRFSVNFQKA AKSFSLKISD SQLGDTAMYF CAPLGLVAGS ARQLTFGSGT QLTVLPDIQN      120
PDPAVYQLRD SKSSDKSVCL FTDFDSQTNV SQSKDSDVYI TDKTVLDMRS MDFKSNSAVA      180
WSNKSDFACA NAFNNSIIPE DTFFPSPESS CDVKLVEKSF ETDTNLNFQN LSVIGFRILL      240
LKVAGFNLLM TLRLWSS                                                     257

SEQ ID NO: 310           moltype = AA  length = 260
FEATURE                  Location/Qualifiers
source                   1..260
                         mol_type = protein
                         organism = Homo sapiens
SEQUENCE: 310
QKITQSQPGM FVQEKEAVTL DCTYDTSDQS YGLFWYKQPS SGEMIFLIYQ GSYDEQNATE       60
GRYSLNFQKA RKSANLVISA SQLGDSAMYF CAMREGSDAG GTSYGKLTFG QGTILTVHPN      120
IQNPDPAVYQ LRDSKSSDKS VCLFTDFDSQ TNVSQSKDSD VYITDKTVLD MRSMDFKSNS      180
AVAWSNKSDF ACANAFNNSI IPEDTFFPSP ESSCDVKLVE KSFETDTNLN FQNLSVIGFR      240
ILLLKVAGFN LLMTLRLWSS                                                  260
```

```
SEQ ID NO: 311            moltype = AA  length = 251
FEATURE                   Location/Qualifiers
source                    1..251
                          mol_type = protein
                          organism = Homo sapiens
SEQUENCE: 311
QKITQTQPGM FVQEKEGVTL DCTYDTSDQS YGLFWYKQPS SGEMIFLIYQ GSYDEQNATE   60
GRYSLNFQKA RKSANLVISA SQLGDSAMYF CGYSNYQLIW GAGTKLIIKP DIQNPDPAVY  120
QLRDSKSSDK SVCLFTDFDS QTNVSQSKDS DVYITDKTVL DMRSMDFKSN SAVAWSNKSD  180
FACANAFNNS IIPEDTFFPS PESSCDVKLV EKSFETDTNL NFQNLSVIGF RILLLKVAGF  240
NLLMTLRLWS S                                                      251

SEQ ID NO: 312            moltype = AA  length = 251
FEATURE                   Location/Qualifiers
source                    1..251
                          mol_type = protein
                          organism = Homo sapiens
SEQUENCE: 312
QSVANPEDQV NVAEGNPLTV KCTYSVSGNP YLFWYVQYPN RGLQFLLKYI TGDNLVKGSY   60
GFEAEFNKSQ TSFHLKKPSA LVSDSALYFC AAPRDDKIIF GKGTRLHILP NIQNPDPAVY  120
QLRDSKSSDK SVCLFTDFDS QTNVSQSKDS DVYITDKTVL DMRSMDFKSN SAVAWSNKSD  180
FACANAFNNS IIPEDTFFPS PESSCDVKLV EKSFETDTNL NFQNLSVIGF RILLLKVAGF  240
NLLMTLRLWS S                                                      251

SEQ ID NO: 313            moltype = AA  length = 251
FEATURE                   Location/Qualifiers
source                    1..251
                          mol_type = protein
                          organism = Homo sapiens
SEQUENCE: 313
QQLNQSPQSM FIQEGERVSM NCTSSSIFNT WLWYKQDPGE GPVLLIALYK AGELTSNGRL   60
TAQFGITRKD SFLNISASIP SDVGIYFCAG GYNYGQNFVF GPGTRLSLVP YIQNPDPAVY  120
QLRDSKSSDK SVCLFTDFDS QTNVSQSKDS DVYITDKTVL DMRSMDFKSN SAVAWSNKSD  180
FACANAFNNS IIPEDTFFPS PESSCDVKLV EKSFETDTNL NFQNLSVIGF RILLLKVAGF  240
NLLMTLRLWS S                                                      251

SEQ ID NO: 314            moltype = AA  length = 259
FEATURE                   Location/Qualifiers
source                    1..259
                          mol_type = protein
                          organism = Homo sapiens
SEQUENCE: 314
QQKEVEQRPG PLSVPEGAIV SLNCTYSNSA FQYFMWYRQY SRKGPELLMY TYSSGNKEDG   60
RFTAQVDKSS KYISLFIRDS QPSDSATYLC AMSGNSGARD YGNNRLAFGK GNQVVVIPNI  120
QNPDPAVYQL RDSKSSDKSV CLFTDFDSQT NVSQSKDSDV YITDKTVLDM RSMDFKSNSA  180
VAWSNKSDFA CANAFNNSII PEDTFFPSPE SSCDVKLVEK SFETDTNLNF QNLSVIGFRI  240
LLLKVAGFNL LMTLRLWSS                                              259

SEQ ID NO: 315            moltype = AA  length = 255
FEATURE                   Location/Qualifiers
source                    1..255
                          mol_type = protein
                          organism = Homo sapiens
SEQUENCE: 315
QTVTQTQPEM SVQEAETVTL SCTYDTSESD YYLFWYKQPP SRQMILVIRQ EAYKQQNATE   60
NRFSVNFQKA AKSFSLKISD SQLGDAAMYF CTFRYGGATN KLIFGTGTLL AVQPNIQNPD  120
PAVYQLRDSK SSDKSVCLFT DFDSQTNVSQ SKDSDVYITD KTVLDMRSMD FKSNSAVAWS  180
NKSDFACANA FNNSIIPEDT FFPSPESSCD VKLVEKSFET DTNLNFQNLS VIGFRILLLK  240
VAGFNLLMTL RLWSS                                                  255

SEQ ID NO: 316            moltype = AA  length = 256
FEATURE                   Location/Qualifiers
source                    1..256
                          mol_type = protein
                          organism = Homo sapiens
SEQUENCE: 316
QKVTQAQTEL SVVEKEDVTL DCVYETRDTT YYLFWYKQPP SGELVFLIRR NSFDEQNEIS   60
GRYSWNFQKS TSSFNFTITA SQVVDSAVYF CALSGRGSEI YKYIFGTGTR LKVLANIQNP  120
DPAVYQLRDS KSSDKSVCLF TDFDSQTNVS QSKDSDVYIT DKTVLDMRSM DFKSNSAVAW  180
SNKSDFACAN AFNNSIIPED TFFPSPESSC DVKLVEKSFE TDTNLNFQNL SVIGFRILLL  240
KVAGFNLLMT LRLWSS                                                 256

SEQ ID NO: 317            moltype = AA  length = 251
FEATURE                   Location/Qualifiers
source                    1..251
                          mol_type = protein
                          organism = Homo sapiens
SEQUENCE: 317
EDVEQSLFLS VREGDTSVIN CTYTDSSSTY LYWYKQEPGA GLQLLTYIFS NMDMKQDQRL   60
```

```
TVLLNKKDKH LSLRIADTQT GDSAIYFCAE KETAGNKLTF GGGTRVLVKP NIQNPDPAVY    120
QLRDSKSSDK SVCLFTDFDS QTNVSQSKDS DVYITDKTVL DMRSMDFKSN SAVAWSNKSD    180
FACANAFNNS IIPEDTFFPS PESSCDVKLV EKSFETDTNL NFQNLSVIGF RILLLKVAGF    240
NLLMTLRLWS S                                                        251

SEQ ID NO: 318          moltype = AA  length = 253
FEATURE                 Location/Qualifiers
source                  1..253
                        mol_type = protein
                        organism = Homo sapiens
SEQUENCE: 318
QNIDQPSEMT ATEGAIVQIN CTYQTSGFNG LFWYQQHAGE APTFLSYNVL DGLEEKGRFS    60
SFLSRSKGYS YLLLKELQMK DSASYLCAVP APYTGTASKL TFGTGTRLQV TLDIQNPDPA    120
VYQLRDSKSS DKSVCLFTDF DSQTNVSQSK DSDVYITDKT VLDMRSMDFK SNSAVAWSNK    180
SDFACANAFN NSIIPEDTFF PSPESSCDVK LVEKSFETDT NLNFQNLSVI GFRILLLKVA    240
GFNLLMTLRL WSS                                                      253

SEQ ID NO: 319          moltype = AA  length = 249
FEATURE                 Location/Qualifiers
source                  1..249
                        mol_type = protein
                        organism = Homo sapiens
SEQUENCE: 319
IQVEQSPPDL ILNEGANSTL RCNFSDSVNN LQWFHQNPWG QLINLFYIPS GTKQNGRLSA    60
TTVATERYSL LYISSSQTTD SGVYFCAVNT GTASKLTFGT GTRLQVTLDI QNPDPAVYQL    120
RDSKSSDKSV CLFTDFDSQT NVSQSKDSDV YITDKTVLDM RSMDFKSNSA VAWSNKSDFA    180
CANAFNNSII PEDTFFPSPE SSCDVKLVEK SFETDTNLNF QNLSVIGFRI LLLKVAGFNL    240
LMTLRLWSS                                                           249

SEQ ID NO: 320          moltype = AA  length = 252
FEATURE                 Location/Qualifiers
source                  1..252
                        mol_type = protein
                        organism = Homo sapiens
SEQUENCE: 320
QLLEQSPQFL SIQEGENLTV YCQSSSVFSS LQWYRQEPGE GPVLLVTVVT GGEVKKLKRL    60
TFQFGDARKD SSLHITAAQP GDTGLYLCAG GLSDSYDKVI FGPGTSLSVI PNIQNPDPAV    120
YQLRDSKSSD KSVCLFTDFD SQTNVSQSKD SDVYITDKTV LDMRSMDFKS NSAVAWSNKS    180
DFACANAFNN SIIPEDTFFP SPESSCDVKL VEKSFETDTN LNFQNLSVIG FRILLLKVAG    240
FNLLMTLRLW SS                                                       252

SEQ ID NO: 321          moltype = AA  length = 258
FEATURE                 Location/Qualifiers
source                  1..258
                        mol_type = protein
                        organism = Homo sapiens
SEQUENCE: 321
QKLTQTQPGM FVQEKEAVTL DCTYDTSDQS YGLFWYKQPS SGEMIFLIYQ GSYDEQNATE    60
GRYSLNFQKA RKSANLVISA SQLGDSAMYF CAMSDPIMDT GRRALTFGSG TRLQVQPNIQ    120
NPDPAVYQLR DSKSSDKSVC LFTDFDSQTN VSQSKDSDVY ITDKTVLDMR SMDFKSNSAV    180
AWSNKSDFAC ANAFNNSIIP EDTFFPSPES SCDVKLVEKS FETDTNLNFQ NLSVIGFRIL    240
LLKVAGFNLL MTLRLWSS                                                 258

SEQ ID NO: 322          moltype = AA  length = 256
FEATURE                 Location/Qualifiers
source                  1..256
                        mol_type = protein
                        organism = Homo sapiens
SEQUENCE: 322
QKITQTQPGM FVQEKEAVSL DCTYDTSDQS YGLFWYKQPS SGEMIFLIYQ GSYDEQNATE    60
GRYSLNFQKA RKSANLVISA SQLGDSAMYF CAINGLPGSA RQLTFGSGTQ LTVLPDIQNP    120
DPAVYQLRDS KSSDKSVCLF TDFDSQTNVS QSKDSDVYIT DKTVLDMRSM DFKSNSAVAW    180
SNKSDFACAN AFNNSIIPED TFFPSPESSC DVKLVEKSFE TDTNLNFQNL SVIGFRILLL    240
KVAGFNLLMT LRLWSS                                                   256

SEQ ID NO: 323          moltype = AA  length = 205
FEATURE                 Location/Qualifiers
source                  1..205
                        mol_type = protein
                        organism = Homo sapiens
SEQUENCE: 323
KQEVTQIPGA LSVPEGENLV LNCSFTDSAI YNLQWFRQDP GKGLTSLLLI QSSQREQTSG    60
RLNASLDKSS GRSTLYIAAS QPGDSATYLC AVLLTGKLIF GQGTTLQVKP NIQKPDPAVY    120
QLRDSKSSDK SVCLFTDFDS QTNVSQSKDS DVYITDKTVL DMRSMDFKSN SAVAWSNKSD    180
FACANAFNNS IIPEDTFFPS PESSC                                         205

SEQ ID NO: 324          moltype = AA  length = 257
FEATURE                 Location/Qualifiers
source                  1..257
```

```
                              mol_type = protein
                              organism = Homo sapiens
SEQUENCE: 324
QTVTQSQPEM SVQEAETVTL SCTYDTSENN YYLFWYKQPP SRQMILVIRQ EAYKQQNATE    60
NRFSVNLQKA AKSFSLKISD SQLGDTAMYF CAPLGLVAGS ARQLTFGSGT QLTVLPDIQN   120
PDPAVYQLRD SKSSDKSVCL FTDFDSQTNV SQSKDSDVYI TDKTVLDMRS MDFKSNSAVA   180
WSNKSDFACA NAFNNSIIPE DTFFPSPESS CDVKLVEKSF ETDTNLNFQN LSVIGFRILL   240
LKVAGFNLLM TLRLWSS                                                  257

SEQ ID NO: 325          moltype = AA    length = 260
FEATURE                 Location/Qualifiers
source                  1..260
                        mol_type = protein
                        organism = Homo sapiens
SEQUENCE: 325
QKITQTQPGM FVQEKEAVTL DCTYDTSDQS YGLFWYKQPS SGEMIFLIYQ GSYDEQNATE    60
GRYSLNFNKA RKSANLVISA SQLGDSAMYF CAMREGSDAG GTSYGKLTFG QGTILTVHPN   120
IQNPDPAVYQ LRDSKSSDKS VCLFTDFDSQ TNVSQSKDSD VYITDKTVLD MRSMDFKSNS   180
AVAWSNKSDF ACANAFNNSI IPEDTFFPSP ESSCDVKLVE KSFETDTNLN FQNLSVIGFR   240
ILLLKVAGFN LLMTLRLWSS                                               260

SEQ ID NO: 326          moltype = AA    length = 251
FEATURE                 Location/Qualifiers
source                  1..251
                        mol_type = protein
                        organism = Homo sapiens
SEQUENCE: 326
QKITQTQPGM FVQEKEAVTL DCTYDTSDQS YGLFWYKQPS SGEMIFLIYQ GSYDEQNATE    60
GKYSLNFQKA RKSANLVISA SQLGDSAMYF CGYSNYQLIW GAGTKLIIKP DIQNPDPAVY   120
QLRDSKSSDK SVCLFTDFDS QTNVSQSKDS DVYITDKTVL DMRSMDFKSN SAVAWSNKSD   180
FACANAFNNS IIPEDTFFPS PESSCDVKLV EKSFETDTNL NFQNLSVIGF RILLLKVAGF   240
NLLMTLRLWS S                                                        251

SEQ ID NO: 327          moltype = AA    length = 251
FEATURE                 Location/Qualifiers
source                  1..251
                        mol_type = protein
                        organism = Homo sapiens
SEQUENCE: 327
QSVAQPEDQV NVAEGNPLTV KCTYSVSGNP YLFWYVQYPN RGLQFLLKYI TGDNLVKGSY    60
GFEAEFNRSQ TSFHLKKPSA LVSDSALYFC AAPRDDKIIF GKGTRLHILP NIQNPDPAVY   120
QLRDSKSSDK SVCLFTDFDS QTNVSQSKDS DVYITDKTVL DMRSMDFKSN SAVAWSNKSD   180
FACANAFNNS IIPEDTFFPS PESSCDVKLV EKSFETDTNL NFQNLSVIGF RILLLKVAGF   240
NLLMTLRLWS S                                                        251

SEQ ID NO: 328          moltype = AA    length = 251
FEATURE                 Location/Qualifiers
source                  1..251
                        mol_type = protein
                        organism = Homo sapiens
SEQUENCE: 328
QQLNQSPQSM FIQEGEDVSM NCTSSSIFNT WLWYKQDPGE GPVLLIALYK AGELTSNGRL    60
TAQFGITRKD SFLNITASIP SDVGIYFCAG GYNYGQNFVF GPGTRLSVLP YIQNPDPAVY   120
QLRDSKSSDK SVCLFTDFDS QTNVSQSKDS DVYITDKTVL DMRSMDFKSN SAVAWSNKSD   180
FACANAFNNS IIPEDTFFPS PESSCDVKLV EKSFETDTNL NFQNLSVIGF RILLLKVAGF   240
NLLMTLRLWS S                                                        251

SEQ ID NO: 329          moltype = AA    length = 259
FEATURE                 Location/Qualifiers
source                  1..259
                        mol_type = protein
                        organism = Homo sapiens
SEQUENCE: 329
QQKEVEQDPG PLSVPEGAIV SLNCTYSNSA FQYFMWYRQY SRKGPELLMY TYSSGNKEDG    60
RFTAQVDKSS KYISLFIRDS NPSDSATYLC AMSGNSGARD YGNNRLAFGK GNQVVVIPNI   120
QNPDPAVYQL RDSKSSDKSV CLFTDFDSQT NVSQSKDSDV YITDKTVLDM RSMDFKSNSA   180
VAWSNKSDFA CANAFNNSII PEDTFFPSPE SSCDVKLVEK SFETDTNLNF QNLSVIGFRI   240
LLLKVAGFNL LMTLRLWSS                                                259

SEQ ID NO: 330          moltype = AA    length = 255
FEATURE                 Location/Qualifiers
source                  1..255
                        mol_type = protein
                        organism = Homo sapiens
SEQUENCE: 330
QTVTQSQPEM SVQEAETVTL SCTYDTSESD YYLFWYKQPP SRQMILVIRQ EAYKQQNATE    60
NRFSVNFQKA AKSFSLKLSD SQLGDAAMYF CTFRYGGATN KLIFGTGTLL AVQPNIQNPD   120
PAVYQLRDSK SSDKSVCLFT DFDSQTNVSQ SKDSDVYITD KTVLDMRSMD FKSNSAVAWS   180
NKSDFACANA FNNSIIPEDT FFPSPESSCD VKLVEKSFET DTNLNFQNLS VIGFRILLLK   240
```

```
VAGFNLLMTL RLWSS                                                          255

SEQ ID NO: 331          moltype = AA  length = 256
FEATURE                 Location/Qualifiers
source                  1..256
                        mol_type = protein
                        organism = Homo sapiens
SEQUENCE: 331
QKVTQAQTEI SVVEKEDVTL DCVYETRDTT YYLFWYKQPP SGELVFLIRR NSFDEQNEIS          60
GRYSWNFQKS TSSFQFTITA SQVVDSAVYF CALSGRGSGT YKYIFGTGTR LKVLANIQNP         120
DPAVYQLRDS KSSDKSVCLF TDFDSQTNVS QSKDSDVYIT DKTVLDMRSM DFKSNSAVAW         180
SNKSDFACAN AFNNSIIPED TFFPSPESSC DVKLVEKSFE TDTNLNFQNL SVIGFRILLL         240
KVAGFNLLMT LRLWSS                                                        256

SEQ ID NO: 332          moltype = AA  length = 251
FEATURE                 Location/Qualifiers
source                  1..251
                        mol_type = protein
                        organism = Homo sapiens
SEQUENCE: 332
EDVEQSLFLS VREGDSSVIN CTYTDSSSTY LYWYKQEPGA GLQLLTYIFS NMDMKQDQRL          60
TVLLNKKDKH LSLRIADSQT GDSAIYFCAE KETAGNKLTF GGGTRVLVKP NIQNPDDAVY         120
QLRDSKSSDK SVCLFTDFDS QTNVSQSKDS DVYITDKTVL DMRSMDFKSN SAVAWSNKSD         180
FACANAFNNS IIPEDTFFPS PESSCDVKLV EKSFETDTNL NFQNLSVIGF RILLLKVAGF         240
NLLMTLRLWS S                                                             251

SEQ ID NO: 333          moltype = AA  length = 253
FEATURE                 Location/Qualifiers
source                  1..253
                        mol_type = protein
                        organism = Homo sapiens
SEQUENCE: 333
QNIDQPTEMT ATEGAIVQIN CTYQTSGFNG LFWYQQHAGE APTFLSYNVL DGLEEKGRFS          60
SFLSRSKGYS YLLIKELQMK DSASYLCAVP APYTGTASKL TFGTGTRLQV TLDIQNPDPA         120
VYQLRDSKSS DKSVCLFTDF DSQTNVSQSK DSDVYITDKT VLDMRSMDFK SNSAVAWSNK         180
SDFACANAFN NSIIPEDTFF PSPESSCDVK LVEKSFETDT NLNFQNLSVI GFRILLLKVA         240
GFNLLMTLRL WSS                                                           253

SEQ ID NO: 334          moltype = AA  length = 249
FEATURE                 Location/Qualifiers
source                  1..249
                        mol_type = protein
                        organism = Homo sapiens
SEQUENCE: 334
IQVEQSPPDL ILQEGANSTL RCNFSDSVNN LQWFHQNPWG QLINLFYIPS GTKQNGRLTA          60
TTVATERYSL LYISSSQTTD SGVYFCAVNT GTASKLTFGT GTRLQVTLDI QNPDPAVYQL         120
RDSKSSDKSV CLFTDFDSQT NVSQKDSDV YITDKTVLDM RSMDFKSNSA VAWSNKSDFA         180
CANAFNNSII PEDTFFPSPE SSCDVKLVEK SFETDTNLNF QNLSVIGFRI LLLKVAGFNL         240
LMTLRLWSS                                                                249

SEQ ID NO: 335          moltype = AA  length = 252
FEATURE                 Location/Qualifiers
source                  1..252
                        mol_type = protein
                        organism = Homo sapiens
SEQUENCE: 335
QLLEQSPQFL SIQEGENLTV YCNSSSVFSS LQWYRQEPGE GPVLLVTVVT GGEVKKLKRL          60
TFQFGDARKD SSLHITAAQP GDTALYLCAG GLSDSYDKVI FGPGTSLSVI PNIQNPDPAV         120
YQLRDSKSSD KSVCLFTDFD SQTNVSQSKD SDVYITDKTV LDMRSMDFKS NSAVAWSNKS         180
DFACANAFNN SIIPEDTFFP SPESSCDVKL VEKSFETDTN LNFQNLSVIG FRILLLKVAG         240
FNLLMTLRLW SS                                                            252

SEQ ID NO: 336          moltype = AA  length = 258
FEATURE                 Location/Qualifiers
source                  1..258
                        mol_type = protein
                        organism = Homo sapiens
SEQUENCE: 336
QKITQTQPGM FVQEKEAVTL DCTYDTSDQS YGLFWYKQPS SGEMIFLIYQ GSYDEQNATE          60
GRYSLNFQKA RKSAQLVISA SQLGDSAMYF CAMSDPIMDT GRRALTFGSG TRLQVQPNIQ         120
NPDPAVYQLR DSKSSDKSVC LFTDFDSQTN VSQSKDSDVY ITDKTVLDMR SMDFKSNSAV         180
AWSNKSDFAC ANAFNNSIIP EDTFFPSPES SCDVKLVEKS FETDTNLNFQ NLSVIGFRIL         240
LLKVAGFNLL MTLRLWSS                                                      258

SEQ ID NO: 337          moltype = AA  length = 256
FEATURE                 Location/Qualifiers
source                  1..256
                        mol_type = protein
                        organism = Homo sapiens
```

```
SEQUENCE: 337
QKITQTQPGM FVQEKEAVTL DCTYDTSDQS YGLFWYKQPS SGEMIFLIYQ GSYDEQNATE   60
GRYSLNFQKA RKSANIVISA SQLGDSAMYF CAINGLPGSA RQLTFGSGTQ LTVLPDIQNP  120
DPAVYQLRDS KSSDKSVCLF TDFDSQTNVS QSKDSDVYIT DKTVLDMRSM DFKSNSAVAW  180
SNKSDFACAN AFNNSIIPED TFFPSPESSC DVKLVEKSFE TDTNLNFQNL SVIGFRILLL  240
KVAGFNLLMT LRLWSS                                                 256

SEQ ID NO: 338          moltype = AA  length = 205
FEATURE                 Location/Qualifiers
source                  1..205
                        mol_type = protein
                        organism = Homo sapiens
SEQUENCE: 338
KQEVTQIPAA LSVPEGENLV LNCSFTDSAI YNLQWFRQDP GKGLTSLLLI QSSQREQTSG   60
RLNASLDKSS GRSTLYIAGS QPGDSATYLC AVLLTGKLIF GQGTTLQVKP NIQKPDDAVY  120
QLRDSKSSDK SVCLFTDFDS QTNVSQSKDS DVYITDKTVL DMRSMDFKSN SAVAWSNKSD  180
FACANAFNNS IIPEDTFFPS PESSC                                       205

SEQ ID NO: 339          moltype = AA  length = 102
FEATURE                 Location/Qualifiers
source                  1..102
                        mol_type = protein
                        organism = Homo sapiens
SEQUENCE: 339
GVSQDPRHKI TKRGQNVTFR CDPISEHNRL YWYRQTLGQG PEFLTYFQNE AQLEKSRLLS   60
DRFSAERPKG SFSTLEIQRT EQGDSAMYLC ASSTDITSYE QY                    102

SEQ ID NO: 340          moltype = AA  length = 103
FEATURE                 Location/Qualifiers
source                  1..103
                        mol_type = protein
                        organism = Homo sapiens
SEQUENCE: 340
GVIQSPRHLI KEKRETATLK CYPIPRHDTV YWYQQGPGQD PQFLISFYEK MQSDKGSIPD   60
RFSAQQFSDY HSELNMSSLE LGDSALYFCA SSPSTGRLNT EAF                   103

SEQ ID NO: 341          moltype = AA  length = 102
FEATURE                 Location/Qualifiers
source                  1..102
                        mol_type = protein
                        organism = Homo sapiens
SEQUENCE: 341
QVTQNPRYLI TVTGKKLTVT CSQNMNHEYM SWYRQDPGLG LRQIYYSMNV EVTDKGDVPE   60
GYKVSRKEKR NFPLILESPS PNQTSLYFCA SREGTGGYQP QH                    102

SEQ ID NO: 342          moltype = AA  length = 102
FEATURE                 Location/Qualifiers
source                  1..102
                        mol_type = protein
                        organism = Homo sapiens
SEQUENCE: 342
GVTQTPKFRV LKTGQSMTLL CAQDMNHEYM YWYRQDPGMG LRLIHYSVGE GTTAKGEVPD   60
GYNVSRLKKQ NFLLGLESAA PSQTSVYFCA SSYLRTGGNE QF                    102

SEQ ID NO: 343          moltype = AA  length = 102
FEATURE                 Location/Qualifiers
source                  1..102
                        mol_type = protein
                        organism = Homo sapiens
SEQUENCE: 343
GVTQTPKHLI TATGQRVTLR CSPRSGDLSV YWYQQSLDQG LQFLIQYYNG EERAKGNILE   60
RFSAQQFPDL HSELNLSSLE LGDSALYFCA SSAGLAGGYE QY                    102

SEQ ID NO: 344          moltype = AA  length = 104
FEATURE                 Location/Qualifiers
source                  1..104
                        mol_type = protein
                        organism = Homo sapiens
SEQUENCE: 344
EVTQTPKHLV MGMTNKKSLK CEQHMGHRAM YWYKQKAKKP PELMFVYSYE KLSINESVPS   60
RFSPECPNSS LLNLHLHALQ PEDSALYLCA SATWEEAGPY NEQF                  104

SEQ ID NO: 345          moltype = AA  length = 103
FEATURE                 Location/Qualifiers
source                  1..103
                        mol_type = protein
                        organism = Homo sapiens
SEQUENCE: 345
GVIQSPRHLI KEKRETATLK CYPIPRHDTV YWYQQGPGQD PQFLISFYEK MQSDKGSIPD   60
```

```
RFSAQQFSDY HSELNMSSLE LGDSALYFCA SRGGWAETPD TQY                    103

SEQ ID NO: 346           moltype = AA  length = 101
FEATURE                  Location/Qualifiers
source                   1..101
                         mol_type = protein
                         organism = Homo sapiens
SEQUENCE: 346
GVIQSPRHLI KEKRETATLK CYPIPRHDTV YWYQQGPGQD PQFLISFYEK MQSDKGSIPD   60
RFSAQQFSDY HSELNMSSLE LGDSALYFCA SSAGTSYNEQ F                      101

SEQ ID NO: 347           moltype = AA  length = 105
FEATURE                  Location/Qualifiers
source                   1..105
                         mol_type = protein
                         organism = Homo sapiens
SEQUENCE: 347
EPEVTQTPSH QVTQMGQEVI LRCVPISNHL YFYWYRQILG QKVEFLVSFY NNEISEKSEI   60
FDDQFSVERP DGSNFTLKIR STKLEDSAMY FCASTVQSPR TNEQF                  105

SEQ ID NO: 348           moltype = AA  length = 102
FEATURE                  Location/Qualifiers
source                   1..102
                         mol_type = protein
                         organism = Homo sapiens
SEQUENCE: 348
GVTQTPKFQV LKTGQSMTLQ CAQDMNHNSM YWYRQDPGMG LRLIYYSASE GTTDKGEVPN   60
GYNVSRLNKR EFSLRLESAA PSQTSVYFCA SSEGYSTYNE QF                     102

SEQ ID NO: 349           moltype = AA  length = 103
FEATURE                  Location/Qualifiers
source                   1..103
                         mol_type = protein
                         organism = Homo sapiens
SEQUENCE: 349
GVTQTPKFQV LKTGQSMTLQ CAQDMNHNSM YWYRQDPGMG LRLIYYSASE GTTDKGEVPN   60
GYNVSRLNKR EFSLRLESAA PSQTSVYFCA SSPRGQGRSY EQY                    103

SEQ ID NO: 350           moltype = AA  length = 102
FEATURE                  Location/Qualifiers
source                   1..102
                         mol_type = protein
                         organism = Homo sapiens
SEQUENCE: 350
EVTQTPKHLV MGMTNKKSLK CEQHMGHRAM YWYKQKAKKP PELMFVYSYE KLSINESVPS   60
RFSPECPNSS LLNLHLHALQ PEDSALYLCA SSQGVGQEYG YT                     102

SEQ ID NO: 351           moltype = AA  length = 103
FEATURE                  Location/Qualifiers
source                   1..103
                         mol_type = protein
                         organism = Homo sapiens
SEQUENCE: 351
GITQSPKYLF RKEGQNVTLS CEQNLNHDAM YWYRQDPGQG LRLIYYSQIV NDFQKGDIAE   60
GYSVSREKKE SFPLTVTSAQ KNPTAFYLCA SKSRGPNLAD TQY                    103

SEQ ID NO: 352           moltype = AA  length = 104
FEATURE                  Location/Qualifiers
source                   1..104
                         mol_type = protein
                         organism = Homo sapiens
SEQUENCE: 352
GVAQSPRYKI IEKRQSVAFW CNPISGHATL YWYQQILGQG PKLLIQFQNN GVVDDSQLPK   60
DRFSAERLKG VDSTLKIQPA KLEDSAVYLC ASSRFVATGT SPLH                   104

SEQ ID NO: 353           moltype = AA  length = 102
FEATURE                  Location/Qualifiers
source                   1..102
                         mol_type = protein
                         organism = Homo sapiens
SEQUENCE: 353
GVTQTPRYLI KTRGQQVTLS CSPISGHRSV SWYQQTPGQG LQFLFEYFSE TQRNKGNFPG   60
RFSGRQFSNS RSEMNVSTLE LGDSALYLCA SSGGPGPSGE QY                     102

SEQ ID NO: 354           moltype = AA  length = 112
FEATURE                  Location/Qualifiers
source                   1..112
                         mol_type = protein
                         organism = Homo sapiens
```

```
SEQUENCE: 354
GVSQEPRHKI TKRGQNVTFR CDPISEHNRL YWYRQTLGQG PEFLTYFQNE AQLEKSRLLS   60
DRFSAERPKG SFSTLEIQRT EQGDSAMYLC ASSTDITSYE QYFGPGTRLT VT           112

SEQ ID NO: 355          moltype = AA   length = 113
FEATURE                 Location/Qualifiers
source                  1..113
                        mol_type = protein
                        organism = Homo sapiens
SEQUENCE: 355
GVIQSPRHLI KEKRESATLK CYPIPRHDTV YWYQQGPGQD PQFLISFYEK MQSDKGSIPD   60
RFSAQQFSDY HSELNMSSLE LGDSALYFCA SSPSTGRLNT EAFFGQGTRL TVV          113

SEQ ID NO: 356          moltype = AA   length = 112
FEATURE                 Location/Qualifiers
source                  1..112
                        mol_type = protein
                        organism = Homo sapiens
SEQUENCE: 356
QVTQNPKYLI TVTGKKLTVT CSQNMNHEYM SWYRQDPGLG LRQIYYSMNV EVTDKGDVPE   60
GYKVSRKEKR NFPLILESPS PNQTSLYFCA SREGTGGYQP QHFGDGTRLS IL           112

SEQ ID NO: 357          moltype = AA   length = 112
FEATURE                 Location/Qualifiers
source                  1..112
                        mol_type = protein
                        organism = Homo sapiens
SEQUENCE: 357
GVTQTPKFRV LKTGQTMTLL CAQDMNHEYM YWYRQDPGMG LRLIHYSVGE GTTAKGEVPD   60
GYNVSRLKKQ NFPLLGLESAA PSQTSVYFCA SSYLRTGGNE QFFGPGTRLT VL          112

SEQ ID NO: 358          moltype = AA   length = 112
FEATURE                 Location/Qualifiers
source                  1..112
                        mol_type = protein
                        organism = Homo sapiens
SEQUENCE: 358
GVTQTPKHLI TATGQRVTLR CTPRSGDLSV YWYQQSLDQG LQFLIQYYNG EERAKGNILE   60
RFSAQQFPDL HSELNLSSLE LGDSALYFCA SSAGLAGGYE QYFGPGTRLT VT           112

SEQ ID NO: 359          moltype = AA   length = 114
FEATURE                 Location/Qualifiers
source                  1..114
                        mol_type = protein
                        organism = Homo sapiens
SEQUENCE: 359
EVTQTPRHLV MGMTNKKSLK CEQHMGHRAM YWYKQKAKKP PELMFVYSYE KLSINESVPS   60
RFSPECPNSS LLNLHLHALQ PEDSALYLCA SATWEEAGPY NEQFFGPGTR LTVL         114

SEQ ID NO: 360          moltype = AA   length = 113
FEATURE                 Location/Qualifiers
source                  1..113
                        mol_type = protein
                        organism = Homo sapiens
SEQUENCE: 360
GVIQSPRHLI KEKRETATLR CYPIPRHDTV YWYQQGPGQD PQFLISFYEK MQSDKGSIPD   60
RFSAQQFSDY HSELNMSSLE LGDSALYFCA SRGGWAETPD TQYFGPGTRL TVL          113

SEQ ID NO: 361          moltype = AA   length = 111
FEATURE                 Location/Qualifiers
source                  1..111
                        mol_type = protein
                        organism = Homo sapiens
SEQUENCE: 361
GVIQSPRHLI KDKRETATLK CYPIPRHDTV YWYQQGPGQD PQFLISFYEK MQSDKGSIPD   60
RFSAQQFSDY HSELNMSSLE LGDSALYFCA SSAGTSYNEQ FFGPGTRLTV L            111

SEQ ID NO: 362          moltype = AA   length = 115
FEATURE                 Location/Qualifiers
source                  1..115
                        mol_type = protein
                        organism = Homo sapiens
SEQUENCE: 362
EPEVTQTPSH QVTQMGQEVI LKCVPISNHL YFYWYRQILG QKVEFLVSFY NNEISEKSEI   60
FDDQFSVERP DGSNFTLKIR STKLEDSAMY FCASTVQSPR TNEQFFGPGT RLTVL        115

SEQ ID NO: 363          moltype = AA   length = 112
FEATURE                 Location/Qualifiers
source                  1..112
```

```
                            mol_type = protein
                            organism = Homo sapiens
SEQUENCE: 363
GVTQTPKFQV LKTGQSMTLQ CIQDMNHNSM YWYRQDPGMG LRLIYYSASE GTTDKGEVPN    60
GYNVSRLNKR EFSLRLESAA PSQTSVYFCA SSEGYSTYNE QFFGPGTRLT VL           112

SEQ ID NO: 364              moltype = AA   length = 113
FEATURE                     Location/Qualifiers
source                      1..113
                            mol_type = protein
                            organism = Homo sapiens
SEQUENCE: 364
GVTQTPKFQV LKSGQSMTLQ CAQDMNHNSM YWYRQDPGMG LRLIYYSASE GTTDKGEVPN    60
GYNVSRLNKR EFSLRLESAA PSQTSVYFCA SSPRGQGRSY EQYFGPGTRL TVT          113

SEQ ID NO: 365              moltype = AA   length = 112
FEATURE                     Location/Qualifiers
source                      1..112
                            mol_type = protein
                            organism = Homo sapiens
SEQUENCE: 365
EVTQTPKHLV QGMTNKKSLK CEQHMGHRAM YWYKQKAKKP PELMFVYSYE KLSINESVPS    60
RFSPECPNSS LLNLHLHALQ PEDSALYLCA SSQGVGQEYG YTFGSGTRLT VV           112

SEQ ID NO: 366              moltype = AA   length = 113
FEATURE                     Location/Qualifiers
source                      1..113
                            mol_type = protein
                            organism = Homo sapiens
SEQUENCE: 366
GITQSPKWLF RKEGQNVTLS CEQNLNHDAM YWYRQDPGQG LRLIYYSQIV NDFQKGDIAE    60
GYSVSREKKE SFPLTVTSAQ KNPTAFYLCA SKSRGPNLAD TQYFGPGTRL TVL          113

SEQ ID NO: 367              moltype = AA   length = 114
FEATURE                     Location/Qualifiers
source                      1..114
                            mol_type = protein
                            organism = Homo sapiens
SEQUENCE: 367
GVAQSPRYKL IEKRQSVAFW CNPISGHATL YWYQQILGQG PKLLIQFQNN GVVDDSQLPK    60
DRFSAERLKG VDSTLKIQPA KLEDSAVYLC ASSRFVATGT SPLHFGNGTR LTVT         114

SEQ ID NO: 368              moltype = AA   length = 112
FEATURE                     Location/Qualifiers
source                      1..112
                            mol_type = protein
                            organism = Homo sapiens
SEQUENCE: 368
GVTQTPRYLI KSRGQQVTLS CSPISGHRSV SWYQQTPGQG LQFLFEYFSE TQRNKGNFPG    60
RFSGRQFSNS RSEMNVSTLE LGDSALYLCA SSGGPGPSGE QYFGPGTRLT VT           112

SEQ ID NO: 369              moltype = AA   length = 112
FEATURE                     Location/Qualifiers
source                      1..112
                            mol_type = protein
                            organism = Homo sapiens
SEQUENCE: 369
GVSQDPRHKI TKRGQNVTFR CDPISEHNRL YWYRQTLGQG PEFLSYFQNE AQLEKSRLLS    60
DRFSAERPKG SFSTLEIQRT EQGDSAMYLC ASSTDITSYE QYFGPGTRLT VT           112

SEQ ID NO: 370              moltype = AA   length = 113
FEATURE                     Location/Qualifiers
source                      1..113
                            mol_type = protein
                            organism = Homo sapiens
SEQUENCE: 370
GVIQSPRHLI KEKRETATLK CYPIPRHDTV YWYQQGPGQD PQFLITFYEK MQSDKGSIPD    60
RFSAQQFSDY HSELNMSSLE LGDSALYFCA SSPSTGRLNT EAFFGQGTRL TVV          113

SEQ ID NO: 371              moltype = AA   length = 112
FEATURE                     Location/Qualifiers
source                      1..112
                            mol_type = protein
                            organism = Homo sapiens
SEQUENCE: 371
QVTQNPRYLI TVTGKKLTVT CSQNMNHEYM SWYQQDPGLG LRQIYYSMNV EVTDKGDVPE    60
GYKVSRKEKR NFPLILESPS PNQTSLYFCA SREGTGGYQP QHFGDGTRLS IL           112

SEQ ID NO: 372              moltype = AA   length = 112
```

```
FEATURE                 Location/Qualifiers
source                  1..112
                        mol_type = protein
                        organism = Homo sapiens
SEQUENCE: 372
GVTQTPKFRV LKTGQSMTLL CAQDMNHEYM YWYRQDPGMG LRLLHYSVGE GTTAKGEVPD   60
GYNVSRLKKQ NFLLGLESAA PSQTSVYFCA SSYLRTGGNE QFFGPGTRLT VL          112

SEQ ID NO: 373          moltype = AA   length = 112
FEATURE                 Location/Qualifiers
source                  1..112
                        mol_type = protein
                        organism = Homo sapiens
SEQUENCE: 373
GVTQTPKHLI TATGQRVTLR CSPRSGDLSV YWYQQTLDQG LQFLIQYYNG EERAKGNILE   60
RFSAQQFPDL HSELNLSSLE LGDSALYFCA SSAGLAGGYE QYFGPGTRLT VT          112

SEQ ID NO: 374          moltype = AA   length = 114
FEATURE                 Location/Qualifiers
source                  1..114
                        mol_type = protein
                        organism = Homo sapiens
SEQUENCE: 374
EVTQTPKHLV MGMTNKKSLK CEQHMGHRAM YWYKQKAKKP PDLMFVYSYE KLSINESVPS   60
RFSPECPNSS LLNLHLHALQ PEDSALYLCA SATWEEAGPY NEQFFGPGTR LTVL        114

SEQ ID NO: 375          moltype = AA   length = 113
FEATURE                 Location/Qualifiers
source                  1..113
                        mol_type = protein
                        organism = Homo sapiens
SEQUENCE: 375
GVIQSPRHLI KEKRETATLK CYPIPRHDTV YWYQQGPGQR PQFLISFYEK MQSDKGSIPD   60
RFSAQQFSDY HSELNMSSLE LGDSALYFCA SRGGWAETPD TQYFGPGTRL TVL         113

SEQ ID NO: 376          moltype = AA   length = 111
FEATURE                 Location/Qualifiers
source                  1..111
                        mol_type = protein
                        organism = Homo sapiens
SEQUENCE: 376
GVIQSPRHLI KEKRETATLK CYPIPRHDTV YWYQQGPGQE PQFLISFYEK MQSDKGSIPD   60
RFSAQQFSDY HSELNMSSLE LGDSALYFCA SSAGTSYNEQ FFGPGTRLTV L           111

SEQ ID NO: 377          moltype = AA   length = 115
FEATURE                 Location/Qualifiers
source                  1..115
                        mol_type = protein
                        organism = Homo sapiens
SEQUENCE: 377
EPEVTQTPSH QVTQMGQEVI LRCVPISNHL YMYWYRQILG QKVEFLVSFY NNEISEKSEI   60
FDDQFSVERP DGSNFTLKIR STKLEDSAMY FCASTVQSPR TNEQFFGPGT RLTVL       115

SEQ ID NO: 378          moltype = AA   length = 112
FEATURE                 Location/Qualifiers
source                  1..112
                        mol_type = protein
                        organism = Homo sapiens
SEQUENCE: 378
GVTQTPKFQV LKTGQSMTLQ CAQDMNHNSF YWYRQDPGMG LRLIYYSASE GTTDKGEVPN   60
GYNVSRLNKR EFSLRLESAA PSQTSVYFCA SSEGYSTYNE QFFGPGTRLT VL          112

SEQ ID NO: 379          moltype = AA   length = 113
FEATURE                 Location/Qualifiers
source                  1..113
                        mol_type = protein
                        organism = Homo sapiens
SEQUENCE: 379
GVTQTPKFQV LKTGQSMTLQ CAQDMNHNSM YWYRQDPGMG LRLIWYSASE GTTDKGEVPN   60
GYNVSRLNKR EFSLRLESAA PSQTSVYFCA SSPRGQGRSY EQYFGPGTRL TVT         113

SEQ ID NO: 380          moltype = AA   length = 112
FEATURE                 Location/Qualifiers
source                  1..112
                        mol_type = protein
                        organism = Homo sapiens
SEQUENCE: 380
EVTQTPKHLV MGMTNKKSLK CEQHMGHRAM YWYKQHAKKP PELMFVYSYE KLSINESVPS   60
RFSPECPNSS LLNLHLHALQ PEDSALYLCA SSQGVGQEYG YTFGSGTRLT VV          112
```

```
SEQ ID NO: 381          moltype = AA   length = 113
FEATURE                 Location/Qualifiers
source                  1..113
                        mol_type = protein
                        organism = Homo sapiens
SEQUENCE: 381
GITQSPKYLF RKEGQNVTLS CEQNLNHDAM YWYRQDPGQA LRLIYYSQIV NDFQKGDIAE   60
GYSVSREKKE SFPLTVTSAQ KNPTAFYLCA SKSRGPNLAD TQYFGPGTRL TVL         113

SEQ ID NO: 382          moltype = AA   length = 114
FEATURE                 Location/Qualifiers
source                  1..114
                        mol_type = protein
                        organism = Homo sapiens
SEQUENCE: 382
GVAQSPRYKI IEKRQSVAFW CNPISGHATM YWYQQILGQG PKLLIQFQNN GVVDDSQLPK   60
DRFSAERLKG VDSTLKIQPA KLEDSAVYLC ASSRFVATGT SPLHFGNGTR LTVT        114

SEQ ID NO: 383          moltype = AA   length = 112
FEATURE                 Location/Qualifiers
source                  1..112
                        mol_type = protein
                        organism = Homo sapiens
SEQUENCE: 383
GVTQTPRYLI KTRGQQVTLS CSPISGHRSV SWYQQSPGQG LQFLFEYFSE TQRNKGNFPG   60
RFSGRQFSNS RSEMNVSTLE LGDSALYLCA SSGGPGPSGE QYFGPGTRLT VT          112

SEQ ID NO: 384          moltype = AA   length = 112
FEATURE                 Location/Qualifiers
source                  1..112
                        mol_type = protein
                        organism = Homo sapiens
SEQUENCE: 384
GVSQDPRHKI TKRGQNVTFR CDPISEHNRL YWYRQTLGQG PEFLTYFQNE AQLEKSRLLT   60
DRFSAERPKG SFSTLEIQRT EQGDSAMYLC ASSTDITSYE QYFGPGTRLT VT          112

SEQ ID NO: 385          moltype = AA   length = 113
FEATURE                 Location/Qualifiers
source                  1..113
                        mol_type = protein
                        organism = Homo sapiens
SEQUENCE: 385
GVIQSPRHLI KEKRETATLK CYPIPRHDTV YWYQQGPGQD PQFLISFYEK MQSDKGSIPD   60
RLSAQQFSDY HSELNMSSLE LGDSALYFCA SSPSTGRLNT EAFFGQGTRL TVV         113

SEQ ID NO: 386          moltype = AA   length = 112
FEATURE                 Location/Qualifiers
source                  1..112
                        mol_type = protein
                        organism = Homo sapiens
SEQUENCE: 386
QVTQNPRYLI TVTGKKLTVT CSQNMNHEYM SWYRQDPGLG LRQIYYSMNV EVTDKGDVPE   60
GYKVSRKERR NFPLILESPS PNQTSLYFCA SREGTGGYQP QHFGDGTRLS IL          112

SEQ ID NO: 387          moltype = AA   length = 112
FEATURE                 Location/Qualifiers
source                  1..112
                        mol_type = protein
                        organism = Homo sapiens
SEQUENCE: 387
GVTQTPKFRV LKTGQSMTLL CAQDMNHEYM YWYRQDPGMG LRLIHYSVGE GTTAKGEVPD   60
GYNVSRLKKQ NFLLGLETAA PSQTSVYFCA SSYLRTGGNE QFFGPGTRLT VL          112

SEQ ID NO: 388          moltype = AA   length = 112
FEATURE                 Location/Qualifiers
source                  1..112
                        mol_type = protein
                        organism = Homo sapiens
SEQUENCE: 388
GVTQTPKHLI TATGQRVTLR CSPRSGDLSV YWYQQSLDQG LQFLIQYYNG EERAKGNILE   60
RFSAMQFPDL HSELNLSSLE LGDSALYFCA SSAGLAGGYE QYFGPGTRLT VT          112

SEQ ID NO: 389          moltype = AA   length = 114
FEATURE                 Location/Qualifiers
source                  1..114
                        mol_type = protein
                        organism = Homo sapiens
SEQUENCE: 389
```

```
EVTQTPKHLV MGMTNKKSLK CEQHMGHRAM YWYKQKAKKP PELMFVYSYE KLSINESVPS    60
RFSPECPNSS LINLHLHALQ PEDSALYLCA SATWEEAGPY NEQFFGPGTR LTVL         114

SEQ ID NO: 390          moltype = AA  length = 113
FEATURE                 Location/Qualifiers
source                  1..113
                        mol_type = protein
                        organism = Homo sapiens
SEQUENCE: 390
GVIQSPRHLI KEKRETATLK CYPIPRHDTV YWYQQGPGQD PQFLISFYEK MQSDKGSLPD    60
RFSAQQFSDY HSELNMSSLE LGDSALYFCA SRGGWAETPD TQYFGPGTRL TVL          113

SEQ ID NO: 391          moltype = AA  length = 111
FEATURE                 Location/Qualifiers
source                  1..111
                        mol_type = protein
                        organism = Homo sapiens
SEQUENCE: 391
GVIQSPRHLI KEKRETATLK CYPIPRHDTV YWYQQGPGQD PQFLISFYEK MQSDKGSIPD    60
RFSAQQFSDY HSELNMTSLE LGDSALYFCA SSAGTSYNEQ FFGPGTRLTV L            111

SEQ ID NO: 392          moltype = AA  length = 115
FEATURE                 Location/Qualifiers
source                  1..115
                        mol_type = protein
                        organism = Homo sapiens
SEQUENCE: 392
EPEVTQTPSH QVTQMGQEVI LRCVPISNHL YFYWYRQILG QKVEFLVSFY NNEISEKSEI    60
FDDQFSVERP DGSNFTLRIR STKLEDSAMY FCASTVQSPR TNEQFFGPGT RLTVL        115

SEQ ID NO: 393          moltype = AA  length = 112
FEATURE                 Location/Qualifiers
source                  1..112
                        mol_type = protein
                        organism = Homo sapiens
SEQUENCE: 393
GVTQTPKFQV LKTGQSMTLQ CAQDMNHNSM YWYRQDPGMG LRLIYYSASE GTTDKGEVPN    60
GYNVTRLNKR EFSLRLESAA PSQTSVYFCA SSEGYSTYNE QFFGPGTRLT VL           112

SEQ ID NO: 394          moltype = AA  length = 113
FEATURE                 Location/Qualifiers
source                  1..113
                        mol_type = protein
                        organism = Homo sapiens
SEQUENCE: 394
GVTQTPKFQV LKTGQSMTLQ CAQDMNHNSM YWYRQDPGMG LRLIYYSASE GTTDKIEVPN    60
GYNVSRLNKR EFSLRLESAA PSQTSVYFCA SSPRGQGRSY EQYFGPGTRL TVT          113

SEQ ID NO: 395          moltype = AA  length = 112
FEATURE                 Location/Qualifiers
source                  1..112
                        mol_type = protein
                        organism = Homo sapiens
SEQUENCE: 395
EVTQTPKHLV MGMTNKKSLK CEQHMGHRAM YWYKQKAKKP PELMFVYSYE KLSINDSVPS    60
RFSPECPNSS LLNLHLHALQ PEDSALYLCA SSQGVGQEYG YTFGSGTRLT VV           112

SEQ ID NO: 396          moltype = AA  length = 113
FEATURE                 Location/Qualifiers
source                  1..113
                        mol_type = protein
                        organism = Homo sapiens
SEQUENCE: 396
GITQSPKYLF RKEGQNVTLS CEQNLNHDAM YWYRQDPGQG LRLIYYSQIV NDFQKGDIAD    60
GYSVSREKKE SFPLTVTSAQ KNPTAFYLCA SKSRGPNLAD TQYFGPGTRL TVL          113

SEQ ID NO: 397          moltype = AA  length = 114
FEATURE                 Location/Qualifiers
source                  1..114
                        mol_type = protein
                        organism = Homo sapiens
SEQUENCE: 397
GVAQSPRYKI IEKRQSVAFW CNPISGHATL YWYQQILGQG PKLLIQFQNN GVVDDSQLPK    60
DRFSAERLKG VDSTLKIMPA KLEDSAVYLC ASSRFVATGT SPLHFGNGTR LTVT         114

SEQ ID NO: 398          moltype = AA  length = 112
FEATURE                 Location/Qualifiers
source                  1..112
                        mol_type = protein
```

```
                        organism = Homo sapiens
SEQUENCE: 398
GVTQTPRYLI KTRGQQVTLS CSPISGHRSV SWYQQTPGQG LQFLFEYFSE TQRNKGNFPG    60
RFSGRQFTNS RSEMNVSTLE LGDSALYLCA SSGGPGPSGE QYFGPGTRLT VT            112

SEQ ID NO: 399           moltype = AA   length = 102
FEATURE                  Location/Qualifiers
source                   1..102
                         mol_type = protein
                         organism = Homo sapiens
SEQUENCE: 399
GVSQEPRHKI TKRGQNVTFR CDPISEHNRL YWYRQTLGQG PEFLTYFQNE AQLEKSRLLS    60
DRFSAERPKG SFSTLEIQRT EQGDSAMYLC ASSTDITSYE QY                       102

SEQ ID NO: 400           moltype = AA   length = 103
FEATURE                  Location/Qualifiers
source                   1..103
                         mol_type = protein
                         organism = Homo sapiens
SEQUENCE: 400
GVIQSPRHLI KEKRESATLK CYPIPRHDTV YWYQQGPGQD PQFLISFYEK MQSDKGSIPD    60
RFSAQQFSDY HSELNMSSLE LGDSALYFCA SSPSTGRLNT EAF                      103

SEQ ID NO: 401           moltype = AA   length = 102
FEATURE                  Location/Qualifiers
source                   1..102
                         mol_type = protein
                         organism = Homo sapiens
SEQUENCE: 401
QVTQNPKYLI TVTGKKLTVT CSQNMNHEYM SWYRQDPGLG LRQIYYSMNV EVTDKGDVPE    60
GYKVSRKEKR NFPLILESPS PNQTSLYFCA SREGTGGYQP QH                       102

SEQ ID NO: 402           moltype = AA   length = 102
FEATURE                  Location/Qualifiers
source                   1..102
                         mol_type = protein
                         organism = Homo sapiens
SEQUENCE: 402
GVTQTPKFRV LKTGQTMTLL CAQDMNHEYM YWYRQDPGMG LRLIHYSVGE GTTAKGEVPD    60
GYNVSRLKKQ NFLLGLESAA PSQTSVYFCA SSYLRTGGNE QF                       102

SEQ ID NO: 403           moltype = AA   length = 102
FEATURE                  Location/Qualifiers
source                   1..102
                         mol_type = protein
                         organism = Homo sapiens
SEQUENCE: 403
GVTQTPKHLI TATGQRVTLR CTPRSGDLSV YWYQQSLDQG LQFLIQYYNG EERAKGNILE    60
RFSAQQFPDL HSELNLSSLE LGDSALYFCA SSAGLAGGYE QY                       102

SEQ ID NO: 404           moltype = AA   length = 104
FEATURE                  Location/Qualifiers
source                   1..104
                         mol_type = protein
                         organism = Homo sapiens
SEQUENCE: 404
EVTQTPRHLV MGMTNKKSLK CEQHMGHRAM YWYKQKAKKP PELMFVYSYE KLSINESVPS    60
RFSPECPNSS LLNLHLHALQ PEDSALYLCA SATWEEAGPY NEQF                     104

SEQ ID NO: 405           moltype = AA   length = 103
FEATURE                  Location/Qualifiers
source                   1..103
                         mol_type = protein
                         organism = Homo sapiens
SEQUENCE: 405
GVIQSPRHLI KEKRETATLR CYPIPRHDTV YWYQQGPGQD PQFLISFYEK MQSDKGSIPD    60
RFSAQQFSDY HSELNMSSLE LGDSALYFCA SRGGWAETPD TQY                      103

SEQ ID NO: 406           moltype = AA   length = 101
FEATURE                  Location/Qualifiers
source                   1..101
                         mol_type = protein
                         organism = Homo sapiens
SEQUENCE: 406
GVIQSPRHLI KDKRETATLK CYPIPRHDTV YWYQQGPGQD PQFLISFYEK MQSDKGSIPD    60
RFSAQQFSDY HSELNMSSLE LGDSALYFCA SSAGTSYNEQ F                        101

SEQ ID NO: 407           moltype = AA   length = 105
FEATURE                  Location/Qualifiers
```

```
source                    1..105
                          mol_type = protein
                          organism = Homo sapiens
SEQUENCE: 407
EPEVTQTPSH QVTQMGQEVI LKCVPISNHL YFYWYRQILG QKVEFLVSFY NNEISEKSEI    60
FDDQFSVERP DGSNFTLKIR STKLEDSAMY FCASTVQSPR TNEQF                   105

SEQ ID NO: 408            moltype = AA   length = 102
FEATURE                   Location/Qualifiers
source                    1..102
                          mol_type = protein
                          organism = Homo sapiens
SEQUENCE: 408
GVTQTPKFQV LKTGQSMTLQ CIQDMNHNSM YWYRQDPGMG LRLIYYSASE GTTDKGEVPN    60
GYNVSRLNKR EFSLRLESAA PSQTSVYFCA SSEGYSTYNE QF                      102

SEQ ID NO: 409            moltype = AA   length = 103
FEATURE                   Location/Qualifiers
source                    1..103
                          mol_type = protein
                          organism = Homo sapiens
SEQUENCE: 409
GVTQTPKFQV LKSGQSMTLQ CAQDMNHNSM YWYRQDPGMG LRLIYYSASE GTTDKGEVPN    60
GYNVSRLNKR EFSLRLESAA PSQTSVYFCA SSPRGQGRSY EQY                     103

SEQ ID NO: 410            moltype = AA   length = 102
FEATURE                   Location/Qualifiers
source                    1..102
                          mol_type = protein
                          organism = Homo sapiens
SEQUENCE: 410
EVTQTPKHLV QGMTNKKSLK CEQHMGHRAM YWYKQKAKKP PELMFVYSYE KLSINESVPS    60
RFSPECPNSS LLNLHLHALQ PEDSALYLCA SSQGVGQEYG YT                      102

SEQ ID NO: 411            moltype = AA   length = 103
FEATURE                   Location/Qualifiers
source                    1..103
                          mol_type = protein
                          organism = Homo sapiens
SEQUENCE: 411
GITQSPKWLF RKEGQNVTLS CEQNLNHDAM YWYRQDPGQG LRLIYYSQIV NDFQKGDIAE    60
GYSVSREKKE SFPLTVTSAQ KNPTAFYLCA SKSRGPNLAD TQY                     103

SEQ ID NO: 412            moltype = AA   length = 104
FEATURE                   Location/Qualifiers
source                    1..104
                          mol_type = protein
                          organism = Homo sapiens
SEQUENCE: 412
GVAQSPRYKL IEKRQSVAFW CNPISGHATL YWYQQILGQG PKLLIQFQNN GVVDDSQLPK    60
DRFSAERLKG VDSTLKIQPA KLEDSAVYLC ASSRFVATGT SPLH                    104

SEQ ID NO: 413            moltype = AA   length = 102
FEATURE                   Location/Qualifiers
source                    1..102
                          mol_type = protein
                          organism = Homo sapiens
SEQUENCE: 413
GVTQTPRYLI KSRGQQVTLS CSPISGHRSV SWYQQTPGQG LQFLFEYFSE TQRNKGNFPG    60
RFSGRQFSNS RSEMNVSTLE LGDSALYLCA SSGGPGPSGE QY                      102

SEQ ID NO: 414            moltype = AA   length = 102
FEATURE                   Location/Qualifiers
source                    1..102
                          mol_type = protein
                          organism = Homo sapiens
SEQUENCE: 414
GVSQDPRHKI TKRGQNVTFR CDPISEHNRL YWYRQTLGQG PEFLSYFQNE AQLEKSRLLS    60
DRFSAERPKG SFSTLEIQRT EQGDSAMYLC ASSTDITSYE QY                      102

SEQ ID NO: 415            moltype = AA   length = 103
FEATURE                   Location/Qualifiers
source                    1..103
                          mol_type = protein
                          organism = Homo sapiens
SEQUENCE: 415
GVIQSPRHLI KEKRETATLK CYPIPRHDTV YWYQQGPGQD PQFLITFYEK MQSDKGSIPD    60
RFSAQQFSDY HSELNMSSLE LGDSALYFCA SSPSTGRLNT EAF                     103
```

```
SEQ ID NO: 416          moltype = AA   length = 102
FEATURE                 Location/Qualifiers
source                  1..102
                        mol_type = protein
                        organism = Homo sapiens
SEQUENCE: 416
QVTQNPRYLI TVTGKKLTVT CSQNMNHEYM SWYQQDPGLG LRQIYYSMNV EVTDKGDVPE     60
GYKVSRKEKR NFPLILESPS PNQTSLYFCA SREGTGGYQP QH                        102

SEQ ID NO: 417          moltype = AA   length = 102
FEATURE                 Location/Qualifiers
source                  1..102
                        mol_type = protein
                        organism = Homo sapiens
SEQUENCE: 417
GVTQTPKFRV LKTGQSMTLL CAQDMNHEYM YWYRQDPGMG LRLLHYSVGE GTTAKGEVPD     60
GYNVSRLKKQ NFLLGLESAA PSQTSVYFCA SSYLRTGGNE QF                        102

SEQ ID NO: 418          moltype = AA   length = 102
FEATURE                 Location/Qualifiers
source                  1..102
                        mol_type = protein
                        organism = Homo sapiens
SEQUENCE: 418
GVTQTPKHLI TATGQRVTLR CSPRSGDLSV YWYQQTLDQG LQFLIQYYNG EERAKGNILE     60
RFSAQQFPDL HSELNLSSLE LGDSALYFCA SSAGLAGGYE QY                        102

SEQ ID NO: 419          moltype = AA   length = 104
FEATURE                 Location/Qualifiers
source                  1..104
                        mol_type = protein
                        organism = Homo sapiens
SEQUENCE: 419
EVTQTPKHLV MGMTNKKSLK CEQHMGHRAM YWYKQKAKKP PDLMFVYSYE KLSINESVPS     60
RFSPECPNSS LLNLHLHALQ PEDSALYLCA SATWEEAGPY NEQF                      104

SEQ ID NO: 420          moltype = AA   length = 103
FEATURE                 Location/Qualifiers
source                  1..103
                        mol_type = protein
                        organism = Homo sapiens
SEQUENCE: 420
GVIQSPRHLI KEKRETATLK CYPIPRHDTV YWYQQGPGQR PQFLISFYEK MQSDKGSIPD     60
RFSAQQFSDY HSELNMSSLE LGDSALYFCA SRGGWAETPD TQY                       103

SEQ ID NO: 421          moltype = AA   length = 101
FEATURE                 Location/Qualifiers
source                  1..101
                        mol_type = protein
                        organism = Homo sapiens
SEQUENCE: 421
GVIQSPRHLI KEKRETATLK CYPIPRHDTV YWYQQGPGQE PQFLISFYEK MQSDKGSIPD     60
RFSAQQFSDY HSELNMSSLE LGDSALYFCA SSAGTSYNEQ F                         101

SEQ ID NO: 422          moltype = AA   length = 105
FEATURE                 Location/Qualifiers
source                  1..105
                        mol_type = protein
                        organism = Homo sapiens
SEQUENCE: 422
EPEVTQTPSH QVTQMGQEVI LRCVPISNHL YMYWYRQILG QKVEFLVSFY NNEISEKSEI     60
FDDQFSVERP DGSNFTLKIR STKLEDSAMY FCASTVQSPR TNEQF                     105

SEQ ID NO: 423          moltype = AA   length = 102
FEATURE                 Location/Qualifiers
source                  1..102
                        mol_type = protein
                        organism = Homo sapiens
SEQUENCE: 423
GVTQTPKFQV LKTGQSMTLQ CAQDMNHNSF YWYRQDPGMG LRLIYYSASE GTTDKGEVPN     60
GYNVSRLNKR EFSLRLESAA PSQTSVYFCA SSEGYSTYNE QF                        102

SEQ ID NO: 424          moltype = AA   length = 103
FEATURE                 Location/Qualifiers
source                  1..103
                        mol_type = protein
                        organism = Homo sapiens
SEQUENCE: 424
GVTQTPKFQV LKTGQSMTLQ CAQDMNHNSM YWYRQDPGMG LRLIWYSASE GTTDKGEVPN     60
```

```
GYNVSRLNKR EFSLRLESAA PSQTSVYFCA SSPRGQGRSY EQY                    103

SEQ ID NO: 425           moltype = AA   length = 102
FEATURE                  Location/Qualifiers
source                   1..102
                         mol_type = protein
                         organism = Homo sapiens
SEQUENCE: 425
EVTQTPKHLV MGMTNKKSLK CEQHMGHRAM YWYKQHAKKP PELMFVYSYE KLSINESVPS   60
RFSPECPNSS LLNLHLHALQ PEDSALYLCA SSQGVGQEYG YT                      102

SEQ ID NO: 426           moltype = AA   length = 103
FEATURE                  Location/Qualifiers
source                   1..103
                         mol_type = protein
                         organism = Homo sapiens
SEQUENCE: 426
GITQSPKYLF RKEGQNVTLS CEQNLNHDAM YWYRQDPGQA LRLIYYSQIV NDFQKGDIAE   60
GYSVSREKKE SFPLTVTSAQ KNPTAFYLCA SKSRGPNLAD TQY                     103

SEQ ID NO: 427           moltype = AA   length = 104
FEATURE                  Location/Qualifiers
source                   1..104
                         mol_type = protein
                         organism = Homo sapiens
SEQUENCE: 427
GVAQSPRYKI IEKRQSVAFW CNPISGHATM YWYQQILGQG PKLLIQFQNN GVVDDSQLPK   60
DRFSAERLKG VDSTLKIQPA KLEDSAVYLC ASSRFVATGT SPLH                    104

SEQ ID NO: 428           moltype = AA   length = 102
FEATURE                  Location/Qualifiers
source                   1..102
                         mol_type = protein
                         organism = Homo sapiens
SEQUENCE: 428
GVTPRYLI KTRGQQVTLS CSPISGHRSV SWYQQSPGQG LQFLFEYFSE TQRNKGNFPG     60
RFSGRQFSNS RSEMNVSTLE LGDSALYLCA SSGGPGPSGE QY                      102

SEQ ID NO: 429           moltype = AA   length = 102
FEATURE                  Location/Qualifiers
source                   1..102
                         mol_type = protein
                         organism = Homo sapiens
SEQUENCE: 429
GVSQDPRHKI TKRGQNVTFR CDPISEHNRL YWYRQTLGQG PEFLTYFQNE AQLEKSRLLT   60
DRFSAERPKG SFSTLEIQRT EQGDSAMYLC ASSTDITSYE QY                      102

SEQ ID NO: 430           moltype = AA   length = 103
FEATURE                  Location/Qualifiers
source                   1..103
                         mol_type = protein
                         organism = Homo sapiens
SEQUENCE: 430
GVIQSPRHLI KEKRETATLK CYPIPRHDTV YWYQQGPGQD PQFLISFYEK MQSDKGSIPD   60
RLSAQQFSDY HSELNMSSLE LGDSALYFCA SSPSTGRLNT EAF                     103

SEQ ID NO: 431           moltype = AA   length = 102
FEATURE                  Location/Qualifiers
source                   1..102
                         mol_type = protein
                         organism = Homo sapiens
SEQUENCE: 431
QVTQNPRYLI TVTGKKLTVT CSQNMNHEYM SWYRQDPGLG LRQIYYSMNV EVTDKGDVPE   60
GYKVSRKERR NFPLILESPS PNQTSLYFCA SREGTGGYQP QH                      102

SEQ ID NO: 432           moltype = AA   length = 102
FEATURE                  Location/Qualifiers
source                   1..102
                         mol_type = protein
                         organism = Homo sapiens
SEQUENCE: 432
GVTQTPKFRV LKTGQSMTLL CAQDMNHEYM YWYRQDPGMG LRLIHYSVGE GTTAKGEVPD   60
GYNVSRLKKQ NFLLGLETAA PSQTSVYFCA SSYLRTGGNE QF                      102

SEQ ID NO: 433           moltype = AA   length = 102
FEATURE                  Location/Qualifiers
source                   1..102
                         mol_type = protein
                         organism = Homo sapiens
```

```
SEQUENCE: 433
GVTQTPKHLI TATGQRVTLR CSPRSGDLSV YWYQQSLDQG LQFLIQYYNG EERAKGNILE    60
RFSAMQFPDL HSELNLSSLE LGDSALYFCA SSAGLAGGYE QY                      102

SEQ ID NO: 434          moltype = AA   length = 104
FEATURE                 Location/Qualifiers
source                  1..104
                        mol_type = protein
                        organism = Homo sapiens
SEQUENCE: 434
EVTQTPKHLV MGMTNKKSLK CEQHMGHRAM YWYKQKAKKP PELMFVYSYE KLSINESVPS    60
RFSPECPNSS LINLHLHALQ PEDSALYLCA SATWEEAGPY NEQF                    104

SEQ ID NO: 435          moltype = AA   length = 103
FEATURE                 Location/Qualifiers
source                  1..103
                        mol_type = protein
                        organism = Homo sapiens
SEQUENCE: 435
GVIQSPRHLI KEKRETATLK CYPIPRHDTV YWYQQGPGQD PQFLISFYEK MQSDKGSLPD    60
RFSAQQFSDY HSELNMSSLE LGDSALYFCA SRGGWAETPD TQY                     103

SEQ ID NO: 436          moltype = AA   length = 101
FEATURE                 Location/Qualifiers
source                  1..101
                        mol_type = protein
                        organism = Homo sapiens
SEQUENCE: 436
GVIQSPRHLI KEKRETATLK CYPIPRHDTV YWYQQGPGQD PQFLISFYEK MQSDKGSIPD    60
RFSAQQFSDY HSELNMTSLE LGDSALYFCA SSAGTSYNEQ F                       101

SEQ ID NO: 437          moltype = AA   length = 105
FEATURE                 Location/Qualifiers
source                  1..105
                        mol_type = protein
                        organism = Homo sapiens
SEQUENCE: 437
EPEVTQTPSH QVTQMGQEVI LRCVPISNHL YFYWYRQILG QKVEFLVSFY NNEISEKSEI    60
FDDQFSVERP DGSNFTLRIR STKLEDSAMY FCASTVQSPR TNEQF                   105

SEQ ID NO: 438          moltype = AA   length = 102
FEATURE                 Location/Qualifiers
source                  1..102
                        mol_type = protein
                        organism = Homo sapiens
SEQUENCE: 438
GVTQTPKFQV LKTGQSMTLQ CAQDMNHNSM YWYRQDPGMG LRLIYYSASE GTTDKGEVPN    60
GYNVTRLNKR EFSLRLESAA PSQTSVYFCA SSEGYSTYNE QF                      102

SEQ ID NO: 439          moltype = AA   length = 103
FEATURE                 Location/Qualifiers
source                  1..103
                        mol_type = protein
                        organism = Homo sapiens
SEQUENCE: 439
GVTQTPKFQV LKTGQSMTLQ CAQDMNHNSM YWYRQDPGMG LRLIYYSASE GTTDKIEVPN    60
GYNVSRLNKR EFSLRLESAA PSQTSVYFCA SSPRGQGRSY EQY                     103

SEQ ID NO: 440          moltype = AA   length = 102
FEATURE                 Location/Qualifiers
source                  1..102
                        mol_type = protein
                        organism = Homo sapiens
SEQUENCE: 440
EVTQTPKHLV MGMTNKKSLK CEQHMGHRAM YWYKQKAKKP PELMFVYSYE KLSINDSVPS    60
RFSPECPNSS LLNLHLHALQ PEDSALYLCA SSQGVGQEYG YT                      102

SEQ ID NO: 441          moltype = AA   length = 103
FEATURE                 Location/Qualifiers
source                  1..103
                        mol_type = protein
                        organism = Homo sapiens
SEQUENCE: 441
GITQSPKYLF RKEGQNVTLS CEQNLNHDAM YWYRQDPGQG LRLIYYSQIV NDFQKGDIAD    60
GYSVSREKKE SFPLTVTSAQ KNPTAFYLCA SKSRGPNLAD TQY                     103

SEQ ID NO: 442          moltype = AA   length = 104
FEATURE                 Location/Qualifiers
source                  1..104
```

```
                          mol_type = protein
                          organism = Homo sapiens
SEQUENCE: 442
GVAQSPRYKI  IEKRQSVAFW  CNPISGHATL  YWYQQILGQG  PKLLIQFQNN  GVVDDSQLPK   60
DRFSAERLKG  VDSTLKIMPA  KLEDSAVYLC  ASSRFVATGT  SPLH                    104

SEQ ID NO: 443            moltype = AA   length = 102
FEATURE                   Location/Qualifiers
source                    1..102
                          mol_type = protein
                          organism = Homo sapiens
SEQUENCE: 443
GVTQTPRYLI  KTRGQQVTLS  CSPISGHRSV  SWYQQTPGQG  LQFLFEYFSE  TQRNKGNFPG   60
RFSGRQFTNS  RSEMNVSTLE  LGDSALYLCA  SSGGPGPSGE  QY                      102

SEQ ID NO: 444            moltype = AA   length = 291
FEATURE                   Location/Qualifiers
source                    1..291
                          mol_type = protein
                          organism = Homo sapiens
SEQUENCE: 444
GVSQEPRHKI  TKRGQNVTFR  CDPISEHNRL  YWYRQTLGQG  PEFLTYFQNE  AQLEKSRLLS   60
DRFSAERPKG  SFSTLEIQRT  EQGDSAMYLC  ASSTDITSYE  QYFGPGTRLT  VTEDLKNVFP  120
PEVAVFEPSE  AEISHTQKAT  LVCLATGFYP  DHVELSWWVN  GKEVHSGVST  DPQPLKEQPA  180
LNDSRYCLSS  RLRVSATFWQ  NPRNHFRCQV  QFYGLSENDE  WTQDRAKPVT  QIVSAEAWGR  240
ADCGFTSESY  QQGVLSATIL  YEILLGKATL  YAVLVSALVL  MAMVKRKDSR  G           291

SEQ ID NO: 445            moltype = AA   length = 290
FEATURE                   Location/Qualifiers
source                    1..290
                          mol_type = protein
                          organism = Homo sapiens
SEQUENCE: 445
GVIQSPRHLI  KEKRESATLK  CYPIPRHDTV  YWYQQGPGQD  PQFLISFYEK  MQSDKGSIPD   60
RFSAQQFSDY  HSELNMSSLE  LGDSALYFCA  SSPSTGRLNT  EAFFGQGTRL  TVVEDLKNVF  120
PPEVAVFEPS  EAEISHTQKA  TLVCLATGFF  PDHVELSWWV  NGKEVHSGVS  TDPQPLKEQP  180
ALNDSRYCLS  SRLRVSATFW  QNPRNHFRCQ  VQFYGLSEND  EWTQDRAKPV  TQIVSAEAWG  240
RADCGFTSVS  YQQGVLSATI  LYEILLGKAT  LYAVLVSALV  LMAMVKRKDF              290

SEQ ID NO: 446            moltype = AA   length = 289
FEATURE                   Location/Qualifiers
source                    1..289
                          mol_type = protein
                          organism = Homo sapiens
SEQUENCE: 446
QVTQNPKYLI  TVTGKKLTVT  CSQNMNHEYM  SWYRQDPGLG  LRQIYYSMNV  EVTDKGDVPE   60
GYKVSRKEKR  NFPLILESPS  PNQTSLYFCA  SREGTGGYQP  QHFGPGTRLS  ILEDLKNVFP  120
PEVAVFEPSE  AEISHTQKAT  LVCLATGFFP  DHVELSWWVN  GKEVHSGVST  DPQPLKEQPA  180
LNDSRYCLSS  RLRVSATFWQ  NPRNHFRCQV  QFYGLSENDE  WTQDRAKPVT  QIVSAEAWGR  240
ADCGFTSVSY  QQGVLSATIL  YEILLGKATL  YAVLVSALVL  MAMVKRKDF               289

SEQ ID NO: 447            moltype = AA   length = 291
FEATURE                   Location/Qualifiers
source                    1..291
                          mol_type = protein
                          organism = Homo sapiens
SEQUENCE: 447
GVTQTPKFRV  LKTGQTMTLL  CAQDMNHEYM  YWYRQDPGMG  LRLIHYSVGE  GTTAKGEVPD   60
GYNVSRLKKQ  NFLLGLESAA  PSQTSVYFCA  SSYLRTGPGT  RLTVLEDLKNVFP           120
PEVAVFEPSE  AEISHTQKAT  LVCLATGFYP  DHVELSWWVN  GKEVHSGVST  DPQPLKEQPA  180
LNDSRYCLSS  RLRVSATFWQ  NPRNHFRCQV  QFYGLSENDE  WTQDRAKPVT  QIVSAEAWGR  240
ADCGFTSESY  QQGVLSATIL  YEILLGKATL  YAVLVSALVL  MAMVKRKDSR  G           291

SEQ ID NO: 448            moltype = AA   length = 291
FEATURE                   Location/Qualifiers
source                    1..291
                          mol_type = protein
                          organism = Homo sapiens
SEQUENCE: 448
GVTQTPKHLI  TATGQRVTLR  CTPRSGDLSV  YWYQQSLDQG  LQFLIQYYNG  EERAKGNILE   60
RFSAQQFPDL  HSELNLSSLE  LGDSALYFCA  SSAGLAGGYE  QYFGPGTRLT  VTEDLKNVFP  120
PEVAVFEPSE  AEISHTQKAT  LVCLATGFYP  DHVELSWWVN  GKEVHSGVST  DPQPLKEQPA  180
LNDSRYCLSS  RLRVSATFWQ  NPRNHFRCQV  QFYGLSENDE  WTQDRAKPVT  QIVSAEAWGR  240
ADCGFTSESY  QQGVLSATIL  YEILLGKATL  YAVLVSALVL  MAMVKRKDSR  G           291

SEQ ID NO: 449            moltype = AA   length = 293
FEATURE                   Location/Qualifiers
source                    1..293
                          mol_type = protein
```

```
                        organism = Homo sapiens
SEQUENCE: 449
EVTQTPRHLV MGMTNKKSLK CEQHMGHRAM YWYKQKAKKP PELMFVYSYE KLSINESVPS   60
RFSPECPNSS LLNLHLHALQ PEDSALYLCA SATWEEAGPY NEQFFGPGTR LTVLEDLKNV  120
FPPEVAVFEP SEAEISHTQK ATLVCLATGF YPDHVELSWW VNGKEVHSGV STDPQPLKEQ  180
PALNDSRYCL SSRLRVSATF WQNPRNHFRC QVQFYGLSEN DEWTQDRAKP VTQIVSAEAW  240
GRADCGFTSE SYQQGVLSAT ILYEILLGKA TLYAVLVSAL VLMAMVKRKD SRG         293

SEQ ID NO: 450          moltype = AA   length = 292
FEATURE                 Location/Qualifiers
source                  1..292
                        mol_type = protein
                        organism = Homo sapiens
SEQUENCE: 450
GVIQSPRHLI KEKRETATLR CYPIPRHDTV YWYQQGPGQD PQFLISFYEK MQSDKGSIPD   60
RFSAQQFSDY HSELNMSSLE LGDSALYFCA SRGGWAETPD TQYFGPGTRL TVLEDLKNVF  120
PPEVAVFEPS EAEISHTQKA TLVCLATGFY PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSES YQQGVLSATI LYEILLGKAT LYAVLVSALV LMAMVKRKDS RG          292

SEQ ID NO: 451          moltype = AA   length = 290
FEATURE                 Location/Qualifiers
source                  1..290
                        mol_type = protein
                        organism = Homo sapiens
SEQUENCE: 451
GVIQSPRHLI KDKRETATLK CYPIPRHDTV YWYQQGPGQD PQFLISFYEK MQSDKGSIPD   60
RFSAQQFSDY HSELNMSSLE LGDSALYFCA SSAGTSYNEQ FFGPGTRLTV LEDLKNVFPP  120
EVAVFEPSEA EISHTQKATL VCLATGFYPD HVELSWWVNG KEVHSGVSTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSRG             290

SEQ ID NO: 452          moltype = AA   length = 294
FEATURE                 Location/Qualifiers
source                  1..294
                        mol_type = protein
                        organism = Homo sapiens
SEQUENCE: 452
EPEVTQTPSH QVTQMGQEVI LKCVPISNHL YFYWYRQILG QKVEFLVSFY NNEISEKSEI   60
FDDQFSVERP DGSNFTLKIR STKLEDSAMY FCASTVQSPR TNEQFFGPGT RLTVLEDLKN  120
VFPPEVAVFE PSEAEISHTQ KATLVCLATG FYPDHVELSW WVNGKEVHSG VSTDPQPLKE  180
QPALNDSRYC LSSRLRVSAT FWQNPRNHFR CQVQFYGLSE NDEWTQDRAK PVTQIVSAEA  240
WGRADCGFTS ESYQQGVLSA TILYEILLGK ATLYAVLVSA LVLMAMVKRK DSRG         294

SEQ ID NO: 453          moltype = AA   length = 291
FEATURE                 Location/Qualifiers
source                  1..291
                        mol_type = protein
                        organism = Homo sapiens
SEQUENCE: 453
GVTQTPKFQV LKTGQSMTLQ CIQDMNHNSM YWYRQDPGMG LRLIYYSASE GTTDKGEVPN   60
GYNVSRLNKR EFSLRLESAA PSQTSVYFCA SSEGYSTYNE QFFGPGTRLT VLEDLKNVFP  120
PEVAVFEPSE AEISHTQKAT LVCLATGFYP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSESY QQGVLSATIL YEILLGKATL YAVLVSALVL MAMVKRKDSR G           291

SEQ ID NO: 454          moltype = AA   length = 292
FEATURE                 Location/Qualifiers
source                  1..292
                        mol_type = protein
                        organism = Homo sapiens
SEQUENCE: 454
GVTQTPKFQV LKSGQSMTLQ CAQDMNHNSM YWYRQDPGMG LRLIYYSASE GTTDKGEVPN   60
GYNVSRLNKR EFSLRLESAA PSQTSVYFCA SSPRGQGRSY EQYFGPGTRL TVTEDLKNVF  120
PPEVAVFEPS EAEISHTQKA TLVCLATGFY PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSES YQQGVLSATI LYEILLGKAT LYAVLVSALV LMAMVKRKDS RG          292

SEQ ID NO: 455          moltype = AA   length = 289
FEATURE                 Location/Qualifiers
source                  1..289
                        mol_type = protein
                        organism = Homo sapiens
SEQUENCE: 455
EVTQTPKHLV QGMTNKKSLK CEQHMGHRAM YWYKQKAKKP PELMFVYSYE KLSINESVPS   60
RFSPECPNSS LLNLHLHALQ PEDSALYLCA SSQGVGQEYG YTFGSGTRLT VVEDLNKVFP  120
PEVAVFEPSE AEISHTQKAT LVCLATGFFP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSVSY QQGVLSATIL YEILLGKATL YAVLVSALVL MAMVKRKDF              289
```

SEQ ID NO: 456          moltype = AA   length = 292
FEATURE                 Location/Qualifiers
source                  1..292
                        mol_type = protein
                        organism = Homo sapiens
SEQUENCE: 456
GITQSPKWLF RKEGQNVTLS CEQNLNHDAM YWYRQDPGQG LRLIYYSQIV NDFQKGDIAE    60
GYSVSREKKE SFPLTVTSAQ KNPTAFYLCA SKSRGPNLAD TQYFGPGTRL TVLEDLKNVF   120
PPEVAVFEPS EAEISHTQKA TLVCLATGFY PDHVELSWWV NGKEVHSGVS TDPQPLKEQP   180
ALNDSRYCLS SRLRVSATFW QNPRNHFRCQ VQFYGLSEND EWTQDRAKPV TQIVSAEAWG   240
RADCGFTSES YQQGVLSATI LYEILLGKAT LYAVLVSALV LMAMVKRKDS RG           292

SEQ ID NO: 457          moltype = AA   length = 291
FEATURE                 Location/Qualifiers
source                  1..291
                        mol_type = protein
                        organism = Homo sapiens
SEQUENCE: 457
GVAQSPRYKL IEKRQSVAFW CNPISGHATL YWYQQILGQG PKLLIQFQNN GVVDDSQLPK    60
DRFSAERLKG VDSTLKIQPA KLEDSAVYLC ASSRFVATGT SPLHFGNGTR LTVTEDLNKV   120
FPPEVAVFEP SEAEISHTQK ATLVCLATGF FPDHVELSWW VNGKEVHSGV STDPQPLKEQ   180
PALNDSRYCL SSRLRVSATF WQNPRNHFRC QVQFYGLSEN DEWTQDRAKP VTQIVSAEAW   240
GRADCGFTSV SYQQGVLSAT ILYEILLGKA TLYAVLVSAL VLMAMVKRKD F            291

SEQ ID NO: 458          moltype = AA   length = 291
FEATURE                 Location/Qualifiers
source                  1..291
                        mol_type = protein
                        organism = Homo sapiens
SEQUENCE: 458
GVTQTPRYLI KSRGQQVTLS CSPISGHRSV SWYQQTPGQG LQFLFEYFSE TQRNKGNFPG    60
RFSGRQFSNS RSEMNVSTLE LGDSALYLCA SSGGPGPSGE QYFGPGTRLT VTEDLKNVFP   120
PEVAVFEPSE AEISHTQKAT LVCLATGFYP DHVELSWWVN GKEVHSGVST DPQPLKEQPA   180
LNDSRYCLSS RLRVSATFWQ NPRNHFRCQV QFYGLSENDE WTQDRAKPVT QIVSAEAWGR   240
ADCGFTSESY QQGVLSATIL YEILLGKATL YAVLVSALVL MAMVKRKDSR G            291

SEQ ID NO: 459          moltype = AA   length = 291
FEATURE                 Location/Qualifiers
source                  1..291
                        mol_type = protein
                        organism = Homo sapiens
SEQUENCE: 459
GVSQDPRHKI TKRGQNVTFR CDPISEHNRL YWYRQTLGQG PEFLSYFQNE AQLEKSRLLS    60
DRFSAERPKG SFSTLEIQRT EQGDSAMYLC ASSTDITSYE QYFGPGTRLT VTEDLKNVFP   120
PEVAVFEPSE AEISHTQKAT LVCLATGFYP DHVELSWWVN GKEVHSGVST DPQPLKEQPA   180
LNDSRYCLSS RLRVSATFWQ NPRNHFRCQV QFYGLSENDE WTQDRAKPVT QIVSAEAWGR   240
ADCGFTSESY QQGVLSATIL YEILLGKATL YAVLVSALVL MAMVKRKDSR G            291

SEQ ID NO: 460          moltype = AA   length = 290
FEATURE                 Location/Qualifiers
source                  1..290
                        mol_type = protein
                        organism = Homo sapiens
SEQUENCE: 460
GVIQSPRHLI KEKRETATLK CYPIPRHDTV YWYQQGPGQD PQFLITFYEK MQSDKGSIPD    60
RFSAQQFSDY HSELNMSSLE LGDSALYFCA SSPSTGRLNT EAFFGQGTRL TVVEDLKNVF   120
PPEVAVFEPS EAEISHTQKA TLVCLATGFF PDHVELSWWV NGKEVHSGVS TDPQPLKEQP   180
ALNDSRYCLS SRLRVSATFW QNPRNHFRCQ VQFYGLSEND EWTQDRAKPV TQIVSAEAWG   240
RADCGFTSVS YQQGVLSATI LYEILLGKAT LYAVLVSALV LMAMVKRKDF              290

SEQ ID NO: 461          moltype = AA   length = 289
FEATURE                 Location/Qualifiers
source                  1..289
                        mol_type = protein
                        organism = Homo sapiens
SEQUENCE: 461
QVTQNPRYLI TVTGKKLTVT CSQNMNHEYM SWYQQDPGLG LRQIYYSMNV EVTDKGDVPE    60
GYKVSRKEKR NFPLILESPS PNQTSLYFCA SREGTGGYQP QHFGDGTRLS ILEDLNKVFP   120
PEVAVFEPSE AEISHTQKAT LVCLATGFFP DHVELSWWVN GKEVHSGVST DPQPLKEQPA   180
LNDSRYCLSS RLRVSATFWQ NPRNHFRCQV QFYGLSENDE WTQDRAKPVT QIVSAEAWGR   240
ADCGFTSVSY QQGVLSATIL YEILLGKATL YAVLVSALVL MAMVKRKDF               289

SEQ ID NO: 462          moltype = AA   length = 291
FEATURE                 Location/Qualifiers
source                  1..291
                        mol_type = protein
                        organism = Homo sapiens
SEQUENCE: 462

```
GVTQTPKFRV LKTGQSMTLL CAQDMNHEYM YWYRQDPGMG LRLLHYSVGE GTTAKGEVPD  60
GYNVSRLKKQ NFLLGLESAA PSQTSVYFCA SSYLRTGGNE QFFGPGTRLT VLEDLKNVFP 120
PEVAVFEPSE AEISHTQKAT LVCLATGFYP DHVELSWWVN GKEVHSGVST DPQPLKEQPA 180
LNDSRYCLSS RLRVSATFWQ NPRNHFRCQV QFYGLSENDE WTQDRAKPVT QIVSAEAWGR 240
ADCGFTSESY QQGVLSATIL YEILLGKATL YAVLVSALVL MAMVKRKDSR G          291

SEQ ID NO: 463            moltype = AA   length = 291
FEATURE                   Location/Qualifiers
source                    1..291
                          mol_type = protein
                          organism = Homo sapiens
SEQUENCE: 463
GVTQTPKHLI TATGQRVTLR CSPRSGDLSV YWYQQTLDQG LQFLIQYYNG EERAKGNILE  60
RFSAQQFPDL HSELNLSSLE LGDSALYFCA SSAGLAGGYE QYFGPGTRLT VTEDLKNVFP 120
PEVAVFEPSE AEISHTQKAT LVCLATGFYP DHVELSWWVN GKEVHSGVST DPQPLKEQPA 180
LNDSRYCLSS RLRVSATFWQ NPRNHFRCQV QFYGLSENDE WTQDRAKPVT QIVSAEAWGR 240
ADCGFTSESY QQGVLSATIL YEILLGKATL YAVLVSALVL MAMVKRKDSR G          291

SEQ ID NO: 464            moltype = AA   length = 293
FEATURE                   Location/Qualifiers
source                    1..293
                          mol_type = protein
                          organism = Homo sapiens
SEQUENCE: 464
EVTQTPKHLV MGMTNKKSLK CEQHMGHRAM YWYKQKAKKP DLMFVYSYE KLSINESVPS   60
RFSPECPNSS LLNLHLHALQ PEDSALYLCA SATWEEAGPY NEQFFGPGTR LTVLEDLKNV 120
FPPEVAVFEP SEAEISHTQK ATLVCLATGF YPDHVELSWW VNGKEVHSGV STDPQPLKEQ 180
PALNDSRYCL SSRLRVSATF WQNPRNHFRC QVQFYGLSEN DEWTQDRAKP VTQIVSAEAW 240
GRADCGFTSE SYQQGVLSAT ILYEILLGKA TLYAVLVSAL VLMAMVKRKD SRG         293

SEQ ID NO: 465            moltype = AA   length = 292
FEATURE                   Location/Qualifiers
source                    1..292
                          mol_type = protein
                          organism = Homo sapiens
SEQUENCE: 465
GVIQSPRHLI KEKRETATLK CYPIPRHDTV YWYQQGPGQR PQFLISFYEK MQSDKGSIPD  60
RFSAQQFSDY HSELNMSSLE LGDSALYFCA SRGGWAETPD TQYFGPGTRL TVLEDLKNVF 120
PPEVAVFEPS EAEISHTQKA TLVCLATGFY PDHVELSWWV NGKEVHSGVS TDPQPLKEQP 180
ALNDSRYCLS SRLRVSATFW QNPRNHFRCQ VQFYGLSEND EWTQDRAKPV TQIVSAEAWG 240
RADCGFTSES YQQGVLSATI LYEILLGKAT LYAVLVSALV LMAMVKRKDS RG          292

SEQ ID NO: 466            moltype = AA   length = 290
FEATURE                   Location/Qualifiers
source                    1..290
                          mol_type = protein
                          organism = Homo sapiens
SEQUENCE: 466
GVIQSPRHLI KEKRETATLK CYPIPRHDTV YWYQQGPGQE PQFLISFYEK MQSDKGSIPD  60
RFSAQQFSDY HSELNMSSLE LGDSALYFCA SSAGTSYNEQ FFGPGTRLTV LEDLKNVFPP 120
EVAVFEPSEA EISHTQKATL VCLATGFYPD HVELSWWVNG KEVHSGVSTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSRG            290

SEQ ID NO: 467            moltype = AA   length = 294
FEATURE                   Location/Qualifiers
source                    1..294
                          mol_type = protein
                          organism = Homo sapiens
SEQUENCE: 467
EPEVTQTPSH QVTQMGQEVI LRCVPISNHL YMYWYRQILG QKVEFLVSFY NNEISEKSEI  60
FDDQFSVERP DGSNFTLKIR STKLEDSAMY FCASTVQSPR TNEQFFGPGT RLTVLEDLKN 120
VFPPEVAVFE PSEAEISHTQ KATLVCLATG FYPDHVELSW WVNGKEVHSG VSTDPQPLKE 180
QPALNDSRYC LSSRLRVSAT FWQNPRNHFR CQVQFYGLSE NDEWTQDRAK PVTQIVSAEA 240
WGRADCGFTS ESYQQGVLSA TILYEILLGK ATLYAVLVSA LVLMAMVKRK DSRG        294

SEQ ID NO: 468            moltype = AA   length = 291
FEATURE                   Location/Qualifiers
source                    1..291
                          mol_type = protein
                          organism = Homo sapiens
SEQUENCE: 468
GVTQTPKFQV LKTGQSMTLQ CAQDMNHNSF YWYRQDPGMG LRLIYYSASE GTTDKGEVPN  60
GYNVSRLNKR EFSLRLESAA PSQTSVYFCA SSEGYSTYNE QFFGPGTRLT VLEDLKNVFP 120
PEVAVFEPSE AEISHTQKAT LVCLATGFYP DHVELSWWVN GKEVHSGVST DPQPLKEQPA 180
LNDSRYCLSS RLRVSATFWQ NPRNHFRCQV QFYGLSENDE WTQDRAKPVT QIVSAEAWGR 240
ADCGFTSESY QQGVLSATIL YEILLGKATL YAVLVSALVL MAMVKRKDSR G          291

SEQ ID NO: 469            moltype = AA   length = 292
```

| FEATURE | Location/Qualifiers |
|---|---|
| source | 1..292 |
| | mol_type = protein |
| | organism = Homo sapiens |

SEQUENCE: 469
```
GVTQTPKFQV LKTGQSMTLQ CAQDMNHNSM YWYRQDPGMG LRLIWYSASE GTTDKGEVPN   60
GYNVSRLNKR EFSLRLESAA PSQTSVYFCA SSPRGQGRSY EQYFGPGTRL TVTEDLKNVF  120
PPEVAVFEPS EAEISHTQKA TLVCLATGFY PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSES YQQGVLSATI LYEILLGKAT LYAVLVSALV LMAMVKRKDS RG          292
```

| SEQ ID NO: 470 | moltype = AA length = 289 |
|---|---|
| FEATURE | Location/Qualifiers |
| source | 1..289 |
| | mol_type = protein |
| | organism = Homo sapiens |

SEQUENCE: 470
```
EVTQTPKHLV MGMTNKKSLK CEQHMGHRAM YWYKQHAKKP PELMFVYSYE KLSINESVPS   60
RFSPECPNSS LLNLHLHALQ PEDSALYLCA SSQGVGQEYG YTFGSGTRLT VVEDLNKVFP  120
PEVAVFEPSE AEISHTQKAT LVCLATGFFP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSVSY QQGVLSATIL YEILLGKATL YAVLVSALVL MAMVKRKDF             289
```

| SEQ ID NO: 471 | moltype = AA length = 292 |
|---|---|
| FEATURE | Location/Qualifiers |
| source | 1..292 |
| | mol_type = protein |
| | organism = Homo sapiens |

SEQUENCE: 471
```
GITQSPKYLF RKEGQNVTLS CEQNLNHDAM YWYRQDPGQA LRLIYYSQIV NDFQKGDIAE   60
GYSVSREKKE SFPLTVTSAQ KNPTAFYLCA SKSRGPNLAD TQYFGPGTRL TVLEDLKNVF  120
PPEVAVFEPS EAEISHTQKA TLVCLATGFY PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSES YQQGVLSATI LYEILLGKAT LYAVLVSALV LMAMVKRKDS RG          292
```

| SEQ ID NO: 472 | moltype = AA length = 291 |
|---|---|
| FEATURE | Location/Qualifiers |
| source | 1..291 |
| | mol_type = protein |
| | organism = Homo sapiens |

SEQUENCE: 472
```
GVAQSPRYKI IEKRQSVAFW CNPISGHATM YWYQQILGQG PKLLIQFQNN GVVDDSQLPK   60
DRFSAERLKG VDSTLKIQPA KLEDSAVYLC ASSRFVATGT SPLHFGNGTR LTVTEDLNKV  120
FPPEVAVFEP SEAEISHTQK ATLVCLATGF FPDHVELSWW VNGKEVHSGV STDPQPLKEQ  180
PALNDSRYCL SSRLRVSATF WQNPRNHFRC QVQFYGLSEN DEWTQDRAKP VTQIVSAEAW  240
GRADCGFTSV SYQQGVLSAT ILYEILLGKA TLYAVLVSAL VLMAMVKRKD F           291
```

| SEQ ID NO: 473 | moltype = AA length = 291 |
|---|---|
| FEATURE | Location/Qualifiers |
| source | 1..291 |
| | mol_type = protein |
| | organism = Homo sapiens |

SEQUENCE: 473
```
GVTQTPRYLI KTRGQQVTLS CSPISGHRSV SWYQQSPGQG LQFLFEYFSE TQRNKGNFPG   60
RFSGRQFSNS RSEMNVSTLE LGDSALYLCA SSGGPGLSGE QYFGPGTRLT VTEDLKNVFP  120
PEVAVFEPSE AEISHTQKAT LVCLATGFYP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSESY QQGVLSATIL YEILLGKATL YAVLVSALVL MAMVKRKDSR G           291
```

| SEQ ID NO: 474 | moltype = AA length = 291 |
|---|---|
| FEATURE | Location/Qualifiers |
| source | 1..291 |
| | mol_type = protein |
| | organism = Homo sapiens |

SEQUENCE: 474
```
GVSQDPRHKI TKRGQNVTFR CDPISEHNRL YWYRQTLGQG PEFLTYFQNE AQLEKSRLLT   60
DRFSAERPKG SFSTLEIQRT EQGDSAMYLC ASSTDITSYE QYFGPGTRLT VTEDLKNVFP  120
PEVAVFEPSE AEISHTQKAT LVCLATGFYP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSESY QQGVLSATIL YEILLGKATL YAVLVSALVL MAMVKRKDSR G           291
```

| SEQ ID NO: 475 | moltype = AA length = 290 |
|---|---|
| FEATURE | Location/Qualifiers |
| source | 1..290 |
| | mol_type = protein |
| | organism = Homo sapiens |

SEQUENCE: 475
```
GVIQSPRHLI KEKRETATLK CYPIPRHDTV YWYQQGPGQD PQFLISFYEK MQSDKGSIPD   60
RLSAQQFSDY HSELNMSSLE LGDSALYFCA SSPSTGRLNT EAFFGQGTRL TVVEDLNKVF  120
```

```
PPEVAVFEPS EAEISHTQKA TLVCLATGFF PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSVS YQQGVLSATI LYEILLGKAT LYAVLVSALV LMAMVKRKDF            290

SEQ ID NO: 476        moltype = AA   length = 289
FEATURE               Location/Qualifiers
source                1..289
                      mol_type = protein
                      organism = Homo sapiens
SEQUENCE: 476
QVTQNPRYLI TVTGKKLTVT CSQNMNHEYM SWYRQDPGLG LRQIYYSMNV EVTDKGDVPE  60
GYKVSRKERR NFPLILESPS PNQTSLYFCA SREGTGGYQP QHFGDGTRLS ILEDLNKVFP  120
PEVAVFEPSE AEISHTQKAT LVCLATGFFP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSVSY QQGVLSATIL YEILLGKATL YAVLVSALVL MAMVKRKDF             289

SEQ ID NO: 477        moltype = AA   length = 291
FEATURE               Location/Qualifiers
source                1..291
                      mol_type = protein
                      organism = Homo sapiens
SEQUENCE: 477
GVTQTPKFRV LKTGQSMTLL CAQDMNHEYM YWYRQDPGMG LRLIHYSVGE GTTAKGEVPD  60
GYNVSRLKKQ NFLLGLETAA PSQTSVYFCA SSYLRTGGNE QFFGPGTRLT VLEDLKNVFP  120
PEVAVFEPSE AEISHTQKAT LVCLATGFYP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSESY QQGVLSATIL YEILLGKATL YAVLVSALVL MAMVKRKDSR G          291

SEQ ID NO: 478        moltype = AA   length = 291
FEATURE               Location/Qualifiers
source                1..291
                      mol_type = protein
                      organism = Homo sapiens
SEQUENCE: 478
GVTQTPKHLI TATGQRVTLR CSPRSGDLSV YWYQQSLDQG LQFLIQYYNG EERAKGNILE  60
RFSAMQFPDL HSELNLSSLE LGDSALYFCA SSAGLAGGYE QYFGPGTRLT VTEDLKNVFP  120
PEVAVFEPSE AEISHTQKAT LVCLATGFYP DHVELSWWVN GKEVHSGVST DPQPLKEQPA  180
LNDSRYCLSS RLRVSATFWQ NPRNHFRCQV QFYGLSENDE WTQDRAKPVT QIVSAEAWGR  240
ADCGFTSESY QQGVLSATIL YEILLGKATL YAVLVSALVL MAMVKRKDSR G          291

SEQ ID NO: 479        moltype = AA   length = 293
FEATURE               Location/Qualifiers
source                1..293
                      mol_type = protein
                      organism = Homo sapiens
SEQUENCE: 479
EVTQTPKHLV MGMTNKKSLK CEQHMGHRAM YWYKQKAKKP PELMFVYSYE KLSINESVPS  60
RFSPECPNSS LINLHLHALQ PEDSALYLCA SATWEEAGPY NEQFFGPGTR LTVLEDLKNV  120
FPPEVAVFEP SEAEISHTQK ATLVCLATGF YPDHVELSWW VNGKEVHSGV STDPQPLKEQ  180
PALNDSRYCL SSRLRVSATF WQNPRNHFRC QVQFYGLSEN DEWTQDRAKP VTQIVSAEAW  240
GRADCGFTSE SYQQGVLSAT ILYEILLGKA TLYAVLVSAL VLMAMVKRKD SRG         293

SEQ ID NO: 480        moltype = AA   length = 292
FEATURE               Location/Qualifiers
source                1..292
                      mol_type = protein
                      organism = Homo sapiens
SEQUENCE: 480
GVIQSPRHLI KEKRETATLK CYPIPRHDTV YWYQQGPGQD PQFLISFYEK MQSDKGSLPD  60
RFSAQQFSDY HSELNMSSLE LGDSALYFCA SRGGWAETPD TQYFGPGTRL TVLEDLKNVF  120
PPEVAVFEPS EAEISHTQKA TLVCLATGFY PDHVELSWWV NGKEVHSGVS TDPQPLKEQP  180
ALNDSRYCLS SRLRVSATFW QNPRNHFRCQ VQFYGLSEND EWTQDRAKPV TQIVSAEAWG  240
RADCGFTSES YQQGVLSATI LYEILLGKAT LYAVLVSALV LMAMVKRKDS RG          292

SEQ ID NO: 481        moltype = AA   length = 290
FEATURE               Location/Qualifiers
source                1..290
                      mol_type = protein
                      organism = Homo sapiens
SEQUENCE: 481
GVIQSPRHLI KEKRETATLK CYPIPRHDTV YWYQQGPGQD PQFLISFYEK MQSDKGSIPD  60
RFSAQQFSDY HSELNMTSLE LGDSALYFCA SSAGTSYNEQ FFGPGTRLTV LEDLKNVFPP  120
EVAVFEPSEA EISHTQKATL VCLATGFYPD HVELSWWVNG KEVHSGVSTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSRG            290

SEQ ID NO: 482        moltype = AA   length = 294
FEATURE               Location/Qualifiers
source                1..294
```

```
                              mol_type = protein
                              organism = Homo sapiens
SEQUENCE: 482
EPEVTQTPSH  QVTQMGQEVI  LRCVPISNHL  YFYWYRQILG  QKVEFLVSFY  NNEISEKSEI    60
FDDQFSVERP  DGSNFTLRIR  STKLEDSAMY  FCASTVQSPR  TNEQFFGPGT  RLTVLEDLKN   120
VFPPEVAVFE  PSEAEISHTQ  KATLVCLATG  FYPDHVELSW  WVNGKEVHSG  VSTDPQPLKE   180
QPALNDSRYC  LSSRLRVSAT  FWQNPRNHFR  CQVQFYGLSE  NDEWTQDRAK  PVTQIVSAEA   240
WGRADCGFTS  ESYQQGVLSA  TILYEILLGK  ATLYAVLVSA  LVLMAMVKRK  DSRG         294

SEQ ID NO: 483            moltype = AA   length = 291
FEATURE                   Location/Qualifiers
source                    1..291
                          mol_type = protein
                          organism = Homo sapiens
SEQUENCE: 483
GVTQTPKFQV  LKTGQSMTLQ  CAQDMNHNSM  YWYRQDPGMG  LRLIYYSASE  GTTDKGEVPN    60
GYNVTRLNKR  EFSLRLESAA  PSQTSVYFCA  SSEGYSTNE   QFFGPGTRLT  VLEDLKNVFP   120
PEVAVFEPSE  AEISHTQKAT  LVCLATGFYP  DHVELSWWVN  GKEVHSGVST  DPQPLKEQPA   180
LNDSRYCLSS  RLRVSATFWQ  NPRNHFRCQV  QFYGLSENDE  WTQDRAKPVT  QIVSAEAWGR   240
ADCGFTSESY  QQGVLSATIL  YEILLGKATL  YAVLVSALVL  MAMVKRKDSR  G            291

SEQ ID NO: 484            moltype = AA   length = 292
FEATURE                   Location/Qualifiers
source                    1..292
                          mol_type = protein
                          organism = Homo sapiens
SEQUENCE: 484
GVTQTPKFQV  LKTGQSMTLQ  CAQDMNHNSM  YWYRQDPGMG  LRLIYYSASE  GTTDKIEVPN    60
GYNVSRLNKR  EFSLRLESAA  PSQTSVYFCA  SSPRGQGRSY  EQYFGPGTRL  TVTEDLKNVF   120
PPEVAVFEPS  EAEISHTQKA  TLVCLATGFY  PDHVELSWWV  NGKEVHSGVS  TDPQPLKEQP   180
ALNDSRYCLS  SRLRVSATFW  QNPRNHFRCQ  VQFYGLSEND  EWTQDRAKPV  TQIVSAEAWG   240
RADCGFTSES  YQQGVLSATI  LYEILLGKAT  LYAVLVSALV  LMAMVKRKDS  RG           292

SEQ ID NO: 485            moltype = AA   length = 289
FEATURE                   Location/Qualifiers
source                    1..289
                          mol_type = protein
                          organism = Homo sapiens
SEQUENCE: 485
EVTQTPKHLV  MGMTNKKSLK  CEQHMGHRAM  YWYKQKAKKP  PELMFVYSYE  KLSINDSVPS    60
RFSPECPNSS  LLNLHLHALQ  PEDSALYLCA  SSQGVGQEYG  YTFGSGTRLT  VVEDLNKVFP   120
PEVAVFEPSE  AEISHTQKAT  LVCLATGFFP  DHVELSWWVN  GKEVHSGVST  DPQPLKEQPA   180
LNDSRYCLSS  RLRVSATFWQ  NPRNHFRCQV  QFYGLSENDE  WTQDRAKPVT  QIVSAEAWGR   240
ADCGFTSVSY  QQGVLSATIL  YEILLGKATL  YAVLVSALVL  MAMVKRKDF                289

SEQ ID NO: 486            moltype = AA   length = 292
FEATURE                   Location/Qualifiers
source                    1..292
                          mol_type = protein
                          organism = Homo sapiens
SEQUENCE: 486
GITQSPKYLF  RKEGQNVTLS  CEQNLNHDAM  YWYRQDPGQG  LRLIYYSQIV  NDFQKGDIAD    60
GYSVSREKKE  SFPLTVTSAQ  KNPTAFYLCA  SKSRGPNLAD  TQYFGPGTRL  TVLEDLKNVF   120
PPEVAVFEPS  EAEISHTQKA  TLVCLATGFY  PDHVELSWWV  NGKEVHSGVS  TDPQPLKEQP   180
ALNDSRYCLS  SRLRVSATFW  QNPRNHFRCQ  VQFYGLSEND  EWTQDRAKPV  TQIVSAEAWG   240
RADCGFTSES  YQQGVLSATI  LYEILLGKAT  LYAVLVSALV  LMAMVKRKDS  RG           292

SEQ ID NO: 487            moltype = AA   length = 291
FEATURE                   Location/Qualifiers
source                    1..291
                          mol_type = protein
                          organism = Homo sapiens
SEQUENCE: 487
GVAQSPRYKI  IEKRQSVAFW  CNPISGHATL  YWYQQILGQG  PKLLIQFQNN  GVVDDSQLPK    60
DRFSAERLKG  VDSTLKIMPA  KLEDSAVYLC  ASSRFVATGT  SPLHFGNGTR  LTVTEDLNKV   120
FPPEVAVFEP  SEAEISHTQK  ATLVCLATGF  FPDHVELSWW  VNGKEVHSGV  STDPQPLKEQ   180
PALNDSRYCL  SSRLRVSATF  WQNPRNHFRC  QVQFYGLSEN  DEWTQDRAKP  VTQIVSAEAW   240
GRADCGFTSV  SYQQGVLSAT  ILYEILLGKA  TLYAVLVSAL  VLMAMVKRKD  F            291

SEQ ID NO: 488            moltype = AA   length = 291
FEATURE                   Location/Qualifiers
source                    1..291
                          mol_type = protein
                          organism = Homo sapiens
SEQUENCE: 488
GVTQTPRYLI  KTRGQQVTLS  CSPISGHRSV  SWYQQTPGQG  LQFLFEYFSE  TQRNKGNFPG    60
RFSGRQFTNS  RSEMNVSTLE  LGDSALYLCA  SSGGPGPSGE  QYFGPGTRLT  VTEDLKNVFP   120
PEVAVFEPSE  AEISHTQKAT  LVCLATGFYP  DHVELSWWVN  GKEVHSGVST  DPQPLKEQPA   180
LNDSRYCLSS  RLRVSATFWQ  NPRNHFRCQV  QFYGLSENDE  WTQDRAKPVT  QIVSAEAWGR   240
```

```
ADCGFTSESY QQGVLSATIL YEILLGKATL YAVLVSALVL MAMVKRKDSR G          291

SEQ ID NO: 489           moltype = AA   length = 8
FEATURE                  Location/Qualifiers
source                   1..8
                         mol_type = protein
                         organism = Homo sapiens
SEQUENCE: 489
GLVAGSAR                                                           8

SEQ ID NO: 490           moltype = AA   length = 8
FEATURE                  Location/Qualifiers
source                   1..8
                         mol_type = protein
                         organism = Homo sapiens
SEQUENCE: 490
GSDAGGTS                                                           8

SEQ ID NO: 491           moltype = AA   length = 8
FEATURE                  Location/Qualifiers
source                   1..8
                         mol_type = protein
                         organism = Homo sapiens
SEQUENCE: 491
GYSNYQLI                                                           8

SEQ ID NO: 492           moltype = AA   length = 8
FEATURE                  Location/Qualifiers
source                   1..8
                         mol_type = protein
                         organism = Homo sapiens
SEQUENCE: 492
APRDDKII                                                           8

SEQ ID NO: 493           moltype = AA   length = 8
FEATURE                  Location/Qualifiers
source                   1..8
                         mol_type = protein
                         organism = Homo sapiens
SEQUENCE: 493
GYNYGQNF                                                           8

SEQ ID NO: 494           moltype = AA   length = 8
FEATURE                  Location/Qualifiers
source                   1..8
                         mol_type = protein
                         organism = Homo sapiens
SEQUENCE: 494
NSGARDYG                                                           8

SEQ ID NO: 495           moltype = AA   length = 8
FEATURE                  Location/Qualifiers
source                   1..8
                         mol_type = protein
                         organism = Homo sapiens
SEQUENCE: 495
RYGGATNK                                                           8

SEQ ID NO: 496           moltype = AA   length = 8
FEATURE                  Location/Qualifiers
source                   1..8
                         mol_type = protein
                         organism = Homo sapiens
SEQUENCE: 496
GRGSGTYK                                                           8

SEQ ID NO: 497           moltype = AA   length = 8
FEATURE                  Location/Qualifiers
source                   1..8
                         mol_type = protein
                         organism = Homo sapiens
SEQUENCE: 497
KETAGNKL                                                           8

SEQ ID NO: 498           moltype = AA   length = 8
FEATURE                  Location/Qualifiers
source                   1..8
                         mol_type = protein
                         organism = Homo sapiens
```

```
SEQUENCE: 498
APYTGTAS                                                                    8

SEQ ID NO: 499         moltype = AA  length = 8
FEATURE                Location/Qualifiers
source                 1..8
                       mol_type = protein
                       organism = Homo sapiens
SEQUENCE: 499
NTGTASKL                                                                    8

SEQ ID NO: 500         moltype = AA  length = 8
FEATURE                Location/Qualifiers
source                 1..8
                       mol_type = protein
                       organism = Homo sapiens
SEQUENCE: 500
GLSDSYDK                                                                    8

SEQ ID NO: 501         moltype = AA  length = 8
FEATURE                Location/Qualifiers
source                 1..8
                       mol_type = protein
                       organism = Homo sapiens
SEQUENCE: 501
DPIMDTGR                                                                    8

SEQ ID NO: 502         moltype = AA  length = 8
FEATURE                Location/Qualifiers
source                 1..8
                       mol_type = protein
                       organism = Homo sapiens
SEQUENCE: 502
NGLPGSAR                                                                    8

SEQ ID NO: 503         moltype = AA  length = 8
FEATURE                Location/Qualifiers
source                 1..8
                       mol_type = protein
                       organism = Homo sapiens
SEQUENCE: 503
VLLTGKLI                                                                    8

SEQ ID NO: 504         moltype = AA  length = 8
FEATURE                Location/Qualifiers
source                 1..8
                       mol_type = protein
                       organism = Homo sapiens
SEQUENCE: 504
STDITSYE                                                                    8

SEQ ID NO: 505         moltype = AA  length = 8
FEATURE                Location/Qualifiers
source                 1..8
                       mol_type = protein
                       organism = Homo sapiens
SEQUENCE: 505
PSTGRLNT                                                                    8

SEQ ID NO: 506         moltype = AA  length = 8
FEATURE                Location/Qualifiers
source                 1..8
                       mol_type = protein
                       organism = Homo sapiens
SEQUENCE: 506
REGTGGYQ                                                                    8

SEQ ID NO: 507         moltype = AA  length = 8
FEATURE                Location/Qualifiers
source                 1..8
                       mol_type = protein
                       organism = Homo sapiens
SEQUENCE: 507
YLRTGGNE                                                                    8

SEQ ID NO: 508         moltype = AA  length = 8
FEATURE                Location/Qualifiers
source                 1..8
                       mol_type = protein
```

-continued

```
                        organism = Homo sapiens
SEQUENCE: 508
AGLAGGYE                                                            8

SEQ ID NO: 509          moltype = AA  length = 8
FEATURE                 Location/Qualifiers
source                  1..8
                        mol_type = protein
                        organism = Homo sapiens
SEQUENCE: 509
TWEEAGPY                                                            8

SEQ ID NO: 510          moltype = AA  length = 8
FEATURE                 Location/Qualifiers
source                  1..8
                        mol_type = protein
                        organism = Homo sapiens
SEQUENCE: 510
GGWAETPD                                                            8

SEQ ID NO: 511          moltype = AA  length = 8
FEATURE                 Location/Qualifiers
source                  1..8
                        mol_type = protein
                        organism = Homo sapiens
SEQUENCE: 511
SAGTSYNE                                                            8

SEQ ID NO: 512          moltype = AA  length = 8
FEATURE                 Location/Qualifiers
source                  1..8
                        mol_type = protein
                        organism = Homo sapiens
SEQUENCE: 512
TVQSPRTN                                                            8

SEQ ID NO: 513          moltype = AA  length = 8
FEATURE                 Location/Qualifiers
source                  1..8
                        mol_type = protein
                        organism = Homo sapiens
SEQUENCE: 513
SEGYSTYN                                                            8

SEQ ID NO: 514          moltype = AA  length = 8
FEATURE                 Location/Qualifiers
source                  1..8
                        mol_type = protein
                        organism = Homo sapiens
SEQUENCE: 514
PRGQGRSY                                                            8

SEQ ID NO: 515          moltype = AA  length = 8
FEATURE                 Location/Qualifiers
source                  1..8
                        mol_type = protein
                        organism = Homo sapiens
SEQUENCE: 515
QGVGQEYG                                                            8

SEQ ID NO: 516          moltype = AA  length = 8
FEATURE                 Location/Qualifiers
source                  1..8
                        mol_type = protein
                        organism = Homo sapiens
SEQUENCE: 516
SRGPNLAD                                                            8

SEQ ID NO: 517          moltype = AA  length = 8
FEATURE                 Location/Qualifiers
source                  1..8
                        mol_type = protein
                        organism = Homo sapiens
SEQUENCE: 517
RFVATGTS                                                            8

SEQ ID NO: 518          moltype = AA  length = 8
FEATURE                 Location/Qualifiers
source                  1..8
```

```
                                        mol_type = protein
                                        organism = Homo sapiens
SEQUENCE: 518
GGPGPSGE                                                                      8

SEQ ID NO: 519                          moltype = AA  length = 10
FEATURE                                 Location/Qualifiers
source                                  1..10
                                        mol_type = protein
                                        organism = Homo sapiens
SEQUENCE: 519
LGLVAGSARQ                                                                   10

SEQ ID NO: 520                          moltype = AA  length = 13
FEATURE                                 Location/Qualifiers
source                                  1..13
                                        mol_type = protein
                                        organism = Homo sapiens
SEQUENCE: 520
REGSDAGGTS YGK                                                               13

SEQ ID NO: 521                          moltype = AA  length = 13
FEATURE                                 Location/Qualifiers
source                                  1..13
                                        mol_type = protein
                                        organism = Homo sapiens
SEQUENCE: 521
SGNSGARDYG NNR                                                               13

SEQ ID NO: 522                          moltype = AA  length = 9
FEATURE                                 Location/Qualifiers
source                                  1..9
                                        mol_type = protein
                                        organism = Homo sapiens
SEQUENCE: 522
SGRGSGTYK                                                                     9

SEQ ID NO: 523                          moltype = AA  length = 10
FEATURE                                 Location/Qualifiers
source                                  1..10
                                        mol_type = protein
                                        organism = Homo sapiens
SEQUENCE: 523
PAPYTGTASK                                                                   10

SEQ ID NO: 524                          moltype = AA  length = 11
FEATURE                                 Location/Qualifiers
source                                  1..11
                                        mol_type = protein
                                        organism = Homo sapiens
SEQUENCE: 524
SDPIMDTGRR A                                                                 11

SEQ ID NO: 525                          moltype = AA  length = 9
FEATURE                                 Location/Qualifiers
source                                  1..9
                                        mol_type = protein
                                        organism = Homo sapiens
SEQUENCE: 525
NGLPGSARQ                                                                     9

SEQ ID NO: 526                          moltype = AA  length = 10
FEATURE                                 Location/Qualifiers
source                                  1..10
                                        mol_type = protein
                                        organism = Homo sapiens
SEQUENCE: 526
SPSTGRLNTE                                                                   10

SEQ ID NO: 527                          moltype = AA  length = 9
FEATURE                                 Location/Qualifiers
source                                  1..9
                                        mol_type = protein
                                        organism = Homo sapiens
SEQUENCE: 527
REGTGGYQP                                                                     9

SEQ ID NO: 528                          moltype = AA  length = 9
FEATURE                                 Location/Qualifiers
```

```
source                          1..9
                                mol_type = protein
                                organism = Homo sapiens
SEQUENCE: 528
SYLRTGGNE                                                                         9

SEQ ID NO: 529                  moltype = AA   length = 9
FEATURE                         Location/Qualifiers
source                          1..9
                                mol_type = protein
                                organism = Homo sapiens
SEQUENCE: 529
SAGLAGGYE                                                                         9

SEQ ID NO: 530                  moltype = AA   length = 11
FEATURE                         Location/Qualifiers
source                          1..11
                                mol_type = protein
                                organism = Homo sapiens
SEQUENCE: 530
ATWEEAGPYN E                                                                     11

SEQ ID NO: 531                  moltype = AA   length = 10
FEATURE                         Location/Qualifiers
source                          1..10
                                mol_type = protein
                                organism = Homo sapiens
SEQUENCE: 531
RGGWAETPDT                                                                       10

SEQ ID NO: 532                  moltype = AA   length = 9
FEATURE                         Location/Qualifiers
source                          1..9
                                mol_type = protein
                                organism = Homo sapiens
SEQUENCE: 532
TVQSPRTNE                                                                         9

SEQ ID NO: 533                  moltype = AA   length = 9
FEATURE                         Location/Qualifiers
source                          1..9
                                mol_type = protein
                                organism = Homo sapiens
SEQUENCE: 533
SEGYSTYNE                                                                         9

SEQ ID NO: 534                  moltype = AA   length = 10
FEATURE                         Location/Qualifiers
source                          1..10
                                mol_type = protein
                                organism = Homo sapiens
SEQUENCE: 534
SPRGQGRSYE                                                                       10

SEQ ID NO: 535                  moltype = AA   length = 9
FEATURE                         Location/Qualifiers
source                          1..9
                                mol_type = protein
                                organism = Homo sapiens
SEQUENCE: 535
SQGVGQEYG                                                                         9

SEQ ID NO: 536                  moltype = AA   length = 10
FEATURE                         Location/Qualifiers
source                          1..10
                                mol_type = protein
                                organism = Homo sapiens
SEQUENCE: 536
KSRGPNLADT                                                                       10

SEQ ID NO: 537                  moltype = AA   length = 10
FEATURE                         Location/Qualifiers
source                          1..10
                                mol_type = protein
                                organism = Homo sapiens
SEQUENCE: 537
SRFVATGTSP                                                                       10

SEQ ID NO: 538                  moltype = AA   length = 9
```

```
FEATURE                 Location/Qualifiers
source                  1..9
                        mol_type = protein
                        organism = Homo sapiens
SEQUENCE: 538
SGGPGPSGE                                                                    9

SEQ ID NO: 539          moltype = AA  length = 25
FEATURE                 Location/Qualifiers
source                  1..25
                        mol_type = protein
                        organism = Homo sapiens
SEQUENCE: 539
QTVTQSQPEM SVQEAETVTL SCTYD                                                  25

SEQ ID NO: 540          moltype = AA  length = 25
FEATURE                 Location/Qualifiers
source                  1..25
                        mol_type = protein
                        organism = Homo sapiens
SEQUENCE: 540
QKITQTQPGM FVQEKEAVTL DCTYD                                                  25

SEQ ID NO: 541          moltype = AA  length = 25
FEATURE                 Location/Qualifiers
source                  1..25
                        mol_type = protein
                        organism = Homo sapiens
SEQUENCE: 541
QKITQTQPGM FVQEKEAVTL DCTYD                                                  25

SEQ ID NO: 542          moltype = AA  length = 25
FEATURE                 Location/Qualifiers
source                  1..25
                        mol_type = protein
                        organism = Homo sapiens
SEQUENCE: 542
QSVAQPEDQV NVAEGNPLTV KCTYS                                                  25

SEQ ID NO: 543          moltype = AA  length = 25
FEATURE                 Location/Qualifiers
source                  1..25
                        mol_type = protein
                        organism = Homo sapiens
SEQUENCE: 543
QQLNQSPQSM FIQEGEDVSM NCTSS                                                  25

SEQ ID NO: 544          moltype = AA  length = 27
FEATURE                 Location/Qualifiers
source                  1..27
                        mol_type = protein
                        organism = Homo sapiens
SEQUENCE: 544
QQKEVEQDPG PLSVPEGAIV SLNCTYS                                                27

SEQ ID NO: 545          moltype = AA  length = 25
FEATURE                 Location/Qualifiers
source                  1..25
                        mol_type = protein
                        organism = Homo sapiens
SEQUENCE: 545
QTVTQSQPEM SVQEAETVTL SCTYD                                                  25

SEQ ID NO: 546          moltype = AA  length = 25
FEATURE                 Location/Qualifiers
source                  1..25
                        mol_type = protein
                        organism = Homo sapiens
SEQUENCE: 546
QKVTQAQTEI SVVEKEDVTL DCVYE                                                  25

SEQ ID NO: 547          moltype = AA  length = 24
FEATURE                 Location/Qualifiers
source                  1..24
                        mol_type = protein
                        organism = Homo sapiens
SEQUENCE: 547
EDVEQSLFLS VREGDSSVIN CTYT                                                   24
```

```
SEQ ID NO: 548        moltype = AA   length = 24
FEATURE               Location/Qualifiers
source                1..24
                      mol_type = protein
                      organism = Homo sapiens
SEQUENCE: 548
QNIDQPTEMT ATEGAIVQIN CTYQ                                                24

SEQ ID NO: 549        moltype = AA   length = 25
FEATURE               Location/Qualifiers
source                1..25
                      mol_type = protein
                      organism = Homo sapiens
SEQUENCE: 549
IQVEQSPPDL ILQEGANSTL RCNFS                                               25

SEQ ID NO: 550        moltype = AA   length = 25
FEATURE               Location/Qualifiers
source                1..25
                      mol_type = protein
                      organism = Homo sapiens
SEQUENCE: 550
QLLEQSPQFL SIQEGENLTV YCNSS                                               25

SEQ ID NO: 551        moltype = AA   length = 25
FEATURE               Location/Qualifiers
source                1..25
                      mol_type = protein
                      organism = Homo sapiens
SEQUENCE: 551
QKITQTQPGM FVQEKEAVTL DCTYD                                               25

SEQ ID NO: 552        moltype = AA   length = 25
FEATURE               Location/Qualifiers
source                1..25
                      mol_type = protein
                      organism = Homo sapiens
SEQUENCE: 552
QKITQTQPGM FVQEKEAVTL DCTYD                                               25

SEQ ID NO: 553        moltype = AA   length = 26
FEATURE               Location/Qualifiers
source                1..26
                      mol_type = protein
                      organism = Homo sapiens
SEQUENCE: 553
KQEVTQIPAA LSVPEGENLV LNCSFT                                              26

SEQ ID NO: 554        moltype = AA   length = 25
FEATURE               Location/Qualifiers
source                1..25
                      mol_type = protein
                      organism = Homo sapiens
SEQUENCE: 554
QTVTQSQPKM SVQEAETVTL SCTYD                                               25

SEQ ID NO: 555        moltype = AA   length = 25
FEATURE               Location/Qualifiers
source                1..25
                      mol_type = protein
                      organism = Homo sapiens
SEQUENCE: 555
QKITQTQPGM FVQEKEAVTL DCTWD                                               25

SEQ ID NO: 556        moltype = AA   length = 25
FEATURE               Location/Qualifiers
source                1..25
                      mol_type = protein
                      organism = Homo sapiens
SEQUENCE: 556
QKITQTQPAM FVQEKEAVTL DCTYD                                               25

SEQ ID NO: 557        moltype = AA   length = 25
FEATURE               Location/Qualifiers
source                1..25
                      mol_type = protein
                      organism = Homo sapiens
SEQUENCE: 557
QSVAQPEDQV NVAEGQPLTV KCTYS                                               25
```

```
SEQ ID NO: 558         moltype = AA  length = 25
FEATURE                Location/Qualifiers
source                 1..25
                       mol_type = protein
                       organism = Homo sapiens
SEQUENCE: 558
QQLNQSPQTM FIQEGEDVSM NCTSS                                              25

SEQ ID NO: 559         moltype = AA  length = 27
FEATURE                Location/Qualifiers
source                 1..27
                       mol_type = protein
                       organism = Homo sapiens
SEQUENCE: 559
QQKEVEQDPG PLSVPEGAIV SLNCTYT                                            27

SEQ ID NO: 560         moltype = AA  length = 25
FEATURE                Location/Qualifiers
source                 1..25
                       mol_type = protein
                       organism = Homo sapiens
SEQUENCE: 560
QTVTQSQPEM SVQEAETFTL SCTYD                                              25

SEQ ID NO: 561         moltype = AA  length = 25
FEATURE                Location/Qualifiers
source                 1..25
                       mol_type = protein
                       organism = Homo sapiens
SEQUENCE: 561
QKVTQAQTEI SWVEKEDVTL DCVYE                                              25

SEQ ID NO: 562         moltype = AA  length = 24
FEATURE                Location/Qualifiers
source                 1..24
                       mol_type = protein
                       organism = Homo sapiens
SEQUENCE: 562
EDVEQSLFIS VREGDSSVIN CTYT                                               24

SEQ ID NO: 563         moltype = AA  length = 24
FEATURE                Location/Qualifiers
source                 1..24
                       mol_type = protein
                       organism = Homo sapiens
SEQUENCE: 563
QNIDQPTEMT GTEGAIVQIN CTYQ                                               24

SEQ ID NO: 564         moltype = AA  length = 25
FEATURE                Location/Qualifiers
source                 1..25
                       mol_type = protein
                       organism = Homo sapiens
SEQUENCE: 564
IQVEQSPPDL ILNEGANSTL RCNFS                                              25

SEQ ID NO: 565         moltype = AA  length = 25
FEATURE                Location/Qualifiers
source                 1..25
                       mol_type = protein
                       organism = Homo sapiens
SEQUENCE: 565
QLLENSPQFL SIQEGENLTV YCNSS                                              25

SEQ ID NO: 566         moltype = AA  length = 25
FEATURE                Location/Qualifiers
source                 1..25
                       mol_type = protein
                       organism = Homo sapiens
SEQUENCE: 566
QKITQTQPGM FVQEKEAVSL DCTYD                                              25

SEQ ID NO: 567         moltype = AA  length = 25
FEATURE                Location/Qualifiers
source                 1..25
                       mol_type = protein
                       organism = Homo sapiens
SEQUENCE: 567
```

-continued

QKITQTQPGM FVQEKEAVTL DCTYN                                         25

SEQ ID NO: 568          moltype = AA  length = 26
FEATURE                 Location/Qualifiers
source                  1..26
                        mol_type = protein
                        organism = Homo sapiens
SEQUENCE: 568
KQEVTQIPAA ISVPEGENLV LNCSFT                                        26

SEQ ID NO: 569          moltype = AA  length = 25
FEATURE                 Location/Qualifiers
source                  1..25
                        mol_type = protein
                        organism = Homo sapiens
SEQUENCE: 569
QTVTNSQPEM SVQEAETVTL SCTYD                                         25

SEQ ID NO: 570          moltype = AA  length = 25
FEATURE                 Location/Qualifiers
source                  1..25
                        mol_type = protein
                        organism = Homo sapiens
SEQUENCE: 570
QKITQSQPGM FVQEKEAVTL DCTYD                                         25

SEQ ID NO: 571          moltype = AA  length = 25
FEATURE                 Location/Qualifiers
source                  1..25
                        mol_type = protein
                        organism = Homo sapiens
SEQUENCE: 571
QKITQTQPGM FVQEKEGVTL DCTYD                                         25

SEQ ID NO: 572          moltype = AA  length = 25
FEATURE                 Location/Qualifiers
source                  1..25
                        mol_type = protein
                        organism = Homo sapiens
SEQUENCE: 572
QSVANPEDQV NVAEGNPLTV KCTYS                                         25

SEQ ID NO: 573          moltype = AA  length = 25
FEATURE                 Location/Qualifiers
source                  1..25
                        mol_type = protein
                        organism = Homo sapiens
SEQUENCE: 573
QQLNQSPQSM FIQEGERVSM NCTSS                                         25

SEQ ID NO: 574          moltype = AA  length = 27
FEATURE                 Location/Qualifiers
source                  1..27
                        mol_type = protein
                        organism = Homo sapiens
SEQUENCE: 574
QQKEVEQRPG PLSVPEGAIV SLNCTYS                                       27

SEQ ID NO: 575          moltype = AA  length = 25
FEATURE                 Location/Qualifiers
source                  1..25
                        mol_type = protein
                        organism = Homo sapiens
SEQUENCE: 575
QTVTQTQPEM SVQEAETVTL SCTYD                                         25

SEQ ID NO: 576          moltype = AA  length = 25
FEATURE                 Location/Qualifiers
source                  1..25
                        mol_type = protein
                        organism = Homo sapiens
SEQUENCE: 576
QKVTQAQTEL SVVEKEDVTL DCVYE                                         25

SEQ ID NO: 577          moltype = AA  length = 24
FEATURE                 Location/Qualifiers
source                  1..24
                        mol_type = protein
                        organism = Homo sapiens

```
SEQUENCE: 577
EDVEQSLFLS VREGDTSVIN CTYT                                                  24

SEQ ID NO: 578          moltype = AA  length = 24
FEATURE                 Location/Qualifiers
source                  1..24
                        mol_type = protein
                        organism = Homo sapiens
SEQUENCE: 578
QNIDQPSEMT ATEGAIVQIN CTYQ                                                  24

SEQ ID NO: 579          moltype = AA  length = 25
FEATURE                 Location/Qualifiers
source                  1..25
                        mol_type = protein
                        organism = Homo sapiens
SEQUENCE: 579
IQVEQSPPDL ILNEGANSTL RCNFS                                                 25

SEQ ID NO: 580          moltype = AA  length = 25
FEATURE                 Location/Qualifiers
source                  1..25
                        mol_type = protein
                        organism = Homo sapiens
SEQUENCE: 580
QLLEQSPQFL SIQEGENLTV YCQSS                                                 25

SEQ ID NO: 581          moltype = AA  length = 25
FEATURE                 Location/Qualifiers
source                  1..25
                        mol_type = protein
                        organism = Homo sapiens
SEQUENCE: 581
QKLTQTQPGM FVQEKEAVTL DCTYD                                                 25

SEQ ID NO: 582          moltype = AA  length = 25
FEATURE                 Location/Qualifiers
source                  1..25
                        mol_type = protein
                        organism = Homo sapiens
SEQUENCE: 582
QKITQTQPGM FVQEKEAVSL DCTYD                                                 25

SEQ ID NO: 583          moltype = AA  length = 26
FEATURE                 Location/Qualifiers
source                  1..26
                        mol_type = protein
                        organism = Homo sapiens
SEQUENCE: 583
KQEVTQIPGA LSVPEGENLV LNCSFT                                                26

SEQ ID NO: 584          moltype = AA  length = 17
FEATURE                 Location/Qualifiers
source                  1..17
                        mol_type = protein
                        organism = Homo sapiens
SEQUENCE: 584
LFWYKQPPSR QMILVIR                                                          17

SEQ ID NO: 585          moltype = AA  length = 17
FEATURE                 Location/Qualifiers
source                  1..17
                        mol_type = protein
                        organism = Homo sapiens
SEQUENCE: 585
LFWYKQPSSG EMIFLIY                                                          17

SEQ ID NO: 586          moltype = AA  length = 17
FEATURE                 Location/Qualifiers
source                  1..17
                        mol_type = protein
                        organism = Homo sapiens
SEQUENCE: 586
LFWYKQPSSG EMIFLIY                                                          17

SEQ ID NO: 587          moltype = AA  length = 17
FEATURE                 Location/Qualifiers
source                  1..17
                        mol_type = protein
```

-continued

```
                    organism = Homo sapiens
SEQUENCE: 587
LFWYVQYPNR GLQFLLK                                                     17

SEQ ID NO: 588         moltype = AA  length = 17
FEATURE                Location/Qualifiers
source                 1..17
                       mol_type = protein
                       organism = Homo sapiens
SEQUENCE: 588
WLWYKQDPGE GPVLLIA                                                     17

SEQ ID NO: 589         moltype = AA  length = 17
FEATURE                Location/Qualifiers
source                 1..17
                       mol_type = protein
                       organism = Homo sapiens
SEQUENCE: 589
FMWYRQYSRK GPELLMY                                                     17

SEQ ID NO: 590         moltype = AA  length = 17
FEATURE                Location/Qualifiers
source                 1..17
                       mol_type = protein
                       organism = Homo sapiens
SEQUENCE: 590
LFWYKQPPSR QMILVIR                                                     17

SEQ ID NO: 591         moltype = AA  length = 17
FEATURE                Location/Qualifiers
source                 1..17
                       mol_type = protein
                       organism = Homo sapiens
SEQUENCE: 591
LFWYKQPPSG ELVFLIR                                                     17

SEQ ID NO: 592         moltype = AA  length = 17
FEATURE                Location/Qualifiers
source                 1..17
                       mol_type = protein
                       organism = Homo sapiens
SEQUENCE: 592
LYWYKQEPGA GLQLLTY                                                     17

SEQ ID NO: 593         moltype = AA  length = 17
FEATURE                Location/Qualifiers
source                 1..17
                       mol_type = protein
                       organism = Homo sapiens
SEQUENCE: 593
LFWYQQHAGE APTFLSY                                                     17

SEQ ID NO: 594         moltype = AA  length = 17
FEATURE                Location/Qualifiers
source                 1..17
                       mol_type = protein
                       organism = Homo sapiens
SEQUENCE: 594
LQWFHQNPWG QLINLFY                                                     17

SEQ ID NO: 595         moltype = AA  length = 17
FEATURE                Location/Qualifiers
source                 1..17
                       mol_type = protein
                       organism = Homo sapiens
SEQUENCE: 595
LQWYRQEPGE GPVLLVT                                                     17

SEQ ID NO: 596         moltype = AA  length = 17
FEATURE                Location/Qualifiers
source                 1..17
                       mol_type = protein
                       organism = Homo sapiens
SEQUENCE: 596
LFWYKQPSSG EMIFLIY                                                     17

SEQ ID NO: 597         moltype = AA  length = 17
FEATURE                Location/Qualifiers
source                 1..17
```

```
                              mol_type = protein
                              organism = Homo sapiens
SEQUENCE: 597
LFWYKQPSSG EMIFLIY                                                    17

SEQ ID NO: 598                moltype = AA  length = 17
FEATURE                       Location/Qualifiers
source                        1..17
                              mol_type = protein
                              organism = Homo sapiens
SEQUENCE: 598
LQWFRQDPGK GLTSLLL                                                    17

SEQ ID NO: 599                moltype = AA  length = 34
FEATURE                       Location/Qualifiers
source                        1..34
                              mol_type = protein
                              organism = Homo sapiens
SEQUENCE: 599
ATENRFSVNF QKAAKSFSLK ISDSQLGDTA MYFC                                 34

SEQ ID NO: 600                moltype = AA  length = 34
FEATURE                       Location/Qualifiers
source                        1..34
                              mol_type = protein
                              organism = Homo sapiens
SEQUENCE: 600
ATEGRYSLNF QKARKSANLV ISASQLGDSA MYFC                                 34

SEQ ID NO: 601                moltype = AA  length = 34
FEATURE                       Location/Qualifiers
source                        1..34
                              mol_type = protein
                              organism = Homo sapiens
SEQUENCE: 601
ATEGRYSLNF QKARKSANLV ISASQLGDSA MYFC                                 34

SEQ ID NO: 602                moltype = AA  length = 34
FEATURE                       Location/Qualifiers
source                        1..34
                              mol_type = protein
                              organism = Homo sapiens
SEQUENCE: 602
KGSYGFEAEF NKSQTSFHLK KPSALVSDSA LYFC                                 34

SEQ ID NO: 603                moltype = AA  length = 34
FEATURE                       Location/Qualifiers
source                        1..34
                              mol_type = protein
                              organism = Homo sapiens
SEQUENCE: 603
TSNGRLTAQF GITRKDSFLN ISASIPSDVG IYFC                                 34

SEQ ID NO: 604                moltype = AA  length = 34
FEATURE                       Location/Qualifiers
source                        1..34
                              mol_type = protein
                              organism = Homo sapiens
SEQUENCE: 604
KEDGRFTAQV DKSSKYISLF IRDSQPSDSA TYLC                                 34

SEQ ID NO: 605                moltype = AA  length = 34
FEATURE                       Location/Qualifiers
source                        1..34
                              mol_type = protein
                              organism = Homo sapiens
SEQUENCE: 605
ATENRFSVNF QKAAKSFSLK ISDSQLGDAA MYFC                                 34

SEQ ID NO: 606                moltype = AA  length = 34
FEATURE                       Location/Qualifiers
source                        1..34
                              mol_type = protein
                              organism = Homo sapiens
SEQUENCE: 606
EISGRYSWNF QKSTSSFNFT ITASQVVDSA VYFC                                 34

SEQ ID NO: 607                moltype = AA  length = 34
FEATURE                       Location/Qualifiers
```

```
source                       1..34
                             mol_type = protein
                             organism = Homo sapiens
SEQUENCE: 607
KQDQRLTVLL NKKDKHLSLR IADTQTGDSA IYFC                              34

SEQ ID NO: 608               moltype = AA  length = 34
FEATURE                      Location/Qualifiers
source                       1..34
                             mol_type = protein
                             organism = Homo sapiens
SEQUENCE: 608
EEKGRFSSFL SRSKGYSYLL LKELQMKDSA SYLC                              34

SEQ ID NO: 609               moltype = AA  length = 34
FEATURE                      Location/Qualifiers
source                       1..34
                             mol_type = protein
                             organism = Homo sapiens
SEQUENCE: 609
KQNGRLSATT VATERYSLLY ISSSQTTDSG VYFC                              34

SEQ ID NO: 610               moltype = AA  length = 34
FEATURE                      Location/Qualifiers
source                       1..34
                             mol_type = protein
                             organism = Homo sapiens
SEQUENCE: 610
KKLKRLTFQF GDARKDSSLH ITAAQPGDTG LYLC                              34

SEQ ID NO: 611               moltype = AA  length = 34
FEATURE                      Location/Qualifiers
source                       1..34
                             mol_type = protein
                             organism = Homo sapiens
SEQUENCE: 611
ATEGRYSLNF QKARKSANLV ISASQLGDSA MYFC                              34

SEQ ID NO: 612               moltype = AA  length = 34
FEATURE                      Location/Qualifiers
source                       1..34
                             mol_type = protein
                             organism = Homo sapiens
SEQUENCE: 612
ATEGRYSLNF QKARKSANLV ISASQLGDSA MYFC                              34

SEQ ID NO: 613               moltype = AA  length = 34
FEATURE                      Location/Qualifiers
source                       1..34
                             mol_type = protein
                             organism = Homo sapiens
SEQUENCE: 613
QTSGRLNASL DKSSGRSTLY IAASQPGDSA TYLC                              34

SEQ ID NO: 614               moltype = AA  length = 34
FEATURE                      Location/Qualifiers
source                       1..34
                             mol_type = protein
                             organism = Homo sapiens
SEQUENCE: 614
ATENRFSVNL QKAAKSFSLK ISDSQLGDTA MYFC                              34

SEQ ID NO: 615               moltype = AA  length = 34
FEATURE                      Location/Qualifiers
source                       1..34
                             mol_type = protein
                             organism = Homo sapiens
SEQUENCE: 615
ATEGRYSLNF NKARKSANLV ISASQLGDSA MYFC                              34

SEQ ID NO: 616               moltype = AA  length = 34
FEATURE                      Location/Qualifiers
source                       1..34
                             mol_type = protein
                             organism = Homo sapiens
SEQUENCE: 616
ATEGKYSLNF QKARKSANLV ISASQLGDSA MYFC                              34

SEQ ID NO: 617               moltype = AA  length = 34
```

```
FEATURE                 Location/Qualifiers
source                  1..34
                        mol_type = protein
                        organism = Homo sapiens
SEQUENCE: 617
KGSYGFEAEF NRSQTSFHLK KPSALVSDSA LYFC                                    34

SEQ ID NO: 618          moltype = AA  length = 34
FEATURE                 Location/Qualifiers
source                  1..34
                        mol_type = protein
                        organism = Homo sapiens
SEQUENCE: 618
TSNGRLTAQF GITRKDSFLN ITASIPSDVG IYFC                                    34

SEQ ID NO: 619          moltype = AA  length = 34
FEATURE                 Location/Qualifiers
source                  1..34
                        mol_type = protein
                        organism = Homo sapiens
SEQUENCE: 619
KEDGRFTAQV DKSSKYISLF IRDSNPSDSA TYLC                                    34

SEQ ID NO: 620          moltype = AA  length = 34
FEATURE                 Location/Qualifiers
source                  1..34
                        mol_type = protein
                        organism = Homo sapiens
SEQUENCE: 620
ATENRFSVNF QKAAKSFSLK LSDSQLGDAA MYFC                                    34

SEQ ID NO: 621          moltype = AA  length = 34
FEATURE                 Location/Qualifiers
source                  1..34
                        mol_type = protein
                        organism = Homo sapiens
SEQUENCE: 621
EISGRYSWNF QKSTSSFQFT ITASQVVDSA VYFC                                    34

SEQ ID NO: 622          moltype = AA  length = 34
FEATURE                 Location/Qualifiers
source                  1..34
                        mol_type = protein
                        organism = Homo sapiens
SEQUENCE: 622
KQDQRLTVLL NKKDKHLSLR IADSQTGDSA IYFC                                    34

SEQ ID NO: 623          moltype = AA  length = 34
FEATURE                 Location/Qualifiers
source                  1..34
                        mol_type = protein
                        organism = Homo sapiens
SEQUENCE: 623
EEKGRFSSFL SRSKGYSYLL IKELQMKDSA SYLC                                    34

SEQ ID NO: 624          moltype = AA  length = 34
FEATURE                 Location/Qualifiers
source                  1..34
                        mol_type = protein
                        organism = Homo sapiens
SEQUENCE: 624
KQNGRLTATT VATERYSLLY ISSSQTTDSG VYFC                                    34

SEQ ID NO: 625          moltype = AA  length = 34
FEATURE                 Location/Qualifiers
source                  1..34
                        mol_type = protein
                        organism = Homo sapiens
SEQUENCE: 625
KKLKRLTFQF GDARKDSSLH ITAAQPGDTA LYLC                                    34

SEQ ID NO: 626          moltype = AA  length = 34
FEATURE                 Location/Qualifiers
source                  1..34
                        mol_type = protein
                        organism = Homo sapiens
SEQUENCE: 626
ATEGRYSLNF QKARKSAQLV ISASQLGDSA MYFC                                    34
```

```
SEQ ID NO: 627           moltype = AA  length = 34
FEATURE                  Location/Qualifiers
source                   1..34
                         mol_type = protein
                         organism = Homo sapiens
SEQUENCE: 627
ATEGRYSLNF QKARKSANIV ISASQLGDSA MYFC                                    34

SEQ ID NO: 628           moltype = AA  length = 34
FEATURE                  Location/Qualifiers
source                   1..34
                         mol_type = protein
                         organism = Homo sapiens
SEQUENCE: 628
QTSGRLNASL DKSSGRSTLY IAGSQPGDSA TYLC                                    34

SEQ ID NO: 629           moltype = AA  length = 11
FEATURE                  Location/Qualifiers
source                   1..11
                         mol_type = protein
                         organism = Homo sapiens
SEQUENCE: 629
FGSGTQLTVL P                                                             11

SEQ ID NO: 630           moltype = AA  length = 11
FEATURE                  Location/Qualifiers
source                   1..11
                         mol_type = protein
                         organism = Homo sapiens
SEQUENCE: 630
FGQGTILTVH P                                                             11

SEQ ID NO: 631           moltype = AA  length = 11
FEATURE                  Location/Qualifiers
source                   1..11
                         mol_type = protein
                         organism = Homo sapiens
SEQUENCE: 631
WGAGTKLIIK P                                                             11

SEQ ID NO: 632           moltype = AA  length = 11
FEATURE                  Location/Qualifiers
source                   1..11
                         mol_type = protein
                         organism = Homo sapiens
SEQUENCE: 632
FGKGTRLHIL P                                                             11

SEQ ID NO: 633           moltype = AA  length = 11
FEATURE                  Location/Qualifiers
source                   1..11
                         mol_type = protein
                         organism = Homo sapiens
SEQUENCE: 633
FGPGTRLSVL P                                                             11

SEQ ID NO: 634           moltype = AA  length = 11
FEATURE                  Location/Qualifiers
source                   1..11
                         mol_type = protein
                         organism = Homo sapiens
SEQUENCE: 634
FGKGNQVVVI P                                                             11

SEQ ID NO: 635           moltype = AA  length = 11
FEATURE                  Location/Qualifiers
source                   1..11
                         mol_type = protein
                         organism = Homo sapiens
SEQUENCE: 635
FGTGTLLAVQ P                                                             11

SEQ ID NO: 636           moltype = AA  length = 11
FEATURE                  Location/Qualifiers
source                   1..11
                         mol_type = protein
                         organism = Homo sapiens
SEQUENCE: 636
FGTGTRLKVL A                                                             11
```

```
SEQ ID NO: 637          moltype = AA  length = 11
FEATURE                 Location/Qualifiers
source                  1..11
                        mol_type = protein
                        organism = Homo sapiens
SEQUENCE: 637
FGGGTRVLVK P                                                              11

SEQ ID NO: 638          moltype = AA  length = 11
FEATURE                 Location/Qualifiers
source                  1..11
                        mol_type = protein
                        organism = Homo sapiens
SEQUENCE: 638
FGTGTRLQVT L                                                              11

SEQ ID NO: 639          moltype = AA  length = 11
FEATURE                 Location/Qualifiers
source                  1..11
                        mol_type = protein
                        organism = Homo sapiens
SEQUENCE: 639
FGTGTRLQVT L                                                              11

SEQ ID NO: 640          moltype = AA  length = 11
FEATURE                 Location/Qualifiers
source                  1..11
                        mol_type = protein
                        organism = Homo sapiens
SEQUENCE: 640
FGPGTSLSVI P                                                              11

SEQ ID NO: 641          moltype = AA  length = 11
FEATURE                 Location/Qualifiers
source                  1..11
                        mol_type = protein
                        organism = Homo sapiens
SEQUENCE: 641
FGSGTRLQVQ P                                                              11

SEQ ID NO: 642          moltype = AA  length = 11
FEATURE                 Location/Qualifiers
source                  1..11
                        mol_type = protein
                        organism = Homo sapiens
SEQUENCE: 642
FGSGTQLTVL P                                                              11

SEQ ID NO: 643          moltype = AA  length = 11
FEATURE                 Location/Qualifiers
source                  1..11
                        mol_type = protein
                        organism = Homo sapiens
SEQUENCE: 643
FGQGTTLQVK P                                                              11

SEQ ID NO: 644          moltype = AA  length = 24
FEATURE                 Location/Qualifiers
source                  1..24
                        mol_type = protein
                        organism = Homo sapiens
SEQUENCE: 644
GVSQDPRHKI TKRGQNVTFR CDPI                                                24

SEQ ID NO: 645          moltype = AA  length = 24
FEATURE                 Location/Qualifiers
source                  1..24
                        mol_type = protein
                        organism = Homo sapiens
SEQUENCE: 645
GVIQSPRHLI KEKRETATLK CYPI                                                24

SEQ ID NO: 646          moltype = AA  length = 24
FEATURE                 Location/Qualifiers
source                  1..24
                        mol_type = protein
                        organism = Homo sapiens
SEQUENCE: 646
```

```
QVTQNPRYLI TVTGKKLTVT CSQN                                              24

SEQ ID NO: 647          moltype = AA   length = 24
FEATURE                 Location/Qualifiers
source                  1..24
                        mol_type = protein
                        organism = Homo sapiens
SEQUENCE: 647
GVTQTPKFRV LKTGQSMTLL CAQD                                              24

SEQ ID NO: 648          moltype = AA   length = 24
FEATURE                 Location/Qualifiers
source                  1..24
                        mol_type = protein
                        organism = Homo sapiens
SEQUENCE: 648
GVTQTPKHLI TATGQRVTLR CSPR                                              24

SEQ ID NO: 649          moltype = AA   length = 24
FEATURE                 Location/Qualifiers
source                  1..24
                        mol_type = protein
                        organism = Homo sapiens
SEQUENCE: 649
EVTQTPKHLV MGMTNKKSLK CEQH                                              24

SEQ ID NO: 650          moltype = AA   length = 24
FEATURE                 Location/Qualifiers
source                  1..24
                        mol_type = protein
                        organism = Homo sapiens
SEQUENCE: 650
GVIQSPRHLI KEKRETATLK CYPI                                              24

SEQ ID NO: 651          moltype = AA   length = 24
FEATURE                 Location/Qualifiers
source                  1..24
                        mol_type = protein
                        organism = Homo sapiens
SEQUENCE: 651
GVIQSPRHLI KEKRETATLK CYPI                                              24

SEQ ID NO: 652          moltype = AA   length = 26
FEATURE                 Location/Qualifiers
source                  1..26
                        mol_type = protein
                        organism = Homo sapiens
SEQUENCE: 652
EPEVTQTPSH QVTQMGQEVI LRCVPI                                            26

SEQ ID NO: 653          moltype = AA   length = 24
FEATURE                 Location/Qualifiers
source                  1..24
                        mol_type = protein
                        organism = Homo sapiens
SEQUENCE: 653
GVTQTPKFQV LKTGQSMTLQ CAQD                                              24

SEQ ID NO: 654          moltype = AA   length = 24
FEATURE                 Location/Qualifiers
source                  1..24
                        mol_type = protein
                        organism = Homo sapiens
SEQUENCE: 654
GVTQTPKFQV LKTGQSMTLQ CAQD                                              24

SEQ ID NO: 655          moltype = AA   length = 24
FEATURE                 Location/Qualifiers
source                  1..24
                        mol_type = protein
                        organism = Homo sapiens
SEQUENCE: 655
EVTQTPKHLV MGMTNKKSLK CEQH                                              24

SEQ ID NO: 656          moltype = AA   length = 24
FEATURE                 Location/Qualifiers
source                  1..24
                        mol_type = protein
                        organism = Homo sapiens
```

```
SEQUENCE: 656
GITQSPKYLF RKEGQNVTLS CEQN                                              24

SEQ ID NO: 657          moltype = AA  length = 24
FEATURE                 Location/Qualifiers
source                  1..24
                        mol_type = protein
                        organism = Homo sapiens
SEQUENCE: 657
GVAQSPRYKI IEKRQSVAFW CNPI                                              24

SEQ ID NO: 658          moltype = AA  length = 24
FEATURE                 Location/Qualifiers
source                  1..24
                        mol_type = protein
                        organism = Homo sapiens
SEQUENCE: 658
GVTQTPRYLI KTRGQQVTLS CSPI                                              24

SEQ ID NO: 659          moltype = AA  length = 24
FEATURE                 Location/Qualifiers
source                  1..24
                        mol_type = protein
                        organism = Homo sapiens
SEQUENCE: 659
GVSQEPRHKI TKRGQNVTFR CDPI                                              24

SEQ ID NO: 660          moltype = AA  length = 24
FEATURE                 Location/Qualifiers
source                  1..24
                        mol_type = protein
                        organism = Homo sapiens
SEQUENCE: 660
GVIQSPRHLI KEKRESATLK CYPI                                              24

SEQ ID NO: 661          moltype = AA  length = 24
FEATURE                 Location/Qualifiers
source                  1..24
                        mol_type = protein
                        organism = Homo sapiens
SEQUENCE: 661
QVTQNPKYLI TVTGKKLTVT CSQN                                              24

SEQ ID NO: 662          moltype = AA  length = 24
FEATURE                 Location/Qualifiers
source                  1..24
                        mol_type = protein
                        organism = Homo sapiens
SEQUENCE: 662
GVTQTPKFRV LKTGQTMTLL CAQD                                              24

SEQ ID NO: 663          moltype = AA  length = 24
FEATURE                 Location/Qualifiers
source                  1..24
                        mol_type = protein
                        organism = Homo sapiens
SEQUENCE: 663
GVTQTPKHLI TATGQRVTLR CTPR                                              24

SEQ ID NO: 664          moltype = AA  length = 24
FEATURE                 Location/Qualifiers
source                  1..24
                        mol_type = protein
                        organism = Homo sapiens
SEQUENCE: 664
EVTQTPRHLV MGMTNKKSLK CEQH                                              24

SEQ ID NO: 665          moltype = AA  length = 24
FEATURE                 Location/Qualifiers
source                  1..24
                        mol_type = protein
                        organism = Homo sapiens
SEQUENCE: 665
GVIQSPRHLI KEKRETATLR CYPI                                              24

SEQ ID NO: 666          moltype = AA  length = 24
FEATURE                 Location/Qualifiers
source                  1..24
                        mol_type = protein
```

```
                                    organism = Homo sapiens
SEQUENCE: 666
GVIQSPRHLI KDKRETATLK CYPI                                                      24

SEQ ID NO: 667          moltype = AA   length = 26
FEATURE                 Location/Qualifiers
source                  1..26
                        mol_type = protein
                        organism = Homo sapiens
SEQUENCE: 667
EPEVTQTPSH QVTQMGQEVI LKCVPI                                                    26

SEQ ID NO: 668          moltype = AA   length = 24
FEATURE                 Location/Qualifiers
source                  1..24
                        mol_type = protein
                        organism = Homo sapiens
SEQUENCE: 668
GVTQTPKFQV LKTGQSMTLQ CIQD                                                      24

SEQ ID NO: 669          moltype = AA   length = 24
FEATURE                 Location/Qualifiers
source                  1..24
                        mol_type = protein
                        organism = Homo sapiens
SEQUENCE: 669
GVTQTPKFQV LKSGQSMTLQ CAQD                                                      24

SEQ ID NO: 670          moltype = AA   length = 24
FEATURE                 Location/Qualifiers
source                  1..24
                        mol_type = protein
                        organism = Homo sapiens
SEQUENCE: 670
EVTQTPKHLV QGMTNKKSLK CEQH                                                      24

SEQ ID NO: 671          moltype = AA   length = 24
FEATURE                 Location/Qualifiers
source                  1..24
                        mol_type = protein
                        organism = Homo sapiens
SEQUENCE: 671
GITQSPKWLF RKEGQNVTLS CEQN                                                      24

SEQ ID NO: 672          moltype = AA   length = 24
FEATURE                 Location/Qualifiers
source                  1..24
                        mol_type = protein
                        organism = Homo sapiens
SEQUENCE: 672
GVAQSPRYKL IEKRQSVAFW CNPI                                                      24

SEQ ID NO: 673          moltype = AA   length = 24
FEATURE                 Location/Qualifiers
source                  1..24
                        mol_type = protein
                        organism = Homo sapiens
SEQUENCE: 673
GVTQTPRYLI KSRGQQVTLS CSPI                                                      24

SEQ ID NO: 674          moltype = AA   length = 17
FEATURE                 Location/Qualifiers
source                  1..17
                        mol_type = protein
                        organism = Homo sapiens
SEQUENCE: 674
LYWYRQTLGQ GPEFLTY                                                              17

SEQ ID NO: 675          moltype = AA   length = 17
FEATURE                 Location/Qualifiers
source                  1..17
                        mol_type = protein
                        organism = Homo sapiens
SEQUENCE: 675
VYWYQQGPGQ DPQFLIS                                                              17

SEQ ID NO: 676          moltype = AA   length = 17
FEATURE                 Location/Qualifiers
source                  1..17
```

```
                              mol_type = protein
                              organism = Homo sapiens
SEQUENCE: 676
MSWYRQDPGL GLRQIYY                                                17

SEQ ID NO: 677                moltype = AA   length = 17
FEATURE                       Location/Qualifiers
source                        1..17
                              mol_type = protein
                              organism = Homo sapiens
SEQUENCE: 677
MYWYRQDPGM GLRLIHY                                                17

SEQ ID NO: 678                moltype = AA   length = 17
FEATURE                       Location/Qualifiers
source                        1..17
                              mol_type = protein
                              organism = Homo sapiens
SEQUENCE: 678
VYWYQQSLDQ GLQFLIQ                                                17

SEQ ID NO: 679                moltype = AA   length = 17
FEATURE                       Location/Qualifiers
source                        1..17
                              mol_type = protein
                              organism = Homo sapiens
SEQUENCE: 679
MYWYKQKAKK PPELMFV                                                17

SEQ ID NO: 680                moltype = AA   length = 17
FEATURE                       Location/Qualifiers
source                        1..17
                              mol_type = protein
                              organism = Homo sapiens
SEQUENCE: 680
VYWYQQGPGQ DPQFLIS                                                17

SEQ ID NO: 681                moltype = AA   length = 17
FEATURE                       Location/Qualifiers
source                        1..17
                              mol_type = protein
                              organism = Homo sapiens
SEQUENCE: 681
VYWYQQGPGQ DPQFLIS                                                17

SEQ ID NO: 682                moltype = AA   length = 17
FEATURE                       Location/Qualifiers
source                        1..17
                              mol_type = protein
                              organism = Homo sapiens
SEQUENCE: 682
FYWYRQILGQ KVEFLVS                                                17

SEQ ID NO: 683                moltype = AA   length = 17
FEATURE                       Location/Qualifiers
source                        1..17
                              mol_type = protein
                              organism = Homo sapiens
SEQUENCE: 683
MYWYRQDPGM GLRLIYY                                                17

SEQ ID NO: 684                moltype = AA   length = 17
FEATURE                       Location/Qualifiers
source                        1..17
                              mol_type = protein
                              organism = Homo sapiens
SEQUENCE: 684
MYWYRQDPGM GLRLIYY                                                17

SEQ ID NO: 685                moltype = AA   length = 17
FEATURE                       Location/Qualifiers
source                        1..17
                              mol_type = protein
                              organism = Homo sapiens
SEQUENCE: 685
MYWYKQKAKK PPELMFV                                                17

SEQ ID NO: 686                moltype = AA   length = 17
FEATURE                       Location/Qualifiers
```

```
source                  1..17
                        mol_type = protein
                        organism = Homo sapiens
SEQUENCE: 686
MYWYRQDPGQ GLRLIYY                                                              17

SEQ ID NO: 687          moltype = AA  length = 17
FEATURE                 Location/Qualifiers
source                  1..17
                        mol_type = protein
                        organism = Homo sapiens
SEQUENCE: 687
LYWYQQILGQ GPKLLIQ                                                              17

SEQ ID NO: 688          moltype = AA  length = 17
FEATURE                 Location/Qualifiers
source                  1..17
                        mol_type = protein
                        organism = Homo sapiens
SEQUENCE: 688
VSWYQQTPGQ GLQFLFE                                                              17

SEQ ID NO: 689          moltype = AA  length = 17
FEATURE                 Location/Qualifiers
source                  1..17
                        mol_type = protein
                        organism = Homo sapiens
SEQUENCE: 689
LYWYRQTLGQ GPEFLSY                                                              17

SEQ ID NO: 690          moltype = AA  length = 17
FEATURE                 Location/Qualifiers
source                  1..17
                        mol_type = protein
                        organism = Homo sapiens
SEQUENCE: 690
VYWYQQGPGQ DPQFLIT                                                              17

SEQ ID NO: 691          moltype = AA  length = 17
FEATURE                 Location/Qualifiers
source                  1..17
                        mol_type = protein
                        organism = Homo sapiens
SEQUENCE: 691
MSWYQQDPGL GLRQIYY                                                              17

SEQ ID NO: 692          moltype = AA  length = 17
FEATURE                 Location/Qualifiers
source                  1..17
                        mol_type = protein
                        organism = Homo sapiens
SEQUENCE: 692
MYWYRQDPGM GLRLLHY                                                              17

SEQ ID NO: 693          moltype = AA  length = 17
FEATURE                 Location/Qualifiers
source                  1..17
                        mol_type = protein
                        organism = Homo sapiens
SEQUENCE: 693
VYWYQQTLDQ GLQFLIQ                                                              17

SEQ ID NO: 694          moltype = AA  length = 17
FEATURE                 Location/Qualifiers
source                  1..17
                        mol_type = protein
                        organism = Homo sapiens
SEQUENCE: 694
MYWYKQKAKK PPDLMFV                                                              17

SEQ ID NO: 695          moltype = AA  length = 17
FEATURE                 Location/Qualifiers
source                  1..17
                        mol_type = protein
                        organism = Homo sapiens
SEQUENCE: 695
VYWYQQGPGQ RPQFLIS                                                              17

SEQ ID NO: 696          moltype = AA  length = 17
```

```
FEATURE                 Location/Qualifiers
source                  1..17
                        mol_type = protein
                        organism = Homo sapiens
SEQUENCE: 696
VYWYQQGPGQ EPQFLIS                                                          17

SEQ ID NO: 697          moltype = AA  length = 17
FEATURE                 Location/Qualifiers
source                  1..17
                        mol_type = protein
                        organism = Homo sapiens
SEQUENCE: 697
MYWYRQILGQ KVEFLVS                                                          17

SEQ ID NO: 698          moltype = AA  length = 17
FEATURE                 Location/Qualifiers
source                  1..17
                        mol_type = protein
                        organism = Homo sapiens
SEQUENCE: 698
FYWYRQDPGM GLRLIYY                                                          17

SEQ ID NO: 699          moltype = AA  length = 17
FEATURE                 Location/Qualifiers
source                  1..17
                        mol_type = protein
                        organism = Homo sapiens
SEQUENCE: 699
MYWYRQDPGM GLRLIWY                                                          17

SEQ ID NO: 700          moltype = AA  length = 17
FEATURE                 Location/Qualifiers
source                  1..17
                        mol_type = protein
                        organism = Homo sapiens
SEQUENCE: 700
MYWYKQHAKK PPELMFV                                                          17

SEQ ID NO: 701          moltype = AA  length = 17
FEATURE                 Location/Qualifiers
source                  1..17
                        mol_type = protein
                        organism = Homo sapiens
SEQUENCE: 701
MYWYRQDPGQ ALRLIYY                                                          17

SEQ ID NO: 702          moltype = AA  length = 17
FEATURE                 Location/Qualifiers
source                  1..17
                        mol_type = protein
                        organism = Homo sapiens
SEQUENCE: 702
MYWYQQILGQ GPKLLIQ                                                          17

SEQ ID NO: 703          moltype = AA  length = 17
FEATURE                 Location/Qualifiers
source                  1..17
                        mol_type = protein
                        organism = Homo sapiens
SEQUENCE: 703
VSWYQQSPGQ GLQFLFE                                                          17

SEQ ID NO: 704          moltype = AA  length = 38
FEATURE                 Location/Qualifiers
source                  1..38
                        mol_type = protein
                        organism = Homo sapiens
SEQUENCE: 704
LEKSRLLSDR FSAERPKGSF STLEIQRTEQ GDSAMYLC                                   38

SEQ ID NO: 705          moltype = AA  length = 37
FEATURE                 Location/Qualifiers
source                  1..37
                        mol_type = protein
                        organism = Homo sapiens
SEQUENCE: 705
SDKGSIPDRF SAQQFSDYHS ELNMSSLELG DSALYFC                                    37
```

```
SEQ ID NO: 706          moltype = AA   length = 37
FEATURE                 Location/Qualifiers
source                  1..37
                        mol_type = protein
                        organism = Homo sapiens
SEQUENCE: 706
TDKGDVPEGY KVSRKEKRNF PLILESPSPN QTSLYFC                                  37

SEQ ID NO: 707          moltype = AA   length = 37
FEATURE                 Location/Qualifiers
source                  1..37
                        mol_type = protein
                        organism = Homo sapiens
SEQUENCE: 707
TAKGEVPDGY NVSRLKKQNF LLGLESAAPS QTSVYFC                                  37

SEQ ID NO: 708          moltype = AA   length = 37
FEATURE                 Location/Qualifiers
source                  1..37
                        mol_type = protein
                        organism = Homo sapiens
SEQUENCE: 708
RAKGNILERF SAQQFPDLHS ELNLSSLELG DSALYFC                                  37

SEQ ID NO: 709          moltype = AA   length = 37
FEATURE                 Location/Qualifiers
source                  1..37
                        mol_type = protein
                        organism = Homo sapiens
SEQUENCE: 709
SINESVPSRF SPECPNSSLL NLHLHALQPE DSALYLC                                  37

SEQ ID NO: 710          moltype = AA   length = 37
FEATURE                 Location/Qualifiers
source                  1..37
                        mol_type = protein
                        organism = Homo sapiens
SEQUENCE: 710
SDKGSIPDRF SAQQFSDYHS ELNMSSLELG DSALYFC                                  37

SEQ ID NO: 711          moltype = AA   length = 37
FEATURE                 Location/Qualifiers
source                  1..37
                        mol_type = protein
                        organism = Homo sapiens
SEQUENCE: 711
SDKGSIPDRF SAQQFSDYHS ELNMSSLELG DSALYFC                                  37

SEQ ID NO: 712          moltype = AA   length = 38
FEATURE                 Location/Qualifiers
source                  1..38
                        mol_type = protein
                        organism = Homo sapiens
SEQUENCE: 712
SEKSEIFDDQ FSVERPDGSN FTLKIRSTKL EDSAMYFC                                 38

SEQ ID NO: 713          moltype = AA   length = 37
FEATURE                 Location/Qualifiers
source                  1..37
                        mol_type = protein
                        organism = Homo sapiens
SEQUENCE: 713
TDKGEVPNGY NVSRLNKREF SLRLESAAPS QTSVYFC                                  37

SEQ ID NO: 714          moltype = AA   length = 37
FEATURE                 Location/Qualifiers
source                  1..37
                        mol_type = protein
                        organism = Homo sapiens
SEQUENCE: 714
TDKGEVPNGY NVSRLNKREF SLRLESAAPS QTSVYFC                                  37

SEQ ID NO: 715          moltype = AA   length = 37
FEATURE                 Location/Qualifiers
source                  1..37
                        mol_type = protein
                        organism = Homo sapiens
SEQUENCE: 715
SINESVPSRF SPECPNSSLL NLHLHALQPE DSALYLC                                  37
```

```
SEQ ID NO: 716          moltype = AA   length = 37
FEATURE                 Location/Qualifiers
source                  1..37
                        mol_type = protein
                        organism = Homo sapiens
SEQUENCE: 716
FQKGDIAEGY SVSREKKESF PLTVTSAQKN PTAFYLC                              37

SEQ ID NO: 717          moltype = AA   length = 38
FEATURE                 Location/Qualifiers
source                  1..38
                        mol_type = protein
                        organism = Homo sapiens
SEQUENCE: 717
VDDSQLPKDR FSAERLKGVD STLKIQPAKL EDSAVYLC                             38

SEQ ID NO: 718          moltype = AA   length = 37
FEATURE                 Location/Qualifiers
source                  1..37
                        mol_type = protein
                        organism = Homo sapiens
SEQUENCE: 718
RNKGNFPGRF SGRQFSNSRS EMNVSTLELG DSALYLC                              37

SEQ ID NO: 719          moltype = AA   length = 38
FEATURE                 Location/Qualifiers
source                  1..38
                        mol_type = protein
                        organism = Homo sapiens
SEQUENCE: 719
LEKSRLLTDR FSAERPKGSF STLEIQRTEQ GDSAMYLC                             38

SEQ ID NO: 720          moltype = AA   length = 37
FEATURE                 Location/Qualifiers
source                  1..37
                        mol_type = protein
                        organism = Homo sapiens
SEQUENCE: 720
SDKGSIPDRL SAQQFSDYHS ELNMSSLELG DSALYFC                              37

SEQ ID NO: 721          moltype = AA   length = 37
FEATURE                 Location/Qualifiers
source                  1..37
                        mol_type = protein
                        organism = Homo sapiens
SEQUENCE: 721
TDKGDVPEGY KVSRKERRNF PLILESPSPN QTSLYFC                              37

SEQ ID NO: 722          moltype = AA   length = 37
FEATURE                 Location/Qualifiers
source                  1..37
                        mol_type = protein
                        organism = Homo sapiens
SEQUENCE: 722
TAKGEVPDGY NVSRLKKQNF LLGLETAAPS QTSVYFC                              37

SEQ ID NO: 723          moltype = AA   length = 37
FEATURE                 Location/Qualifiers
source                  1..37
                        mol_type = protein
                        organism = Homo sapiens
SEQUENCE: 723
RAKGNILERF SAMQFPDLHS ELNLSSLELG DSALYFC                              37

SEQ ID NO: 724          moltype = AA   length = 37
FEATURE                 Location/Qualifiers
source                  1..37
                        mol_type = protein
                        organism = Homo sapiens
SEQUENCE: 724
SINESVPSRF SPECPNSSLI NLHLHALQPE DSALYLC                              37

SEQ ID NO: 725          moltype = AA   length = 37
FEATURE                 Location/Qualifiers
source                  1..37
                        mol_type = protein
                        organism = Homo sapiens
SEQUENCE: 725
```

```
SDKGSLPDRF SAQQFSDYHS ELNMSSLELG DSALYFC                              37

SEQ ID NO: 726         moltype = AA   length = 37
FEATURE                Location/Qualifiers
source                 1..37
                       mol_type = protein
                       organism = Homo sapiens
SEQUENCE: 726
SDKGSIPDRF SAQQFSDYHS ELNMTSLELG DSALYFC                              37

SEQ ID NO: 727         moltype = AA   length = 38
FEATURE                Location/Qualifiers
source                 1..38
                       mol_type = protein
                       organism = Homo sapiens
SEQUENCE: 727
SEKSEIFDDQ FSVERPDGSN FTLRIRSTKL EDSAMYFC                             38

SEQ ID NO: 728         moltype = AA   length = 37
FEATURE                Location/Qualifiers
source                 1..37
                       mol_type = protein
                       organism = Homo sapiens
SEQUENCE: 728
TDKGEVPNGY NVTRLNKREF SLRLESAAPS QTSVYFC                              37

SEQ ID NO: 729         moltype = AA   length = 37
FEATURE                Location/Qualifiers
source                 1..37
                       mol_type = protein
                       organism = Homo sapiens
SEQUENCE: 729
TDKIEVPNGY NVSRLNKREF SLRLESAAPS QTSVYFC                              37

SEQ ID NO: 730         moltype = AA   length = 37
FEATURE                Location/Qualifiers
source                 1..37
                       mol_type = protein
                       organism = Homo sapiens
SEQUENCE: 730
SINDSVPSRF SPECPNSSLL NLHLHALQPE DSALYLC                              37

SEQ ID NO: 731         moltype = AA   length = 37
FEATURE                Location/Qualifiers
source                 1..37
                       mol_type = protein
                       organism = Homo sapiens
SEQUENCE: 731
FQKGDIADGY SVSREKKESF PLTVTSAQKN PTAFYLC                              37

SEQ ID NO: 732         moltype = AA   length = 38
FEATURE                Location/Qualifiers
source                 1..38
                       mol_type = protein
                       organism = Homo sapiens
SEQUENCE: 732
VDDSQLPKDR FSAERLKGVD STLKIMPAKL EDSAVYLC                             38

SEQ ID NO: 733         moltype = AA   length = 37
FEATURE                Location/Qualifiers
source                 1..37
                       mol_type = protein
                       organism = Homo sapiens
SEQUENCE: 733
RNKGNFPGRF SGRQFTNSRS EMNVSTLELG DSALYLC                              37

SEQ ID NO: 734         moltype = AA   length = 10
FEATURE                Location/Qualifiers
source                 1..10
                       mol_type = protein
                       organism = Homo sapiens
SEQUENCE: 734
FGPGTRLTVT                                                            10

SEQ ID NO: 735         moltype = AA   length = 10
FEATURE                Location/Qualifiers
source                 1..10
                       mol_type = protein
                       organism = Homo sapiens
```

```
SEQUENCE: 735
FGQGTRLTVV                                                                      10

SEQ ID NO: 736         moltype = AA   length = 10
FEATURE                Location/Qualifiers
source                 1..10
                       mol_type = protein
                       organism = Homo sapiens
SEQUENCE: 736
FGDGTRLSIL                                                                      10

SEQ ID NO: 737         moltype = AA   length = 10
FEATURE                Location/Qualifiers
source                 1..10
                       mol_type = protein
                       organism = Homo sapiens
SEQUENCE: 737
FGPGTRLTVL                                                                      10

SEQ ID NO: 738         moltype = AA   length = 10
FEATURE                Location/Qualifiers
source                 1..10
                       mol_type = protein
                       organism = Homo sapiens
SEQUENCE: 738
FGPGTRLTVT                                                                      10

SEQ ID NO: 739         moltype = AA   length = 10
FEATURE                Location/Qualifiers
source                 1..10
                       mol_type = protein
                       organism = Homo sapiens
SEQUENCE: 739
FGPGTRLTVL                                                                      10

SEQ ID NO: 740         moltype = AA   length = 10
FEATURE                Location/Qualifiers
source                 1..10
                       mol_type = protein
                       organism = Homo sapiens
SEQUENCE: 740
FGPGTRLTVL                                                                      10

SEQ ID NO: 741         moltype = AA   length = 10
FEATURE                Location/Qualifiers
source                 1..10
                       mol_type = protein
                       organism = Homo sapiens
SEQUENCE: 741
FGPGTRLTVL                                                                      10

SEQ ID NO: 742         moltype = AA   length = 10
FEATURE                Location/Qualifiers
source                 1..10
                       mol_type = protein
                       organism = Homo sapiens
SEQUENCE: 742
FGPGTRLTVL                                                                      10

SEQ ID NO: 743         moltype = AA   length = 10
FEATURE                Location/Qualifiers
source                 1..10
                       mol_type = protein
                       organism = Homo sapiens
SEQUENCE: 743
FGPGTRLTVL                                                                      10

SEQ ID NO: 744         moltype = AA   length = 10
FEATURE                Location/Qualifiers
source                 1..10
                       mol_type = protein
                       organism = Homo sapiens
SEQUENCE: 744
FGPGTRLTVT                                                                      10

SEQ ID NO: 745         moltype = AA   length = 10
FEATURE                Location/Qualifiers
source                 1..10
                       mol_type = protein
```

```
                        organism = Homo sapiens
SEQUENCE: 745
FGSGTRLTVV                                                                        10

SEQ ID NO: 746          moltype = AA  length = 10
FEATURE                 Location/Qualifiers
source                  1..10
                        mol_type = protein
                        organism = Homo sapiens
SEQUENCE: 746
FGPGTRLTVL                                                                        10

SEQ ID NO: 747          moltype = AA  length = 10
FEATURE                 Location/Qualifiers
source                  1..10
                        mol_type = protein
                        organism = Homo sapiens
SEQUENCE: 747
FGNGTRLTVT                                                                        10

SEQ ID NO: 748          moltype = AA  length = 10
FEATURE                 Location/Qualifiers
source                  1..10
                        mol_type = protein
                        organism = Homo sapiens
SEQUENCE: 748
FGPGTRLTVT                                                                        10

SEQ ID NO: 749          moltype = AA  length = 189
FEATURE                 Location/Qualifiers
source                  1..189
                        mol_type = protein
                        organism = Homo sapiens
SEQUENCE: 749
MTDKTEKVAV DPETVFKRPR ECDSPSYQKR QRMALLARKQ GAGDSLIAGS AMSKAKKLMT                   60
GHAIPPSQLD SQIDDFTGFS KDRMMQKPGS NAPVGGNVTS SFSGDDLECR ETASSPKSQR                  120
EINADIKRKL VKELRCVGQK YEKIFEMLEG VQGPTAVRKR FFESIIKEAA RCMRRDFVKH                  180
LKKKLKRMI                                                                        189

SEQ ID NO: 750          moltype = AA  length = 141
FEATURE                 Location/Qualifiers
source                  1..141
                        mol_type = protein
                        organism = Homo sapiens
SEQUENCE: 750
DIQNPDPAVY QLRDSKSSDK SVCLFTDFDS QTNVSQSKDS DVYITDKTVL DMRSMDFKSN                   60
SAVAWSNKSD FACANAFNNS IIPEDTFFPS PESSCDVKLV EKSFETDTNL NFQNLSVIGF                  120
RILLLKVAGF NLLMTLRLWS S                                                           141

SEQ ID NO: 751          moltype = AA  length = 141
FEATURE                 Location/Qualifiers
source                  1..141
                        mol_type = protein
                        organism = Homo sapiens
SEQUENCE: 751
NIQNPDPAVY QLRDSKSSDK SVCLFTDFDS QTNVSQSKDS DVYITDKTVL DMRSMDFKSN                   60
SAVAWSNKSD FACANAFNNS IIPEDTFFPS PESSCDVKLV EKSFETDTNL NFQNLSVIGF                  120
RILLLKVAGF NLLMTLRLWS S                                                           141
```